(12) United States Patent
Diels et al.

(10) Patent No.: US 8,338,422 B2
(45) Date of Patent: Dec. 25, 2012

(54) INDOLIN-2-ONES AND AZA-INDOLIN-2-ONES

(75) Inventors: Gaston Stanislas Marcella Diels, Ravels (BE); Marc Gustaaf Celine Verdonck, Gierle (BE); Peter Jacobus Johannes Antonius Buijnsters, Etten Leur (BE); Kristof Van Emelen, Sint-Niklaas (BE)

(73) Assignee: Janssen Pharmaceutica NV, Beerse (BE)

( * ) Notice: Subject to any disclaimer, the term of this patent is extended or adjusted under 35 U.S.C. 154(b) by 266 days.

(21) Appl. No.: 12/663,158

(22) PCT Filed: Jun. 20, 2008

(86) PCT No.: PCT/EP2008/057909
§ 371 (c)(1),
(2), (4) Date: Dec. 4, 2009

(87) PCT Pub. No.: WO2008/155421
PCT Pub. Date: Dec. 24, 2008

(65) Prior Publication Data
US 2010/0190786 A1    Jul. 29, 2010

(30) Foreign Application Priority Data

Jun. 21, 2007 (EP) .................................. 07110764

(51) Int. Cl.
C07D 209/34 (2006.01)
C07D 471/04 (2006.01)
C07D 487/04 (2006.01)
A61K 31/404 (2006.01)
A61K 31/407 (2006.01)
A61P 35/00 (2006.01)

(52) U.S. Cl. ........ 514/249; 514/257; 514/410; 540/457; 540/458

(58) Field of Classification Search .................. 540/457, 540/458; 514/249, 257, 410
See application file for complete search history.

(56) References Cited

FOREIGN PATENT DOCUMENTS

| WO | WO 00/55159 A | 9/2000 |
|----|---------------|--------|
| WO | WO 01/16130 A | 3/2001 |
| WO | WO 01/27081 | 4/2001 |
| WO | WO 02/20479 A | 3/2002 |
| WO | WO 2004/013099 | 2/2004 |
| WO | WO 2004/026829 A | 4/2004 |
| WO | WO 2006/067165 | 6/2006 |

OTHER PUBLICATIONS

"Heterocyclic Compounds"—Fused pyrimidines, vol. 24 (part 4), pp. 261-304, Wiley-Interscience, (1992).
Barr, F.A. et al, Nat. Rev. Mol. Cell Biol. 2004, vol. 5.: 429-441.
Burns, Timothy F. et al, Mol.Cell. Biol. 2003, vol. 23, No. 16:5556-5571.
Carvajal, Richard D. et al, Clin. Cancer Res 2006;12(23): pp. 6869-6875.
Cook, Neil D. et al, Advances in Experimental Medicine and Biology, 1991, 36: pp. 525-528.
Castedo, M., et al, Oncogene, 2004, 23: 2825-2837.
Nagamatsu, Tomohisa et al, J. Chem. Soc., Perkin Trans. vol. 1; 2001:130-137.
Greene, Theodora W. et al, In Protective Groups in Organic Synthesis; 3rd edition, 1998. Note:Title Page and Table of Content provided only; please advise if additional portions should be submitted.
Li, Jun et al, Neoplasia; Apr. 2005: 7(4):pp. 312-323.
Spankuch-Schmitt, Birgit et al, Oncogene, May 9, 2002; 21(20):3162-3171.
Rodems, Steven M. et al, Assay Drug Develop. Technol. 2002; 1:9-19.
Nagamatsu, Tomohisa et al, Chem. Pharm. Bull., 1993, vol. 41(2):362-368.
Wang, Qi et al, Mol. Cell. Biol. 2002, 22(10): 3450-3459.
Yuan, Juping et al, Cancer Research. 2002, 62:4186-4190.
International Search Report PCT/EP2008/057909, mailed Dec. 4, 2008.

*Primary Examiner* — Bruck Kifle

(57) ABSTRACT

The present invention relates to compounds or pharmaceutically-acceptable salts thereof, processes for preparing them, pharmaceutical compositions containing them and their use in therapy. The invention particularly relates to certain indolin-2-ones and aza-indolin-2-ones which possess anti-tumor activity and are accordingly useful in methods of treatment of the human or animal body, in particular such compounds are useful in the treatment of pathological processes which involve an aberrant cellular proliferation, such as tumor growth, rheumatoid arthritis, restenosis and atherosclerosis.

19 Claims, No Drawings

INDOLIN-2-ONES AND AZA-INDOLIN-2-ONES

CROSS REFERENCE TO RELATED APPLICATIONS

This application is a national stage of PCT Application No. PCT/EP2008/057909, filed Jun. 20, 2008, which claims priority for EPO Patent Application No. 07110764.3, filed Jun. 21, 2007, all of which are hereby incorporated by reference in their entirety.

The present invention relates to compounds and pharmaceutically-acceptable salts thereof, processes for preparing them, pharmaceutical compositions containing them and their use in therapy. The invention particularly relates to certain indolin-2-ones and aza-indolin-2-ones which possess anti-tumour activity and are accordingly useful in methods of treatment of the human or animal body, in particular such compounds are useful in the treatment of pathological processes which involve an aberrant cellular proliferation, such as tumor growth, rheumatoid arthritis, restenosis and atherosclerosis.

BACKGROUND OF THE INVENTION

The main goal of a mitotic cell is to equally seggregate its chromosomes and centrosomes between two daughter cells. The careful orchestration of cytoskeletal and chromosomal events requires coordinated action by members of the CDK (cyclin-dependent kinase), Plk (polo-like kinase) and Aurora kinase families. The study of these kinases, their regulatory subunits and substrates has attracted considerable attention in recent years, in part because they are all candidate targets for cancer therapy. Indeed, during mitosis, a spectacular reorganization of the cytoskeleton occurs that builds a bipolar microtubule spindle that assures proper segregation of chromosomes and requires a number of precisely coordinated cell-cycle events to occur. By the end of S-phase, the cell must have duplicated its centrosome and replicated its DNA. At the end of prophase, the duplicated and matured centrosomes must have become separated. During prometaphase, the two centrosomes and the chromosomes nucleate highly dynamic mitotic microtubules that assemble a bipolar spindle. During progression from prometaphase to metaphase, the chromosomes must become bi-orientated and aligned at the metaphase plate. Bi-orientation is achieved by microtubule-organized attachment of kinetochore pairs to opposite centrosomes. During this process, the mitotic checkpoint is continuously activated; it controls microtubule attachment to the kinetochores and tension. When these two conditions are satisfied, the checkpoint signals are switched off, the chromatids separate and anaphase proceeds. In telophase, nuclear division occurs and the cell undergoes cytokinesis. Finally, each daughter cell receives one set of chromosomes and one centrosome.

Considering the complexity of mitosis, not surprisingly there are many mitotic defects that can lead to the formation of aneuploid daughter cells, i.e. cells that possess an altered content of DNA (abnormal number of chromosomes). To prevent the appearance of such aneuploid cells, the cell will enter into mitotic catastrophe, i.e. a type of cell death as a result of DNA damage or deranged spindle formation coupled to the debilitation of different checkpoint mechanisms that would normally arrest progression into mitosis and hence suppress catastrophic events until repair has been achieved. Cells that fail to execute mitotic catastrophe in response to mitotic failure are likely to divide asymmetrically, with the consequent generation of aneuploid cells.

Most tumors develop in an (oligo) clonal and stochastic manner, through a multi-step process. It is accordingly a hypothesis that one of the mechanisms that contribute to oncogenesis consists of 'cytogenetic catastrophe', i.e. the failure to activate mitotic catastrophe in response to mitotic failure (Castedo, M., et al., Oncogene (2004) 23, 2825-2837). In these circumstances aneuploidization could result from the asymmetric division of polyploid cells, generated from an illicit cell fusion, as it may occur in vivo or from endoreplication/endomitosis. Indeed, polyploidy is frequently observed in neoplasia and constitutes a negative prognostic factor, while aneuploidy is a near to general characteristic of cancer.

As already mentioned above, the networks of kinases that regulate the mitotic events are all candidate targets for cancer therapy. For example, Aurora A is an oncogenic serine/threonine kinase that plays a role in centrosome separation and in the formation of the mitotic bipolar spindle. Aurora B is required for chromosome alignment, kinetochore-microtubule bi-orientation, activation of the spindle assembly checkpoint and cytokinesis. Both Aurora A and B are upregulated in various cancers, Aurora A is commonly amplified in melanoma and cancers of the breast, colon, pancreas, ovaries, bladder, liver and stomach. Aurora B is frequently increased in tumors such as colorectal cancer and high-grade gliomas, and Aurora B overexpression in CHO cells results in an increased invasiveness, suggesting a role for Aurora B in tumorigenesis (Carvajal, R. D. et al., Clin. Cancer Res. (2006) 12(23), 6869-6875).

Another member of the kinases involved in cellular mitosis, are the cyclin-dependent kinases CDKs. The family of cyclin-dependent kinases lies at the core of the machinery that drives the cell division. It is for example, well established that CDK1, formerly called Cdc2, interacts with its obligate allosteric activator, cyclin B1 to form an active heterodimer, the 'mitosis-promoting factor'. The mitosis-promoting factor induces mitosis by phosphorylating and activating enzymes regulating chromatin condensation, nuclear membrane breakdown, mitosis-specific microtubule reorganization and actin cytoskeleton allowing for mitotic rounding up of the cell. Aberrant mitotic entry, for example before the completion of DNA replication, can result in cytogenic catastrophe as observed in many tumor cells. Obviously, this requires the activation of CDK1, and it is currently assumed that premature entry of active CDK1/cyclin B1 complex into the nucleus suffices to cause premature chromatin condensation that may result in aneuploidization (Castedo M. et al., supra). This increasing body of evidence provides a link between tumor development and CDK related malfunctions and led to an intense search for inhibitors of the CDK family as an approach to cancer therapy.

Final members of the kinases involved in cellular mitosis are Polo-like kinases (PLKs). PLKs are key enzymes that control mitotic entry of proliferating cells and regulate many aspects of mitosis necessary for successful cytokinesis, including centrosome duplication and maturation; DNA damage checkpoint activation; bipolar spindle formation; Golgi fragmentation and assembly; and chromosome segregation (Barr, F. A. et al., Nat. Rev. Mol. Cell. Biol. 2004, 5, 429-441). Given the established role of PLKs as mitotic regulators, they have been regarded as validated mitotic cancer targets for a number of years. In addition, recent studies demonstrate that changes of intracellular levels of PLKs are involved in the control of cell growth. For example, PLK1 when fused to an antennapedia peptide and efficiently internalized into cells caused an inhibition of cancer cell proliferation (Yuan, J., et al., Cancer Res. 62, 2002, 4186-4190), whereas downregulation of PLK1 by antisense induced the growth inhibition of cancer cells (Spankuch-Schmitt, B., et al., Oncogene 21, 2002, 3162-3171). PLK2 was recently found to be a novel p53 target gene and RNAi silencing of PLK2 leads to mitotic catastrophe in taxol-exposed cells (Burns, T F., et al., Mol Cell Biol. 23, 2003, 5556-5571). For PLK3 it was found that it induces cell cycle arrest and apoptosis through perturbation of microtubule structure (Wang, Q., et al., Mol Cell Biol. 22, 2002, 3450-3459) and PLK4 was shown to be transcriptionally repressed by p53 and induces apoptosis upon RNAi silencing (Li, J., et al., Neoplasia 7, 2005, 312-323). Thus confirming that targeting PLKs with conventional small-molecule agents may be a valid and effective anticancer strategy with potential to synergize with established DNA-damage and antimitotic chemotherapies. PLK4 was also found to be required for centriole duplication and flagella development. The absence of centrioles, and hence basal bodies, compromises the meiotic divisions and the formation of sperm axonemes. This implies a possible use of PLK4 antagonists as male contraceptives.

We have now found that, certain indolin-2-ones and aza-indolin-2-ones possess potent anti-tumor activity. Without wishing to imply that the compounds disclosed in the present invention possess pharmacological activity only by virtue of an effect on a single biological process, it is believed that the compounds provide an anti-tumor effect by way of inhibition of one or more of protein kinases that are involved in the regulation of cellular mitosis and which lead to cytogenetic catastrophe in case of aberrant activity.

The compounds of the present invention, were also found to have Glycogen synthase kinase-3 (GSK-3) inhibitory activity and are accordingly useful in the prevention or treatment of diseases mediated through GSK-3 activity such as bipolar disorder (in particular manic depression), diabetes, Alzheimer's disease, leukopenia, FTDP-17 (Fronto-temporal dementia associated with Parkinson's disease), cortico-basal degeneration, progressive supranuclear palsy, multiple system atrophy, Pick's disease, Niemann Pick's disease type C, Dementia Pugilistica, dementia with tangles only, dementia with tangles and calcification, Downs syndrome, myotonic dystrophy, Parkinsonism-dementia complex of Guam, aids related dementia, Postencephalic Parkinsonism, prion diseases with tangles, subacute sclerosing panencephalitis, frontal lobe degeneration (FLD), argyrophilic grains disease, subacutesclerotizing panencephalitis (SSPE) (late complication of viral infections in the central nervous system), inflammatory diseases, depression, cancer, dermatological disorders such as baldness, neuroprotection, schizophrenia, pain, in particular neuropathic pain. GSK3 inhibitors can also be used to inhibit sperm motility and can therefore be used as male contraceptives. Therefore, the invention also provides the use of the macrocyclic indolin-2-ones and aza-indolin-2-ones as male contraceptives.

In particular, the compounds of the present invention are useful in the prevention or treatment of Alzheimer's disease; diabetes, in particular type 2 diabetes (non insulin dependent diabetes); bipolar disorder; cancer including lung cancer (especially non small-cell lung cancer), breast cancer, liver cancer, ovarian cancer, prostate cancer, pancreatic cancer, colorectal cancer, gastrointestinal cancer such as colon, bladder, rectal or stomach cancer and papillary carcinomas (such as papillary thyroid cancer) as well as in squamous cell cancers of the head and neck and in oesophageal cancers including oropharyngeal cancer; pain, in particular neuropathic pain; depression; inflammatory diseases including allergies and asthma, MS, RA, arteriosclerosis, arthritis or IBD.

DESCRIPTION OF THE INVENTION

The present invention concerns macrocyclic indolin-2-ones and aza-indolin-2-ones having potent anti-tumor activity. The invention further relates to methods for their preparation and pharmaceutical compositions comprising them. The invention also relates to the use of the macrocyclic indolin-2-ones and aza-indolin-2-ones compounds for the manufacture of a medicament for the treatment of cell proliferative disorders, including cancer, rheumatoid arthritis, restenosis and atherosclerosis. In the treatment of cancers, said cancers include lung cancer (especially non small-cell lung cancer), breast cancer, liver cancer, ovarian cancer, prostate cancer, pancreatic cancer, colorectal cancer, gastrointestinal cancer such as colon, rectal or stomach cancer and papillary carcinomas (such as papillary thyroid cancer) as well as in squamous cell cancers of the head and neck and in oesophageal cancers including oropharyngeal cancer. In a further aspect, the invention also provides the use of the macrocyclic indolin-2-ones and aza-indolin-2-ones compounds as male contraceptives.

Boehringer Ingelheim International GmbH has disclosed indolinones as useful compounds in the treatment of fybrotic diseases (PCT Int. Pat. Publ. WO 2006067165). Active compounds contain either a tetrazole group or a nitrile function at the pyrimidine C-5 position. A variety of (hetero)arylalkylamino groups are tolerated at C-2, whereas the C-4 substituent does not appear to be critical for PLK1 inhibitory activity.

Indolinones have been described in WO 01/27081 and WO 04/13099 as having valuable pharmacological properties, in particular an inhibiting effect on various kinases, especially receptor tyrosine kinases such as VEGFR as well as complexes of CDKs with their specific cyclins.

The present invention relates to compounds of formula

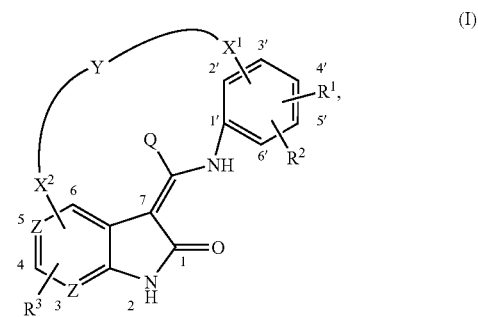

(I)

a N-oxide form, a quaternary amine or a stereochemically isomeric form thereof, wherein
Z represents N or CH;
Y represents —$C_{1-6}$alkanediyl-O—;
  —$C_{1-6}$alkanediyl-NR$^{15}$—;
  —$C_{1-6}$alkanediyl-NR$^{24}$—CO—$C_{1-6}$alkanediyl-;
  —NR$^5$—CO—$C_{1-6}$alkanediyl-;
  —NR$^{20}$—CO—$C_{1-6}$alkanediyl-NR$^4$—;
  —NR$^7$—$C_{1-6}$alkanediyl-NR$^8$—CO—$C_{1-6}$alkanediyl;
  —NR$^{25}$—CO—$C_{1-6}$alkanediyl-NR$^{26}$—$C_{1-6}$alkanediyl;
  —NR$^{16}$—$C_{1-6}$alkanediyl-NR$^{17}$—CO—$C_{1-6}$alkanediyl-NR$^{21}$—;
  —NR$^9$—CO—$C_{1-6}$alkanediyl-NR$^{10}$—CO—$C_{1-6}$alkanediyl-NR$^{11}$;

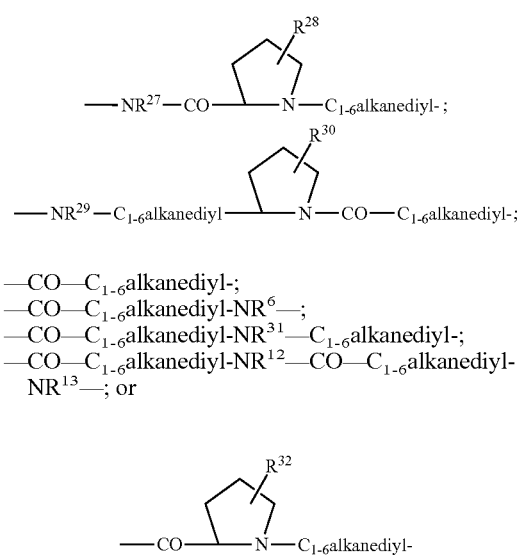

wherein each of said $C_{1-6}$alkanediyl may optionally be substituted with hydroxy or $Ar^{11}$;
$X^1$ represents a $C_{1-4}$alkanediyl, —O— or —S(O)$_2$—;
$X^2$ represents a $C_{1-4}$alkanediyl, Het$^1$, $C_{2-4}$alkenediyl, or —$C_{1-4}$alkanediyl-NR$^{14}$—;
Q represents hydrogen, $C_{1-4}$alkyl or Ar;
$R^1$ and $R^2$ each independently represent hydrogen; halo; $C_{1-4}$alkyl optionally substituted with one or where possible two, three or more substituents selected from the group consisting of halo, Ar$^3$ and Het$^3$; Ar$^1$—$C_{3-6}$cycloalkyl-O—; $C_{1-4}$alkyl-O— optionally substituted with one or where possible two, three or more substituents selected from the group consisting of halo, Ar$^4$ and Het$^4$; Ar$^2$—O—; —NR$^{18}$R$^{19}$; Het$^2$; cyano or —NR$^{33}$—W$^1$—Ar$^{10}$;
$R^3$ represents hydrogen, $C_{1-4}$alkyl-, Ar$^5$, Het$^5$, —NR$^{23}$R$^{22}$, $C_{1-4}$alkyl-O—, Ar$^6$—O—, $C_{1-4}$alkyl-S—, Ar$^7$—S—, $C_{1-4}$alkyl-S(O)$_{1-2}$—, Ar$^8$—S(O)$_{1-2}$—;
$R^4$, $R^5$, $R^6$, $R^7$, $R^8$, $R^9$, $R^{10}$, $R^{11}$, $R^{12}$, $R^{13}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{29}$ and $R^{31}$ each independently represent hydrogen; $C_{1-4}$alkyl; $C_{3-6}$cycloalkyl; $C_{1-4}$alkyl substituted with $C_{1-4}$alkyloxy, morpholinyl, piperazinyl or $C_{1-4}$alkylpiperazinyl wherein the $C_{1-4}$alkyl substituted on the piperazinyl may optionally be further substituted with one or where possible two, three or more substituents selected from the group consisting of halo, Ar$^9$ and Het$^6$;
$R^{14}$ and $R^{33}$ each independently represent hydrogen or $C_{1-4}$alkyl;
$R^{28}$, $R^{30}$ and $R^{32}$ each independently represent hydrogen or OH;
$W^1$ represents —CO—NH—, —CO—, —SO$_2$— or —$C_{1-4}$alkanediyl-;
Het$^1$ represents piperidinyl, piperazinyl, pyrrolidinyl or azetidinyl;
Het$^2$ and Het$^5$ each independently represent morpholinyl, thiomorpholinyl, pyrrolidinyl, piperazinyl or piperidinyl wherein said Het$^2$ and Het$^5$ are optionally substituted with one or where possible two or more substituents selected from $C_{1-4}$alkyl, $C_{3-6}$cycloalkyl, hydroxy$C_{1-4}$alkyl or $C_{1-4}$alkyloxy$C_{1-4}$alkyl;
Het$^3$, Het$^4$ and Het$^6$ each independently represent morpholinyl, thiomorpholinyl, pyrrolidinyl, piperazinyl or piperidinyl wherein said Het$^3$, Het$^4$ and Het$^6$ are optionally substituted with one or where possible two or more substituents selected from $C_{1-4}$alkyl, $C_{3-6}$cycloalkyl, hydroxy$C_{1-4}$alkyl or $C_{1-4}$alkyloxy$C_{1-4}$alkyl;

Ar represents an aryl or heteroaryl ring selected from the group consisting of phenyl, naphthyl, quinolinyl, benzoxazolyl, pyridyl, pyrazinyl, furanyl, thienyl, pyrimidinyl, isoxazolyl, isothiazolyl, oxazolyl, thiazolyl, pyrrolyl, pyrazolyl, indolyl, pyridazinyl, benzimidazolyl, benzothienyl and benzothiazolyl;
Ar$^1$, Ar$^2$, Ar$^3$, Ar$^4$ and Ar$^9$ each independently represent an aryl or heteroaryl ring system selected from the group consisting of phenyl, naphthyl, quinolinyl, benzoxazolyl, pyridyl, pyrazinyl, furanyl, thienyl, pyrimidinyl, isoxazolyl, isothiazolyl, oxazolyl, thiazolyl, pyrrolyl, pyrazolyl, indolyl, pyridazinyl, benzimidazolyl, benzothienyl and benzothiazolyl;
Ar$^5$, Ar$^6$, Ar$^7$ and Ar$^8$ each independently represent an aryl or heteroaryl ring system selected from the group consisting of phenyl, naphthyl, quinolinyl, benzoxazolyl, pyridyl, pyrazinyl, furanyl, thienyl, pyrimidinyl, isoxazolyl, isothiazolyl, oxazolyl, thiazolyl, pyrrolyl, pyrazolyl, indolyl, pyridazinyl, benzimidazolyl, benzothienyl and benzothiazolyl;
Ar$^{10}$ and Ar$^{11}$ each independently represent a ring system selected from the group consisting of phenyl and $C_{3-6}$cycloalkyl;
or a pharmaceutically acceptable addition salt or solvate thereof.
In one aspect, the present invention relates to compounds of formula

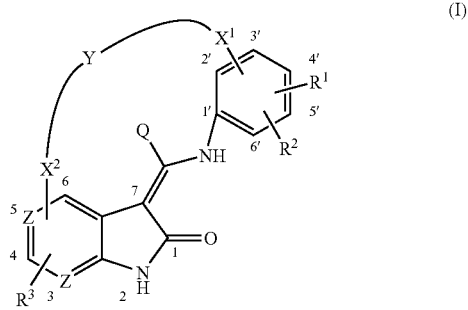

(I)

the N-oxide forms, the pharmaceutically acceptable addition salts, the quaternary amines and the stereochemically isomeric forms thereof, wherein
Z represents N or CH;
Y represents —NR$^{20}$—CO—$C_{1-6}$alkanediyl-NR$^4$—; —NR$^5$—CO—$C_{1-6}$alkanediyl-; —CO—$C_{1-6}$alkanediyl-NR$^6$—; —NR$^7$—$C_{1-6}$alkanediyl-NR$^8$—CO—$C_{1-6}$alkanediyl-; —CO—$C_{1-6}$alkanediyl-; —$C_{1-6}$alkanediyl-O—; —$C_{1-6}$alkanediyl-NR$^{15}$—; —NR$^9$—CO—$C_{1-6}$alkanediyl-NR$^{10}$—CO—$C_{1-6}$alkanediyl-NR$^{11}$—; —CO—$C_{1-6}$alkanediyl-NR$^{12}$—CO—$C_{1-6}$alkanediyl-NR$^{13}$—; —NR$^{16}$—$C_{1-6}$alkanediyl-NR$^{17}$—CO—$C_{1-6}$alkanediyl-NR$^{21}$—;
$X^1$ represents a $C_{1-4}$alkanediyl, —O— or —S(O)$_2$—;
$X^2$ represents a $C_{1-4}$alkanediyl, Het$^1$, $C_{2-4}$alkynediyl, or —$C_{1-4}$alkanediyl-NR$^{14}$—;
Q represents hydrogen, $C_{1-4}$alkyl or Ar;
$R^1$ and $R^2$ each independently represent hydrogen; halo; $C_{1-4}$alkyl optionally substituted with one or where possible two, three or more substituents selected from the group consisting of halo, Ar$^3$ and Het$^3$; Ar$^1$—$C_{3-6}$cycloalkyl-O—; $C_{1-4}$alkyl-O— optionally substituted with one or where possible two, three or more substituents selected from the group consisting of halo, Ar$^4$ and Het$^4$; Ar$^2$—O—; —NR$^{18}$R$^{19}$; Het$^2$ or cyano;

$R^3$ represents hydrogen, $C_{1-4}$alkyl, $Ar^5$, $Het^5$, —$NR^{23}R^{22}$, $C_{1-4}$alkyl-O—, $Ar^6$—O—, $C_{1-4}$alkyl-S—, $Ar^7$—S—, $C_{1-4}$alkyl-S(O)$_{1-2}$—, $Ar^8$—S(O)$_{1-2}$—;

$R^4, R^5, R^6, R^7, R^8, R^9, R^{10}, R^{11}, R^{12}, R^{13}, R^{15}, R^{16}, R^{17}, R^{18}, R^{19}, R^{20}, R^{21}, R^{22}$ and $R^{23}$ each independently represent hydrogen; $C_{1-4}$alkyl; $C_{3-6}$cycloalkyl; $C_{1-4}$alkyl substituted with morpholinyl, piperazinyl or $C_{1-4}$alkylpiperazinyl wherein the $C_{1-4}$alkyl substituted on the piperazinyl may optionally be further substituted with one or where possible two, three or more substituents selected from the group consisting of halo, $Ar^9$ and $Het^6$;

$R^{14}$ represents hydrogen or $C_{1-4}$alkyl;

$Het^1$ represents piperidinyl, piperazinyl, pyrrolidinyl or azetidinyl;

$Het^2$ and $Het^5$ each independently represent morpholinyl, thiomorpholinyl, pyrrolidinyl, piperazinyl or piperidinyl wherein said $Het^2$ and $Het^5$ are optionally substituted with one or where possible two or more substituents selected from $C_{1-4}$alkyl, $C_{3-6}$cycloalkyl, hydroxy$C_{1-4}$alkyl or $C_{1-4}$alkyloxy$C_{1-4}$alkyl;

$Het^3$, $Het^4$ and $Het^6$ each independently represent morpholinyl, thiomorpholinyl, pyrrolidinyl, piperazinyl or piperidinyl wherein said $Het^3$, $Het^4$ and $Het^6$ are optionally substituted with one or where possible two or more substituents selected from $C_{1-4}$alkyl, $C_{3-6}$cycloalkyl, hydroxy$C_{1-4}$alkyl or $C_{1-4}$alkyloxy$C_{1-4}$alkyl;

Ar represents an aryl or heteroaryl ring system selected from the group consisting of phenyl, naphthyl, quinolinyl, benzoxazolyl, pyridyl, pyrazinyl, furanyl, thienyl, pyrimidinyl, isoxazolyl, isothiazolyl, oxazolyl, thiazolyl, pyrrolyl, pyrazolyl, indolyl, pyridazinyl, benzimidazolyl, benzothienyl and benzothiazolyl;

$Ar^1, Ar^2, Ar^3, Ar^4$ and $Ar^9$ each independently represent an aryl or heteroaryl ring system selected from the group consisting of phenyl, naphthyl, quinolinyl, benzoxazolyl, pyridyl, pyrazinyl, furanyl, thienyl, pyrimidinyl, isoxazolyl, isothiazolyl, oxazolyl, thiazolyl, pyrrolyl, pyrazolyl, indolyl, pyridazinyl, benzimidazolyl, benzothienyl and benzothiazolyl;

$Ar^5, Ar^6, Ar^7$ and $Ar^8$ each independently represent an aryl or heteroaryl ring system selected from the group consisting of phenyl, naphthyl, quinolinyl, benzoxazolyl, pyridyl, pyrazinyl, furanyl, thienyl, pyrimidinyl, isoxazolyl, isothiazolyl, oxazolyl, thiazolyl, pyrrolyl, pyrazolyl, indolyl, pyridazinyl, benzimidazolyl, benzothienyl and benzothiazolyl;

In another aspect, the present invention relates to the compounds of formula (I) wherein Z represents N, hereinafter referred to as the compounds of formula (Ia);

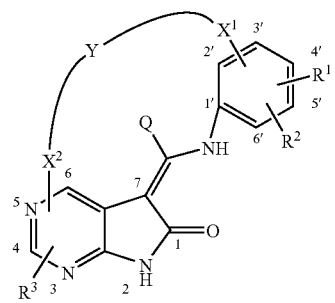
(Ia)

the N-oxide forms, the pharmaceutically acceptable addition salts, the quaternary amines and the stereochemically isomeric forms thereof, wherein Y represents —$NR^{20}$—CO—$C_{1-6}$alkanediyl-$NR^4$—; —$NR^5$—CO—$C_{1-6}$alkanediyl-; —CO—$C_{1-6}$alkanediyl-$NR^6$—; —$NR^7$—$C_{1-6}$alkanediyl-$NR^8$—CO—$C_{1-6}$alkanediyl-; —CO—$C_{1-6}$alkanediyl-; —$C_{1-6}$alkanediyl-O—; —$C_{1-6}$alkanediyl-$NR^{15}$—; —$NR^9$—CO—$C_{1-6}$alkanediyl-$NR^{10}$—CO—$C_{1-6}$alkanediyl-$NR^{11}$—; —CO—$C_{1-6}$alkanediyl-$NR^{12}$—CO—$C_{1-6}$alkanediyl-$NR^{13}$—; —$NR^{16}$—$C_{1-6}$alkanediyl-$NR^{17}$—CO—$C_{1-6}$alkanediyl-$NR^{21}$—;

$X^1$ represents a $C_{1-4}$alkanediyl, —O— or —S(O)$_2$—;

$X^2$ represents a $C_{1-4}$alkanediyl, $Het^1$, $C_{2-4}$alkynediyl, or —$C_{1-4}$alkanediyl-$NR^{14}$—;

Q represents hydrogen, $C_{1-4}$alkyl or Ar;

$R^1$ and $R^2$ each independently represent hydrogen; halo; $C_{1-4}$alkyl optionally substituted with one or where possible two, three or more substituents selected from the group consisting of halo, $Ar^3$ and $Het^3$; $Ar^1$—$C_{3-6}$cycloalkyl-O—; $C_{1-4}$alkyl-O— optionally substituted with one or where possible two, three or more substituents selected from the group consisting of halo, $Ar^4$ and $Het^4$; $Ar^2$—O—; —$NR^{18}R^{19}$; $Het^2$ or cyano;

$R^3$ represents hydrogen, $C_{1-4}$alkyl-, $Ar^5$, $Het^5$, —$NR^{23}R^{22}$, $C_{1-4}$alkyl-O—, $Ar^6$—O—, $C_{1-4}$alkyl-S—, $Ar^7$—S—, $C_{1-4}$alkyl-S(O)$_{1-2}$—, $Ar^8$—S(O)$_{1-2}$—;

$R^4, R^5, R^6, R^7, R^8, R^9, R^{10}, R^{11}, R^{12}, R^{13}, R^{15}, R^{16}, R^{17}, R^{18}, R^{19}, R^{20}, R^{21}, R^{22}$ and $R^{23}$ each independently represent hydrogen; $C_{1-4}$alkyl; $C_{3-6}$cycloalkyl; $C_{1-4}$alkyl substituted with morpholinyl, piperazinyl or $C_{1-4}$alkylpiperazinyl wherein the $C_{1-4}$alkyl substituted on the piperazinyl may optionally be further substituted with one or where possible two, three or more substituents selected from the group consisting of halo, $Ar^9$ and $Het^6$;

$R^{14}$ represents hydrogen or $C_{1-4}$alkyl;

$Het^1$ represents piperidinyl, piperazinyl, pyrrolidinyl or azetidinyl;

$Het^2$ and $Het^5$ each independently represent morpholinyl, thiomorpholinyl, pyrrolidinyl, piperazinyl or piperidinyl wherein said $Het^2$ and $Het^5$ are optionally substituted with one or where possible two or more substituents selected from $C_{1-4}$alkyl, $C_{3-6}$cycloalkyl, hydroxy$C_{1-4}$alkyl or $C_{1-4}$alkyloxy$C_{1-4}$alkyl;

$Het^3$, $Het^4$ and $Het^6$ each independently represent morpholinyl, thiomorpholinyl, pyrrolidinyl, piperazinyl or piperidinyl wherein said $Het^3$, $Het^4$ and $Het^6$ are optionally substituted with one or where possible two or more substituents selected from $C_{1-4}$alkyl, $C_{3-6}$cycloalkyl, hydroxy$C_{1-4}$alkyl or $C_{1-4}$alkyloxy$C_{1-4}$alkyl;

Ar represents an aryl or heteroaryl ring selected from the group consisting of phenyl, naphthyl, quinolinyl, benzoxazolyl, pyridyl, pyrazinyl, furanyl, thienyl, pyrimidinyl, isoxazolyl, isothiazolyl, oxazolyl, thiazolyl, pyrrolyl, pyrazolyl, indolyl, pyridazinyl, benzimidazolyl, benzothienyl and benzothiazolyl;

$Ar^1, Ar^2, Ar^3, Ar^4$ and $Ar^9$ each independently represent an aryl or heteroaryl ring system selected from the group consisting of phenyl, naphthyl, quinolinyl, benzoxazolyl, pyridyl, pyrazinyl, furanyl, thienyl, pyrimidinyl, isoxazolyl, isothiazolyl, oxazolyl, thiazolyl, pyrrolyl, pyrazolyl, indolyl, pyridazinyl, benzimidazolyl, benzothienyl and benzothiazolyl;

$Ar^5, Ar^6, Ar^7$ and $Ar^8$ each independently represent an aryl or heteroaryl ring system selected from the group consisting of phenyl, naphthyl, quinolinyl, benzoxazolyl, pyridyl, pyrazinyl, furanyl, thienyl, pyrimidinyl, isoxazolyl, isothiazolyl, oxazolyl, thiazolyl, pyrrolyl, pyrazolyl, indolyl, pyridazinyl, benzimidazolyl, benzothienyl and benzothiazolyl;

In another aspect, the present invention relates to the compounds of formula (I) wherein Z represents CH, hereinafter referred to as the compounds of formula (Ib);

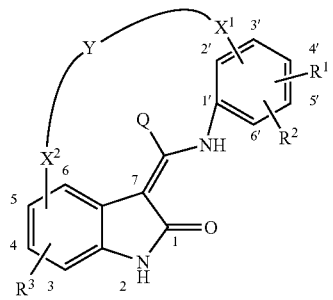

(Ib)

the N-oxide forms, the pharmaceutically acceptable addition salts, the quaternary amines and the stereochemically isomeric forms thereof, wherein Y represents —NR$^{20}$—CO—C$_{1-6}$alkanediyl-NR$^4$—; —NR$^5$—CO—C$_{1-6}$alkanediyl-; —CO—C$_{1-6}$alkanediyl-NR$^6$—; —NR$^7$—C$_{1-6}$alkanediyl-NR$^8$—CO—C$_{1-6}$alkanediyl-; —CO—C$_{1-6}$alkanediyl-; —C$_{1-6}$alkanediyl-O—; —C$_{1-6}$alkanediyl-NR$^{15}$—; —NR$^9$—CO—C$_{1-6}$alkanediyl-NR$^{10}$—CO—C$_{1-6}$alkanediyl-NR$^{11}$—; —CO—C$_{1-6}$alkanediyl-NR$^{12}$—CO—C$_{1-6}$alkanediyl-NR$^{13}$—; —NR$^{16}$—C$_{1-6}$alkanediyl-NR$^{17}$—CO—C$_{1-6}$alkanediyl-NR$^{21}$—;

X$^1$ represents a C$_{1-4}$alkanediyl, —O— or —S(O)$_2$—;

X$^2$ represents a C$_{1-4}$alkanediyl, Het$^1$, C$_{2-4}$alkynediyl, or —C$_{1-4}$alkanediyl-NR$^{14}$—;

Q represents hydrogen, C$_{1-4}$alkyl or Ar;

R$^1$ and R$^2$ each independently represent hydrogen; halo; C$_{1-4}$alkyl optionally substituted with one or where possible two, three or more substituents selected from the group consisting of halo, Ar$^3$ and Het$^3$; Ar$^1$—C$_{3-6}$cycloalkyl-O—; C$_{1-4}$alkyl-O— optionally substituted with one or where possible two, three or more substituents selected from the group consisting of halo, Ar$^4$ and Het$^5$; Ar$^2$—O—; —NR$^{18}$R$^{19}$; Het$^2$ or cyano;

R$^3$ represents hydrogen, C$_{1-4}$alkyl-, Ar$^5$, Het$^5$, —NR$^{23}$R$^{22}$, C$_{1-4}$alkyl-O—, Ar$^6$—O—, C$_{1-4}$alkyl-S—, Ar$^7$—S—, C$_{1-4}$alkyl-S(O)$_{1-2}$—, Ar$^8$—S(O)$_{1-2}$—;

R$^4$, R$^5$, R$^6$, R$^7$, R$^8$, R$^9$, R$^{10}$, R$^{11}$, R$^{12}$, R$^{13}$, R$^{15}$, R$^{16}$, R$^{17}$, R$^{18}$, R$^{19}$, R$^{20}$, R$^{21}$, R$^{22}$ and R$^{23}$ each independently represent hydrogen; C$_{1-4}$alkyl; C$_{3-6}$cycloalkyl; C$_{1-4}$-alkyl substituted with morpholinyl, piperazinyl or C$_{1-4}$alkylpiperazinyl wherein the C$_{1-4}$alkyl substituted on the piperazinyl may optionally be further substituted with one or where possible two, three or more substituents selected from the group consisting of halo, Ar$^9$ and Het$^6$;

R$^{14}$ represents hydrogen or C$_{1-4}$alkyl;

Het$^1$ represents piperidinyl, piperazinyl, pyrrolidinyl or azetidinyl;

Het$^2$ and Het$^5$ each independently represent morpholinyl, thiomorpholinyl, pyrrolidinyl, piperazinyl or piperidinyl wherein said Het$^2$ and Het$^5$ are optionally substituted with one or where possible two or more substituents selected from C$_{1-4}$alkyl, C$_{3-6}$cycloalkyl, hydroxyC$_{1-4}$alkyl or C$_{1-4}$alkyloxyC$_{1-4}$alkyl;

Het$^3$, Het$^4$ and Het$^6$ each independently represent morpholinyl, thiomorpholinyl, pyrrolidinyl, piperazinyl or piperidinyl wherein said Het$^3$, Het$^4$ and Het$^6$ are optionally substituted with one or where possible two or more substituents selected from C$_{1-4}$alkyl, C$_{3-6}$cycloalkyl, hydroxyC$_{1-4}$alkyl or C$_{1-4}$alkyloxyC$_{1-4}$alkyl;

Ar represents an aryl or heteroaryl ring system selected from the group consisting of phenyl, naphthyl, quinolinyl, benzoxazolyl, pyridyl, pyrazinyl, furanyl, thienyl, pyrimidinyl, isoxazolyl, isothiazolyl, oxazolyl, thiazolyl, pyrrolyl, pyrazolyl, indolyl, pyridazinyl, benzimidazolyl, benzothienyl and benzothiazolyl;

Ar$^1$, Ar$^2$, Ar$^3$, Ar$^4$ and Ar$^9$ each independently represent an aryl or heteroaryl ring system selected from the group consisting of phenyl, naphthyl, quinolinyl, benzoxazolyl, pyridyl, pyrazinyl, furanyl, thienyl, pyrimidinyl, isoxazolyl, isothiazolyl, oxazolyl, thiazolyl, pyrrolyl, pyrazolyl, indolyl, pyridazinyl, benzimidazolyl, benzothienyl and benzothiazolyl;

Ar$^5$, Ar$^6$, Ar$^7$ and Ar$^8$ each independently represent an aryl or heteroaryl ring system selected from the group consisting of phenyl, naphthyl, quinolinyl, benzoxazolyl, pyridyl, pyrazinyl, furanyl, thienyl, pyrimidinyl, isoxazolyl, isothiazolyl, oxazolyl, thiazolyl, pyrrolyl, pyrazolyl, indolyl, pyridazinyl, benzimidazolyl, benzothienyl and benzothiazolyl;

As used herein;

C$_{1-4}$alkyl as a group or part of a group defines straight or branched chain saturated hydrocarbon radicals having from 1 to 4 carbon atoms such as methyl, ethyl, propyl, 1-methylethyl, butyl;

C$_{1-4}$alkanediyl as a group or part of a group defines straight or branched chain saturated bivalent hydrocarbon radicals having from 1 to 4 carbon atoms such as methylene, ethanediyl, propanediyl, 1-methylethanediyl, butanediyl;

C$_{1-6}$alkanediyl as a group or part of a group defines straight or branched chain saturated hydrocarbon radicals having from 1 to 6 carbon atoms such as the groups defined for C$_{1-4}$alkyl and pentyl, hexyl, 2-methylbutyl and the like;

halo is generic to fluoro, chloro, bromo and iodo. As used in the foregoing and hereinafter, polyhaloC$_{1-6}$alkyl or polyhaloC$_{1-4}$alkyl as a group or part of a group is defined as mono- or polyhalosubstituted C$_{1-6}$alkyl or C$_{1-4}$alkyl, for example methyl with one or more fluoro atoms, for example, difluoromethyl or trifluoromethyl, 1,1-difluoro-ethyl and the like. In case more than one halogen atom is attached to an alkyl group within the definition of polyhaloC$_{1-4}$alkyl or polyhaloC$_{1-6}$alkyl, they may be the same or different.

C$_{2-4}$alkynyl as a group or part of a group defines straight and branched chain hydrocarbon radicals containing at least one triple bond and having from 2 to 4 carbon atoms such as, for example, 2-propynyl, 3-butynyl and the like;

C$_{2-4}$alkynediyl as a group or part of a group defines straight and branched chain bivalent hydrocarbon radicals containing at least one triple bond and having from 2 to 4 carbon atoms such as, for example, 2-propyndiyl, 3-butyndiyl and the like;

C$_{3-6}$cycloalkyl is generic to cyclopropyl, cyclobutyl, cyclopentyl and cyclohexyl;

As used herein, the term CO represents a carbonyl moiety; S(O)$_{1-2}$ is generic to sulfoxide (when only one oxygen atom is attached to a sulfur atom) and sulfonyl (when two oxygen atoms are attached to a sulfur atom).

Lines drawn into ring systems indicate that the bond may be attached to any suitable ring atom.

The heterocycles as mentioned in the above definitions and hereinafter, are meant to include all possible isomeric forms thereof, for instance pyrrolyl also includes 2H-pyrrolyl; triazolyl includes 1,2,4-triazolyl and 1,3,4-triazolyl; oxadiazolyl includes 1,2,3-oxadiazolyl, 1,2,4-oxadiazolyl, 1,2,5-oxadiazolyl and 1,3,4-oxadiazolyl; thiadiazolyl includes 1,2,3-thiadiazolyl, 1,2,4-thiadiazolyl, 1,2,5-thiadiazolyl and 1,3,4-thiadiazolyl; pyranyl includes 2H-pyranyl and 4H-pyranyl; benzodioxanyl includes 1,4 and 1,3 benzodioxanyl; pyrrolidinonyl includes 2-pyrrolidinonyl and 3-pyrrolidinonyl; tetrahydroquinolinyl includes 1,2,3,4-tetrahydroquinolinyl and 5,6,7,8-tetrahydroquinolinyl.

Further, the heterocycles as mentioned in the above definitions and hereinafter may be attached to the remainder of the molecule of formula (I) through any ring carbon or heteroatom as appropriate. Thus, for example, when the heterocycle is imidazolyl, it may be a 1-imidazolyl, 2-imidazolyl, 3-imidazolyl, 4-imidazolyl and 5-imidazolyl; when it is thiazolyl, it may be 2-thiazolyl, 4-thiazolyl and 5-thiazolyl; when it is triazolyl, it may be 1,2,4-triazol-1-yl, 1,2,4-triazol-3-yl, 1,2,4-triazol-5-yl, 1,3,4-triazol-1-yl and 1,3,4-triazol-2-yl; when it is benzothiazolyl, it may be 2-benzothiazolyl, 4-benzothiazolyl, 5-benzothiazolyl, 6-benzothiazolyl and 7-benzothiazolyl.

When any variable occurs more than one time in any constituent, each definition is independent.

It will be appreciated that some of the compounds of formula (I), (Ia) or (Ib) may contain one or more centers of chirality and can occur in stereochemically isomeric forms.

The term "stereochemically isomeric forms" as used hereinbefore or hereinafter defines all the possible stereoisomeric forms which the compounds of formula (I), (Ia) or (Ib) and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I), (Ia) or (Ib) and their N-oxides, salts, solvates, quaternary amines substantially free, i.e. associated with less than 10%, preferably less than 5%, in particular less than 2% and most preferably less than 1% of the other isomers. Stereochemically isomeric forms of the compounds of formula (I), (Ia) or (Ib) are obviously intended to be embraced within the scope of this invention.

For therapeutic use, salts of the compounds of formula (I), (Ia) or (Ib) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove or hereinafter are meant to comprise the therapeutically active non-toxic acid and base addition salt forms which the compounds of formula (I), (Ia) or (Ib) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I), (Ia) or (Ib) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term addition salt as used hereinabove also comprises the solvates which the compounds of formula (I), (Ia) or (Ib) as well as the salts thereof, are able to form. Such solvates are for example hydrates, alcoholates and the like.

The term "quaternary amine" as used hereinbefore defines the quaternary ammonium salts which the compounds of formula (I), (Ia) or (Ib) are able to form by reaction between a basic nitrogen of a compound of formula (I), (Ia) or (Ib) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include for example chloro, bromo, iodo, trifluoroacetate and acetate. The counterion of choice can be made using ion exchange resin columns.

The N-oxide forms of the present compounds are meant to comprise the compounds of formula (I), (Ia) or (Ib) wherein one or several tertiary nitrogen atoms are oxidized to the so-called N-oxide.

Some of the compounds of formula (I), (Ia) or (Ib) may also exist in their tautomeric form. Such forms although not explicitly indicated in the above formula are intended to be included within the scope of the present invention.

The chemical names of the macrocyclic compounds of the present invention were generated according to the nomenclature rules agreed upon by the Chemical Abstracts Service (CAS). In case of tautomeric forms, the name of the depicted tautomeric from of the structure was generated. However it should be clear for the present invention that the other, non-depicted tautomeric form is also included within the scope of the present invention.

For example, the chemical names for the compounds below are generated as:

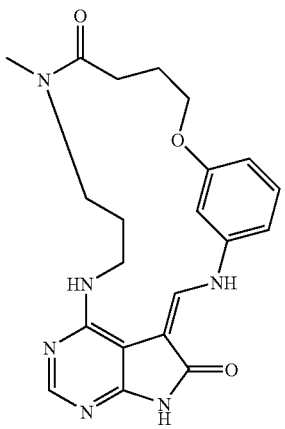

20,16-metheno-16H-15-oxa-2,3,5,6,10,21-hexaazacycloeicos[1,2,3-cd]indene-1,11(2H,12H)-dione,6,7,8,9,10,13,14,21-octahydro-10-methyl-

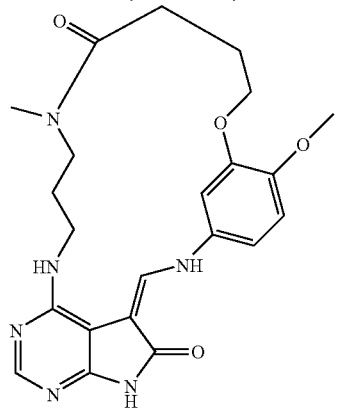

20,16-metheno-16H-15-oxa-2,3,5,6,10,21-hexaazacycloeicos[1,2,3-cd]indene-1,11(2H,12H)-dione,6,7,8,9,10,13,14,21-octahydro-17-methoxy-10-methyl- A first group of compounds are those compounds of formula (I) wherein one or more of the following restrictions apply;
(i) Z represents N or CH;
(ii) Y represents —$NR^{20}$—CO—$C_{1-6}$alkanediyl-$NR^4$—; —$NR^5$—CO—$C_{1-6}$alkanediyl-; —CO—$C_{1-6}$alkanediyl-$NR^6$—; —CO—$C_{1-6}$alkanediyl-; —$NR^9$—CO—$C_{1-6}$alkanediyl-$NR^{10}$—CO—$C_{1-6}$alkanediyl-$NR^{11}$—; or —CO—$C_{1-6}$alkanediyl-$NR^{12}$—CO—$C_{1-6}$alkanediyl-$NR^{13}$—;
(iii) $X^1$ represents $C_{1-4}$alkanediyl, —O— or —$S(O)_2$—;
(iv) $X^2$ represents $Het^1$, $C_{2-4}$alkynediyl, or —$C_{1-4}$alkanediyl-$NR^{14}$—;
(v) Q represents hydrogen;
(vi) $R^1$ and $R^2$ each independently represent hydrogen, halo, $C_{1-4}$alkanediyl-O—, cyano or $Het^2$; in particular $R^1$ represents $Het^2$, $C_{1-4}$alkanediyl-O—, cyano or halo and $R^2$ represents hydrogen, halo or $C_{1-4}$alkanediyl-O—;
(vii) $R^3$ represents hydrogen;
(viii) $R^5$, $R^9$, $R^{10}$, $R^{12}$ and $R^{20}$ each independently represent hydrogen, $C_{1-4}$alkyl or $C_{1-4}$alkyl substituted with morpholinyl or piperazinyl; in particular $R^5$, $R^9$, $R^{12}$ and $R^{20}$ each independently represent hydrogen or $C_{1-4}$alkyl and $R^{10}$ represents hydrogen, $C_{1-4}$alkyl or $C_{1-4}$alkyl substituted with morpholinyl or piperazinyl; more in particular $R^{10}$ represents $C_{1-4}$alkyl substituted with morpholinyl;
(ix) $R^4$, $R^6$, $R^{11}$ and $R^{13}$ each independently represent hydrogen or $C_{1-4}$alkyl;
(x) $R^{14}$ represents hydrogen or $C_{1-4}$alkyl;
(xi) $Het^1$ represents piperidinyl or piperazinyl;
(xii) $Het^2$ represents morpholinyl;

It is also an object of the present invention to provide those compounds of formula (I) wherein one or more of the following restrictions apply;
(i) Z represents N or CH;
(ii) Y represents —$NR^{20}$—CO—$C_{1-6}$alkanediyl-$NR^4$—; —$NR^5$—CO—$C_{1-6}$alkanediyl-; —CO—$C_{1-6}$alkanediyl-$NR^6$—; —CO—$C_{1-6}$alkanediyl-; or —$NR^9$—CO—$C_{1-6}$alkanediyl-$NR^{10}$—CO—$C_{1-6}$alkanediyl-$NR^{11}$—;
(iii) $X^1$ represents $C_{1-4}$alkanediyl, —O— or —$S(O)_2$—;
(iv) $X^2$ represents $Het^1$, $C_{2-4}$alkynediyl or —$C_{1-4}$alkanediyl-$NR^{14}$—;
(v) Q represents hydrogen;
(vi) $R^1$ represents hydrogen, $Het^2$, $C_{1-4}$alkanediyl-O—, cyano or halo;
(vii) $R^2$ represents hydrogen or $C_{1-4}$alkanediyl-O—;
(viii) $R^3$ represents hydrogen;
(ix) $R^5$, $R^9$, $R^{10}$ and $R^{20}$ each independently represent hydrogen or $C_{1-4}$alkyl; in particular $R^5$, $R^9$, $R^{10}$ and $R^{20}$ each independently represent hydrogen, methyl or isopropyl;
(x) $R^4$, $R^6$ and $R^{11}$ each independently represent $C_{1-4}$alkyl; in particular methyl or isopropyl;
(xi) $R^{14}$ represents hydrogen or $C_{1-4}$alkyl;
(xii) $Het^1$ represents piperazinyl;
(xiii) $Het^2$ represents morpholinyl.

It is also an object of the present invention to provide those compounds of formula (I) wherein one or more of the following restrictions apply;
(i) Z represents N or CH;
(ii) Y represents —$NR^{20}$—CO—$C_{1-6}$alkanediyl-$NR^4$—; —$NR^5$—CO—$C_{1-6}$alkanediyl-; or —CO—$C_{1-6}$alkanediyl-;
(iii) $X^1$ represents $C_{1-4}$alkanediyl, —O— or —$S(O)_2$—;
(iv) $X^2$ represents $Het^1$, $C_{2-4}$alkynediyl or —$C_{1-4}$alkanediyl-$NR^{14}$—;
(v) Q represents hydrogen;
(vi) $R^1$ represents hydrogen, $Het^2$, $C_{1-4}$alkanediyl-O—, cyano or halo;
(vii) $R^2$ represents hydrogen;
(viii) $R^3$ represents hydrogen;
(ix) $R^5$, $R^9$, $R^{10}$ and $R^{20}$ each independently represent hydrogen or $C_{1-4}$alkyl; in particular $R^5$, $R^9$, $R^{10}$ and $R^{20}$ each independently represent hydrogen, methyl or isopropyl;
(x) $R^4$, $R^6$ and $R^{11}$ each independently represent $C_{1-4}$alkyl; in particular methyl or isopropyl;
(xi) $R^{14}$ represents hydrogen or $C_{1-4}$alkyl;
(xii) $Het^1$ represents piperazinyl;
(xiii) $Het^2$ represents morpholinyl.

Also of interest are those compounds of formula (I) wherein one or more of the following restrictions apply;

(i) Z represents N;
(ii) Y represents —$NR^5$—CO—$C_{1-6}$alkanediyl- with $R^5$ being selected from hydrogen, methyl or isopropyl;
(iii) $X^1$ represents —O—;
(iv) $X^2$ represents —$C_{1-4}$alkanediyl-$NR^{14}$— with $R^{14}$ being selected from hydrogen or methyl;
(v) $R^1$ represents hydrogen, $C_{1-4}$alkanediyl-O—, or halo; in particular $R^1$ represents hydrogen, methoxy, ethoxy or halo;
(vi) $R^2$ and $R^3$ represent hydrogen.

An interesting embodiment of the present invention concerns those compounds of formula (Ia) wherein one or more of the following restrictions apply:
(i) Y represents —$NR^{20}$—CO—$C_{1-6}$alkanediyl-$NR^4$—; —$NR^5$—CO—$C_{1-6}$alkanediyl-; —CO—$C_{1-6}$alkanediyl-$NR^6$—; —CO—$C_{1-6}$alkanediyl-; —$NR^9$—CO—$C_{1-6}$alkanediyl-$NR^{10}$—CO—$C_{1-6}$alkanediyl-$NR^{11}$—; or —CO—$C_{1-6}$alkanediyl-$NR^{12}$—CO—$C_{1-6}$alkanediyl-$NR^{13}$—; in particular Y represents —$NR^{20}$—CO—$C_{1-6}$alkanediyl-$NR^4$—; —$NR^5$—CO—$C_{1-6}$alkanediyl-; —CO—$C_{1-6}$alkanediyl-$NR^6$— or —CO—$C_{1-6}$alkanediyl-;
(ii) $X^1$ represents $C_{1-4}$alkanediyl, —O— or $S(O)_2$—;
(iii) $X^2$ represents $Het^1$, $C_{2-4}$alkynediyl, or —$C_{1-4}$alkanediyl-$NR^{14}$—; in particular $X^2$ represents $Het^1$ or —$C_{1-4}$alkanediyl-$NR^{14}$—;
(iv) Q represents hydrogen;
(v) $R^1$ and $R^2$ each independently represent hydrogen, halo, $C_{1-4}$alkanediyl-O—, cyano or $Het^2$; in particular $R^1$ represents $Het^2$, $C_{1-4}$alkanediyl-O—, cyano or halo and $R^2$ represents hydrogen, halo or $C_{1-4}$alkanediyl-O—;
(vi) $R^3$ represents hydrogen;
(vii) $R^5$, $R^9$, $R^{10}$, $R^{12}$ and $R^{20}$ each independently represent hydrogen, $C_{1-4}$alkyl or $C_{1-4}$alkyl substituted with morpholinyl or piperazinyl; in particular $R^5$, $R^9$, $R^{10}$, $R^{12}$ and $R^{20}$ each independently represent hydrogen, or $C_{1-4}$alkyl;
(viii) $R^4$, $R^6$, $R^{11}$ and $R^{13}$ each independently represent hydrogen or $C_{1-4}$alkyl;
(ix) $R^{14}$ represents hydrogen or $C_{1-4}$alkyl;
(x) $Het^1$ represents piperidinyl or piperazinyl;
(xi) $Het^2$ represents morpholinyl.

A further embodiment of the compounds of formula (Ia) are those wherein one or more of the following further restrictions apply;
(i) $R^1$ represents hydrogen, morpholinyl, halo, cyano or methoxy;
(ii) $R^2$ represents hydrogen, halo or methoxy; in particular $R^2$ represents hydrogen;
(iii) $R^3$ represents hydrogen;
(iv) $R^5$, $R^9$, $R^{10}$, $R^{12}$ and $R^{20}$ each independently represent hydrogen, or $C_{1-4}$alkyl; in particular $R^5$, $R^9$, $R^{10}$, $R^{12}$ and $R^{20}$ each independently represent hydrogen, methyl or isopropyl; more in particular $R^5$ and $R^{20}$ each independently represent hydrogen, or $C_{1-4}$alkyl; even more in particular $R^5$ and $R^{20}$ each independently represent hydrogen or methyl;
(v) $R^4$, $R^6$, $R^{11}$ and $R^{13}$ each independently represent hydrogen or $C_{1-4}$alkyl; in particular $R^4$, $R^6$, $R^{11}$ and $R^{13}$ each independently represents hydrogen or methyl; more in particular $R^4$ represents hydrogen or $C_{1-4}$alkyl; even more in particular $R^4$ represents hydrogen or methyl;
(vi) $R^{14}$ represents hydrogen or $C_{1-4}$alkyl; in particular $R^{14}$ represents hydrogen or methyl;
(vii) $Het^1$ represents piperazinyl.

Also of interest are those compounds of formula (Ia) wherein one or more of the following restrictions apply;
(i) Y represents —$NR^5$—CO—$C_{1-6}$alkanediyl- with $R^5$ being selected from hydrogen, methyl or isopropyl;
(ii) $X^1$ represents —O—;
(iii) $X^2$ represents —$C_{1-6}$alkanediyl-$NR^{14}$— with $R^{14}$ being selected from hydrogen or methyl;
(iv) $R^1$ represents hydrogen, $C_{1-4}$alkanediyl-O—, or halo; in particular $R^1$ represents hydrogen, methoxy, ethoxy or halo;
(v) $R^2$ and $R^3$ represent hydrogen.

An even further interesting embodiment of the present invention concerns those compounds of formula (I) wherein one or more of the following restrictions apply:
(i) Y represents —$NR^{20}$—CO—$C_{1-6}$alkanediyl-$NR^4$—; —$NR^5$—CO—$C_{1-6}$alkanediyl-; or —CO—$C_{1-6}$alkanediyl-; in particular Y represents —$NR^5$—CO—$C_{1-6}$alkanediyl-;
(ii) $X^1$ represents $C_{1-4}$alkanediyl, —O— or —$S(O)_2$—; in particular $X^1$ represents —O—;
(iii) $X^2$ represents $Het^1$, $C_{2-4}$alkynediyl, or —$C_{1-4}$alkanediyl-$NR^{14}$—; in particular $X^2$ represents —$C_{1-4}$alkanediyl-$NR^{14}$—;
(iv) Q represents hydrogen;
(v) $R^1$ and $R^2$ each independently represent hydrogen, halo, $C_{1-4}$alkanediyl-O—, cyano or $Het^2$; in particular $R^1$ represents $Het^2$, $C_{1-4}$alkanediyl-O—, cyano or halo and $R^2$ represents hydrogen; in an even further embodiment $R^1$ and $R^2$ each independently represent hydrogen, halo, or $C_{1-4}$alkanediyl-O—;
(vi) $R^3$ represents hydrogen;
(vii) $R^5$ and $R^{20}$ each independently represent hydrogen or $C_{1-4}$alkyl;
(viii) $R^4$ represents hydrogen or $C_{1-4}$alkyl;
(ix) $R^{14}$ represents hydrogen or $C_{1-4}$alkyl;
(x) $Het^1$ represents piperidinyl or piperazinyl; in particular $Het^1$ represents piperazinyl;
(xi) $Het^2$ represents morpholinyl;

Another particular embodiment of the present invention concerns those compounds of formula (Ib) wherein one of the following restrictions apply:
(i) Y represents —$NR^{20}$—CO—$C_{1-6}$alkanediyl-$NR^4$—; —$NR^5$—CO—$C_{1-6}$alkanediyl-; —CO—$C_{1-6}$alkanediyl-$NR^6$—; —CO—$C_{1-6}$alkanediyl-; —$NR^9$—CO—$C_{1-6}$alkanediyl-$NR^{10}$—CO—$C_{1-6}$alkanediyl-$NR^{11}$—; or —CO—$C_{1-6}$alkanediyl-$NR^{12}$—CO—$C_{1-6}$alkanediyl-$NR^{13}$—; in particular Y represents —$NR^{20}$—CO—$C_{1-6}$alkanediyl-$NR^4$—; —CO—$C_{1-6}$alkanediyl-$NR^6$—; —CO—$C_{1-6}$alkanediyl-; —$NR^9$—CO—$C_{1-6}$alkanediyl-$NR^{10}$—CO—$C_{1-6}$alkanediyl-$NR^{11}$—; or —CO—$C_{1-6}$alkanediyl-$NR^{12}$—CO—$C_{1-6}$alkanediyl-$NR^{13}$—; more in particular Y represents —$NR^{20}$—CO—$C_{1-6}$alkanediyl-$NR^4$—; —CO—$C_{1-6}$alkanediyl-$NR^6$—; —$NR^9$—CO—$C_{1-6}$alkanediyl-$NR^{10}$—CO—$C_{1-6}$alkanediyl-$NR^{11}$—; or —CO—$C_{1-6}$alkanediyl-$NR^{12}$—CO—$C_{1-6}$alkanediyl-$NR^{13}$—; more in particular Y represents —$NR^{20}$—CO—$C_{1-6}$alkanediyl-$NR^4$—; —CO—$C_{1-6}$alkanediyl-$NR^6$—;

—NR$^9$—CO—C$_{1-6}$alkanediyl-NR$^{10}$—CO—C$_{1-6}$alkanediyl-NR$^{11}$—; or
—CO—C$_{1-6}$alkanediyl-NR$^{12}$—CO—C$_{1-6}$alkanediyl-NR$^{13}$—;

(ii) X$^1$ represents C$_{1-4}$alkanediyl, —O— or —S(O)$_2$—; in particular X$^1$ represents —S(O)$_2$—;

(iii) X$^2$ represents Het$^1$, C$_{2-4}$alkynediyl, or —C$_{1-4}$alkanediyl-NR$^{14}$—; in particular X$^2$ represents Het$^1$ or C$_{2-4}$alkynediyl;

(iv) Q represents hydrogen;

(v) R$^1$ and R$^2$ each independently represent hydrogen, halo, C$_{1-4}$alkanediyl-O—, cyano or Het$^2$; in particular R$^1$ represents Het$^2$, C$_{1-4}$alkanediyl-O—, cyano or halo and R$^2$ represents hydrogen, halo or C$_{1-4}$alkanediyl-O—; more in particular R$^1$ and R$^2$ represent hydrogen;

(vi) R$^3$ represents hydrogen;

(viii) R$^5$, R$^9$, R$^{10}$, R$^{12}$, and R$^{20}$ each independently represent hydrogen, C$_{1-4}$alkanediyl or C$_{1-4}$alkanediyl substituted with morpholinyl or piperazinyl; in particular R$^5$, R$^9$, R$^{10}$, R$^{12}$ and R$^{20}$ each independently represent hydrogen, or C$_{1-4}$alkanediyl; in particular R$^5$, R$^9$, R$^{12}$ and R$^{20}$ each independently represent hydrogen or C$_{1-4}$alkanediyl and R$^{10}$ represents hydrogen, C$_{1-4}$alkanediyl or C$_{1-4}$alkanediyl substituted with morpholinyl or piperazinyl; more in particular R$^{10}$ represents C$_{1-4}$alkanediyl substituted with morpholinyl;

(viii) R$^4$, R$^6$, R$^{11}$ and R$^{13}$ each independently represent hydrogen or C$_{1-4}$alkyl;

(ix) R$^{14}$ represents hydrogen or C$_{1-4}$alkyl;

(x) Het$^1$ represents piperidinyl or piperazinyl; in particular piperazinyl;

(xi) Het$^2$ represents morpholinyl;

Also an interesting embodiment of the present invention concerns those compounds of formula (Ib) wherein one or more of the following restrictions apply;

(i) Y represents —NR$^{20}$—CO—C$_{1-6}$alkanediyl-NR$^4$—; —CO—C$_{1-6}$alkanediyl-NR$^6$—; or
—NR$^9$—CO—C$_{1-6}$alkanediyl-NR$^{10}$—CO—C$_{1-6}$alkanediyl-NR$^{11}$—;

(ii) X$^1$ represents C$_{1-4}$alkanediyl, —O— or S(O)$_2$—; in particular X$^1$ represents —S(O)$_2$—;

(iii) X$^2$ represents Het$^1$, C$_{2-4}$alkynediyl, or —C$_{1-4}$alkanediyl-NR$^{14}$—; in particular X$^2$ represents Het$^1$ or C$_{2-4}$alkynediyl;

(iv) Q represents hydrogen;

(v) R$^1$ and R$^2$ each independently represent hydrogen;

(vi) R$^3$ represents hydrogen;

(vii) R$^9$, R$^{10}$ and R$^{20}$ each independently represent hydrogen, C$_{1-4}$alkanediyl or C$_{1-4}$alkanediyl substituted with morpholinyl or piperazinyl; in particular R$^9$, R$^{10}$ and R$^{20}$ each independently represent hydrogen, or C$_{1-4}$alkyl;

(viii) R$^4$ and R$^6$ each independently represent hydrogen or C$_{1-4}$alkyl;

(ix) R$^{14}$ represents hydrogen or C$_{1-4}$alkyl;

(x) Het$^1$ represents piperidinyl or piperazinyl;

(xi) Het$^2$ represents morpholinyl.

Also of interest are those compounds of formula (Ib) wherein one or more of the following restrictions apply;

(i) R$^1$ represents hydrogen, morpholinyl, halo, cyano or methoxy; in particular hydrogen (ii) R$^2$ represents hydrogen, halo or methoxy; in particular R$^2$ represents hydrogen;

(iii) R$^3$ represents hydrogen;

(iv) R$^9$, R$^{10}$ and R$^{20}$ each independently represent hydrogen, methyl or isopropyl; more in particular R$^9$, R$^{10}$ and R$^{20}$ each independently represent hydrogen or methyl;

(v) R$^4$ and R$^6$ each independently represents hydrogen or methyl;

(vi) R$^{14}$ represents hydrogen or methyl;

(vii) Het$^1$ represents piperazinyl.

Another interesting embodiment of the present invention concerns those compounds of formula (I), (Ia) or (Ib) wherein; Y represents —NR$^5$—CO—C$_{1-6}$alkanediyl-; X$^1$ represents —O—; X$^2$ represents —C$_{1-4}$alkanediyl-NR$^{14}$—; R$^5$ represents hydrogen or C$_{1-4}$alkyl and R$^{14}$ represents hydrogen or C$_{1-4}$alkyl. More in particular, those compounds of formula (I), (Ia) or (Ib) wherein Y represents —NR$^5$—CO—(CH$_2$)$_{3-4}$—; X$^1$ represents —O—; X$^2$ represents —(CH$_2$)$_3$—NR$^{14}$—; R$^5$ represents hydrogen, methyl or isopropyl and R$^{14}$ represents hydrogen or methyl.

A further interesting embodiment of the present invention concerns those compounds of formula (I), (Ia) or (Ib) wherein X$^1$ is attached at position 2', R$^1$ is at position 3' and X$^2$ is at position 6.

In a further interesting embodiment of the present invention the compounds are selected from:

6,9-ethano-17,20-etheno-1H-16-oxa-2,3,5,6,9,21-hexaazacycloeicos[1,2,3-cd]indene-1,10(11H)-dione, 18-chloro-2,7,8,12,13,14,15,21-octahydro- 1H-6,9-ethano-16,20-metheno-10H-15-oxa-2,3,5,6,9,21-hexaazacycloeicos[1,2,3-cd]indene-1,10-dione, 19-chloro-2,7,8,11,12,13,14,21-octahydro- 1H-6,9-ethano-16,20-metheno-10H-15-oxa-2,3,5,6,9,21-hexaazacycloeicos[1,2,3-cd]indene-1,10-dione, 17-chloro-2,7,8,11,12,13,14,21-octahydro- 1H-6,9-ethano-17,21-metheno-16-thia-2,3,5,6,9,15,22-heptaazacycloheneicos[1,2,3-cd]indene-1,10(11H)-dione, 2,7,8,12,13,14,15,22-octahydro-, 16,16-dioxide 1H-6,9-ethano-17,21-metheno-16-oxa-2,3,5,6,9,22-hexaazacycloheneicos[1,2,3-cd]indene-1,10(11H)-dione, 18-chloro-2,7,8,12,13,14,15,22-octahydro- 1H-6,9-ethano-15,19-metheno-14-oxa-2,3,5,6,9,20-hexaazacyclononadec[1,2,3-cd]indene-16-carbonitrile, 2,7,8,10,11,12,13,20-octahydro-1,10-dioxo- 1H-6,9-ethano-16,20-metheno-10H-15-oxa-2,3,5,6,9,21-hexaazacycloeicos[1,2,3-cd]indene-17-carbonitrile, 2,7,8,11,12,13,14,21-octahydro-1,10-dioxo- 1H-6,9-ethano-16,20-metheno-2,3,5,6,9,14,21-heptaazacycloeicos[1,2,3-cd]indene-1,10(11H)-dione, 2,7,8,12,13,14,15,21-octahydro-14-methyl- 10H-6,9-ethano-21,17-metheno-1H-2,3,5,6,9,15,22-heptaazacycloheneicos[1,2,3-cd]indene-1,10-dione, 18-fluoro-2,7,8,11,12,13,14,15,16,22-decahydro-15-(1-methylethyl)-

20,16-metheno-16H-15-oxa-2,3,5,6,10,21-hexaazacycloeicos[1,2,3-cd]indene-1,11(2H,12H)-dione, 6,7,8,9,10,13,14,21-octahydro-17-methoxy-6,10-dimethyl- 1H-19,15-metheno-14-oxa-2,3,5,6,9,20-hexaazacyclononadec[1,2,3-cd]indene-1,10(11H)-dione, 2,6,7,8,9,12,13,20-octahydro-16-methoxy-6-methyl-9-(1-methylethyl)-

20,16-metheno-16H-15-oxa-2,3,5,6,10,21-hexaazacycloeicos[1,2,3-cd]indene-1,11(2H,12H)-dione, 6,7,8,9,10,13,14,21-octahydro-17-methoxy-10-methyl- 20,16-metheno-16H-15-oxa-2,3,5,6,10,21-hexaazacycloeicos[1,2,3-cd]indene-1,11(2H,12H)-dione, 6,7,8,9,10,13,14,21-octahydro-10-methyl- 1H-21,17-metheno-16-oxa-2,3,5,6,9,22-hexaazacyclohene-
icos[1,2,3-cd]indene-1,10(11H)-dione, 2,6,7,8,9,12,13,
14,15,22-decahydro-18-methoxy-9-methyl- 20,16-metheno-16H-15-oxa-2,3,5,6,9,21-hexaazacycloe-
icos[1,2,3-cd]indene-1,10-dione, 2,6,7,8,9,11,12,13,14,
21-decahydro-17-methoxy-9-methyl- 1H-21,17-metheno-16-oxa-2,3,5,6,9,22-hexaazacyclohene-
icos[1,2,3-cd]indene-1,10(11H)-dione, 18-chloro-2,6,7,8,
9,12,13,14,15,22-decahydro-6-methyl- 20,16-metheno-16H-15-oxa-2,3,5,6,10,21-hexaazacycloe-
icos[1,2,3-cd]indene-1,11(2H,12H)-dione, 17-chloro-6,7,
8,9,10,13,14,21-octahydro-10-methyl- 21,17-metheno-17H-2,3,5,6,10,15,22-heptaazacyclohene-
icos[1,2,3-cd]indene-1,11(2H,12H)-dione, 6,7,8,9,10,13,
14,15,16,22-decahydro-10,15-dimethyl- 1H-19,15-metheno-14-oxa-2,3,5,6,9,20-hexaazacyclonona-
dec[1,2,3-cd]indene-1,10(11H)-dione, 2,6,7,8,9,12,13,
20-octahydro-9-methyl-16-(4-morpholinyl)-

21,17-metheno-17H-2,3,5,6,10,15,22-heptaazacyclohene-
icos[1,2,3-cd]indene-1,11(2H,12H)-dione, 6,7,8,9,10,13,
14,15,16,22-decahydro-18,19-dimethoxy-10,15-dim-
ethyl- 21,17-metheno-17H-2,3,5,6,10,15,22-heptaazacyclohene-
icos[1,2,3-cd]indene-1,11(2H,12H)-dione, 6,7,8,9,10,13,
14,15,16,22-decahydro-10,15-dimethyl-18-(4-morpholi-
nyl)- or a N-oxide, a pharmaceutically acceptable addition salt, a quaternary amine and a stereochemically isomeric form thereof.

In a particular embodiment of the present invention the compounds are selected from:

1H-21,17-metheno-16-oxa-2,3,5,6,9,22-hexaazacyclohene-
icos[1,2,3-cd]indene-1,10(11H)-dione, 18-chloro-2,6,7,8,
9,12,13,14,15,22-decahydro-6-methyl- 20,16-metheno-16H-15-oxa-2,3,5,6,10,21-hexaazacycloe-
icos[1,2,3-cd]indene-1,11(2H,12H)-dione, 6,7,8,9,10,13,
14,21-octahydro-10-methyl- 1H-21,17-metheno-16-oxa-2,3,5,6,9,22-hexaazacyclohene-
icos[1,2,3-cd]indene-1,10(11H)-dione, 2,6,7,8,9,12,13,
14,15,22-decahydro-18-methoxy-9-methyl- 20,16-metheno-16H-15-oxa-2,3,5,6,9,21-hexaazacycloe-
icos[1,2,3-cd]indene-1,10-dione, 2,6,7,8,9,11,12,13,14,
21-decahydro-17-methoxy-9-methyl- 20,16-metheno-16H-15-oxa-2,3,5,6,10,21-hexaazacycloe-
icos[1,2,3-cd]indene-1,11(2H,12H)-dione, 6,7,8,9,10,13,
14,21-octahydro-17-methoxy-6,10-dimethyl- 1H-19,15-metheno-14-oxa-2,3,5,6,9,20-hexaazacyclonona-
dec[1,2,3-cd]indene-1,10(11H)-dione, 2,6,7,8,9,12,13,
20-octahydro-16-methoxy-6-methyl-9-(1-methylethyl)-

20,16-metheno-16H-15-oxa-2,3,5,6,10,21-hexaazacycloe-
icos[1,2,3-cd]indene-1,11(2H,12H)-dione, 6,7,8,9,10,13,
14,21-octahydro-17-methoxy-10-methyl- or or an N-oxide, a pharmaceutically acceptable addition salt, a quaternary amine and a stereochemically isomeric form thereof.

A further interesting embodiment of the present invention concerns those compounds of formula (I), including the N-oxide forms and stereochemically isomers thereof, selected from the group consisting of;

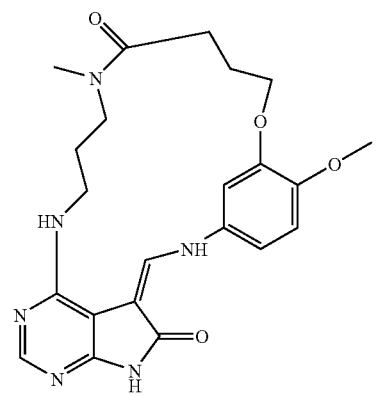

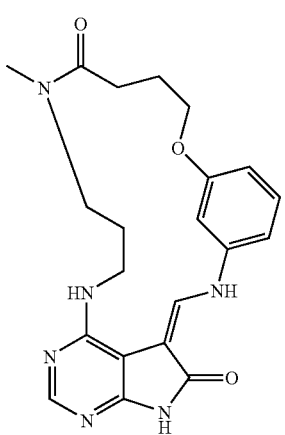

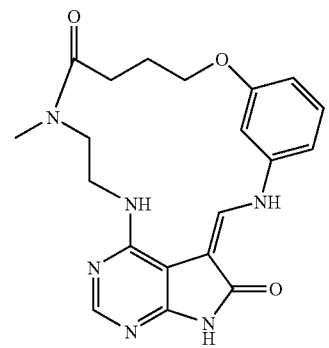

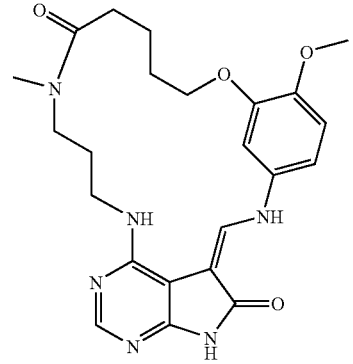

21
-continued
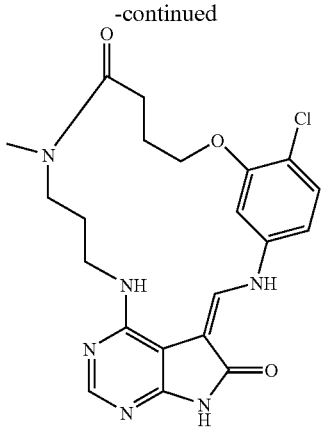
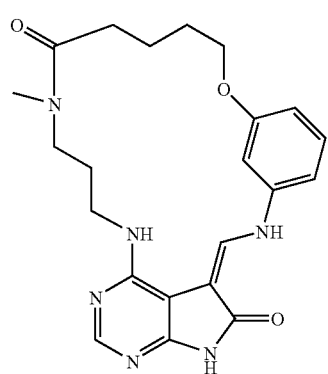
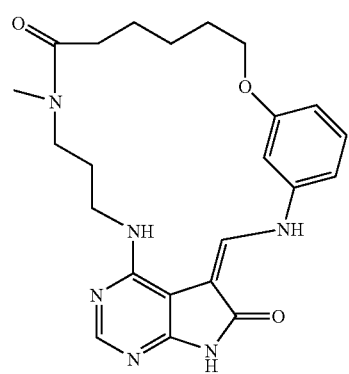
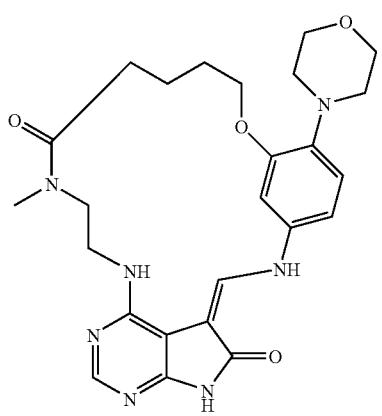
22
-continued
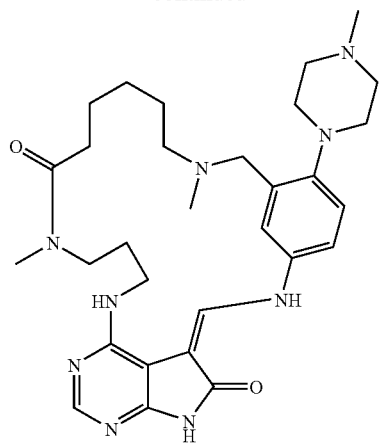
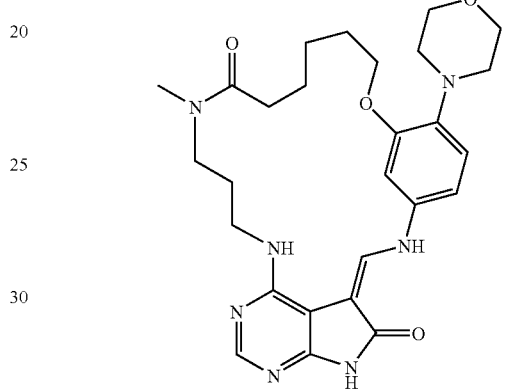
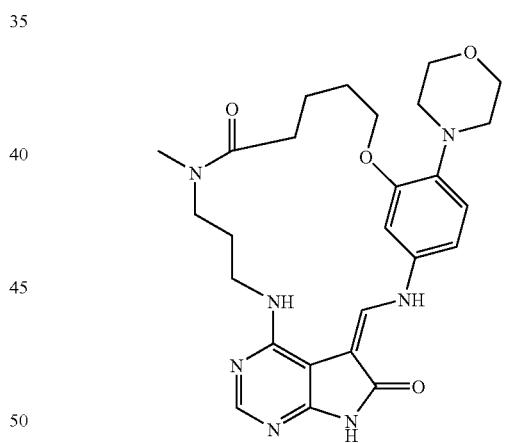
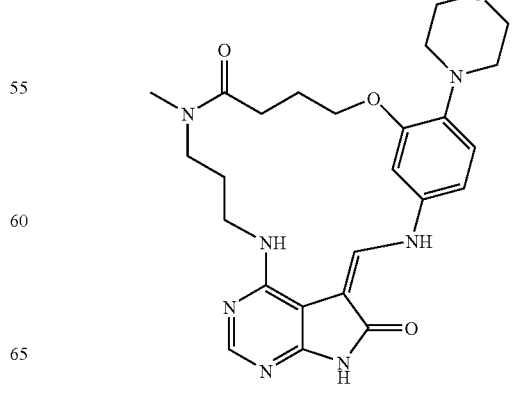

23
-continued
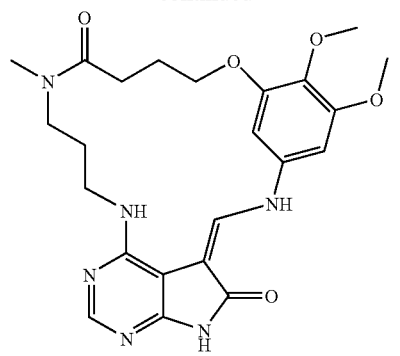
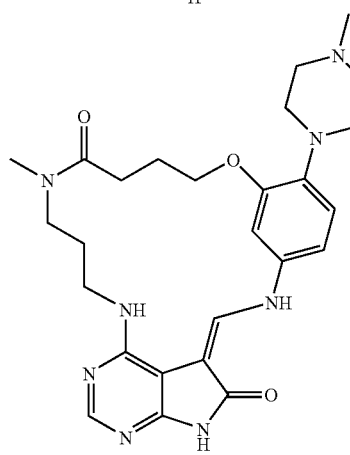
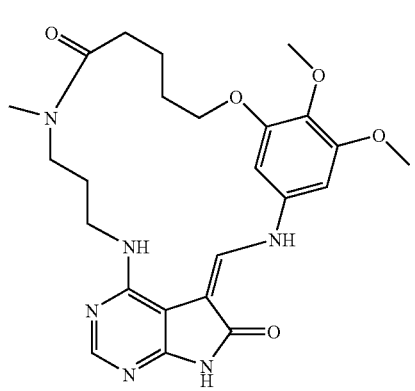
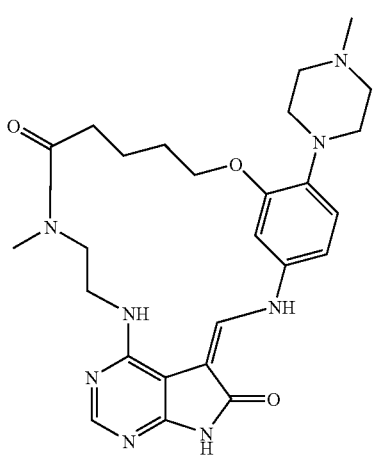
24
-continued
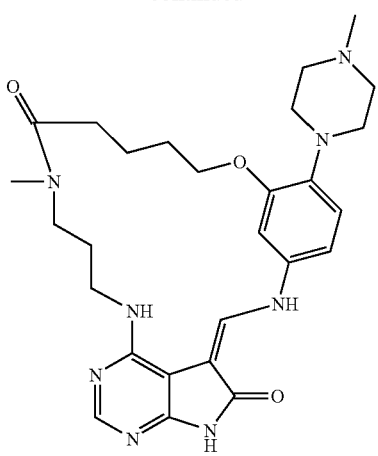
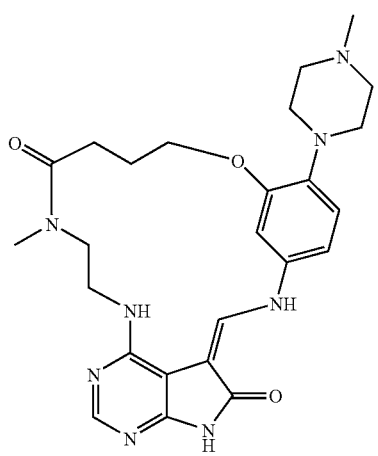
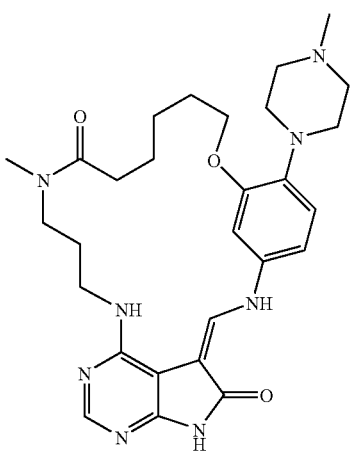

-continued

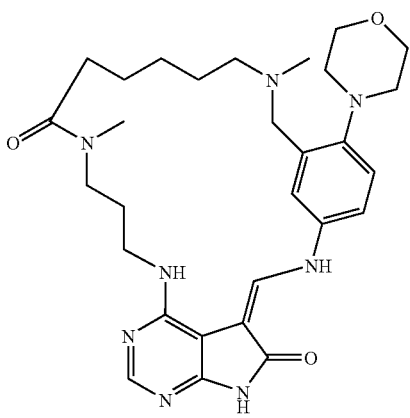

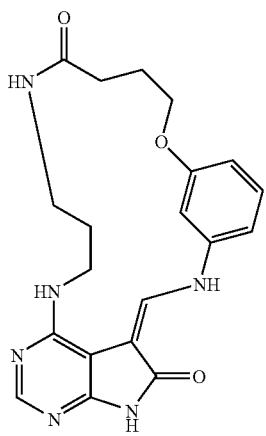

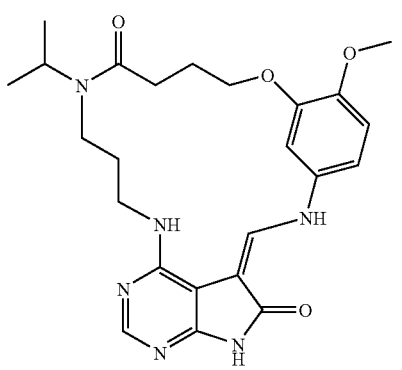

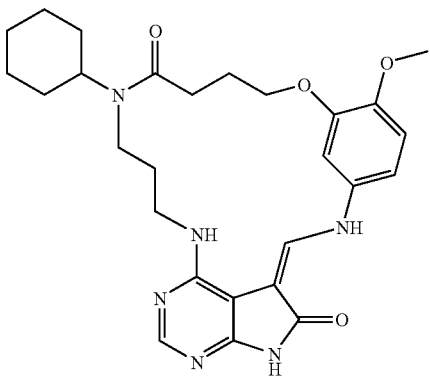

-continued

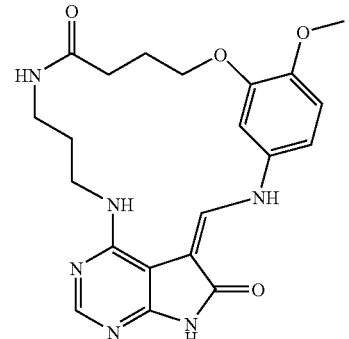

or the pharmaceutically acceptable addition salts and solvates thereof.

The compounds of this invention can be prepared by any of several standard synthetic processes commonly used by those skilled in the art of organic chemistry and described for instance in the following references; "Heterocyclic Compounds" Vol. 24 (part 4) p 261-304 Fused pyrimidines, Wiley—Interscience; Chem. Pharm. Bull., Vol 41(2) 362-368 (1993); J. Chem. Soc., Perkin Trans. 1, 2001, 130-137. The compounds are generally prepared from starting materials which are either commercially available or prepared by standard means obvious to those skilled in the art.

In the general schemes described below, all substituents are defined as in the general formula (I), unless otherwise mentioned or indicated.

Referring to Scheme 1, compounds of Formula (I) wherein $X^2$ is an amine either as —$C_{1-4}$alkanediyl-$NR^{14}$— or as part of $Het^1$, and wherein Y represents —$NR^{20}$—CO—$C_{1-6}$alkanediyl-$NR^4$—; —$NR^5$—CO—$C_{1-6}$alkanediyl-; —CO—$C_{1-6}$alkanediyl-$NR^6$—; —$NR^7$—$C_{1-6}$alkanediyl-$NR^8$—CO—$C_{1-6}$alkanediyl-; —CO—$C_{1-6}$alkanediyl-; —$NR^9$—CO—$C_{1-6}$alkanediyl-$NR^{10}$—CO—$C_{1-6}$alkanediyl-$NR^{11}$—; —CO—$C_{1-6}$alkanediyl-$NR^{17}$—CO—$C_{1-6}$alkanediyl-$NR^{21}$— or —$NR^{16}$—$C_{1-6}$alkanediyl-$NR^{17}$—CO—$C_{1-6}$alkanediyl-$NR^{21}$—;

are generally prepared by reacting the 4-chloro-pyrrolo[2,3-d]pyrimidine derivatives (IIa) or the 4-iodo-isatine derivatives (IIb), with an appropriate amine (III) using art known conditions.

Scheme 1

Scheme 1A (intermediates of formula (IV) where Z is N)

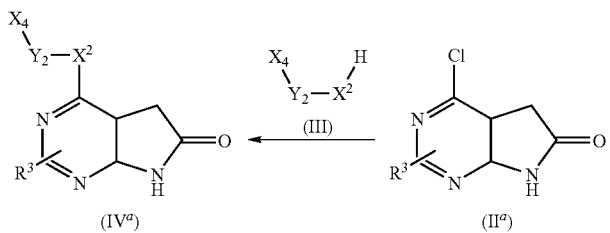

Scheme 1B (intermediates of formula (IV) where Z is CH)

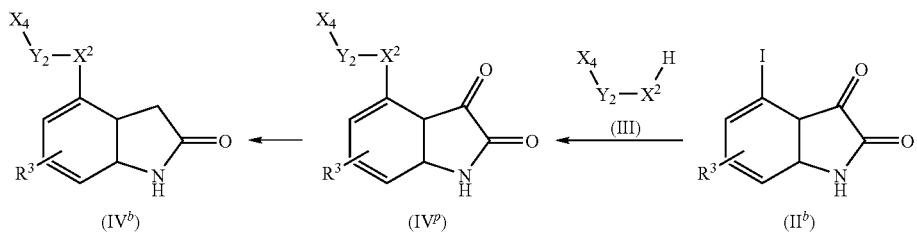

Scheme 1C

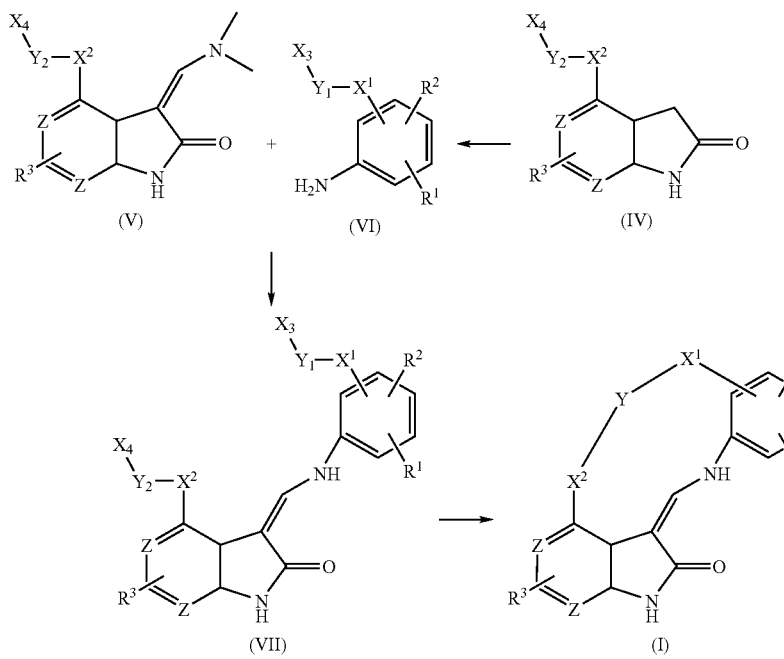

$X^2$ is an appropriate amine, either as $C_{1-4}$alkanediyl-$NR^{14}$— or as part of $Het^1$;

Z represents N or CH; $Y_1$ and $Y_2$ each independently represent e.g. a direct bond;

—$NR^{20}$—; —$NR^5$—; —CO—$C_{1-6}$alkanediyl-; —$NR^7$—$C_{1-6}$alkanediyl-$NR^8$—;

—$NR^9$—CO—$C_{1-6}$alkanediyl-$NR^{10}$—; —CO—$C_{1-6}$alkanediyl-$NR^{10}$—CO—$C_{1-6}$alkanediyl —$NR^{11}$—, —$NR^{25}$—CO—$C_{1-6}$alkanediyl, —$NR^{26}$—$C_{1-6}$alkanediyl —$NR^9$, —$NR^{16}$—$C_{1-6}$alkanediyl-$NR^{17}$— or —CO—$C_{1-6}$alkanediyl-$NR^w$—

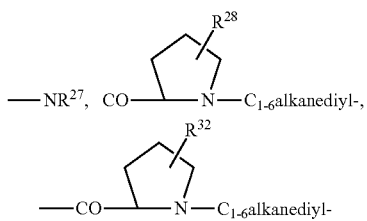

wherein $R^w$ represents $R^4$, $R^6$, $R^{11}$, $R^{13}$, $R^{21}$ and wherein $R^4$, $R^5$, $R^6$, $R^7$, $R^8$, $R^9$, $R^{10}$, $R^{11}$, $R^{12}$, $R^{13}$, $R^{16}$, $R^{17}$, $R^{20}$, $R^{21}$, $R^{25}$, $R^{26}$, $R^{27}$, $R^{28}$, $R^{29}$, $R^{30}$, $R^{32}$ and $R^{31}$ are defined as for the compounds of formula (I);

$X_3$ and $X_4$ together with the functional moiety to which they are attached represent a protected functional group, such as for example a tert-butoxy carbonyl (Boc) protected primary or secondary amine or an ester, which upon reaction (after deprotection) produce together with the $Y_1$ respectively $Y_2$ substituent to which they are attached, the bivalent Y radical that is defined as —$C_{1-6}$alkanediyl-O—;
—$C_{1-6}$alkanediyl-$NR^{15}$—;
—$C_{1-6}$alkanediyl-$NR^{24}$—CO—$C_{1-6}$alkanediyl-;
—$NR^5$—CO—$C_{1-6}$alkanediyl-;
—$NR^{20}$—CO—$C_{1-6}$alkanediyl-$NR^4$—;
—$NR^7$—$C_{1-6}$alkanediyl-$NR^8$—CO—$C_{1-6}$alkanediyl;
—$NR^{25}$—CO—$C_{1-6}$alkanediyl-$NR^{26}$—$C_{1-6}$alkanediyl;
—$NR^{16}$—$C_{1-6}$alkanediyl-$NR^{17}$—CO—$C_{1-6}$alkanediyl-$NR^{21}$—;
—$NR^9$—CO—$C_{1-6}$alkanediyl-$NR^{10}$—CO—$C_{1-6}$alkanediyl-$NR^{11}$—;

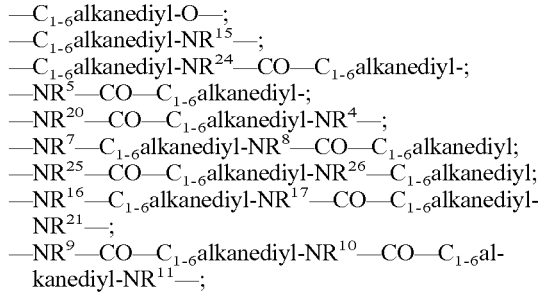

—CO—$C_{1-6}$alkanediyl-;
—CO—$C_{1-6}$alkanediyl-$NR^6$—;
—CO—$C_{1-6}$alkanediyl-$NR^{31}$—$C_{1-6}$alkanediyl-;
—CO—$C_{1-6}$alkanediyl-$NR^{12}$—CO—$C_{1-6}$alkanediyl-$NR^{13}$—; or

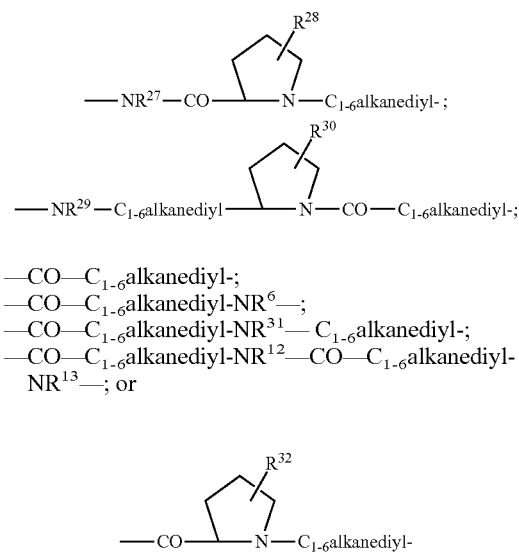

wherein each of said $C_{1-6}$alkanediyl may optionally be substituted with hydroxy or $Ar^{11}$;

In case of the 4-chloro-pyrrolo[2,3-d]pyrimidine derivatives (Scheme 1A, II$^a$), the amine is for example, coupled by stirring the reagentia at an elevated temperature (70-100° C.) optionally in an appropriate solvent such as propane-2-ol, 1-butanol or DMSO in the presence of a base such as for example triethylamine, N-ethyl-N-(1-methylethyl)-2-propaneamine (DIPEA) and alike to yield the intermediate of formula (IV$^a$). In case of the 4-iodo-isatine derivative (Scheme 1B, II$^b$), the coupling of the amine is catalysed using copper or nickel salts such as for example $Cu_2O$, CuI or $Ni(CO)_4$. Reduction of the isatine derivative (IV$^F$), such as for example using the Wolff-Kishner reduction in which the isatine derivative is heated with hydrazine hydrate, optionally in the presence of a base such as NaOH or KOH, yields the intermediate of formula (IV$^b$). The thus obtained common intermediates of formula (IV) are subsequently converted into the dimethyl ene-amine scaffolds (V) by reaction with an excess dimethylformamide dimethylacetal (DMFDMA) at room temperature. Further reaction with an appropriate aniline (VI) yields the open intermediates of formula (VII). This transamination reaction is done using art known conditions, such as for example using acidic catalysed conditions (HCl and alike) in a suitable polar solvent such as ethanol, propane-2-ol, 1-butanol, acetonitrile and alike at elevated temperatures (60-90° C. or reflux temperatures). Deprotection of the intermediates of formula (VII) as described in *Protective Groups in Organic Synthesis* by T. W. Greene and P. G. M. Wuts, 3$^{rd}$ edition, 1998 followed by ring closure under standard conditions give the macrocyclic compounds (I) of the present invention. Ring closure is typically performed in the presence of a coupling reagent such as for example 1,3-dicyclohexylcarbodiimide (DCC), N,N'-carbonyldiimidazole (CDI), Benzotriazol-1-yl-oxytripyrrolidino-phosphonium hexafluorophosphate (PyBOP), 1-[bis(dimethylamino)methylene]-1H-benzotriazolium hexafluorophosphate(1-)-3-oxide (HBTU) or 1-(3-dimethylaminopropyl)-3-ethylcarbodiimide (EDCI) in the presence or absence of hydroxybenzotriazole (HOBt).

For those compounds where $X^1$ represents —O—, the suitable substituted anilines of formula (VI$^a$) are generally prepared from the commercially available nitro-phenols (X) and the α, ω-protected (esters) halogenated carboxylic acids (XI) under alkaline conditions in a reaction inert solvent, for example, using dimethylacetamide (DMA) in the presence of $K_2CO_3$. The resulting nitro-phenyl derivative (XII) is subsequently reduced according to standard conditions, for example, using iron/HCl, to yield the substituted anilines of formula (VI$^a$) (Scheme 2).

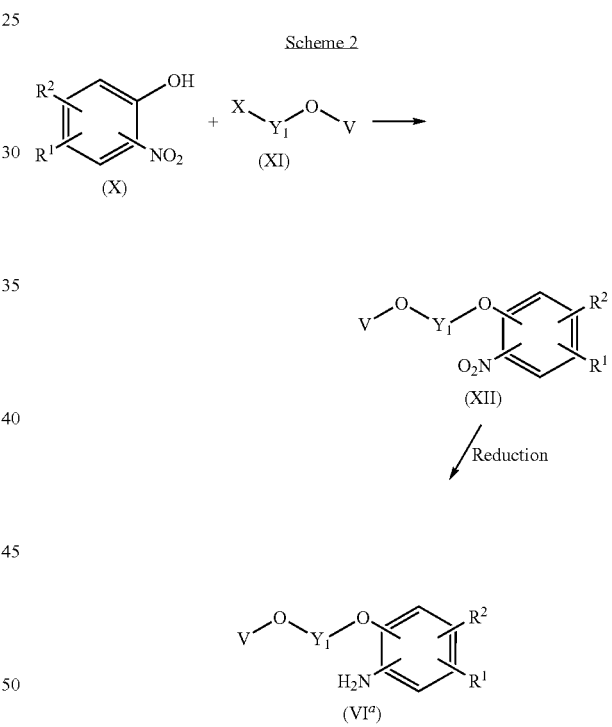

X represents a halogen such as for example, Cl, Br, and I; V represents hydrogen or a protective group such as for example methyl, ethyl or t-butyl; other substituents are defined as in Scheme 1.

For those compounds where $X^1$ represents a $C_{1-4}$alkanediyl, the suitable substituted anilines of formula (VI$^b$) are generally prepared from the commercially available 2- or 3-nitro-benzaldehydes (XIII) and the amine substituted esters (XIV) by reductive amination under standard conditions (Scheme 3), for example using $NaBH_4$ and $NaBH(OAc)_3$ as reducing agents in ethanol as solvent, yielding the nitro-benzylamines of formula (XVI). The thus obtained intermediate of formula (XVI) is subsequently reduced according to standard conditions, for example, using hydrogenolysis ($H_2$, Pt/C, thiophene, MeOH) or tin (II) chloride ($SnCl_2.H_2O$, EtOH) to yield the substituted anilines of formula (VI$^b$).

Scheme 3

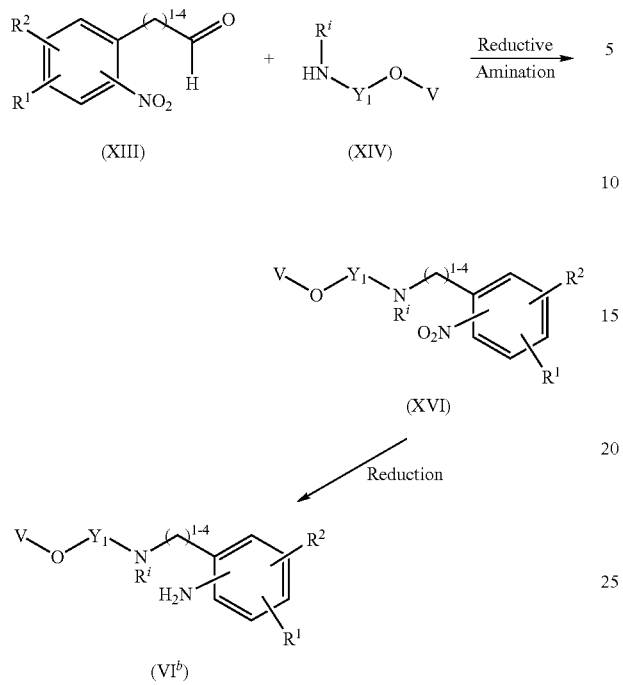

V represents a protective group such as for example methyl, ethyl or t-butyl. For clarity of Scheme 3, the functional group $R^i$—NH— which is part of $Y_1$ ($Y_1$ can be defined as in Scheme 1 hereinbefore, except for the case $Y_1$ is a direct bond and additionally $Y_1$ can also represent —$NR^{15}$—) was shown explicitly in Scheme 3. $R^i$ corresponds to any one of $R^4, R^5, R^6, R^7, R^8, R^9, R^{10}, R^{11}, R^{12}, R^{13}, R^{15}, R^{16}, R^{17}, R^{20}$ or $R^{21}$ as defined for the compounds of formula (I) hereinbefore. Other substituents are defined as in Scheme 1.

For those compounds of formula (I) wherein $X^1$ represents —$SO_2$— and $Y^1$ represents CO—$C_{1-6}$alkanediyl-$NR^w$— or —CO—$C_{1-6}$alkanediyl-$NR^{10}$—CO—$C_{1-6}$alkanediyl-$NR^{11}$—, the anilines of formula (VI$^c$) are generally prepared from the commercially available 2- or 3-nitro-benzenesulfonylchloride (XVII) by the treatment with an appropriate amine (XVIII) under standard conditions, also known as the Hinsberg test, i.e. the reaction is conducted in aqueous base (NaOH or KOH), and the benzenesulfonyl chloride reagent is present as an insoluble oil. The sulfonamide derivative (XIX) from secundary amines will be recovered as an insoluble solid. The sulfonamide derivative from primary amines is acidic and will dissolve in the aqueous base. Acidification of this solution then precipitates the sulfonamide of the primary-amine. The resulting sulfonamide derivative (XIX) is subsequently reduced according to standard conditions, for example, using iron/HCl, to yield the substituted anilines of formula (VI$^c$) (Scheme 4).

Scheme 4

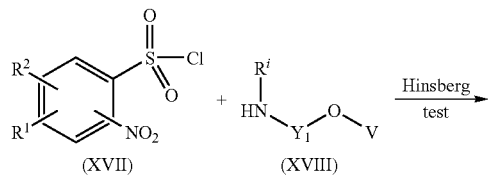

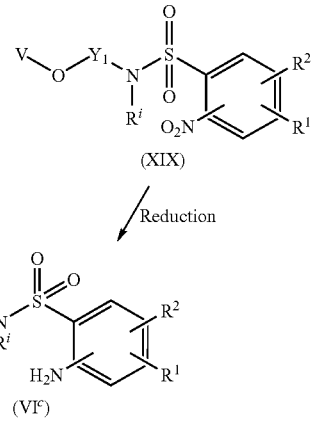

V represents a protective group such as for example methyl, ethyl or t-butyl. For clarity of Scheme 4, the functional group $R^i$—NH— which is part of $Y_1$ ($Y_1$ can be defined as in Scheme 1 hereinbefore, except for the case $Y_1$ is a direct bond and additionally $Y_1$ can also represent —$NR^{15}$—) was shown explicitly in Scheme 4. $R^i$ corresponds to any one of $R^4, R^5, R^6, R^7, R^8, R^9, R^{10}, R^{11}, R^{12}, R^{13}, R^{15}, R^{16}, R^{17}, R^{20}$ or $R^{21}$ as defined for the compounds of formula (I) hereinbefore. Other substituents are defined as in Scheme 1.

For those compounds of formula (Ia) wherein $X^2$ is an appropriate amine, either as $C_{1-4}$alkanediyl-$NR^{14}$— or as part of Het$^1$, the pyrrolo[2,3-d]pyrimidine derivatives of formula (IV$^a$) are obtained by reacting the 4-chloro-pyrrolo[2,3-d]pyrimidine derivatives (II$^a$), with an appropriate amine (III) using art known conditions, such as for example, by stirring the reagentia at an elevated temperature (70-100° C.) optionally in an appropriate solvent such as propane-2-ol, 1-butanol or DMSO in the presence of a base such as for example triethylamine, N-ethyl-N-(1-methylethyl)-2-propaneamine (DIPEA) and alike (Scheme 5).

Scheme 5

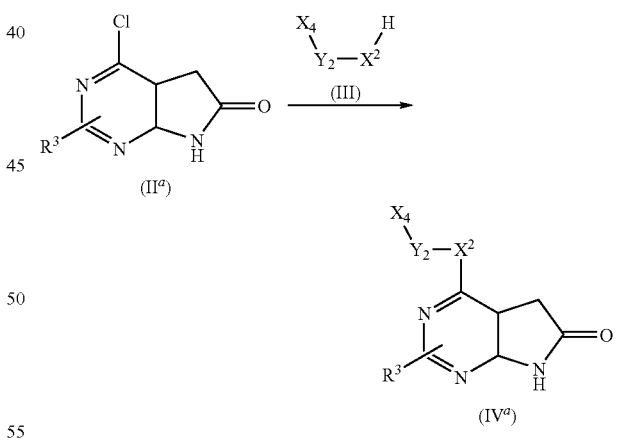

For those compounds of formula (Ib) wherein $X^2$ represents an appropriate amine, either as $C_{1-4}$alkanediyl-$NR^{14}$— or as part of Het$^1$, the 2-oxindole derivatives of formula (IV$^b$) are obtained by reacting the 4-iodo-isatine derivatives (II$^b$), with an appropriate amine (III) using art known conditions, such as for example, by stirring the reagentia under copper or nickel catalysed conditions (for example using copper or nickel salts such as for example Cu$_2$O, CuI or Ni(CO)$_4$) at an elevated temperature (70-100° C.) optionally in an appropriate solvent such as propane-2-ol, 1-butanol or DMSO in the presence of a base such as for example triethylamine, N-ethyl-N-(1-methylethyl)-2-propaneamine (DIPEA) and alike. Subsequent reduction of the Isatine derivative (IV$^p$) yields the 2-oxindole derivatives of formula (IV$^b$) (Scheme 6).

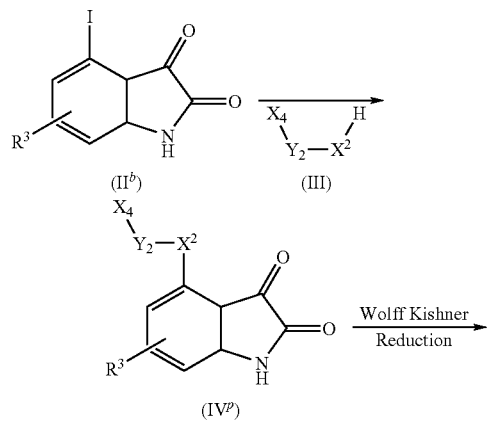

For those compounds of formula (Ib) wherein X$^2$ represents C$_{2-4}$alkynediyl, the sequential build-up of the molecules differs from the general synthesis Scheme 1. In a first step, the 4-iodo oxindole derivative (In is treated with the excess of DMFDMA (supra) followed by the transamination reaction with the aniline (VI) using art known conditions as provided in Scheme 1 hereinbefore. Only then the C$_{2-4}$alkynediyl is introduced by using a compound of general formula (XX) using for example the Sonogashira reaction as discussed in Scheme 6 hereinbefore. Deprotection and ring closure (supra) yields the compounds of formula (Ib) wherein X$^2$ represents C$_{2-4}$alkynediyl (Scheme 7).

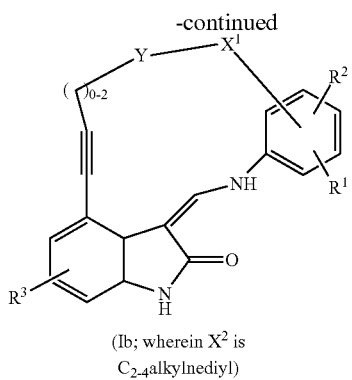

(Ib; wherein $X^2$ is $C_{2-4}$alkylnediyl)

$X^2$ is of $C_{2-4}$alkynediyl; Z represents N or CH; $Y_1$ and $Y_2$ each independently represent —$NR^{20}$—; —$NR^5$—; —CO—$C_{1-6}$alkanediyl-; —$NR^7$—$C_{1-6}$alkanediyl-$NR^8$—; —$NR^9$—CO—$C_{1-6}$alkanediyl-$NR^{10}$—; —CO—$C_{1-6}$alkanediyl-$NR^{10}$—CO—$C_{1-6}$alkanediyl-$NR^{11}$—; —$NR^9$, —$NR^{16}$—$C_{1-6}$alkanediyl-$NR^{17}$— or —CO—$C_{1-6}$alkanediyl-$NR^w$— wherein $R^w$ represents $R_4$, $R_6$, $R_{11}$, $R_{12}$, $R_{13}$, $R_{21}$ and wherein R4, R5, R6, R7, R8, R9, R10, R11, R12, R13, R16, R17, R20 and R21 are defined as for the compounds of formula (I); X3 and X4 together with the functional moiety to which they are attached represent a protected functional group, such as for example a tert-butoxy carbonyl (Boc) proctected primary or secondary amine or an ester, which upon reaction (after deprotection) produce together with the Y1 respectively Y2 substituent to which they are attached, the bivalent Y radical that is defined as —$NR^{20}$—CO—$C_{1-6}$alkanediyl-$NR^4$—; —$NR^5$—CO—$C_{1-6}$alkanediyl-; —CO—$C_{1-6}$alkanediyl-$NR^6$—; —$NR^7$—$C_{1-6}$alkanediyl-$NR^8$—CO—$C_{1-6}$alkanediyl-; —CO—$C_{1-6}$alkanediyl-; —$NR^9$—CO—$C_{1-6}$alkanediyl-$NR^{10}$—CO—$C_{1-6}$alkanediyl-$NR^{11}$—; —CO—$C_{1-6}$alkanediyl-$NR^{12}$—CO—$C_{1-6}$alkanediyl-$NR^{13}$— or —$NR^{16}$—$C_{1-6}$alkanediyl-$NR^{17}$—CO—$C_{1-6}$alkanediyl-$NR^{21}$—;

More specific examples for the synthesis of compounds of formula (I) are provided in the examples hereinafter.

Where necessary or desired, any one or more of the following further steps in any order may be performed:
(i) removing any remaining protecting group(s);
(ii) converting a compound of formula (I) or a protected form thereof into a further compound of formula (I) or a protected form thereof;
(iii) converting a compound of formula (I) or a protected form thereof into a N-oxide, a salt, a quaternary amine or a solvate of a compound of formula (I) or a protected form thereof;
(iv) converting a N-oxide, a salt, a quaternary amine or a solvate of a compound of formula (I) or a protected form thereof into a compound of formula (I) or a protected form thereof;
(v) converting a N-oxide, a salt, a quaternary amine or a solvate of a compound of formula (I) or a protected form thereof into another N-oxide, a pharmaceutically acceptable addition salt a quaternary amine or a solvate of a compound of formula (I) or a protected form thereof;
(vi) where the compound of formula (I) is obtained as a mixture of (R) and (S) enantiomers resolving the mixture to obtain the desired enantiomer.

Compounds of formula (I), N-oxides, addition salts, quaternary amines and stereochemically isomeric forms thereof can be converted into further compounds according to the invention using procedures known in the art.

It will be appreciated by those skilled in the art that in the processes described above the functional groups of intermediate compounds may need to be blocked by protecting groups.

Functional groups, which are desirable to protect, include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include $C_{(1-6)}$ alkyl or benzyl esters.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarbo-peroxoic acid, e.g. 3-chlorobenzenecarbo-peroxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydro-carbons, e.g. dichloromethane, and mixtures of such solvents.

We have now surprisingly found that, the indolin-2-ones and aza-indolin-2-ones as defined hereinbefore possess potent anti-tumour activity. Without wishing to imply that the compounds disclosed in the present invention possess pharmacological activity only by virtue of an effect on a single biological process, it is believed that the compounds provide an anti-tumour effect by way of inhibition of one or more of protein kinases that are involved in the regulation of cellular mitosis and which lead to cytogenetic catastrophe in case of aberrant activity.

It is thus an object of the present invention to provide the compounds of the present invention for use as a medicine. As used herein the compounds of the present invention includes the compounds of formula (I), (Ia) or (Ib) as defined hereinbefore, including all subgroups and combinations thereof.

In one aspect, the compounds of the present invention may be useful for the treatment or prevention of cell proliferative disorders, including cancer, rheumatoid arthritis, restenosis and atherosclerosis. In the treatment of cancers said cancers include lung cancer (especially non small-cell lung cancer), breast cancer, liver cancer, ovarian cancer, prostate cancer, pancreatic cancer, colorectal cancer, gastrointestinal cancer such as colon, rectal or stomach cancer and papillary carcinomas (such as papillary thyroid cancer) as well as in squamous cell cancers of the head and neck and in oesophageal cancers including oropharyngeal cancer. In a further aspect, the invention also provides the use of the macrocyclic indolin-2-ones and aza-indolin-2-ones compounds as male contraceptives.

In a further objective of the present invention the compounds of the present invention may be useful in the treatment of diseases mediated through GSK-3 activity such as bipolar disorder (in particular manic depression), diabetes, Alzheimer's disease, leukopenia, FTDP-17 (Fronto-temporal dementia associated with Parkinson's disease), cortico-basal degeneration, progressive supranuclear palsy, multiple system atrophy, Pick's disease, Niemann Pick's disease type C, Dementia Pugilistica, dementia with tangles only, dementia with tangles and calcification, Downs syndrome, myotonic dystrophy, Parkinsonism-dementia complex of Guam, aids related dementia, Postencephalic Parkinsonism, prion diseases with tangles, subacute sclerosing panencephalitis, frontal lobe degeneration (FLD), argyrophilic grains disease, subacutesclerotizing panencephalitis (SSPE) (late complication of viral infections in the central nervous system), inflammatory diseases, depression, cancer, dermatological disorders such as baldness, neuroprotection, schizophrenia, pain, in particular neuropathic pain. GSK3 inhibitors can also be used to inhibit sperm motility and can therefore be used as male contraceptives.

Accordingly, the compounds of the present invention can be administered to mammals, preferably humans, for the treatment of a variety of conditions and disorders, including, but not limited to Alzheimer's disease; diabetes, in particular type 2 diabetes (non insulin dependent diabetes); bipolar disorder; cancer including lung cancer (especially non small-cell lung cancer), breast cancer, liver cancer, ovarian cancer, prostate cancer, pancreatic cancer, colorectal cancer, gastrointestinal cancer such as colon, bladder, rectal or stomach cancer and papillary carcinomas (such as papillary thyroid cancer) as well as in squamous cell cancers of the head and neck and in oesophageal cancers including oropharyngeal cancer; pain, in particular neuropathic pain; depression; inflammatory diseases including allergies and asthma, MS, RA, arteriosclerosis, arthritis or IBD. The compounds of the present invention can be administered to mammals, preferably humans as male contraceptives.

The compounds of the present invention may be administered alone or in combination with one or more additional therapeutic agents. Combination therapy includes administration of a single pharmaceutical dosage formulation which contains a compound of Formula (I), (Ia) or (Ib) and one or more additional therapeutic agents, as well as administration of the compound of Formula (I), (Ia) or (Ib) and each additional therapeutic agents in its own separate pharmaceutical dosage formulation. For example, a compound of Formula (I), (Ia) or (Ib) and a therapeutic agent may be administered to the patient together in a single oral dosage composition such as a tablet or capsule, or each agent may be administered in separate oral dosage formulations.

Where separate dosage formulations are used, the compounds of the present invention and one or more additional therapeutic agents may be administered at essentially the same time (e.g., concurrently) or at separately staggered times (e.g., sequentially).

For example the compounds of the present invention could be used in combination with other anti-cancer agents. Examples of anti-cancer agents are:
  platinum coordination compounds for example cisplatin, carboplatin or oxalyplatin;
  taxane compounds for example paclitaxel or docetaxel;
  topoisomerase I inhibitors such as camptothecin compounds for example irinotecan or topotecan;
  topoisomerase II inhibitors such as anti-tumour podophyllotoxin derivatives for example etoposide or teniposide;
  anti-tumour vinca alkaloids for example vinblastine, vincristine or vinorelbine;
  anti-tumour nucleoside derivatives for example 5-fluorouracil, gemcitabine or capecitabine;
  alkylating agents such as nitrogen mustard or nitrosourea for example cyclophosphamide, chlorambucil, carmustine or lomustine;
  anti-tumour anthracycline derivatives for example daunorubicin, doxorubicin, idarubicin or mitoxantrone;
  HER2 antibodies for example trastuzumab;
  estrogen receptor antagonists or selective estrogen receptor modulators for example tamoxifen, toremifene, droloxifene, faslodex or raloxifene;
  aromatase inhibitors such as exemestane, anastrozole, letrazole and vorozole;
  differentiating agents such as retinoids, vitamin D and retinoic acid metabolism blocking agents (RAMBA) for example accutane;
  DNA methyl transferase inhibitors for example azacytidine;
  kinase inhibitors for example flavoperidol, imatinib mesylate or gefitinib;
  farnesyltransferase inhibitors for example tipifarnib;
  Histone Deacetylase (HDAC) inhibitors for example sodium butyrate, suberoylanilide hydroxamide acid (SAHA), R306465, JNJ26481585 and trichostatin A;
  Inhibitors of the ubiquitin-proteasome pathway for example PS-341, MLN 0.41 or bortezomib;
  Yondelis;
  Telomerase inhibitors for example telomestatin;
  Matrix metalloproteinase inhibitors for example batimastat, marimastat, prinostat and metastat.

The term "platinum coordination compound" is used herein to denote any tumour cell growth inhibiting platinum coordination compound which provides platinum in the form of an ion.

The term "taxane compounds" indicates a class of compounds having the taxane ring system and related to or derived from extracts from certain species of yew (Taxus) trees.

The term "topisomerase inhibitors" is used to indicate enzymes that are capable of altering DNA topology in eukaryotic cells. They are critical for important cellular functions and cell proliferation. There are two classes of topoisomerases in eukaryotic cells, namely type I and type II. Topoisomerase I is a monomeric enzyme of approximately 100,000 molecular weight. The enzyme binds to DNA and introduces a transient single-strand break, unwinds the double helix (or allows it to unwind) and subsequently reseals the break before dissociating from the DNA strand. Topisomerase II has a similar mechanism of action which involves the induction of DNA strand breaks or the formation of free radicals.

The term "camptothecin compounds" is used to indicate compounds that are related to or derived from the parent camptothecin compound which is a water-insoluble alkaloid derived from the Chinese tree Camptothecin acuminata and the Indian tree Nothapodytes foetida.

The term "podophyllotoxin compounds" is used to indicate compounds that are related to or derived from the parent podophyllotoxin, which is extracted from the mandrake plant.

The term "anti-tumour vinca alkaloids" is used to indicate compounds that are related to or derived from extracts of the periwinkle plant (Vinca rosea).

The term "alkylating agents" encompass a diverse group of chemicals that have the common feature that they have the capacity to contribute, under physiological conditions, alkyl groups to biologically vital macromolecules such as DNA. With most of the more important agents such as the nitrogen mustards and the nitrosoureas, the active alkylating moieties are generated in vivo after complex degradative reactions, some of which are enzymatic. The most important pharmacological actions of the alkylating agents are those that disturb the fundamental mechanisms concerned with cell proliferation in particular DNA synthesis and cell division. The capacity of alkylating agents to interfere with DNA function and integrity in rapidly proliferating tissues provides the basis for their therapeutic applications and for many of their toxic properties.

The term "anti-tumour anthracycline derivatives" comprise antibiotics obtained from the fungus Strep. peuticus var. caesius and their derivatives, characterized by having a tetracycline ring structure with an unusual sugar, daunosamine, attached by a glycosidic linkage.

Amplification of the human epidermal growth factor receptor 2 protein (HER 2) in primary breast carcinomas has been shown to correlate with a poor clinical prognosis for certain patients. Trastuzumab is a highly purified recombinant DNA-derived humanized monoclonal IgG1 kappa antibody that binds with high affinity and specificity to the extracellular domain of the HER2 receptor.

Many breast cancers have estrogen receptors and growth of these tumours can be stimulated by estrogen. The terms "estrogen receptor antagonists" and "selective estrogen receptor modulators" are used to indicate competitive inhibitors of estradiol binding to the estrogen receptor (ER). Selective estrogen receptor modulators, when bound to the ER, induces a change in the three-dimensional shape of the receptor, modulating its binding to the estrogen responsive element (ERE) on DNA.

In postmenopausal women, the principal source of circulating estrogen is from conversion of adrenal and ovarian androgens (androstenedione and testosterone) to estrogens (estrone and estradiol) by the aromatase enzyme in peripheral tissues. Estrogen deprivation through aromatase inhibition or inactivation is an effective and selective treatment for some postmenopausal patients with hormone-dependent breast cancer.

The term "antiestrogen agent" is used herein to include not only estrogen receptor antagonists and selective estrogen receptor modulators but also aromatase inhibitors as discussed above.

The term "differentiating agents" encompass compounds that can, in various ways, inhibit cell proliferation and induce differentiation. Vitamin D and retinoids are known to play a major role in regulating growth and differentiation of a wide variety of normal and malignant cell types. Retinoic acid metabolism blocking agents (RAMBA's) increase the levels of endogenous retinoic acids by inhibiting the cytochrome P450-mediated catabolism of retinoic acids.

DNA methylation changes are among the most common abnormalities in human neoplasia. Hypermethylation within the promotors of selected genes is usually associated with inactivation of the involved genes. The term "DNA methyl transferase inhibitors" is used to indicate compounds that act through pharmacological inhibition of DNA methyl transferase and reactivation of tumour suppressor gene expression.

The term "kinase inhibitors" comprises potent inhibitors of kinases that are involved in cell cycle progression and programmed cell death (apoptosis).

The term "farnesyltransferase inhibitors" is used to indicate compounds that were designed to prevent farnesylation of Ras and other intracellular proteins. They have been shown to have effect on malignant cell proliferation and survival.

The term "histone deacetylase inhibitor" or "inhibitor of histone deacetylase" is used to identify a compound, which is capable of interacting with a histone deacetylase and inhibiting its activity, more particularly its enzymatic activity. Inhibiting histone deacetylase enzymatic activity means reducing the ability of a histone deacetylase to remove an acetyl group from a histone.

The term "other inhibitors of the ubiquitin-proteasome pathway" is used to identify compounds that inhibit the targeted destruction of cellular proteins in the proteasome, including cell cycle regulatory proteins.

The term "telomerase inhibitor" refers to compounds which target, decrease or inhibit the activity of telomerase, especially compounds which inhibit the telomerase receptor.

The term "matrix metalloproteinase inhibitor" includes but is not limited to, collagen peptidomimetic and non-peptidomimetic inhibitors.

The compounds of the present invention can be used as "radiosensitizer" and/or "chemosensitizer".

Radiosensitizers are known to increase the sensitivity of cancerous cells to the toxic effects of ionizing radiation. Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogs of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease. Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumor with or without additional radiation; or other therapeutically effective compounds for treating cancer or other disease. Examples of additional therapeutic agents that may be used in conjunction with radiosensitizers include, but are not limited to: 5-fluorouracil, leucovorin, 5'-amino-5' deoxythymidine, oxygen, carbogen, red cell transfusions, perfluorocarbons (e.g., Fluosol 10 DA), 2,3-DPG, BW12C, calcium channel blockers, pentoxyfylline, antiangiogenesis compounds, hydralazine, and LBSO. Examples of chemotherapeutic agents that may be used in conjunction with radiosensitizers include, but are not limited to: adriamycin, camptothecin, carboplatin, cisplatin, daunorubicin, docetaxel, doxorubicin, interferon (alpha, beta, gamma), interleukin 2, irinotecan, paclitaxel, topotecan, and therapeutically effective analogs and derivatives of the same.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumor or other therapeutically effective compounds for treating cancer or other disease.

In view of the above described pharmacological properties, the compounds of formula (I), (Ia) or (Ib) or any subgroup thereof, their N-oxides, pharmaceutically acceptable addition salts, quaternary amines and stereochemically isomeric forms, may be used as a medicine. In particular, the present compounds can be used for the manufacture of a medicament for treatment of any one of the disease conditions mentioned hereinbefore. In particular for the manufacture of a medicament for the treatment of Alzheimer's disease; diabetes, in particular type 2 diabetes (non insulin dependent diabetes); bipolar disorder; cancer including lung cancer (especially non small-cell lung cancer), breast cancer, liver cancer, ovarian cancer, prostate cancer, pancreatic cancer, colorectal cancer, gastrointestinal cancer such as colon, bladder, rectal or stomach cancer and papillary carcinomas (such as papillary thyroid cancer) as well as in squamous cell cancers of the head and neck and in oesophageal cancers including oropharyngeal cancer; pain, in particular neuropathic pain; depression; inflammatory diseases including allergies and asthma, MS, RA, arteriosclerosis, arthritis or IBD.

In view of the utility of the compounds of formula (I), (Ia) or (Ib), there is provided a method of treating warm-blooded animals, including humans, suffering from or a method of preventing warm-blooded animals, including humans, to suffer from any one of the diseases mentioned hereinbefore, such as Alzheimer's disease; diabetes, in particular type 2 diabetes (non insulin dependent diabetes); bipolar disorder; cancer including lung cancer (especially non small-cell lung cancer), breast cancer, liver cancer, ovarian cancer, prostate cancer, pancreatic cancer, colorectal cancer, gastrointestinal cancer such as colon, bladder, rectal or stomach cancer and papillary carcinomas (such as papillary thyroid cancer) as well as in squamous cell cancers of the head and neck and in oesophageal cancers including oropharyngeal cancer; pain, in particular neuropathic pain; depression; inflammatory diseases including allergies and asthma, MS, RA, arteriosclerosis, arthritis or IBD. Said methods comprise the administration, i.e. the systemic or topical administration, preferably oral administration, of an effective amount of a compound of formula (I), (Ia) or (Ib), a N-oxide form, a pharmaceutically acceptable addition salt, a quaternary amine or a possible stereoisomeric form thereof, to warm-blooded animals, including humans.

One skilled in the art will recognize that a therapeutically effective amount of the compounds of the present invention is the amount sufficient to have anti-tumour activity and that this amount varies inter alias, depending on the type of disease, the concentration of the compound in the therapeutic formulation, and the condition of the patient. Generally, the amount of a compound of the present invention to be administered as a therapeutic agent for treating cell proliferative disorders such as cancer, rheumatoid arthritis, restenosis and atherosclerosis will be determined on a case by case by an attending physician.

Generally, a suitable dose is one that results in a concentration of the compounds of the present invention at the treatment site in the range of 0.5 nM to 200 µM, and more usually 5 nM to 50 µM. To obtain these treatment concentrations, a patient in need of treatment likely will be administered between 0.01 mg/kg to 250 mg/kg body weight, in particular from 0.1 mg/kg to 50 mg/kg body weight. The amount of a compound according to the present invention, also referred to here as the active ingredient, which is required to achieve a therapeutically effect will be, of course vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to admission. As described herein below, suitable pharmaceutical formulations are prepared by known procedures using well known and readily available ingredients.

The present invention also provides compositions for preventing or treating cell proliferative diseases, such as cancer, rheumatoid arthritis, restenosis and atherosclerosis. Said compositions comprising a therapeutically effective amount of a compound of formula (I), (Ia) or (Ib) and a pharmaceutically acceptable carrier or diluent.

In a further aspect the present invention also provides compositions for preventing or treating diseases mediated through GSK-3 activity such as bipolar disorder (in particular manic depression), diabetes, Alzheimer's disease, leukopenia, FTDP-17 (Fronto-temporal dementia associated with Parkinson's disease), cortico-basal degeneration, progressive supranuclear palsy, multiple system atrophy, Pick's disease, Niemann Pick's disease type C, Dementia Pugilistica, dementia with tangles only, dementia with tangles and calcification, Downs syndrome, myotonic dystrophy, Parkinsonism-dementia complex of Guam, aids related dementia, Postencephalic Parkinsonism, prion diseases with tangles, subacute sclerosing panencephalitis, frontal lobe degeneration (FLD), argyrophilic grains disease, subacutesclerotizing panencephalitis (SSPE) (late complication of viral infections in the central nervous system), inflammatory diseases, depression, cancer, dermatological disorders such as baldness, neuroprotection, schizophrenia, pain, in particular neuropathic pain. Said compositions comprising a therapeutically effective amount of a compound of formula (I), (Ia) or (Ib) and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound of formula (I), (Ia) or (Ib) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The following examples illustrate the present invention.

EXPERIMENTAL PART

In obtaining the compounds described in the examples below, the following experimental protocols were followed unless otherwise indicated. Unless otherwise stated, reaction mixtures were magnetically stirred at room temperature. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure.

It was observed that the compounds embraced within the scope of this invention can switch between the Z and E configuration, depending on the conditions under which the Z/E determination is measured. As a consequence, the compounds from the present invention occur as a mixture of Z and E isomers. The ratio of Z and E isomers vary depending on parameters such as e.g. solvent and temperature. When a Z/E ratio was reported in the examples below or in the tables or in the analytical part, such ratio was measured by NMR in a DMSO-d6 solution at room temperature after equilibrium. When no Z/E ratio is reported in the examples below or in the tables or in the analytical part, the compound is a Z/E mixture. For simplicity the compounds are always drawn as the Z-isomer, however both Z and E isomers are part of the present invention.

Hereinafter, the term "DMA" means N,N-dimethylacetamide, "DIPEA" means N-ethyl-N-(1-methylethyl)-2-propanamine, "DCM" means dichloromethane, "MeOH" means methanol, "EtOAc" means ethyl acetate, "HBTU" means 1-[bis(dimethylamino)methylene]-1H-benzotriazolium-hexafluorophosphate(1-)-3-oxide, "DMF" means N,N-dimethylformamide, "TFA" means trifluoroacetic acid, "PyBOP" means 1-benzotriazolyloxytripyrrolidinylphosphonium hexafluorophosphate, "EtOH" means ethanol, "X-Phos" means 2-(dicyclohexylphosphino)-2',4',6'-tri(isopropyl)biphenyl, "DIPE" means diisopropyl ether, "THF" means tetrahydrofuran, "EDCI" means 1-(3-dimethylaminopropyl)-3-ethylcarbodiimide hydrochloride, "HOBt-"means 1-hydroxybenzotriazole, "DMSO-d6" means deuterated dimethyl sulfoxide, "NMR" means Nuclear Magnetic Resonance and "LCMS" means Liquid Chromatography/Mass spectrometry.

Extrelut™ is a product of Merck KgaA, Darmstadt, Germany, and is a short column comprising diatomaceous earth.

A. PREPARATION OF THE INTERMEDIATES

Example A1 a) Preparation of Intermediate 1

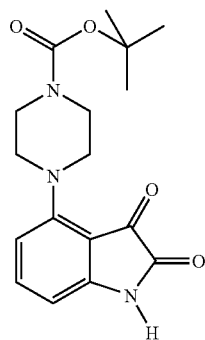

A mixture of 4-iodo-1H-indole-2,3-dione (0.07 mol), 1-piperazinecarboxylic acid, 1,1-dimethylethyl ester (0.124 mol), Cu₂O (0.100 g) in DIPEA (25 ml) and DMA (500 ml) was stirred for 20 hours at 125° C. The solvent was evaporated. The residue was diluted with water and this mixture was extracted with DCM (3×). The combined organic layers were dried (MgSO₄), filtered and the solvent was evaporated. The residue was purified over silica gel on a glass filter (eluent: DCM/MeOH 96.5/3.5). The product fractions were collected and the solvent was evaporated. This residue (18 g) was crystallized from CH₃CN. The precipitate was filtered off and dried. Yield: 13.6 g of intermediate 1 (58.6%).

b) Preparation of Intermediate 2

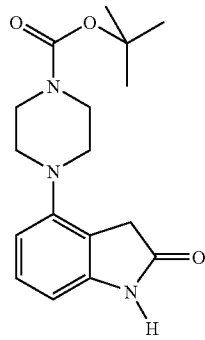

A mixture of intermediate 1 (0.054 mol) in hydrazine monohydrate (60 ml) and EtOH (240 ml) was stirred and heated for one hour at 150° C. in a microwave oven. The solvent was evaporated. The residue was extracted with DCM (3×). The separated organic layer was dried (MgSO₄), filtered and the solvent evaporated. The residue was suspended in water. The precipitate was filtered off, washed with water and dried in vacuo. Yield: 14.4 g of intermediate 2.

c) Preparation of Intermediate 3

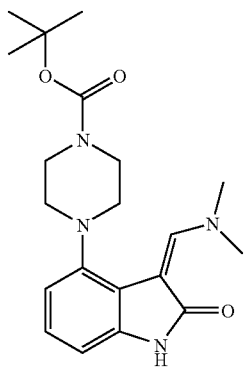

A mixture of intermediate 2 (0.045 mol) and 1,1-dimethoxy-N,N-dimethylmethanamine (0.060 mol) in DMF (100 ml) was stirred for 3 hours at room temperature. The reaction mixture was diluted with water (700 ml). The resulting precipitate was filtered off and dried (vacuum). Yield: 13 g of intermediate 3.

Example A2 a) Preparation of Intermediate 4

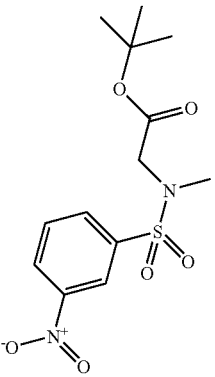

A mixture of N-methylglycine 1,1-dimethylethyl ester hydrochloride (0.01 mol), NaOH (0.8 mol) in H₂O (125 ml) and toluene (200 ml) was stirred at room temperature. 3-nitrobenzenesulfonyl chloride (0.01 mol) was added and the reaction mixture was stirred for 60 minutes at 90° C. The reaction mixture was cooled. The layers were separated. The aqueous phase was extracted once more with toluene. The combined organic layers were dried (MgSO₄), filtered and the solvent was evaporated. The residue was crystallized from DIPE. The precipitate was filtered off and dried (vacuum). Yield: 27.7 g of intermediate 4 (83.9%).

b) Preparation of Intermediate 5

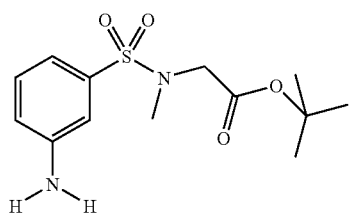

A mixture of intermediate 4 (0.084 mol) in THF (500 ml) was hydrogenated at room temperature with Pd/C (10%) (5 g) as a catalyst. After uptake of $H_2$ (3 equiv), the catalyst was filtered off over Dicalite and the filtrate was evaporated. The residue was crystallized from DIPE. The precipitate was filtered off and dried (vacuum). Yield: 22.6 g of intermediate 5 (89.7%).

Example A3 a) Preparation of Intermediate 6

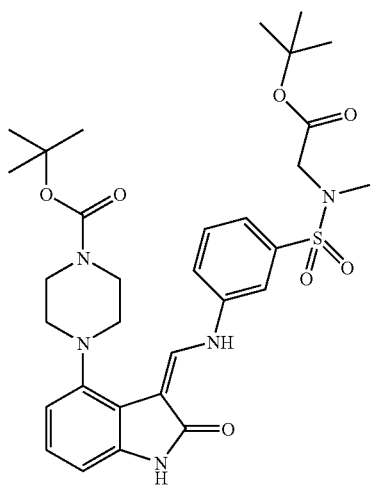

A mixture of intermediate 3 (0.0053 mol), intermediate 5 (1.6 g) and HCl/2-propanol (1 ml) in EtOH (100 ml) was stirred and refluxed for 20 hours. The solvent was evaporated. The residue was diluted with water and alkalized with 1 N NaOH. This mixture was extracted with DCM (2×). The separated organic layer was washed with water, dried ($MgSO_4$), filtered and the solvent evaporated. The residue was purified by column chromatography over silica gel (eluent: DCM/MeOH 97/3). The product fractions were collected and the solvent was evaporated. The residue (3 g) was crystallized from $CH_3CN$. A first fraction was recrystallized from DIPE, filtered off and dried. Yield: 0.25 g of crude product (LCMS: 43% intermediate 5 and 50% intermediate 6). A second fraction was recrystallized from DIPE, filtered off and dried. Yield: 0.7 g of intermediate 6.

b) Preparation of Intermediate 7

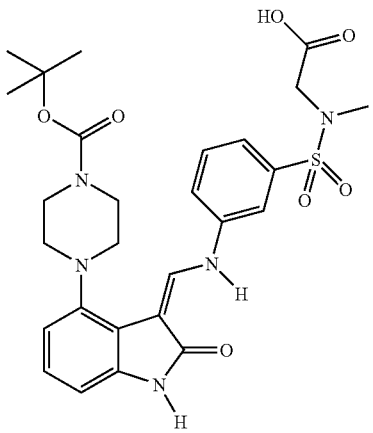

A mixture of intermediate 6 (0.7 g; result from second fraction in A3.a) in a NaOH solution (20 ml; 1 N), THF (40 ml) and MeOH (20 ml) was stirred for 3 hours at room temperature. The reaction mixture was neutralized with HCl (20 ml; 1 N). The solvent was partially evaporated until precipitation resulted. The precipitate was filtered off and dried (vacuum). Yield: Intermediate 7(a). The same procedure was repeated with intermediate 6 (0.25 g, crude result from first fraction in A3.a), yielding a second amount of intermediate 7(b). Both fractions intermediate 7 (a)+(b) were combined, yielding 0.75 g (88%) of intermediate 7.

Example A4 a) Preparation of Intermediate 8

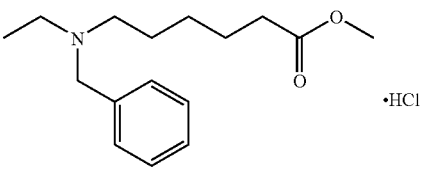

A mixture of 6-oxohexanoic acid methyl ester (crude), N-ethylbenzenemethanamine (16.2 g, 0.12 mol) and MeOH (200 ml) was reacted with Pd/C 10% (2 g) as a catalyst in the presence of a thiophene solution (1 ml; 4% in DIPE). After uptake of $H_2$ (1 equivalent), the reaction mixture was filtered through a small plug of Dicalite and the solvent was evaporated. DCM (100 ml) was added to the residue and acetyl chloride (0.6 ml) was added to scavenge the excess of N-ethylbenzenemethanamine. The solvent was evaporated and MeOH (100 ml) was added to the residue. This mixture was ice-cooled and $SOCl_2$ was added (7.5 g, 0.12 mol). The reaction mixture was concentrated and the concentrate was washed 3 times with toluene (100 ml). Then all solvents were evaporated. Yield: 27 g of intermediate 8 (HCl-salt).

b) Preparation of Intermediate 9

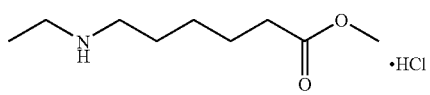

A mixture of intermediate 8 (27 g, 0.09 mol) in MeOH (250 ml) was hydrogenated with Pd/C 10% (2 g) as a catalyst. After uptake of $H_2$, the catalyst was filtered off and the filtrate was evaporated. The crude intermediate 9 (white solid; HCl-salt) was used as such in the next reaction step.

Example A5 a) Preparation of Intermediate 10

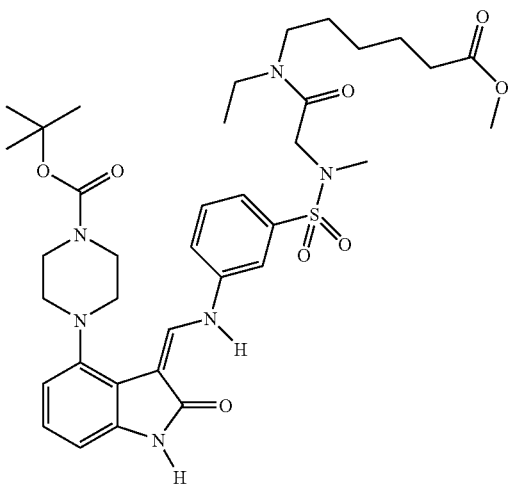

A mixture of intermediate 7 (0.00065 mil), intermediate 9 (q.s.) EDCI (0.15 g), HOBt (0.10 g) and $Et_3N$ (1 ml) in DCM (50 ml) was stirred at room temperature for 4 days.

The reaction mixture was washed with $H_2O$, dried ($MgSO_4$), filtered and the solvent was evaporated. The residue was purified by short column chromatography (eluent: DCM/MeOH 95/5). The product fractions were collected and the solvent was evaporated. Yield: 0.47 g of intermediate 10.

b) Preparation of Intermediate 11

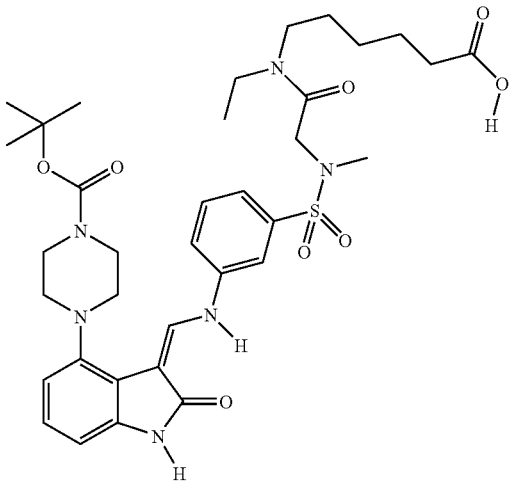

A mixture of intermediate 10 (0.00065 mol) in a NaOH solution (15 ml; 1 N), THF (30 ml) and MeOH (15 ml) was stirred at room temperature for 4 hours. The reaction mixture was neutralized with HCl 1 N (15 ml). The reaction mixture was concentrated by evaporation of part of the solvent, until an oily precipitation resulted. The supernatant was decanted off. Yield: 0.45 g of intermediate 11 (oily).

c) Preparation of Intermediate 12

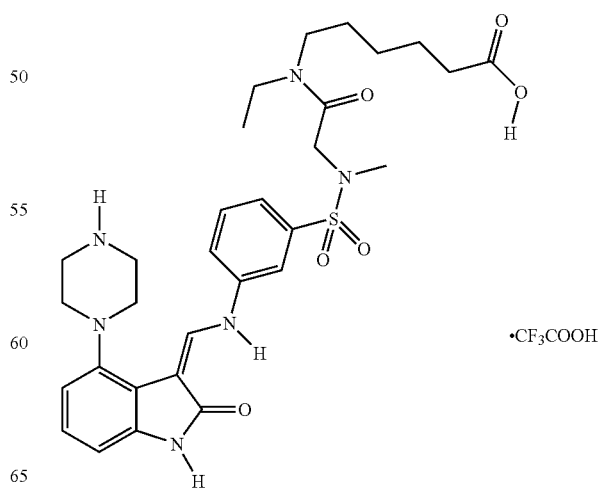

A mixture of intermediate 11 (0.00063 mol) in 20% TFA/DCM (20 ml) was stirred at room temperature for 2 hours. The solvent was evaporated. Yield: 0.5 g of intermediate 12 (.TFA).

Example A6 a) Preparation of Intermediate 14

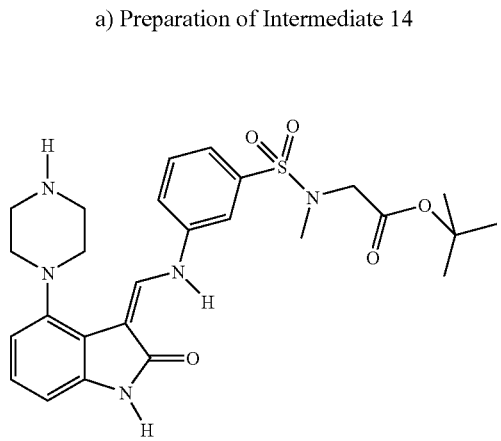

A mixture of intermediate 3 (0.0026 mol), intermediate 5 (0.0026 mol) and HCl/2-propanol (1 ml) in EtOH (100 ml) was stirred and refluxed for 20 hours. Then an additional amount of HCl/2-propanol (2 ml) was added. The reaction mixture was stirred and refluxed for 1 hour. The solvent was evaporated. The residue was diluted with $H_2O/NH_4OH$. The product was extracted tree times with DCM. The separated organic layer was washed with $H_2O$, dried ($MgSO_4$), filtered and the organic solvent was evaporated. The residue was purified by column chromatography over silica gel (eluent: DCM/(MeOH/$NH_3$) 95/5). The product fractions were collected and the solvent was evaporated. Yield: 0.55 g of intermediate 14 (30-40%).

c) Preparation of Intermediate 15

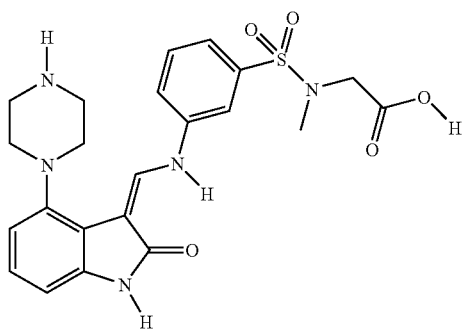

A mixture of intermediate 14 (0.001 mol) in 20% TFA/DCM (50 ml) was stirred at room temperature for 20 hours. The solvent was evaporated. NaOH (20 ml; 1 N), THF (40 ml) and MeOH (20 ml) were added to the residue and the mixture was stirred at room temperature for 2 hours. The reaction mixture was neutralized with 20 ml HCl (1 N). The reaction mixture was concentrated by evaporation until a precipitate resulted. The precipitate was filtered off, washed with $H_2O$ and dried (vacuum). Yield: 0.28 g of intermediate 15 (59.6%).

Example A7 a) Preparation of Intermediate 16

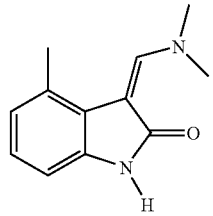

A mixture of 1,3-dihydro-4-iodo-2H-indol-2-one (0.0036 mol) and 1,1-dimethoxy-N,N-dimethylmethanamine (0.6 ml) in DMF (20 ml) was stirred at room temperature for 3 hours. The reaction mixture was diluted with $H_2O$ (200 ml). The precipitate was filtered off and dried (vacuum). Yield: 1 g of intermediate 16 (86.9%).

b) Preparation of Intermediate 17

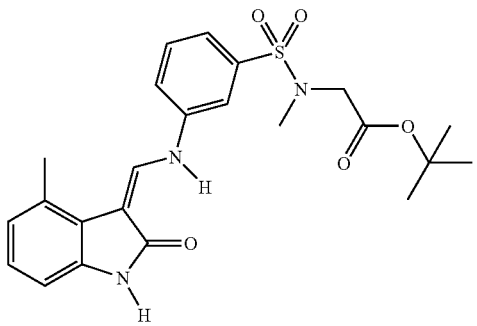

A mixture of intermediate 16 (0.017 mol) and intermediate 5 (0.018 mol) in EtOH (100 ml) was stirred and refluxed for 20 hours. The reaction mixture was cooled. The precipitate was filtered off, washed with a small amount of ethanol and dried (vacuum). Yield: 7.15 g of intermediate 17 (73.8%).

c) Preparation of Intermediate 18

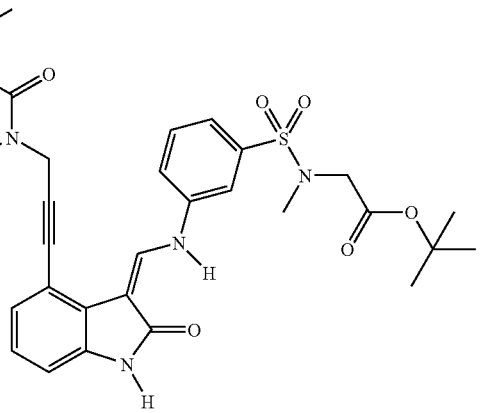

A mixture of intermediate 17 (0.002 mol), CuI (0.020 g) and dichloro(triphenylphosphine)palladium (0.070 g) in Et₃N (15 ml) and DMF (5 ml) was stirred at 40° C. A solution of N-2-propyn-1-yl-carbamic acid, 1,1-dimethylethyl ester (0.005 mol) in DMF (5 ml) was added dropwise at 40° C. and the reaction mixture was stirred for 45 minutes at 50° C. The mixture was poured out into H₂O. This mixture was extracted with EtOAc (3×). The combined organic layers were dried (MgSO₄), filtered and the solvent was evaporated. The residue was purified by column chromatography over silica gel (eluent: DCM/MeOH 96.5/3.5). The product fractions were collected and the solvent was evaporated. The residue (1.5 g) was crystallized from CH₃CN. The precipitate was filtered off and dried (vacuum). Yield: 0.8 g of intermediate 18 (67.2%).

d) Preparation of Intermediate 19

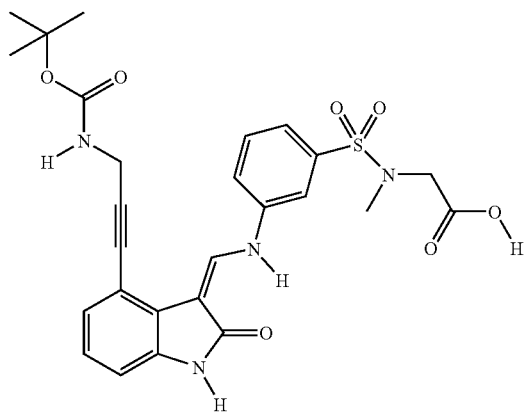

A mixture of intermediate 18 (0.00008 mol) in NaOH (2 ml; 1 N), THF (4 ml) and MeOH (1 ml) was stirred at room temperature for 4 hours. The reaction mixture was neutralized with 2 ml HCl (1 N). DCM (5 ml) was added to the mixture. The reaction mixture was filtered over Extrelut™ and the filtrate was blown dry under N₂ gas. Yield: 0.04 g of intermediate 19.

e) Preparation of Intermediate 20

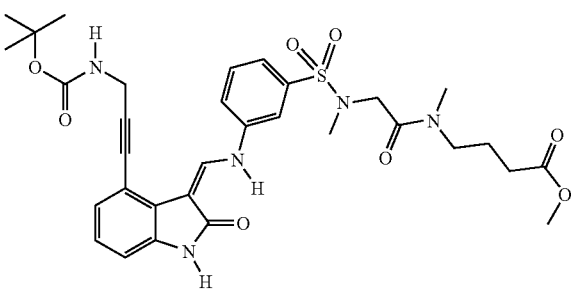

A mixture of intermediate 19 (0.0015 mol), 4-(methylamino)-butanoic acid, methyl ester, hydrochloride (0.0017 mol), EDCI (0.0017 mol), HOBt (0.0017 ml) and Et₃N (0.007 mol) in DCM (50 ml) was stirred at room temperature for 90 hours. The reaction mixture was diluted with DCM/MeOH and washed with H₂O. The organic layer was separated, dried (MgSO₄), filtered and the organic solvent was evaporated. The residue was suspended in hot CH₃CN and stirred for 30 minutes (cooled to room temperature). The precipitate was filtered off and dried (vacuum). Yield: 0.5 g of (51%)., yielding of intermediate 20.

f) Preparation of Intermediate 21

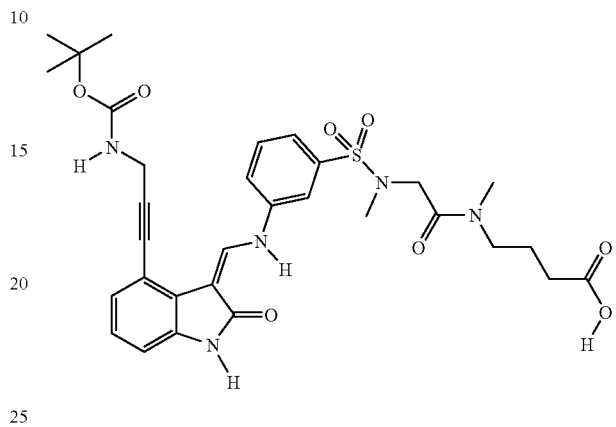

A mixture of intermediate 20 (0.00077 mol) in NaOH (20 ml; 1 N), 1,4-dioxane (40 ml) and MeOH (20 ml) was stirred at room temperature for 3 hours. The reaction mixture was neutralized with HCl (20 ml; 1 N). The reaction mixture was diluted with H₂O (100 ml) and extracted 3 times with DCM. The combined organic layers were dried (MgSO₄), filtered and the solvent was evaporated. Yield: 0.5 g of intermediate 21 (93%).

g) Preparation of Intermediate 22

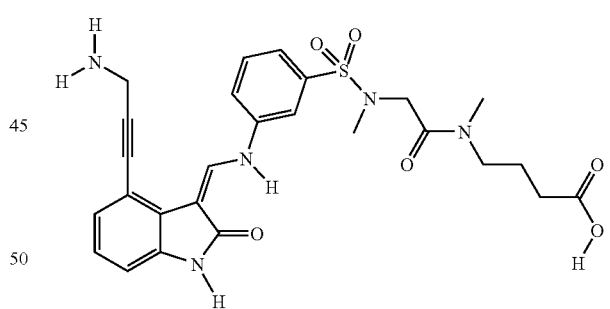

A mixture of intermediate 21 (0.00077 mol) in 20% TFA/DCM (30 ml) was stirred at room temperature for 1 hour. The solvent was evaporated. The residue was suspended in DIPE. The precipitate was filtered off and dried (vacuum). This fraction was purified by reversed-phase column chromatography (Shandon Hyperprep® C18 BDS (Base Deactivated Silica) 8 μm, 250 g, I.D. 5 cm). The mentioned mobile phases were used to apply a gradient (phase A: 90% of a 0.5% NH₄OAc solution in water+10% CH₃CN; phase B: CH₃OH (optional); phase C: CH₃CN). Two product fraction groups were collected and the solvents of the main product fraction was partially evaporated. The concentrate was taken up in H₂O and extracted with DCM. The separated organic layer was dried (MgSO$_4$), filtered and the solvent was evaporated. This main product fraction yielded 0.1 g of intermediate 22.

Example A8 a) Preparation of Intermediate 23

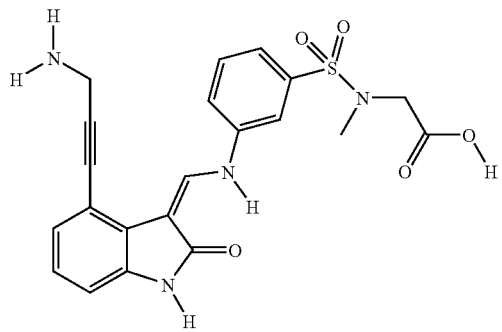

A mixture of intermediate 19 (0.000074 mol) in 20% TFA/DCM (5 ml) was stirred at room temperature for 3 hours. The solvent was evaporated. Yield: 0.040 g of intermediate 23.

Example A9 a) Preparation of Intermediate 24

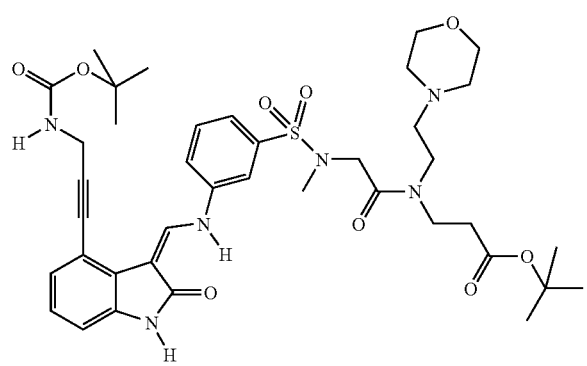

A mixture of intermediate 19 (0.0015 mol), N-[2-(4-morpholinyl)ethyl]-β-Alanine 0.2HCl (0.0017 mol), EDCI (0.0017 mol), HOBt (0.0017 ml) and Et$_3$N (0.007 mol) in DCM (50 ml) was stirred at room temperature for 90 hours. The reaction mixture was washed with water. The organic layer was separated, dried (MgSO$_4$), filtered and the solvent was evaporated. The residue was purified by short column chromatography over silica gel (eluent: DCM/MeOH 90/10). The product fractions were collected and the solvent was evaporated. The residue (1 g) was the residue was crystallized from CH$_3$CN/DIPE. The precipitate was filtered off and dried. Yield: 0.5 g of intermediate 24.

b) Preparation of Intermediate 25

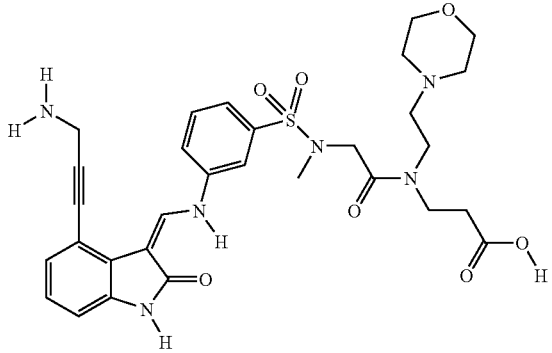

A mixture of intermediate 24 (0.00064 mol) in 5 TFA/DCM (50 ml) was stirred at room temperature for 20 hours. Then 20% TFA/DCM (7.5 ml) was added and the reaction mixture was stirred for another 20 hours at room temperature. The solvent was evaporated. Yield: 0.60 g of intermediate 25 (LCMS: 70% P).

Example A10

Preparation of Intermediate 26

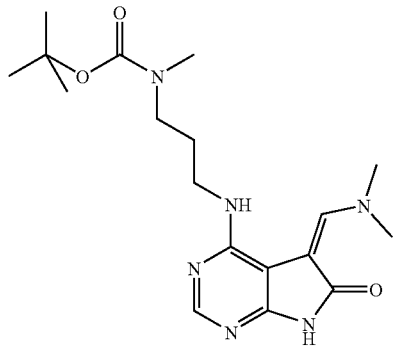

4-Chloro-1,5-dihydro-6H-pyrrolo[2,3-d]pyrimidin-6-one (0.0241 mol) was dissolved in DMA (96 ml) under N$_2$ atmosphere. DIPEA (0.0289 mol) was added and the mixture was stirred for 5 minutes. (4-aminobutyl)methyl-carbamic acid, 1,1-dimethylethyl ester (0.0265 mol) was added and the reaction mixture was stirred for 15 hours at 100° C. under N$_2$ atmosphere. Then the mixture was cooled to 25-30° C. 1,1-dimethoxy-N,N-dimethylmethanamine (0.073 mol) was added in one portion and the reaction mixture was stirred for 3 hours at room temperature. The reaction mixture was poured out into a saturated aqueous NaCl solution. This mixture was extracted with EtOAc. The organic layer was separated, washed with a saturated aqueous NaCl solution, dried (MgSO$_4$), filtered and the solvent was evaporated. The residue was purified by flash column chromatography over silica gel (eluent: DCM/MeOH 50/1 up to 10/1). The product fractions were collected and the solvent was evaporated. Yield: 2.97 g of intermediate 26 (33%).

Example A11 a) Preparation of Intermediate 27

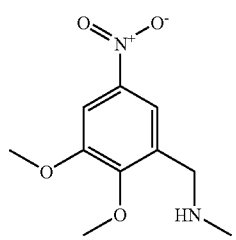

2,3-Dimethoxy-5-nitrobenzaldehyde (5.5 g, 26 mmol, 1.0 eq.) was dissolved in MeOH (47 ml) and THF (7.8 ml). NaHCO$_3$ (3.5 g, 83.4 mmol, 3.2 eq.) and methanamine, hydrochloride (2.12 g, 31.3 mmol, 1.2 eq.) were added. The mixture was stirred at 80° C. for 4 hours. After cooling to room temperature, sodium borohydride (1.19 g, 31.3 mmol, 1.2 eq.) was added portionwise, and the mixture was stirred overnight. Then the mixture was partitioned between EtOAc and brine. The layers were separated and the organic layer dried over MgSO$_4$, filtered and concentrated. The resulting product was dried under high vacuum to afford 6.0 g of intermediate 27 (used as such in the next reaction steps).

b) Preparation of Intermediate 28

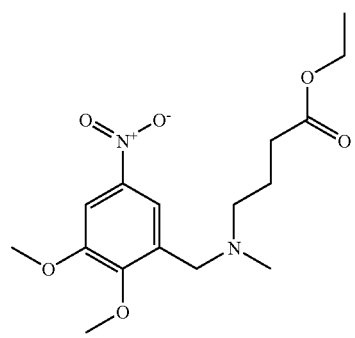

Intermediate 27 (2.0 g, 8.85 mmol, 1.0 eq.) was dissolved in DMA (30 ml). 4-Bromobutanoic acid ethyl ester (1.8 g, 9.3 mmol, 1.05 eq.) was added and the mixture was stirred. Then Na$_2$CO$_3$ (1.050 g, 9.75 mmol, 1.1. eq.) was added and the mixture was stirred overnight at 70° C. The mixture was partitioned between EtOAc and brine. The layers were separated and the organic layer dried over MgSO$_4$, filtered and concentrated. The resulting product was dried under high vacuum to yield intermediate 28 (used as such in the next reaction steps).

c) Preparation of Intermediate 29

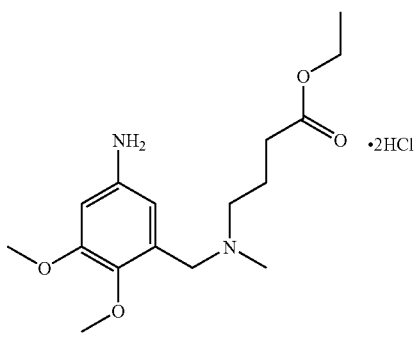

Intermediate 28 (8.5 mmol) was dissolved in EtOAc (150 ml). Vanadium pentoxide (0.100 g) and a thiophene solution (2 ml; 2% in DIPE) were added, followed by Pt/C 5% (2.0 g) as the catalyst. After N$_2$ purge, a H$_2$ atmosphere was introduced through a gas-bag. The reaction mixture was hydrogenated for 20 hours at room temperature. Then the catalyst was filtered off over a celite-pad. HCl/Dioxane (6 ml, 4 N) was added to the filtrate and the resulting mixture was concentrated under reduced pressure. THF was added to the residue and the resulting solid was filtered, washed with DIPE and dried to afford 1.4 g of intermediate 29 (94% purity LCMS; 43% yield over 2 reaction steps; 0.2HCl).

d) Preparation of Intermediate 30

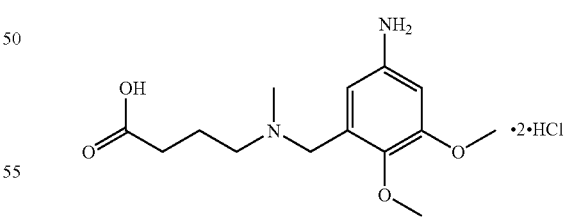

Intermediate 29 (1.4 g, 3.6 mmol) was dissolved in H$_2$O (5 ml) and dioxane (5 ml). HCl (37%; 2.5 ml) was added to the solution and the mixture was stirred for 15 hours at 50° C. The solvent was evaporated and the residue was stirred in THF (40 ml). The resulting solid was filtered, washed with DIPE and dried to afford 1.39 g of intermediate 30 (85% purity LCMS; 0.2HCl).

Example A12 a) Preparation of Intermediate 31

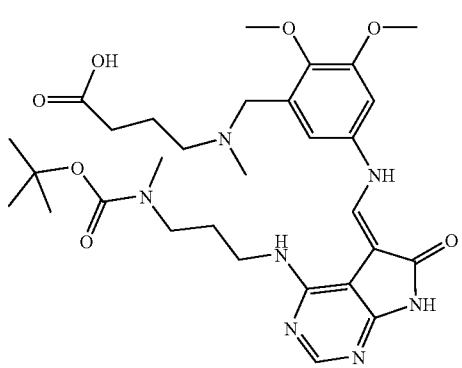

A mixture of intermediate 26 (0.15 g, 0.000398 mol), intermediate 30 (0.000478 mol; 0.2HCl) and MgSO$_4$ (0.2 g) in DMA (2 ml) was heated overnight at 80° C. The solvent was evaporated and the crude residue was purified by flash column chromatography (eluent: DCM/MeOH). Yield: intermediate 31 (used as such in the next reaction step).

b) Preparation of Intermediate 32

TFA (5 ml) was added to intermediate 31 (0.00025 mol; crude) and the mixture was stirred for 6 hours at room temperature. Then the solvent was evaporated and the crude intermediate 32 was used as such in the next reaction step.

Example A13 a) Preparation of Intermediate 33

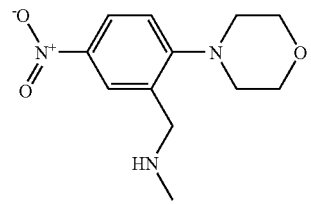

NaHCO$_3$ (35.5 g, 0.424 mol) was dissolved in MeOH (750 ml). 2-(4-morpholinyl)-5-nitro-benzaldehyde (50 g, 0.212 mol) and methanamine (127 ml, 0.254 mol; 2 M solution in THF) were added to the solution. The reaction mixture was refluxed for 4 hours and was then cooled at 5° C. NaBH$_4$ (9.6 g, 0.254 mol) was added portionwise during 30 minutes while the mixture was cooled at 10° C. The mixture was stirred at room temperature for 2 hours and then H$_2$O (few drops) was added. The mixture was concentrated to remove most of the MeOH. The resulting mixture was extracted with DCM. The combined organic layers were washed with brine, dried (MgSO$_4$), filtered and the solvent was evaporated. Yield: 41.8 g of intermediate 33 (78.5%).

b) Preparation of Intermediate 34

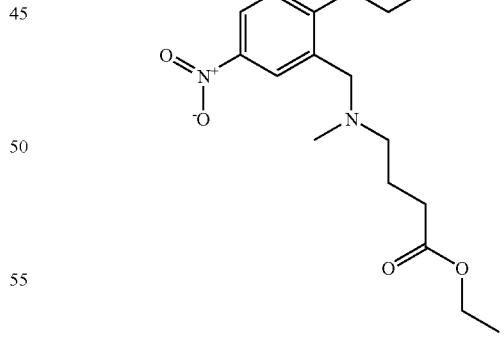

Intermediate 33 (10 g, 0.04 mol), 4-bromo-butanoic acid ethyl ester (7.8 g, 0.04 mol) and K$_2$CO$_3$ (11 g, 0.08 mol) were added to acetone (500 ml) and the reaction mixture was stirred and refluxed for 12 hours. The solution was filtered and the filtrate's solvent was evaporated. The residue was purified by column chromatography. The product fractions were collected and the solvent was evaporated. Yield: 11 g of intermediate 34 (76%).

c) Preparation of Intermediate 35

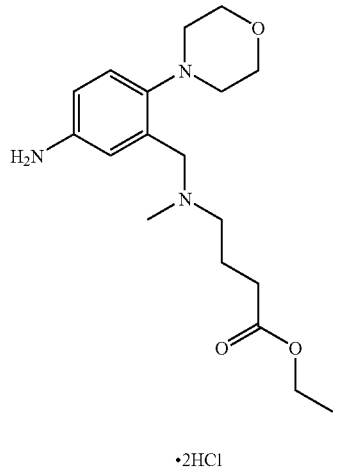

•2HCl

A mixture of intermediate 34 (11 g, 0.0313 mol) in THF (350 ml) was hydrogenated for 12 hours at room temperature with Raney nickel (6 g, 0.0171 mol; catalyst). After an uptake of $H_2$ (3 eq, 1 atm), the catalyst was filtered off and the solvent was evaporated. The residue was dissolved in a solution of HCl in 1,4-dioxane (30 ml) and stirred at room temperature for 10 minutes. The solvent was evaporated. This residue was stirred in ether and the precipitate was filtered off. Yield: 10 g of intermediate 35 (100%; 0.2HCl).

d) Preparation of Intermediate 36

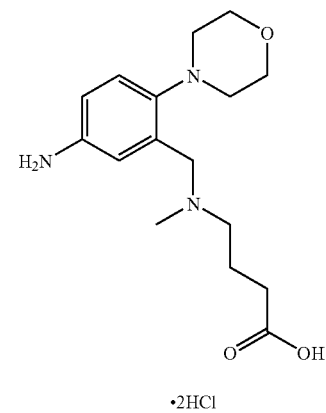

•2HCl

Intermediate 35 (2 g, 4.9 mmol) was dissolved in $H_2O$ (10 ml) and dioxane (10 ml). HCl (10 ml; 37%) was added and the mixture was stirred for 10 hours at 50° C. The solvent was evaporated and the residue was stirred in THF (40 ml). The resulting solid was filtered, washed with DIPE and dried to yield 1.42 g of intermediate 36 (76%; 0.2HCl; 98% purity by LCMS).

Example A14 a) Preparation of Intermediate 37

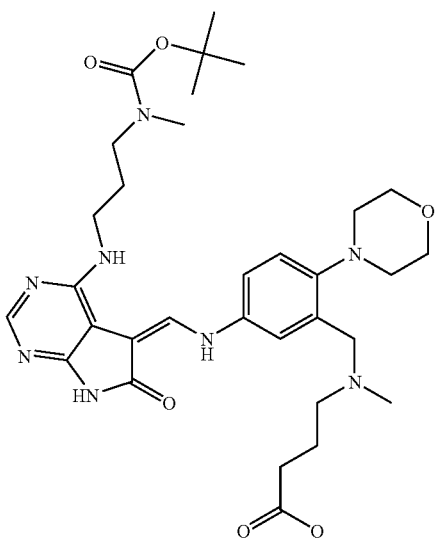

A mixture of intermediate 26 (0.15 g, 0.000398 mol), intermediate 36 (1,2 eq, 0.0004776 mol; 0.2HCl) and $MgSO_4$ (0.2 g) in DMA (2 ml) was heated overnight at 80° C. The solvent was evaporated and the crude was purified by flash column chromatography (eluent: DCM/MeOH). The desired fractions were collected and the solvent was evaporated. Yield: Intermediate 37.

b) Preparation of Intermediate 38

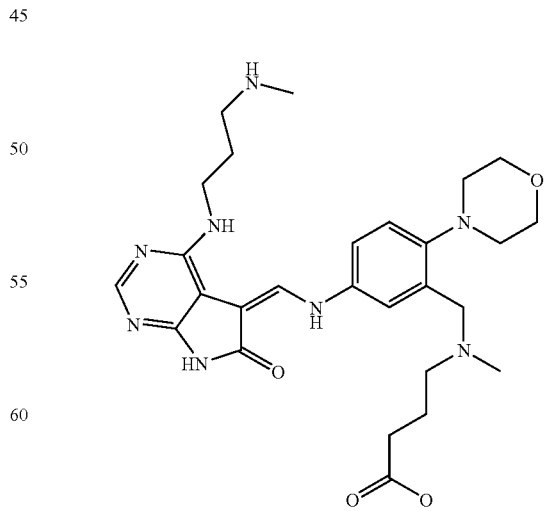

TFA/DCM (5 ml) was added to intermediate 37 (0.00025 mol; crude) and the mixture was stirred for 6 hours at room Example A15 a) Preparation of Intermediate 39

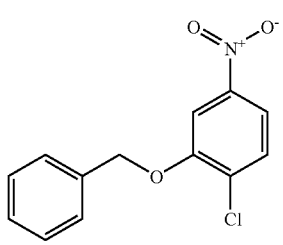

2-Chloro-5-nitrophenol (0.048 mol) and K$_2$CO$_3$ (0.053 mol) were dissolved in DMF (75 ml) and the solution was stirred at room temperature. A solution of (chloromethyl)benzene (0.057 mol) in DMF (75 ml) was added dropwise to the reaction mixture. When the reaction was finished, H$_2$O (q.s.) was added and the product precipitated. The solid was filtered off, washed with H$_2$O and dried. Yield: 1'1.7 g of intermediate 39 (92.4%).

b) Preparation of Intermediate 40

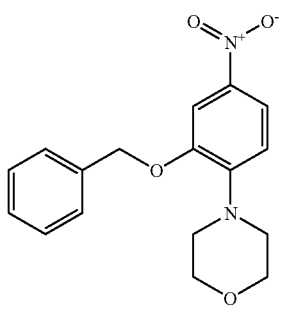

Intermediate 39 (4 g, 15.1 mmol, 1.0 eq.) was dissolved in toluene (100 ml). Morpholine (1.85 g, 21 mmol, 1.4 eq.) was added and the mixture was stirred. Cs$_2$CO$_3$ (6.9 g, 21 mmol, 1.4 eq.) was added and the mixture was stirred at 40° C. for 20 minutes under N$_2$ bubling. Palladium acetate (Pd(OAc)$_2$) (140 mg, catalytic) and X-Phos (40 mg, Catalytic), were added and the mixture was stirred under N$_2$ at reflux overnight. Then the mixture was partitioned between toluene and brine. The layers were separated and the organic layer dried over MgSO$_4$, filtered and concentrated. The resulting product was dried under high vacuum to afford 6.3 g of intermediate 40 (used as such in the next reaction steps).

c) Preparation of Intermediate 41

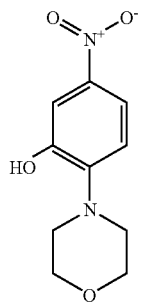

Intermediate 40 (crude, 0.015 mol theoretical) was mixed with a HCl solution in dioxane (q.s.; 7 M), and the mixture was stirred for 30 hours at 100° C. in a sealed tube. After completion of the reaction, the reaction mixture was concentrated and the crude intermediate 41 was used as such in the next reaction steps.

d) Preparation of Intermediate 42

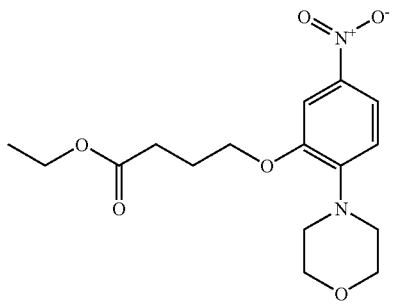

Intermediate 41 (15 mmol, 1.0 eq.) was dissolved in DMA (30 ml). 4-Bromobutanoic acid ethyl ester (3.2 g, 16.5 mmol, 1.1 eq.) was added and the solution was stirred. Cs$_2$CO$_3$ (10 g, 30 mmol, 2.0 eq.) was added and the mixture was stirred overnight at 60° C. Then the mixture was partitioned between EtOAc and brine. The layers were separated and the organic layer dried over MgSO$_4$, filtered and concentrated. The resulting product was dried under high vacuum to afford 5.3 g of intermediate 42 (used as such in the next reaction steps).

e) Preparation of Intermediate 43

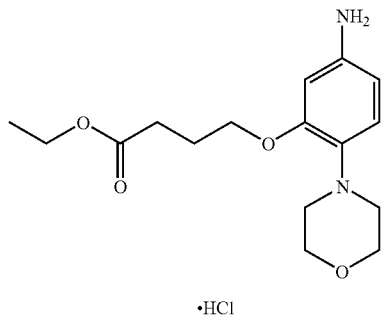

·HCl

Intermediate 42 (15 mmol) was dissolved in EtOH (200 ml). A solution of thiophene (2% in DIPE) (2 ml) was added, followed by addition of Pd/C 10% (2.0 g) as catalyst. After $N_2$ purge, a $H_2$ atmosphere was introduced through a gas-bag. The reaction mixture was then hydrogenated for 20 hours at room temperature. The catalyst was filtered over a celite-pad. HCl/dioxane (6 ml, 4 N) was added to the filtrate and the mixture was concentrated under reduced pressure. THF was added to the residue and the resulting solid was filtered, washed with DIPE and dried to yield 4.4 g of intermediate 43 (hydrochloride) (94% purity LCMS; 85% yield over 4 reaction steps).

f) Preparation of Intermediate 44

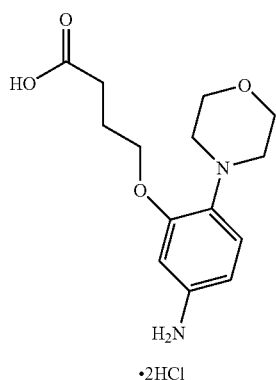

·2HCl

Intermediate 43 (2 g, 5.8 mmol) was dissolved in $H_2O$ (10 ml) and dioxane (10 ml). HCl (10 ml; 37%) was added and the mixture was stirred at 50° C. for 10 hours. The solvent was evaporated and the residue was stirred in THF (40 ml). The resulting solid was filtered, washed with DIPE and dried to afford 1.39 g of intermediate 44 (hydrochloride) (91% purity LCMS; 76% yield).

Example A16 a) Preparation of Intermediate 45

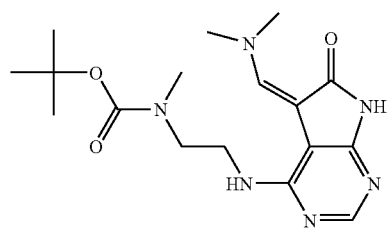

4-Chloro-1,5-dihydro-6H-pyrrolo[2,3-d]pyrimidin-6-one (2.22 g, 0.0131 mol) was dissolved in DMA (52 ml) under an stream of $N_2$. DIPEA was added and the reaction mixture was stirred for 5 minutes. N-(2-aminoethyl)-N-methylcarbamic acid 1,1-dimethylethyl ester (0.0144 mol, 1.1 eq.) was added and the reaction mixture was stirred overnight at 100° C. under $N_2$. The reaction mixture was cooled down to 25° C. 1,1-dimethoxy-N,N-dimethyl-methanamine (0.03927 mol, 3 eq.) was added in one portion and the reaction mixture was stirred at room temperature for 3 hours. The mixture was poured into brine and the product was extracted with EtOAc (3×). The combined organic layers were dried over $MgSO_4$, filtered and concentrated. The resulting residue was purified by flash-chromatography on silica gel (eluent: DCM/MeOH 50:1 until 30:1). The desired fractions were concentrated to afford pure 1.09 g intermediate 45 (36%).

b) Preparation of Intermediate 46

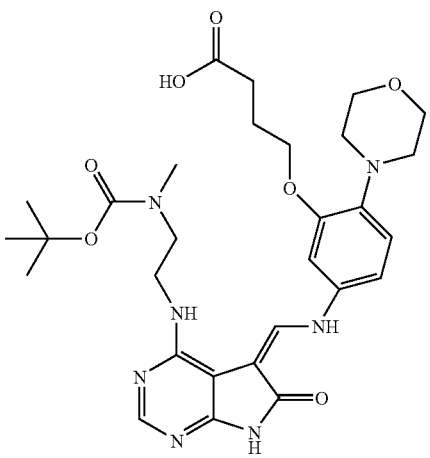

A mixture of intermediate 45 (0.00041 mol), intermediate 44 (1.2 equiv; 0.00049 mol) and $MgSO_4$ (0.2 g) in DMA (2 ml) was stirred overnight at 80° C. The mixture was filtered and the solvent was evaporated. The residue was purified by flash column chromatography over silica gel (eluent: DCM/MeOH gradient). The product fractions were collected and the solvent was evaporated. Yield: Intermediate 46.

c) Preparation of Intermediate 47

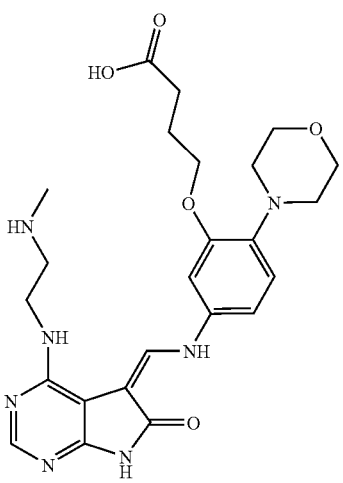

TFA (5 ml) was added to intermediate 46 (0.00025 mol). The resultant reaction mixture was stirred for 6 hours at room temperature. The solvent was evaporated, yielding intermediate 47 (used in the next reaction step, without further purification).

Example A17 a) Preparation of Intermediate 52

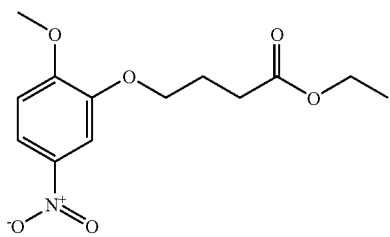

A mixture of 2-methoxy-5-nitrophenol (0.059 mol), K$_2$CO$_3$ (0.065 mol) and 4-chloro-butanoic acid ethyl ester (0.066 mol) in DMF (120 ml) was stirred overnight at 60° C., then cooled and poured out into H$_2$O. The precipitate was filtered off and dried in vacuo. Yield: 8.05 g of intermediate 52 (96%).

b) Preparation of Intermediate 53

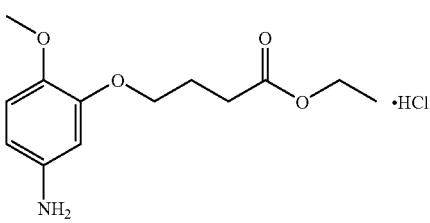

A mixture of intermediate 52 (14 g, 0.0494 mol) in EtOH (250 ml) was hydrogenated at room temperature with Pd/C 10% (2 g) as a catalyst in the presence of a thiophene solution (2 ml; 4% in DIPE). After uptake of H$_2$, the catalyst was filtered off and the filtrate was acidified with HCl/2-propanol. The mixture was evaporated and the residue was stirred in DIPE. The precipitate was filtered off and dried. Yield: 13.3 g of intermediate 53.

c) Preparation of Intermediate 54

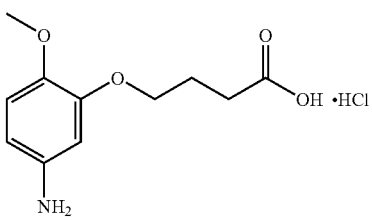

A mixture of intermediate 53 (2.4 g, 0.01 mol), dioxane (40 ml), H$_2$O (40 ml) and HCl (20 ml; 36%) was stirred for 4 hours at 50° C. and was then stirred overnight at room temperature. The solvent was evaporated. Toluene was added 2× to the residue and the solvent was evaporated each time. The residue was stirred in DIPE. The precipitate was filtered off and dried. Yield: 2.5 g of intermediate 54 (.HCl).

Example A 18 a) Preparation of Intermediate 48

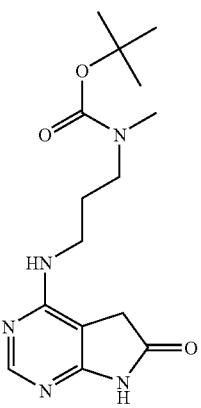

Reaction under N$_2$ atmosphere. A mixture of 4-chloro-1, 5-dihydro-6H-pyrrolo[2,3-d]pyrimidin-6-one (0.001 mol), N-(3-aminopropyl)-N-methylcarbamic acid, 1,1-dimethylethyl ester (0.0012 mol) and DIPEA (0.0015 mol) in DMA (3 ml) was stirred for 16 hours at 100° C. Then the mixture was allowed to cool to room temperature. Yield: Intermediate 48 (Mixture, used in next reaction step without further purification).

b) Preparation of Intermediate 49

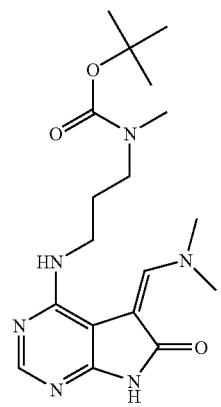

The crude mixture intermediate 48 obtained in the previous procedure was treated with 1,1-dimethoxy-N,N-dimethylmethanamine (0.003 mol). This mixture was stirred for 4 hours. The mixture was poured out into $H_2O$ and was then extracted with DCM. The separated organic layer was dried, filtered and the solvent evaporated. The residue was purified over silica gel on a glass filter (eluent: DCM/MeOH 95/5). The product fractions were collected and the solvent was evaporated. Yield: 0.343 g of intermediate 49 (91%).

c) Preparation of Intermediate 50

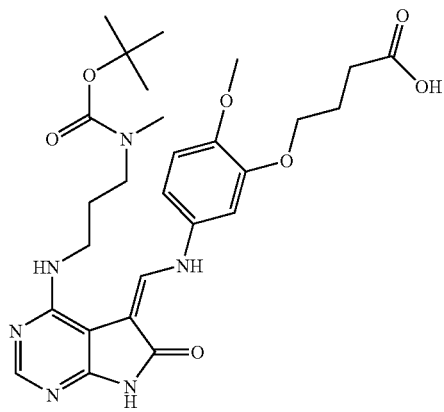

A mixture of intermediate 49 (0.0009 mol) and intermediate 54 (0.0009 mol) in t-butanol (5 ml) was stirred for 16 hours at 80° C. Then the mixture was cooled to room temperature and the solvent was evaporated. Yield: Intermediate 50 (quantitative yield; used in next reaction step, without further purification).

d) Preparation of Intermediate 51

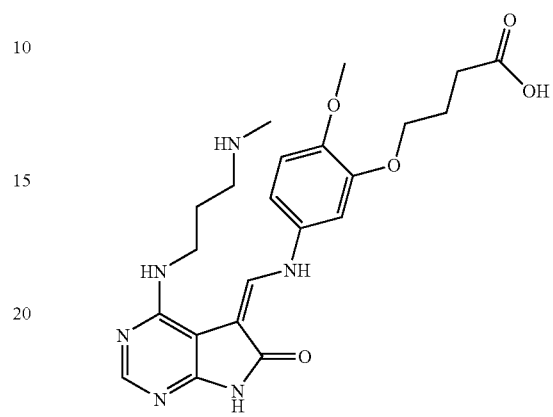

A mixture of intermediate 50 (0.0009 mol) in 20% TFA/DCM (20 ml) was stirred for 16 hours at 25° C. The solvent was evaporated. The residue was purified by reversed-phase high-performance liquid chromatography (Shandon Hyperprep® C18 BDS (Base Deactivated Silica) 8 μm, 250 g, I.D. 5 cm). The mentioned mobile phases were used to apply a gradient (phase A: a 0.25% $NH_4HCO_3$ solution in water; phase B: MeOH (optional); phase C: $CH_3CN$). The product fractions were collected and the solvent was evaporated. Yield: 0.059 g of intermediate 51 (14.4%).

Example A19

Preparation of Intermediate 55

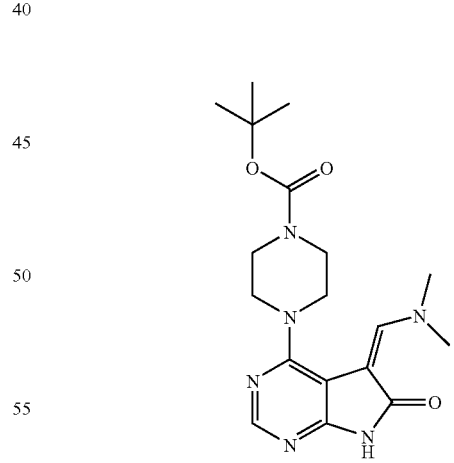

A mixture of 4-chloro-1,5-dihydro-6H-pyrrolo[2,3-d]pyrimidin-6-one (0.169 g, 0.0010 mol), 1-piperazinecarboxylic acid, 1,1-dimethylethyl ester (0.186 g, 0.0010 mol), $Et_3N$ (0.110 g, 0.0011 mol) and DMA (2 ml) was stirred for 16 hours at 100° C. The reaction mixture was cooled and then 1,1-dimethoxy-N,N-dimethylmethanamine (0.360 g, 0.0030 mol) was added. The reaction mixture was stirred over the weekend and then water was added. This mixture was extracted 3× with EtOAc. The separated organic layer was washed 2× with H₂O, dried, filtered and the solvent was evaporated. The residue was purified over silica gel (glass filter and eluent: DCM/MeOH 95/5). The product fractions were collected and the solvent was evaporated. Yield: 0.225 g of intermediate 55 (60%).

Example A20 a) Preparation of Intermediate 56

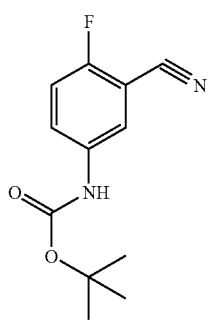

A mixture of 5-amino-2-fluorobenzonitrile monohydrochloride (0.15 mol), Et₃N (0.18 mol) and N,N-dimethyl-4-pyridinamine (catalytic quantity) in DCM (q.s.) was stirred at room temperature. Dicarbonic acid, bis(1,1-dimethylethyl) ester (0.16 mol) was added portionwise. The reaction mixture was stirred overnight. NH₃/MeOH was added and the mixture was stirred overnight. The solvent was evaporated. The residue was purified over silica gel on a glass filter (eluent: DCM/MeOH 99/1). The product fractions were collected and the solvent was evaporated. Yield: 18.3 g of intermediate 56.

b) Preparation of Intermediate 57

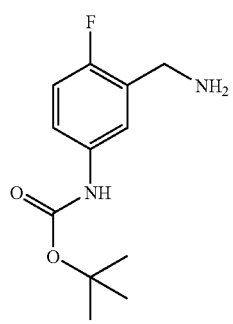

First input: A mixture of intermediate 56 (0.01 mol) in MeOH (q.s.) was hydrogenated at room temperature with Raney Nickel as a catalyst. After uptake of H₂ (2 eq.), the catalyst was filtered off, giving filtrate (I). Second input: A mixture of intermediate 56 (0.066 mol) in NH₃/MeOH (q.s.) was hydrogenated at room temperature with Raney Nickel as a catalyst. After uptake of H₂ (2 eq.), the catalyst was filtered off, giving filtrate (II). Filtrates (I) and (II) were combined.

The solvent was evaporated. The residue was stirred in DIPE. The precipitate was filtered off and dried. Yield: 11.3 g of intermediate 57 (62%).

c) Preparation of Intermediate 58

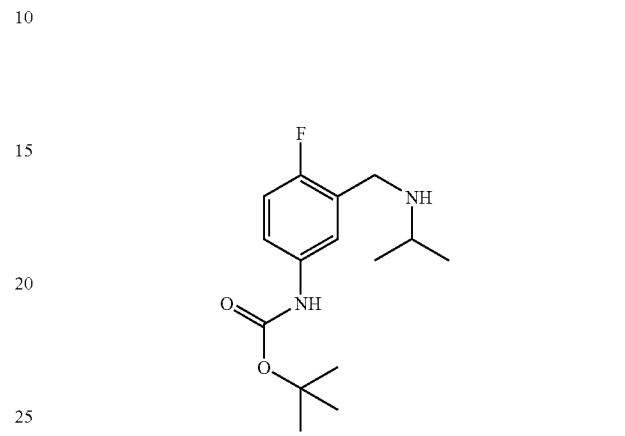

A mixture of intermediate 57 (0.01 mol) and acetone (0.750 g) in MeOH (100 ml) was hydrogenated at 50° C. (atmospheric pressure) with Pd/C 10% (0.5 G) as a catalyst in the presence of a thiophene solution (0.5 ml; 4% in DIPE). After uptake of H₂ (1 eq.), the catalyst was filtered off and the filtrate was evaporated. The residue was taken up into DCM. The solid was filtered off and the filtrate's solvent was evaporated. Yield: 2.6 g of intermediate 58 (92%).

d) Preparation of Intermediate 59

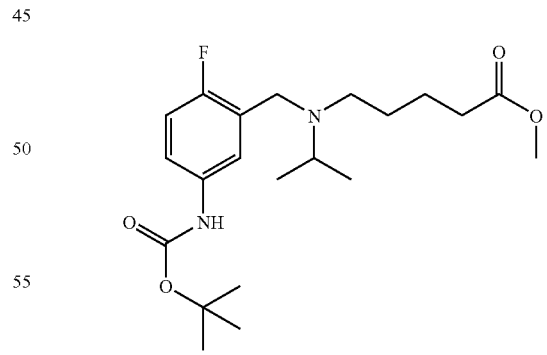

A mixture of intermediate 58 (0.00815 mol), 5-bromopentanoic acid, methyl ester (0.00815 mol) and DIPEA (1.58 g) in DMA (25 ml) was stirred for 5 days at 60° C. More 5-bromo-pentanoic acid, methyl ester (0.5 g) was added and the reaction mixture was stirred over the weekend at 60° C. The mixture was poured out into H₂O. This mixture was extracted with EtOAc (3×), washed with H₂O (2×), dried, filtered and the solvent evaporated. The residue was purified by high-performance liquid chromatography (HPLC). The product fractions were collected and worked-up. Yield: 2.55 g of intermediate 59 (79%).

e) Preparation of Intermediate 60

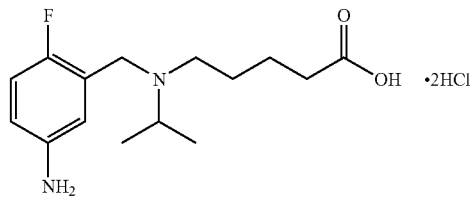

A mixture of intermediate 59 (0.0064 mol) in 1,4-dioxane (40 ml), H$_2$O (40 ml) and HCl (20 ml; 36%) was stirred for 16 hours at 50° C. The solvent was evaporated. Yield: 2.8 g of intermediate 60 (0.2HCl; quantitative yield; used in next reaction step, without further purification).

f) Preparation of Intermediate 61

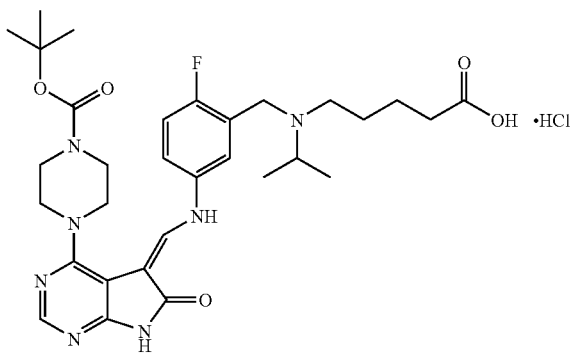

A mixture of intermediate 55 (0.0005 mol) and intermediate 60 (0.0005 mol) in t-butanol (5 ml) was stirred for 16 hours at 80° C. The solvent was evaporated. Yield: Intermediate 61 (quantitative yield; used in next reaction step, without further purification).

g) Preparation of Intermediate 62

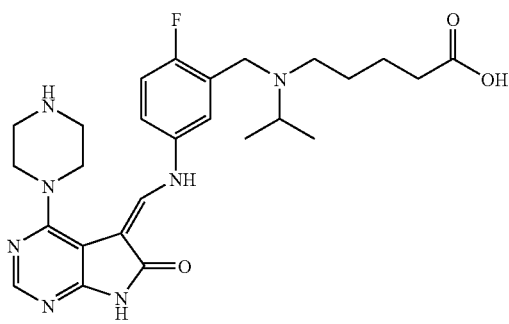

A mixture of intermediate 61 (0.0005 mol) in 20% TFA/DCM (20 ml) was stirred for 16 hours at room temperature (25° C.). The solvent was evaporated. The residue was purified by HPLC. The product fractions were collected and worked-up. Yield: 0.100 g of intermediate 62 (39.1%).

Example A21 a) Preparation of Intermediate 63

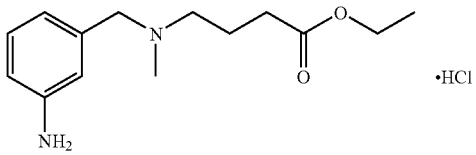

A mixture of N-methyl-3-nitro-benzenemethanamine, monohydrochloride (0.02 mol), 4-bromobutanoic acid, ethyl ester (0.021 mol) and Na$_2$CO$_3$ (0.022 mol) in DMA (30 ml) was stirred for 16 hours at 70° C. The mixture was cooled, then poured out into H$_2$O and the mixture was extracted 3× with EtOAc. The combined organic layers were washed with H$_2$O (2×), dried (MgSO$_4$), filtered and the solvent was evaporated. Yield: 5.6 g of intermediate 63 (quantitative yield; used in next reaction step, without further purification).

b) Preparation of Intermediate 64

A mixture of intermediate 63 (0.02 mol) in EtOAc (200 ml) was hydrogenated at room temperature with Pt/C (2 g) as a catalyst and V$_2$O$_5$ (0.200 g) as a co-catalyst in the presence of a thiophene solution (2 ml; 4% in DIPE). After uptake of H$_2$ (3 eq.), the catalyst was filtered off and the filtrate's solvent was evaporated. The residue was taken up in DIPE (100 ml) and converted into the hydrochloric acid salt (1:1) with 6 N HCl/2-propanol (10 ml). The resultant oil's organic layer was decanted off. To the residue, DIPE (100 ml) was added. The c) Preparation of Intermediate 65

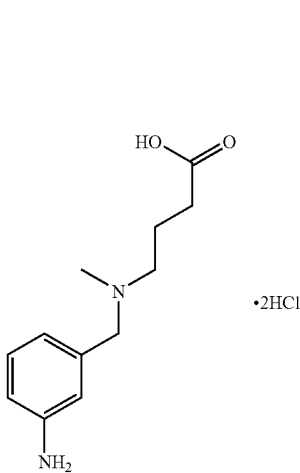

·2HCl

A mixture of intermediate 64 (0.02 mol) in 1,4-dioxane (30 ml), H₂O (30 ml) and HCl (30 ml; 36%) was stirred for 3 hours at 50° C. The solvent was evaporated. The residue was stirred in THF, then filtered off and dried. Yield: 5.1 g of intermediate 65 (0.2HCl).

d) Preparation of Intermediate 66

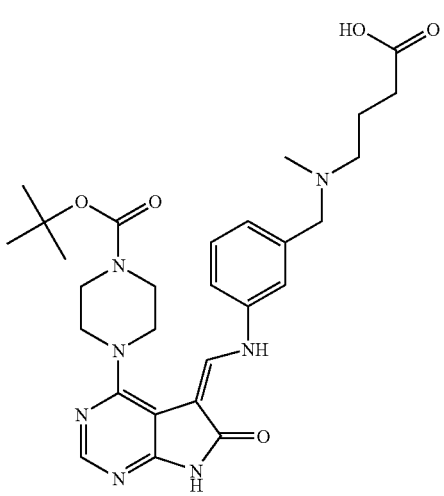

A mixture of intermediate 55 (0.0005 mol) and intermediate 65 (0.0005 mol) in t-butanol (5 ml) was stirred for 16 hours at 80° C. The solvent was evaporated. Yield: Intermediate 66 (used in next reaction step, without further purification).

e) Preparation of Intermediate 67

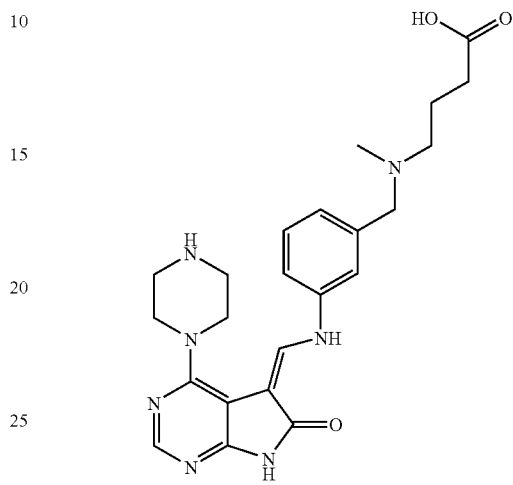

A solution of intermediate 66 (0.0005 mol) in 20% TFA/DCM (20 ml) was stirred over the weekend at room temperature. The solvent was evaporated. The residue was purified by reversed-phase high-performance liquid chromatography (Shandon Hyperprep® C18 BDS (Base Deactivated Silica) 8 µm, 250 g, I.D. 5 cm). The mentioned mobile phases were used to apply a gradient (phase A: a 0.25% NH₄HCO₃ solution in water; phase B: MeOH (optional); phase C: CH₃CN). The product fractions were collected and the solvent was evaporated. The residue (0.080 g) was stirred in DIPE. The resulting precipitate was filtered off and dried. Yield: 0.055 g of intermediate 67 (24%).

Example A22 a) Preparation of Intermediate 68

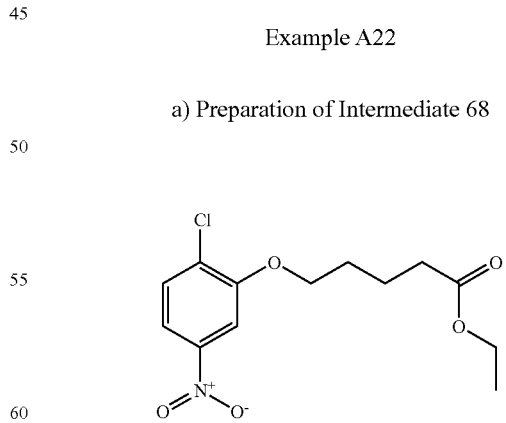

Reaction under N₂ atmosphere. A mixture of 2-chloro-5-nitrophenol (0.029 mol), 5-bromopentanoic acid, ethyl ester (0.032 mol) and K₂CO₃ (0.032 mol) in DMA (150 ml) was stirred overnight at 60° C. The reaction mixture was cooled. H₂O was added. This mixture was extracted with EtOAc (3×).

The separated organic layer was washed with H$_2$O (2×), dried, filtered and the solvent evaporated. Yield: 8.7 g of intermediate 68 (100%).

b) Preparation of Intermediate 69

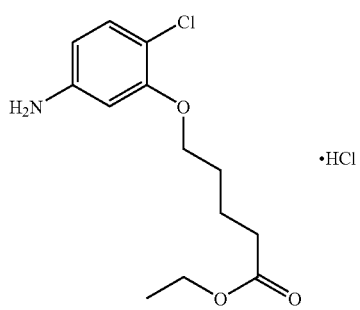

A mixture of intermediate 68 (0.029 mol) in EtOAc (100 ml) was hydrogenated with Pt/C 10% (2 g) as a catalyst and V$_2$O$_5$ (0.200 g) as a co-catalyst in the presence of a thiophene solution (2 ml; 4% in DIPE). After uptake of H$_2$ (3 eq.), the catalyst was filtered off. The filter residue was washed with EtOH and the filtrate was treated with HCl/2-propanol (1.5 ml). The solvent was evaporated. Yield: 9 g of intermediate 69 (.HCl; quantitative yield; used in next reaction step, without further purification).

c) Preparation of Intermediate 70

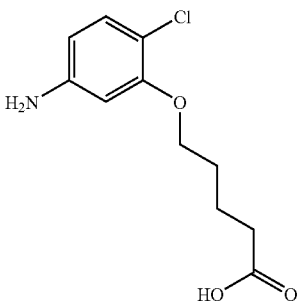

A mixture of intermediate 69 (0.029 mol) in H$_2$O (40 ml), 1,4-dioxane (40 ml) and HCl (40 ml; 36%) was stirred for 4 hours at 50° C. The solvent was evaporated. The residue was stirred in D1PE and CH$_3$CN. The precipitate was filtered off and dried. This fraction (15.5 g) was taken up into H$_2$O, NH$_4$HCO$_3$ was added. This mixture was extracted with DCM. The separated organic layer was dried, filtered and the solvent evaporated. Yield: 0.7 g of intermediate 70 (10%).

d) Preparation of Intermediate 71

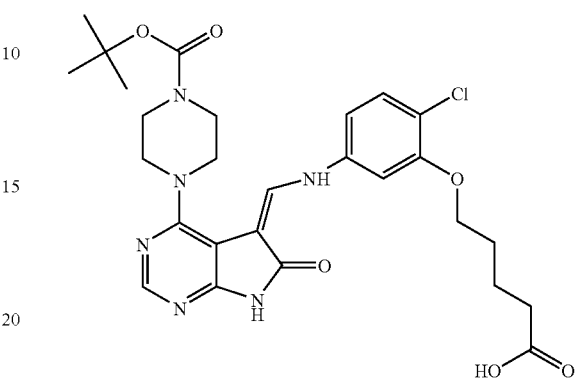

Two different reaction mixtures. Reaction mixture A: Mixture of intermediate 55 (0.0001 mol), intermediate 70 (0.0001 mol) and HCl/2-propanol (5 drops) in t-butanol (3 ml) was stirred for 16 hours at 80° C., then over the weekend at 80° C. Reaction mixture B: A mixture of intermediate 55 (0.0004 mol), intermediate 70 (0.0004 mol) and HCl/2-propanol (20 drops) in t-butanol (5 ml) was stirred over the weekend at 80° C. The two reaction mixtures were combined. The solvent was evaporated. The residue was stirred in boiling CH$_3$CN. The mixture was cooled and the precipitate was filtered off and dried. Yield: 0.180 g of intermediate 71 (78%; Z/E 85/15).

e) Preparation of Intermediate 72

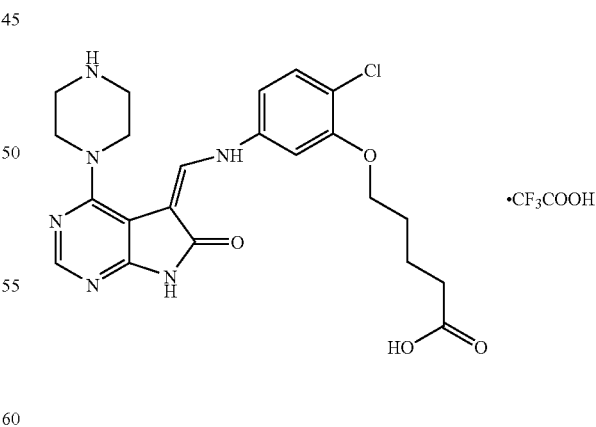

A solution of intermediate 71 (0.00024 mol) in 20% TFA/DCM (20 ml) was stirred overnight at room temperature. The solvent was evaporated. The residue was stirred in DIPE. The precipitate was filtered off and dried. Yield: 0.158 g of intermediate 72 (93.6%; .CF; Z/E±89/11).

Example A23 a) Preparation of Intermediate 73

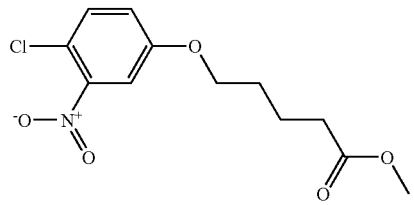

Reaction under N$_2$ atmosphere. A mixture of 4-chloro-3-nitrophenol (0.055 mol), 5-bromopentanoic acid, methyl ester (0.055 mol) and K$_2$CO$_3$ (0.055 mol) in DMA (50 ml) was stirred for 16 hours at 60° C. The reaction mixture was cooled. H$_2$O was added. This mixture was extracted with EtOAc (3×). The separated organic layer was washed with H$_2$O (2×), dried, filtered and the solvent evaporated. Yield: 16.5 g of intermediate 73 (100%).

b) Preparation of Intermediate 74

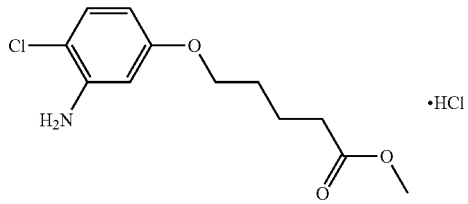

A mixture of intermediate 73 (0.05 mol) in THF (150 ml) was hydrogenated at room temperature with Pt/C (2 g) as a catalyst and V$_2$O$_5$ (0.100 g) as a co-catalyst in the presence of a thiophene solution (2 ml; 4% in DIPE). After uptake of H$_2$ (3 eq.), the catalyst was filtered off. The filter residue was washed with EtOH and the filtrate was treated with HCl/2-propanol. The solvent was evaporated. The residue was stirred in DIPE. The precipitate was filtered off and dried. Yield: 14.5 g of intermediate 74 (100%; .HCl).

c) Preparation of Intermediate 75

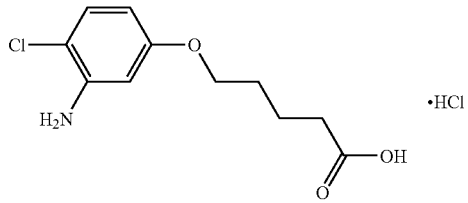

A mixture of intermediate 74 (0.01 mol) in 1,4-dioxane (20 ml), H$_2$O (20 ml) and HCl (10 ml; 36%) was stirred for 6 hours at 50° C. More HCl (10 ml; 36%) was added and the reaction mixture was stirred for 2 hours at 50° C. The solvent was evaporated. The residue was stirred in CH$_3$CN, then filtered off and dried. Yield: 2.67 g of intermediate 75 (96.4%).

d) Preparation of Intermediate 76

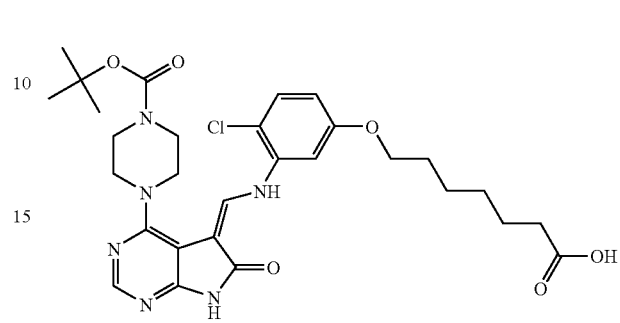

A mixture of intermediate 55 (0.001 mol) and intermediate 75 (0.002 mol) in t-butanol (10 ml) was stirred for 16 hours at 80° C. The solvent was evaporated. The restudies was stirred in boiling CH$_3$CN (4 ml). The mixture was cooled and the precipitate was filtered off and dried. Yield: 0.186 g of intermediate 76 (32.5%).

e) Preparation of Intermediate 77

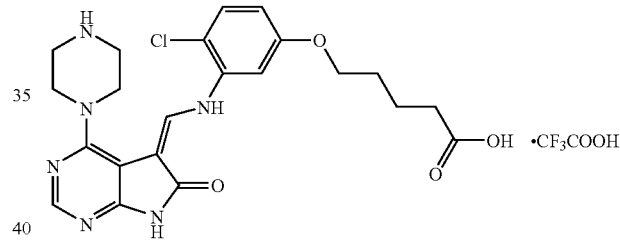

A solution of intermediate 76 (0.000324 mol) in 20% TFA/DCM (25 ml) was stirred over the weekend at room temperature (25° C.). The solvent was evaporated. The residue was stirred in CH$_3$CN. The precipitate was filtered off and dried. Yield: 0.065 g of intermediate 77 (34.2%; .CF$_3$COOH).

Example A24 a) Preparation of Intermediate 78

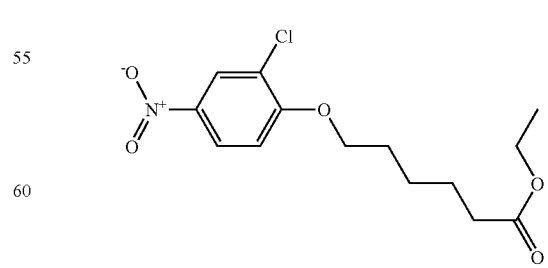

A mixture of 2-chloro-4-nitrophenol (0.05 mol), 6-bromohexanoic acid, ethyl ester (0.055 mol) and K$_2$CO$_3$ (0.055 mol) in DMA (50 ml) was stirred for 16 hours at 60° C. The mixture was cooled. H₂O was added. This mixture was extracted with EtOAc (3×). The combined organic layers were washed with water (2×), then dried (MgSO₄), filtered and the solvent was evaporated. Yield: 15.8 g of intermediate 78 (quantitative yield; used in next reaction step, without further purification).

b) Preparation of Intermediate 79

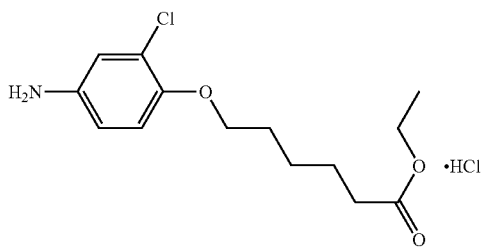

A mixture of intermediate 78 (0.05 mol) in EtOAc (200 ml) was hydrogenated at room temperature with Pt/C (2 g) as a catalyst and V₂O₅ (0.200 g) as a co-catalyst in the presence of a thiophene solution (2 ml; 4% in DIPE). After uptake of HCl/2 (3 eq.), the catalyst was filtered off. The filter residue was rinsed with EtOH. HCl/2-propanol (25 ml) was added. The solvent was evaporated. The residue was stirred in DIPE. The precipitate was filtered off and dried. Yield: 15.3 g of intermediate 79 (95.6%; .HCl).

c) Preparation of Intermediate 80

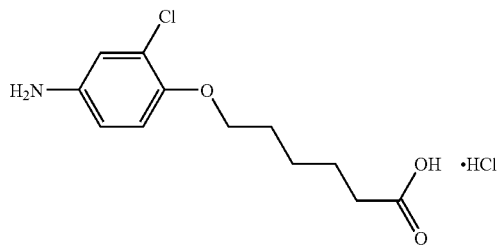

A mixture of intermediate 79 (0.01 mol) in 1,4-dioxane (20 ml), H₂O (20 ml) and HCl (10 ml; 36%) was stirred for 6 hours at 50° C. The solvent was evaporated. CH₃CN was added, then evaporated again (2×). The residue was stirred in DIPE, filtered off and dried. Yield: 2.75 g of intermediate 80 (94.5%; .HCl).

d) Preparation of Intermediate 81

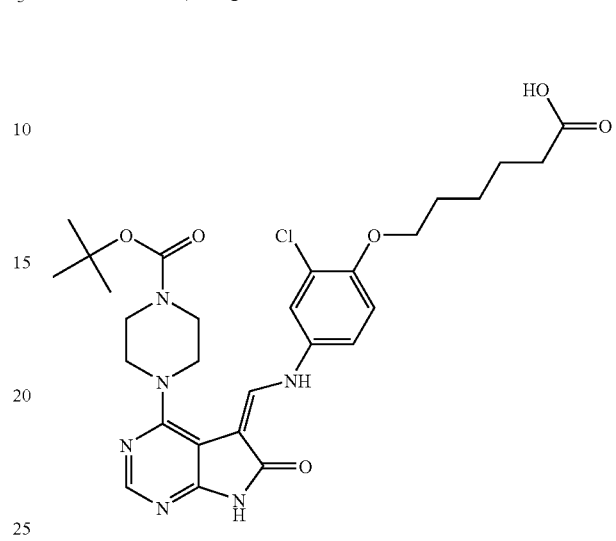

A mixture of intermediate 55 (0.0010 mol) and intermediate 80 (0.0012 mol) in t-butanol (20 ml) was stirred for 16 hours at 80° C. The solvent was evaporated. The residue was stirred in boiling CH₃CN, then cooled and the resulting precipitate was filtered off and dried. Yield: 0.265 g of intermediate 81 (45%).

e) Preparation of Intermediate 82

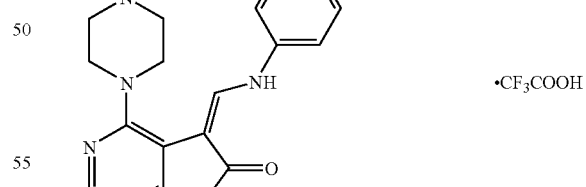

A solution of intermediate 81 (0.000443 mol) in 20% TFA/DCM (25 ml) was stirred for 16 hours at room temperature. The solvent was evaporated. The residue was stirred in DIPE. The precipitate was filtered off and dried. Yield: 0.225 g of intermediate 82 (84.6%; .CF₃COOH).

Example A25 a) Preparation of Intermediate 83

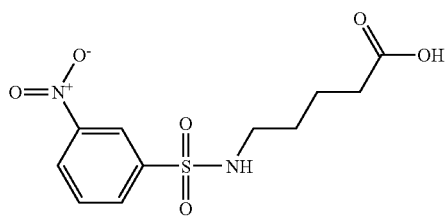

NaOH (0.1 mol; 50%) and 5-amino-entanoic acid (0.05 mol) were added to $H_2O$ (100 ml). The mixture was stirred. A solution of 3-nitrobenzenesulfonyl chloride (0.05 mol) in THF (30 ml) was added dropwise in 30 minutes while the reaction mixture was kept at room temperature on a waterbath). Then the reaction mixture was stirred for 2 hours at room temperature. HCl (9 ml; chemical pure) was added dropwise and the reaction mixture was stirred for one hour at room temperature. The resulting precipitate was filtered off, washed with $H_2O$ and dried (50° C.). Yield: 10.5 g of intermediate 83 (67%)

b) Preparation of Intermediate 84

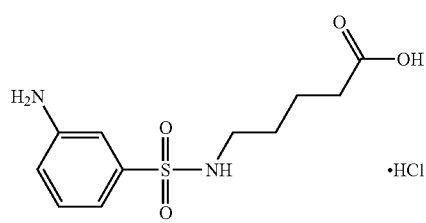

A mixture of intermediate 83 (0.0066 mol) in THF (100 ml) was hydrogenated at room temperature with Pd/C 10% (0.5 g) as a catalyst and $V_2O_5$ (0.050 g) as a co-catalyst in the presence of thiophene (0.5 ml; 4% in DIPE). After uptake of $H_2$ (3 eq.), the catalyst was filtered off and the filtrate was evaporated. The residue was dissolved in $CH_3CN$ and converted into the hydrochloric acid salt (1:1) with HCl/2-propanol. The precipitate was filtered off and dried. Yield: 1.8 g of intermediate 84 (90%; .HCl).

c) Preparation of Intermediate 85

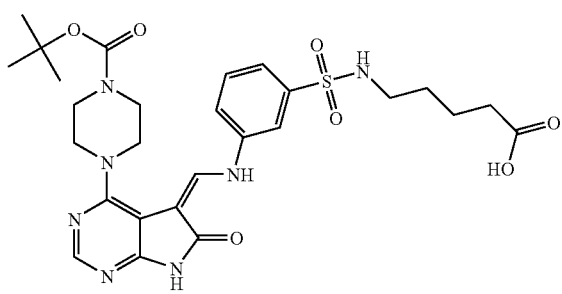

A mixture of intermediate 55 (0.001 mol), intermediate 84 (0.001 mol) and HCl/2-propanol (q.s.) in t-butanol (20 ml) was stirred for 16 hours at 80° C. The solvent was evaporated. The residue was stirred in boiling $CH_3CN$, then cooled and the resulting precipitate was filtered off and dried. Yield: 0.100 g of intermediate 85 (16.7%).

d) Preparation of Intermediate 86

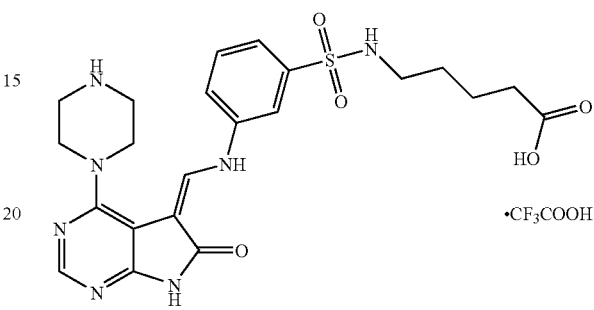

A solution of intermediate 84 (0.000167 mol) in 20% TFA/DCM (20 ml) was stirred for 16 hours at room temperature. The solvent was evaporated. The residue was stirred in DIPE. The precipitate was filtered off and dried. Yield: 0.075 g of intermediate 86 (73%; .$CF_3COOH$).

Example A26 a) Preparation of Intermediate 87

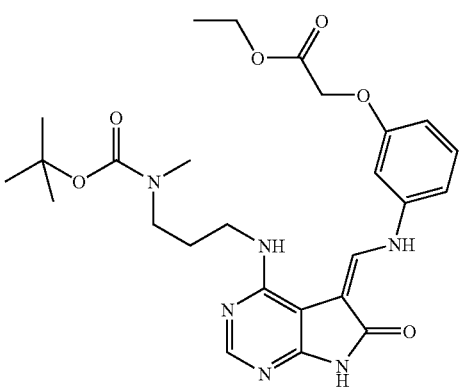

A mixture of intermediate 49 (10.63 mmol), 2-(3-aminophenoxy)-acetic acid ethyl ester (12.75 mmol) $CH_3CN$ (20 ml), HCl (4N in 1,4-dioxane; 10.63 mmol) DMA (20 ml) and anhydrous $MgSO_4$ (10 g) was heated overnight at 80° C. The reaction crude was poured onto brine and extracted with EtOAc. The organic layer was washed several times with more brine solution, then dried over anhydrous $MgSO_4$ and evaporated to dryness. The resulting residue was purified by flash chromatography (eluent: DCM/MeOH gradient to 19:1), yielding 3.92 μg (70%) of intermediate 87.

b) Preparation of Intermediate 88

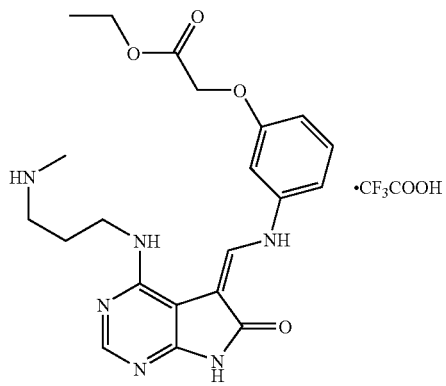

Intermediate 87 (7.5 mmol) was dissolved in a mixture of DCM (50 ml) and TFA (50 ml) and the solution was stirred at room temperature for 5 hours. The reaction mixture was evaporated to dryness yielding intermediate 88.

c) Preparation Of Intermediate 89

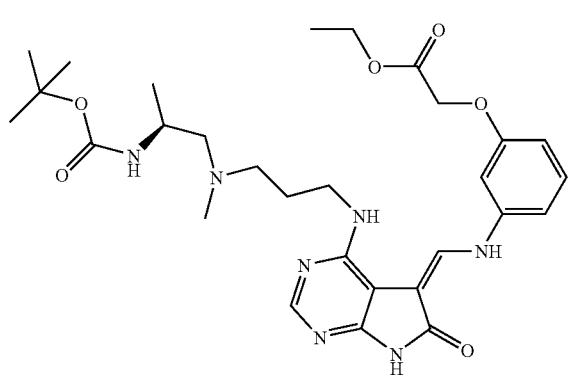

Intermediate 88 (2.5 mmol), N-[(1S)-1-methyl-2-oxoethyl]-carbamic acid 1,1-dimethylethyl ester (3.0 mmol) and sodium triacetoxyborohydride, 95% (3.75 mmol) were dissolved in 1,2-dichloroethane (25 ml) and DMA (5 ml). The reaction mixture was stirred overnight at room temperature. ½ equivalent of N-[(1S)-1-methyl-2-oxoethyl]-carbamic acid 1,1-dimethylethyl ester and ½ equivalent of sodium triacetoxyborohydride, 95% were added and the mixture was stirred for 3 additional hours. The reaction crude was poured onto NaHCO₃ sat. solution and extracted with EtOAc, then washed with brine solution. The organic layer was dried over anhydrous MgSO₄ and concentrated to dryness, yielding 1.35 g (92%) yielding of intermediate 89.

d) Preparation of Intermediate 90

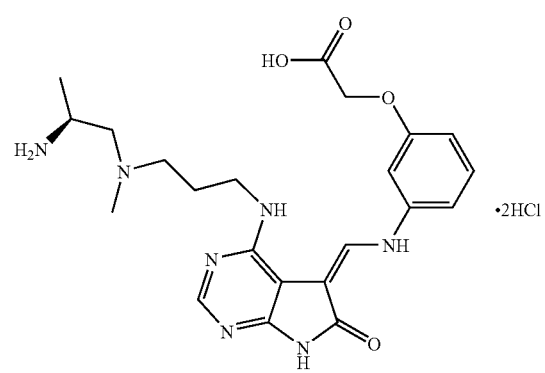

Intermediate 89 (2.3 mmol) was dissolved in 1,4-dioxane (100 ml) and HCl 5% (20 ml) and the reaction mixture was stirred at room temperature for 20 hours. The reaction mixture was concentrated to dryness. The product was stirred in DIPE, filtered off and dried (vacuum, room temperature) and was used as such in the next reaction step (intermediate 90).

Example A27 a) Preparation of Intermediate 91

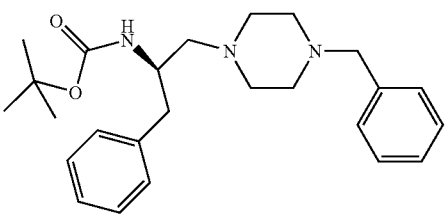

A solution of 1-(phenylmethyl)piperazine (0.0036 mol), N-[(1R)-1-formyl-2-phenylethyl]-carbamic acid 1,1-dimethylethyl ester (0.0044 mol) and sodium triacetoxyborohydride (0.0054 mol) in DCM (18 ml) was stirred overnight at room temperature. The crude reaction mixture was poured out onto a saturated aqueous NaHCO₃ solution and extracted with DCM. The separated organic layer was dried over MgSO₄, filtered and evaporated to dryness. The residue was dried (vacuum, room temperature), yielding 1.47 g of a brown oil as intermediate 91.

b) Preparation of Intermediate 92

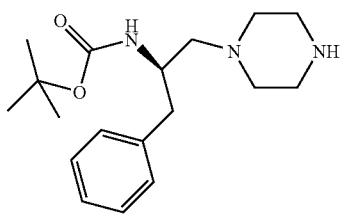

A solution of intermediate 91 (3.6 mmol) in EtOAc (q.s.) was degassed and purged with $N_2$. The catalyst Pd/C 10% (q.s.) was added and the solution was degassed and purged again with $N_2$, then with $H_2$. The reaction mixture was stirred at room temperature overnight under 1 atm $H_2$ gas. After uptake of $H_2$ (1 equiv.), the catalyst was filtered off through Celite, washed with MeOH and the filtrate was concentrated to dryness. The residue was dried (vacuum, room temperature), yielding 1.12 g (97%) of intermediate 92.

c) Preparation of Intermediate 93

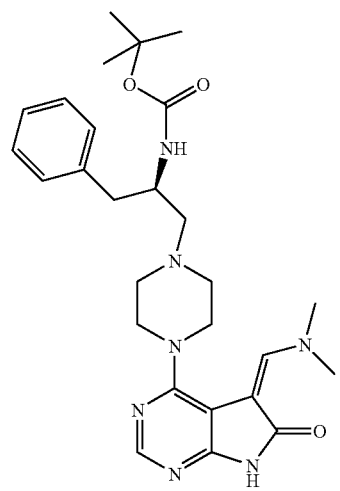

4-chloro-5,7-dihydro-6H-pyrrolo[2,3-d]pyrimidin-6-one (3.2 mmol) was dissolved in DMA 99% (15 ml) at room temperature under $N_2$ atmosphere. Then DIPEA (3.85 mmol) was added and the mixture was stirred for 5 minutes. Finally, intermediate 92 (3.5 mmol) was added and the resulting mixture was stirred at 100° C. for 15 hours under $N_2$ atmosphere. The reaction mixture was cooled to 25-30° C., DMFDMA (9.6 mmol) was added and the mixture was stirred at room temperature for 3 hours. The reaction mixture was poured onto brine and extracted several times with ethylacetate (6×300 ml). The organic layers were combined and washed with brine, dried over anhydrous $MgSO_4$, filtered and evaporated to dryness. The residue was purified by flash chromatography on silica gel (gradient elution: DCM/MeOH). The product fractions were collected and the solvent was evaporated. The product was dried (vacuum, room temperature) yielding 0.756 mol (47%) of a brown oil as intermediate 93.

d) Preparation of Intermediate 94

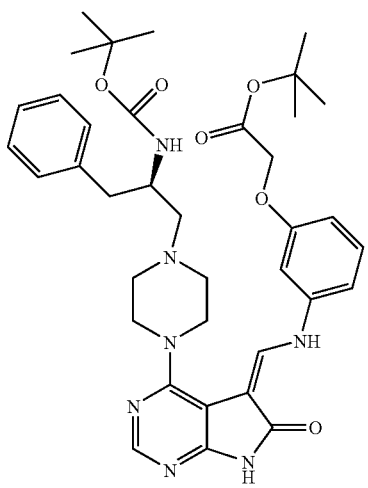

Intermediate 93 (1.48 mmol), 2-(3-aminophenoxy)-acetic acid 1,1-dimethylethyl ester (1.63 mmol), $CH_3CN$ (9 ml), HCl (4N in 1,4-dioxane, 1.63 mmol)), DMA (9 ml) and anhydrous $MgSO_4$ (1.48 g) were heated overnight at 80° C. The reaction mixture was poured onto brine and extracted with EtOAc. The organic layer was washed several times with more brine solution, then dried over anhydrous $MgSO_4$ and evaporated to dryness. The residue was purified by flash chromatography on silica gel (eluent: hexane/EtOAc gradient 9:1 to 4:1). The product fractions were collected and the solvent was evaporated, yielding 0.69 g (68%) of intermediate 94.

e) Preparation of Intermediate 95

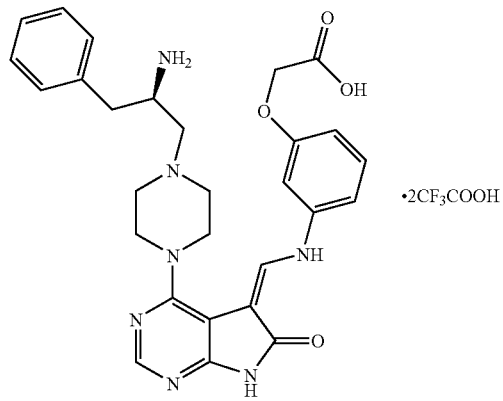

Intermediate 94 (1.02 mmol) was dissolved in DCM (100 ml) and TFA (100 ml), then the mixture was stirred at room temperature for 5 hours. The solvent was evaporated. The residue stirred in DIPE, filtered off and dried under vacuum, yielding intermediate 95 used as such in following step.

Example A28 a) Preparation of Intermediate 96

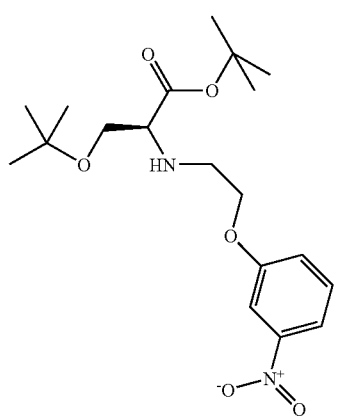

A mixture of o-tBu-L-Ser-tBu ester (8.7 mmol) and triethylamine (20.1 mmol) in $CH_3CN$ (20 ml), 1-(2-bromoethoxy)-3-nitrobenzene (6.7 mmol) was added and the mixture was stirred overnight at 60° C. The reaction crude was poured onto a brine solution and extracted several times with ethyl acetate. The organic extracts were combined and washed with water, dried over anhydrous $MgSO_4$ and concentrated to dryness. The residue was purified by flash chromatography on silica gel (eluent: hexane/EtOAc from 9:1 to 1:1). The product fractions were collected and the solvent was evaporated, yielding 1.9 g (74%) of intermediate 96.

b) Preparation of Intermediate 97

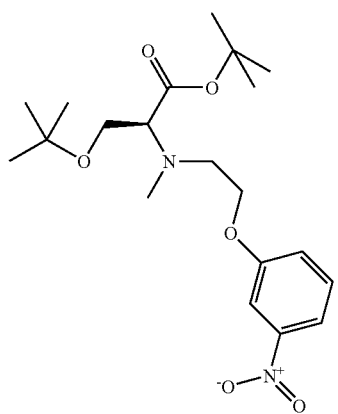

Intermediate 96 (5.18 mmol) was dissolved in 1,2-dichloroethane (16 ml), formaldehyde, 37 wt % solution. in water, stab. with 10-15% MeOH (7.77 mmol) and sodium triacetoxyborohydride, 95% (10.36 mmol) were added and the mixture was stirred overnight at room temperature. Another 3 equivalents of formaldehyde, 37 wt % solution. in water, stab. with 10-15% MeOH and sodium triacetoxyborohydride, 95% were added. The reaction mixture was partitioned between a saturated $NaHCO_3$ solution. and EtOAc, The organic layer was separated, dried over $MgSO_4$ and concentrated to dryness. The product fraction was dried (vacuum, room temperature), yielding 2.0 g (97%) of intermediate 97.

c) Preparation of Intermediate 98

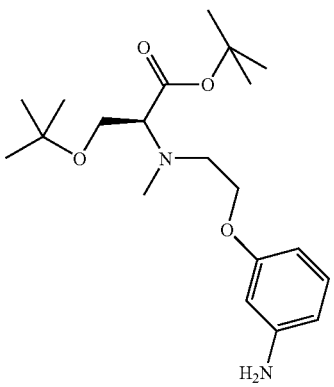

Intermediate 97 (5.2 mmol) was dissolved in EtOAc (50 ml) and the solution was degassed and purged with $N_2$. The catalyst Pd/C 10% (0.20 g) was added and the solution was degassed and purged again with $N_2$, then with $H_2$. The reaction mixture was stirred overnight at room temperature under 1 atm $H_2$ gas, then filtered through Celite and washed with MeOH. The filtrate was concentrated to dryness, yielding 1.90 g of intermediate 98.

d) Preparation of Intermediate 99

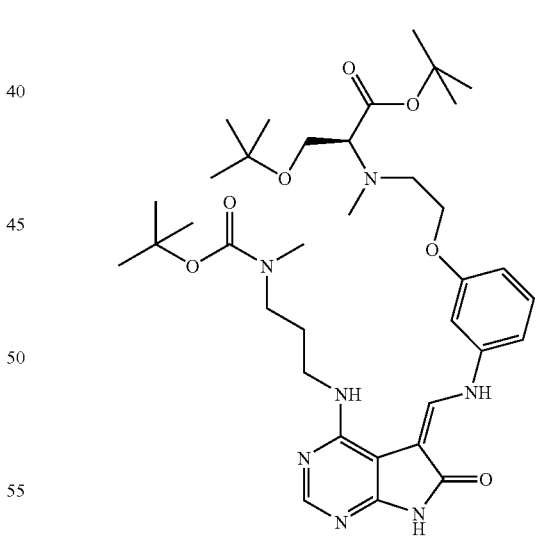

Intermediate 49 (2.2 mmol), intermediate 98 (2.6 mmol), $CH_3CN$ (5 ml) and HCl (4N in 1,4-dioxane; 2.6 mmol) were added to a mixture of DMA (5 ml) and anhydrous $MgSO_4$ (2 g) and then the reaction mixture was heated overnight at 80° C. The reaction crude was poured onto a brine solution and extracted with EtOAc. The organic layer was then washed several times with more brine solution, dried over $MgSO_4$ and concentrated to dryness. The residue was purified by flash chromatography (eluent: DCM/MeOH 49:1). The product fractions were collected and the solvent was evaporated, yielding 0.78 g (51%) of intermediate 99.

e) Preparation of Intermediate 100

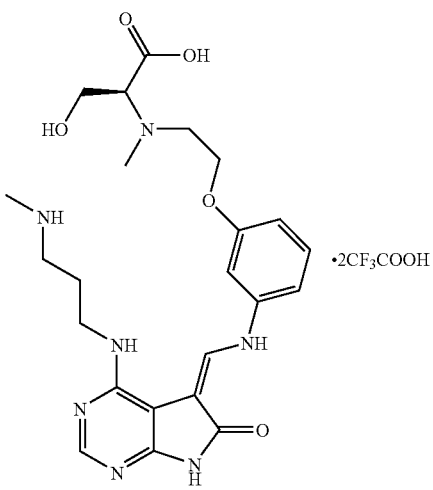

Intermediate 99 (1.12 mmol) was dissolved in TFA (112 ml) and DCM (112 ml) and then the mixture was stirred at room temperature for 5 hours. The solvent was evaporated and the residue was stirred in DIPE, filtered off and dried yielding intermediate 100 which was used as such in the following step.

Example A29 a) Preparation of Intermediate 101

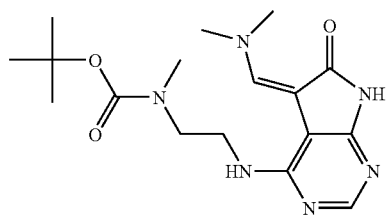

4-chloro-5,7-dihydro-6H-Pyrrolo[2,3-d]pyrimidin-6-one (0.04128 mol) was dissolved in DMA (165.12 ml) at room temperature, under $N_2$ atmosphere. Then, DIPEA (1.2 equiv, 0.04954 mol) was added and the mixture was stirred for 5 minutes. Finally, N-(2-aminoethyl)-N-methyl-carbamic acid 1,1-dimethylethyl ester (1.1 equiv, 0.04540 mol) was added and the resulting reaction mixture was stirred overnight at 100° C. under $N_2$ atmosphere. The reaction mixture was cooled to 25-30° C. DMFDMA (3 equiv, 0.12384 mol) was added in one portion and the reaction mixture was stirred at room temperature for 3 hours. The reaction mixture was poured out into brine and extracted with EtOAc (6×300 ml). The organic layers were combined, washed with brine, dried over anhydrous $MgSO_4$, filtered and concentrated to dryness. The residue was purified by flash column chromatography over silica gel (eluent: DCM/MeOH gradient: 40:1-30:1-20:1-10:1). The product fractions were collected and the solvent was evaporated. The residue was dried (vacuum, room temperature), yielding 5.4 g (36%) of a brown solid as intermediate 101.

Example A30 a) Preparation of Intermediate 102

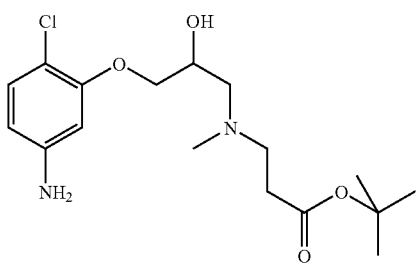

N-methyl-β-Alanine 1,1-dimethylethyl ester hydrochloride (1:1) (0.022 mol) was added to a solution of [(2-chloro-5-nitrophenoxy methyl]oxirane (0.022 mol) and DIPEA (0.022 mol) in EtOH (100 ml). The reaction mixture was stirred and refluxed for 15 hours. The solvent was evaporated. The residue was partitioned between EtOAc and brine. The separated organic layer was dried, filtered and the solvent evaporated, yielding 3.0 g of intermediate 102 which was used in the next reaction step, without further purification.

b) Preparation of Intermediate 103

Intermediate 102 (0.0077 mol) was dissolved in EtOAc. A thiophene solution (2% in D1PE; 1 ml was added. The solution was degassed and purged with $N_2$. $V_2O_5$ (0.1 g) was added. Catalyst Pt/$C_5$% (0.4 g) was added and the solution was degassed, purged with $N_2$, then with $H_2$. The reaction mixture was hydrogenated overnight at room temperature under 1 atm $H_2$ gas. After uptake of $H_2$ (3 equiv), the catalyst was filtered off through Celite. The filter residue was washed with methanol and the filtrate was evaporated. The residue was purified by column, chromatography over silica gel (gradient elution with DCM/MeOH). The product fractions were collected and the solvent was evaporated, yielding 2.67 g (97%) of intermediate 103.

c) Preparation of Intermediate 104

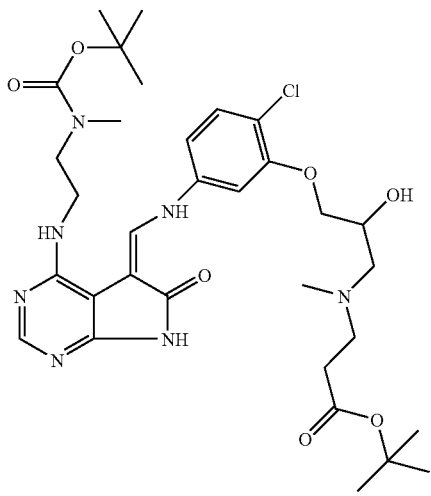

A mixture of intermediate 101 (0.0025 mol), intermediate 103 (0.0025 mol), anhydrous MgSO$_4$ (2.5 g) and HCl (4N in 1,4-dioxane; 0.75 ml) in a mixture of CH$_3$CN (7 ml) and DMA (7 ml) was stirred overnight at 80° C. The crude reaction mixture was poured out into brine, then extracted with EtOAc. The separated organic layer was washed several times with brine, dried over anhydrous MgSO$_4$, filtered and evaporated to dryness. The residue was purified by flash column chromatography over silica gel (gradient elution with DCM/MeOH). The product fractions were collected and the solvent was evaporated, yielding 1.00 g (70%) of intermediate 104.

d) Preparation of Intermediate 105

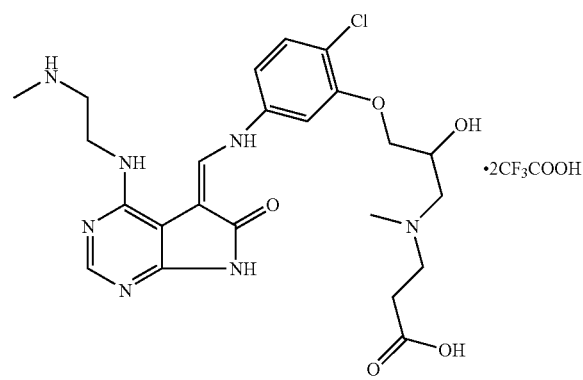

Intermediate 104 (0.00061 mol) was dissolved in DCM (60 ml) and treated with TFA (60 ml). The resultant reaction mixture was stirred for 5 hours at room temperature. The solvent was evaporated. The residue was triturated under DIPE, filtered off and dried under high-vacuum, yielding intermediate 105 used in next reaction step, without further purification.

Example A31 a) Preparation of Intermediate 106

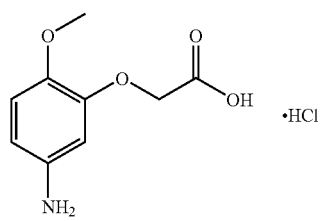

(5-Amino-2-methoxyphenoxy)acetic acid ethyl ester (0.00888 mol) was dissolved in HCl (4N in 1,4-dioxane; 45 ml). The reaction solution was stirred overnight at 55° C. The solvent was evaporated and the crude residue was dried under vacuum yielding 2.05 g of intermediate 106 which was used in the next reaction step without further purification.

Example A32 a) Preparation of Intermediate 107

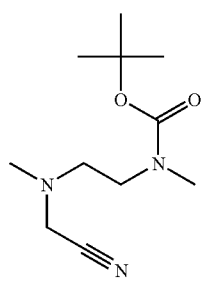

A solution of 2-chloro-acetonitrile (0.045 mol) in CH$_3$CN (50 ml) was added to a solution of N-methyl-N-[2-(methylamino)ethyl]-carbamic acid 1,1-dimethylethyl ester (0.045 mol) and K$_2$CO$_3$ (0.045 mol) in CH$_3$CN (100 ml). The reaction mixture was stirred for 27 hours at room temperature. The solvent was evaporated. Water was added and this mixture was extracted three times with DCM. The separated organic layer was dried over MgSO$_4$, filtered and the solvent evaporated yielding 10.2 g (99.7%) of intermediate 107 which was used in the next reaction step without further purification.

b) Preparation of Intermediate 108

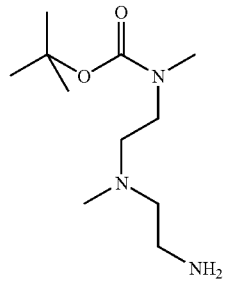

A mixture of intermediate 107 (0.045 mol) in NH$_3$/MeOH (250 ml) was hydrogenated with Raney Nickel under H$_2$ atmosphere. After uptake of H$_2$ (2 equiv.), the catalyst was filtered off and the filtrate was evaporated, yielding intermediate 108 which was used in the next reaction step without further purification.

c) Preparation of Intermediate 109

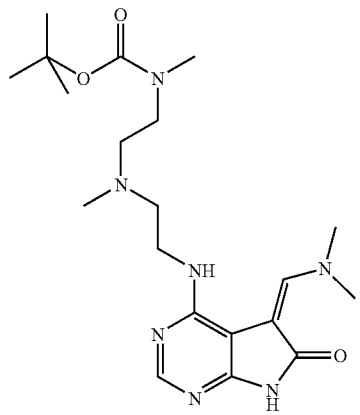

4-Chloro-5,7-dihydro-6H-pyrrolo[2,3-d]pyrimidin-6-one (0.0082 mol) was dissolved in DMA (32 ml) under N$_2$. DIPEA (0.0017 mol) was added and the reaction mixture was stirred for 5 minutes. Intermediate 108 (0.0090 mol) was added and the reaction mixture was stirred overnight at 100° C. under N$_2$. The mixture was cooled to 25° C. DMFDMA (0.0346 mol) was added and the mixture was stirred at room temperature for 3 hours. The reaction mixture was poured onto brine and extracted with EtOAc (3 times). The combined organic phases were dried over MgSO$_4$ anhydrous, filtered and concentrated. The residue was purified by flash chromatography (eluent: DCM/MeOH. gradient 50:1 to 30:1). The collected product fractions were evaporated to dryness, yielding 1.04 g (30%) of intermediate 109.

d) Preparation of Intermediate 110

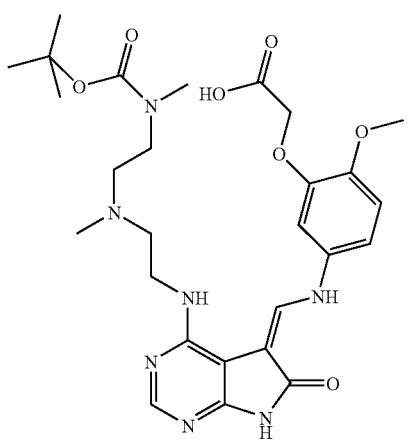

Intermediate 109 (0.0010 mol) was dissolved in DMA (4 ml). Intermediate 106 (0.0011 mol) was added. The reaction mixture was shaken overnight at 80° C. Another 0.3 equivalents of intermediate 106 was added and the reaction mixture was stirred at 80° C. for 20 additional hours. DMA was evaporated and the crude residue was purified by flash chromatography (eluent: DCM/MeOH, gradient 20:1 to 7:1). The product fractions were collected and the solvent was evaporated to dryness, yielding 0.44 g (80%) of intermediate 110.

e) Preparation of Intermediate 111

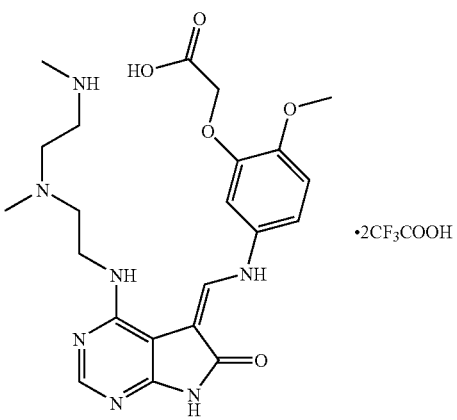

Intermediate 110 (0.0008 mol) was dissolved in DCM (5 ml) and TFA (5 ml). The reaction solution was stirred at room temperature overnight. The reaction mixture was evaporated to dryness and the crude residue was dried in vacuum yielding an oil as intermediate 111 which was used as such in the next step.

Example A33 a) Preparation of Intermediate 112

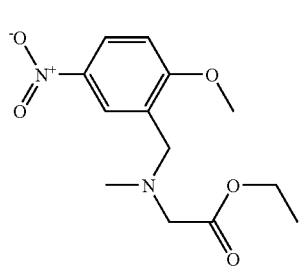

A mixture of 2-methoxy-N-methyl-5-nitrobenzenemethanamine (0.00761 mol), 2-bromo-acetic acid ethyl ester (0.01529 mol) and $Cs_2CO_3$ (0.02293 mol) in DMF (22.93 ml) was stirred overnight at 80° C. $Cs_2CO_3$ was filtered off and the DMF was evaporated. The crude residue was purified by flash chromatography (eluent: DCM/MeOH; gradient 50:1 to 30:1). The combined product fractions were evaporated to dryness, yielding 0.92 g (32%) of intermediate 112.

b) Preparation of Intermediate 113

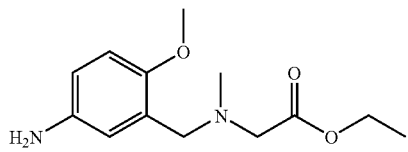

Intermediate 112 (0.00326 mol) was dissolved in EtOAc (10 ml). A thiophene solution 4% in DIPE (3 ml) and $V_2O_5$ (0.013 g) were added and $N_2$ was flushed through the mixture. Pt/C (0.09 g) was added slowly and the reaction mixture was stirred overnight under one atmosphere of $H_2$. Pt/C was removed by filtration over Celite. The solvent was evaporated and the crude was used in the next step without further purification, yielding 0.82 g of intermediate 113.

c) Preparation of Intermediate 114

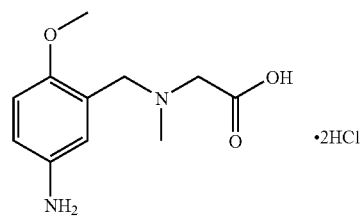

Intermediate 113 (0.00325 mol) was dissolved in HCl (4N in 1,4-dioxane; 16.25 ml) and the reaction solution was stirred overnight at 55° C. The solvent was evaporated and the crude residue was dried under vacuum yielding 1.00 g of intermediate 114.

d) Preparation of Intermediate 115

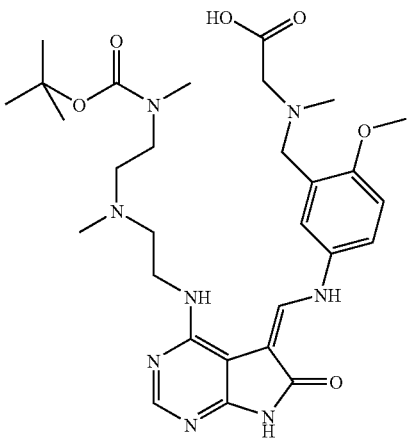

Intermediate 109 (0.0010 mol) was dissolved in DMA (4 ml). Intermediate 114 (0.0012 mol) and anhydrous $MgSO_4$ were added. The reaction mixture was shaken overnight at 80° C. Another 0.3 equivalents of intermediate 114 were added and the reaction was stirred at 80° C. for 20 additional hours. The anhydrous $MgSO_4$ anhydrous was removed by filtration. The DMA was evaporated and the crude residue was purified by flash chromatography (eluent: DCM/MeOH; gradient in 20:1 to 7:1). The product fractions were collected and the solvent was evaporated to dryness, yielding 0.28 g (47%) of intermediate 115.

e) Preparation of Intermediate 116

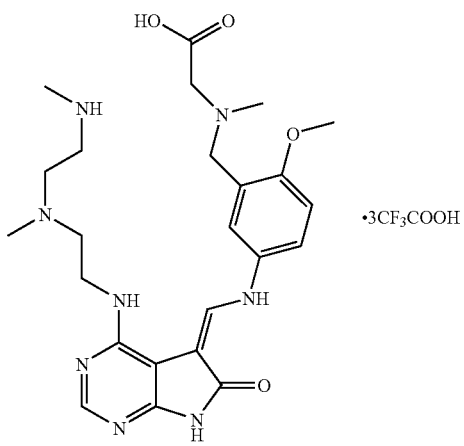

Intermediate 115 (0.0005 mol) was dissolved in DCM (5 ml). And TFA (5 ml). The reaction solution was stirred at room temperature overnight. The reaction mixture was evaporated to dryness and the crude residue was dried under high vacuum. The resulting oil was used as such in the next reaction step as intermediate 116.

Example A34 a) Preparation of Intermediate 117

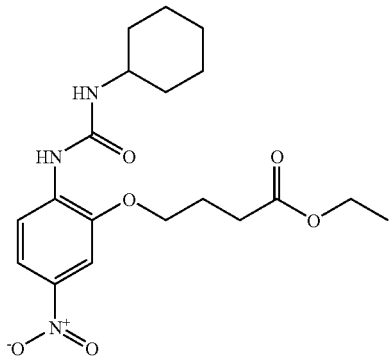

K$_2$CO$_3$ (0.036 mol) was added to a solution of N-cyclohexyl-N'-(2-hydroxy-4-nitrophenyl)-urea (0.018 mol) and 4-bromo-butanoic acid ethyl ester (0.018 mol) in DMF (30 ml). The reaction mixture was stirred for 16 hours at 50° C., then cooled to room temperature. The mixture was poured out into water and extracted with EtOAc (3×100 ml). The organic layers were combined, washed with a 10% aqueous K$_2$CO$_3$ solution, then with brine, dried over Na$_2$SO$_4$, filtered and the solvent was evaporated. The residue was stirred in DIPE, filtered off and dried, yielding 6.2 g (87.5%) of intermediate 117.

b) Preparation of Intermediate 118

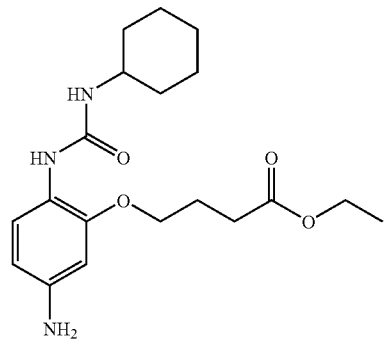

A solution of NH$_4$Cl (0.014 mol) in H$_2$O (20 ml) was added to a mixture of intermediate 117 (0.012 mol) and Fe (0.06 mol) in THF (50 ml). The reaction mixture was stirred and refluxed for 4 hours, then filtered hot. EtOAc (200 ml) was added to the filtrate. The organic layer was separated, washed with a 2N aqueous Na$_2$CO$_3$ solution, with brine, then dried over Na$_2$SO$_4$, filtered and the solvent was evaporated yielding 3.31 g (77.3%) of intermediate 118.

c) Preparation of Intermediate 119

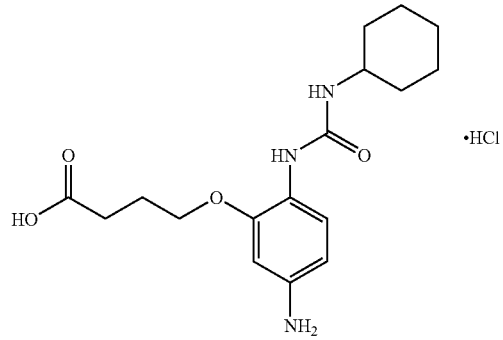

Intermediate 118 (6.3 mmol) was dissolved in HCl (4N in dioxane, 55 ml) and the solution was heated overnight at 60° C. The reaction mixture was concentrated to dryness, yielding 2.34 g (100%) of intermediate 119.

d) Preparation of Intermediate 120

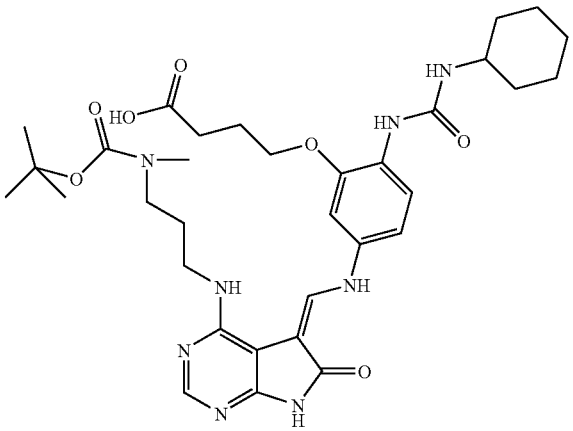

Intermediate 49 (2.4 mmol) and intermediate 119 (2.98 mmol), MgSO$_4$ (0.6 g) in DMA (15 ml) were heated overnight at 80° C. The reaction mixture was concentrated to dryness and purified by column chromatography on silica e) Preparation of Intermediate 121

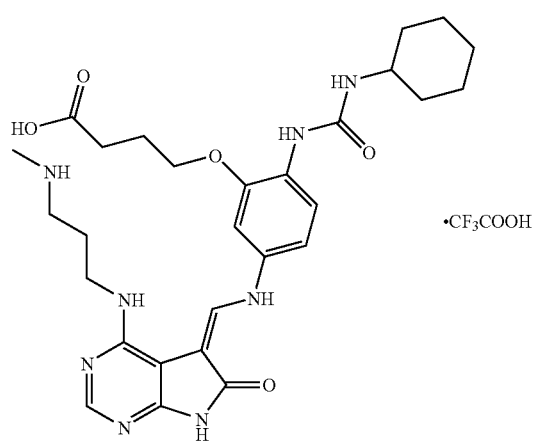

Intermediate 120 (1.1 mmol) was dissolved in DCM (20 ml) and TFA (6 ml) and the solution was stirred overnight at room temperature. The reaction mixture was concentrated to dryness yielding 1.12 g of a brown solid as intermediate 121 which was used as a crude in the next step.

Example A35 a) Preparation of Intermediate 122

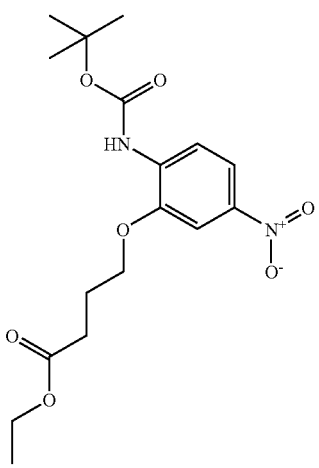

(2-Hydroxy-4-nitrophenyl)-carbamic acid 1,1-dimethylethyl ester (0.0787 mol), $K_2CO_3$ (0.1023 mol) and 4-bromobutanoic acid ethyl ester (0.08653 mol) were mixed in DMA (236 ml) and the reaction mixture was stirred overnight at 60° C. The mixture was stirred for 12 hours and was then poured into a saturated aqueous NaCl aqueous solution. This mixture was extracted with EtOAc, then the organic layers were washed with brine, dried over $MgSO_4$, filtered off and concentrated. The residue was purified by flash chromatography (eluent: hexane/EtOAc gradient: 40:1-30:1-20:1). The product fractions were collected and the solvent was evaporated. The residue was dried (vacuum, room temperature) yielding 12 g (41%) of a yellow solid as intermediate 122.

b) Preparation of Intermediate 123

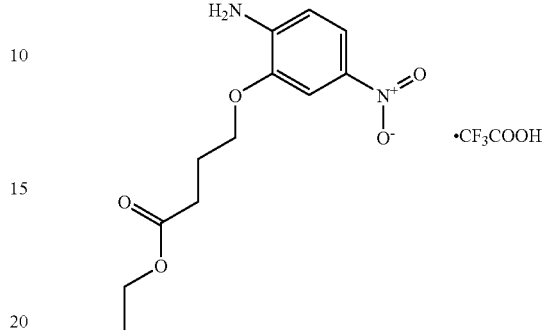

Intermediate 122 (32.5 mmol) in TFA (12 ml) and DCM (30 ml) was stirred at room temperature for 3 hours. The reaction mixture was concentrated to dryness, yielding 12.5 g (100%) of intermediate 123 which was used without further purification in the next step.

c) Preparation of Intermediate 124

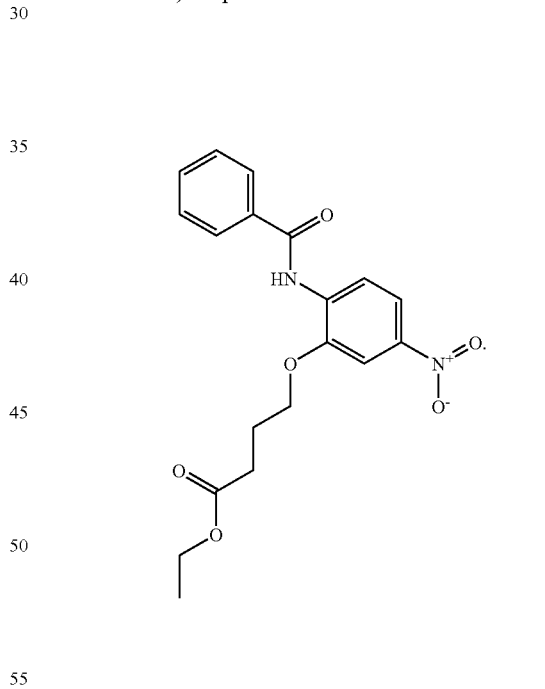

Intermediate 123 (32.6 mmol) was dissolved in THF (150 ml) and triethylamine (13.6 ml) was added. The mixture was stirred at room temperature for 15 minutes and benzoyl chloride (42.5 mmol) was added dropwise over 20 minutes. The reaction mixture was stirred overnight at room temperature. More benzoyl chloride (0.6 eq. more) and triethylamine (1.2 eq.) were added. The reaction mixture was stirred over the weekend and then concentrated to dryness. The residue was partitioned between DCM/$H_2O$ (300 ml, 1:1) and the aqueous layer was extracted with more DCM. The organic extracts were washed with H₂O, dried and concentrated to dryness, yielding 1.5 g (15%) of intermediate 124.

d) Preparation of Intermediate 125

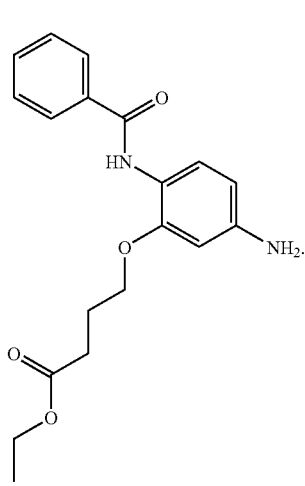

Intermediate 124 (4 mmol) was dissolved in THF (100 ml) and the solution was hydrogenated with Pt/C₅% as a catalyst under 1 atm. H₂. The catalyst was filtered through Celite and the filtrate concentrated to dryness, yielding 1.4 g (100%) of intermediate 125.

e) Preparation of Intermediate 126

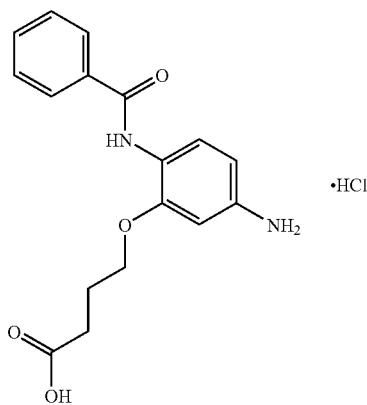

Intermediate 125 (4 mmol) was dissolved in HCl (4M in dioxane; 30 ml) and the solution was heated overnight at 60° C. The reaction mixture was concentrated to dryness and the residue was triturated with DIPE, yielding 1.1 g (78%) of intermediate 126.

f) Preparation of Intermediate 127

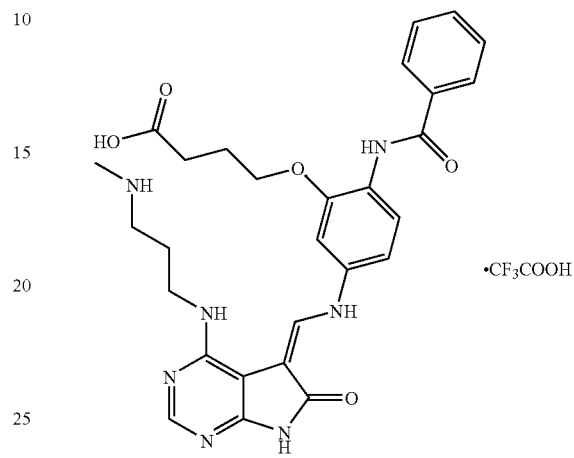

Intermediate 126 (2.0 mmol) and intermediate 49 (1.6 mmol) and MgSO₄ (2.0 g) in CH₃CN (30 ml) and DMA (30 ml) were heated overnight at 80° C. Extra DMA was added and the reaction mixture was heated at 80° C. during 20 hours. The reaction mixture was concentrated to dryness and the residue was re-dissolved in DCM and filtered again. TFA (5 ml) was added to the filtrate. The reaction mixture was stirred at room temperature for 16 hours and concentrated to dryness, yielding intermediate 127 which was used as such in the next reaction step.

Example A36 a) Preparation of Intermediate 128

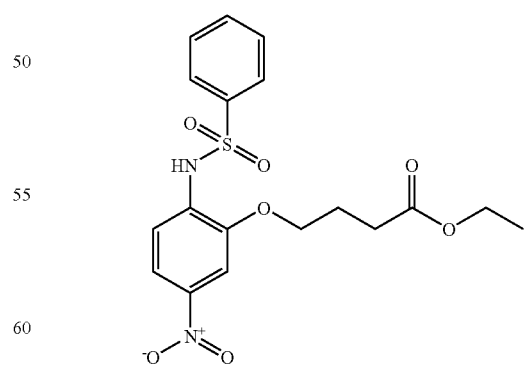

A mixture of 4-(2-amino-5-nitrophenoxy)-butanoic acid ethyl ester (0.0447 mol) and benzenesulfonyl chloride (0.0447 mol) in pyridine (50 ml) was stirred overnight at 110° C. The solvent was evaporated. The residue was stirred with petroleum ether filtered off and dried, yielding 22 g of intermediate 128 which was used in the next reaction step without further purification.

b) Preparation of Intermediate 129

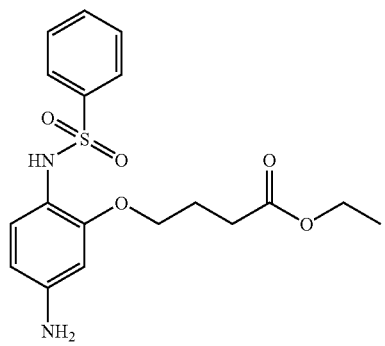

A mixture of intermediate 128 (0.039 mol) in EtOH (200 ml) was stirred and hydrogenated for 48 hours with Pd/C 10% (2 g) as a catalyst. After uptake of $H_2$ (3 equiv), the catalyst was filtered off and the filtrate was evaporated The residue was stirred in diethyl ether filtered off and dried. The residue was purified by column chromatography over silica gel. The product fractions were collected and the solvent was evaporated, yielding 3.5 g (23.8%) of intermediate 129.

c) Preparation of Intermediate 130

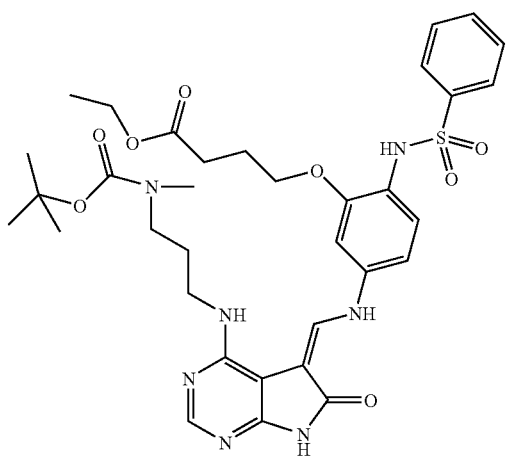

Intermediate 49 (1.6 mmol), intermediate 129 (2 mmol), HCl (2 mmol of 4N in dioxane), $MgSO_4$ (19.2 mmol) in $CH_3CN$ (32 ml) and DMA, 99% (32 ml) was stirred overnight at 80° C. The reaction mixture was poured onto brine and extracted with ethylacetate several times. The organic layers were combined and washed with brine, dried over anhydrous $MgSO_4$, filtered and concentrated to dryness. The residue was purified by flash chromatography on silica gel. The product fractions were collected and the solvent was evaporated. The residue was dried (vacuum, room temperature), yielding 1.4 g of intermediate 130 as a yellow solid.

d) Preparation of Intermediate 131

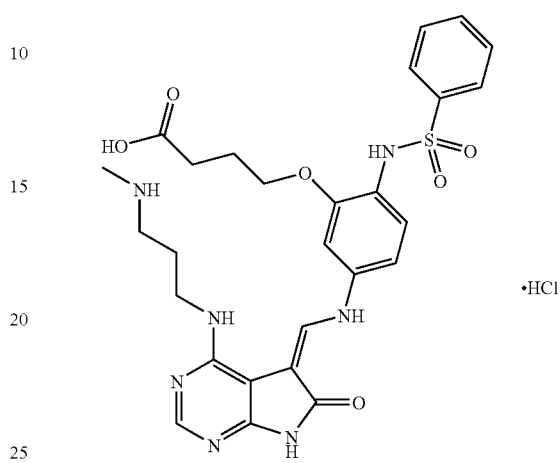

Intermediate 130 (1.6 mmol) was dissolved in 37% HCl (1.6 ml) and dioxane (16 ml) and the reaction mixture was stirred at room temperature for 15 hours. The mixture was concentrated to dryness. The product was stirred in DIPE filtered off and dried (vacuum, room temperature), yielding intermediate 131 which was used as such in the next step.

Example A37 a) Preparation of Intermediate 132

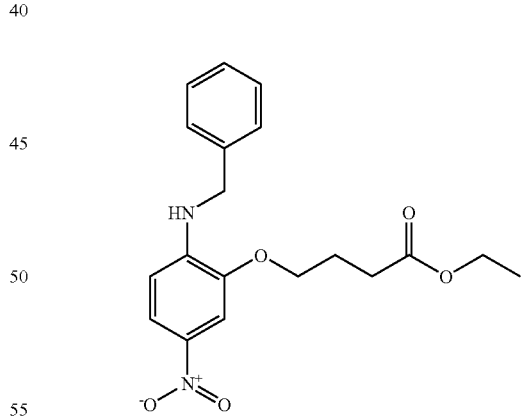

A mixture of 4-(2-amino-5-nitrophenoxy)-butanoic acid ethyl ester (0.0664 mol) and benzaldehyde (0.07 mol) in DCM (200 ml) was stirred at room temperature under $N_2$ atmosphere. HOAc (0.0664 mol) was added. $NaBH(OAc)_3$ (0.066 mol) was added portionwise and the reaction mixture was stirred overnight at room temperature. A saturated aqueous $NaHCO_3$ solution was added. This mixture was extracted with DCM. The separated organic layer was dried, filtered and the solvent evaporated. The residue was purified by column chromatography over silica gel (eluent: petroleum ether/

EtOAc gradient). The product fractions were collected and the solvent was evaporated, yielding 18 g (75.6%) of intermediate 132.

b) Preparation of Intermediate 133

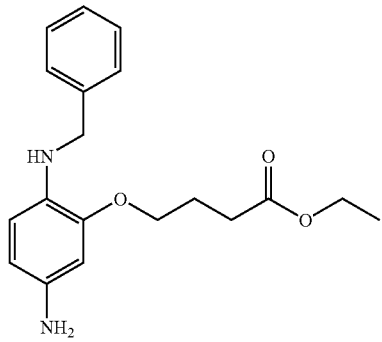

A mixture of intermediate 132 (0.05 mol), Fe (0.25 mol) and NH$_4$Cl (0.055 mol) in THF (200 ml) and H$_2$O (60 ml) was stirred and refluxed overnight. The reaction mixture was filtered through Celite and the layers were separated. The organic layer was evaporated. The residue was purified by column chromatography. The product fractions were collected and the solvent was evaporated, yielding 4.79 g (28.7%) of intermediate 133.

c) Preparation of Intermediate 134

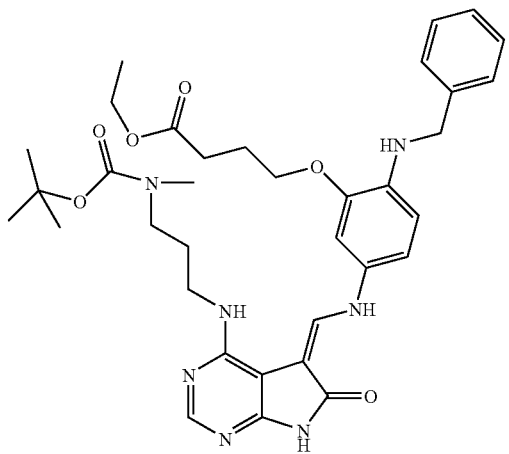

Intermediate 49 (2.97 mmol) and intermediate 133 (3.7 mmol) in DMA (60 ml), 1 ml of 4N HCl in dioxane and anhydrous MgSO$_4$ (35 mmol) was stirred overnight at 80° C. The reaction mixture was poured onto brine and extracted with ethylacetate several times. The organic layers were combined and washed with brine, dried over anhydrous MgSO$_4$, filtered and concentrated to dryness. The product was purified by flash column chromatography on silica gel, (eluent: DCM/ CH$_3$OH gradient: 50:1-40:1-30:1-20:1-10:1). The product fractions were collected and the solvent was evaporated. The product was dried (vacuum, room temperature) yielding 240 mg (13%) of a brown solid as intermediate 134.

d) Preparation of Intermediate 135

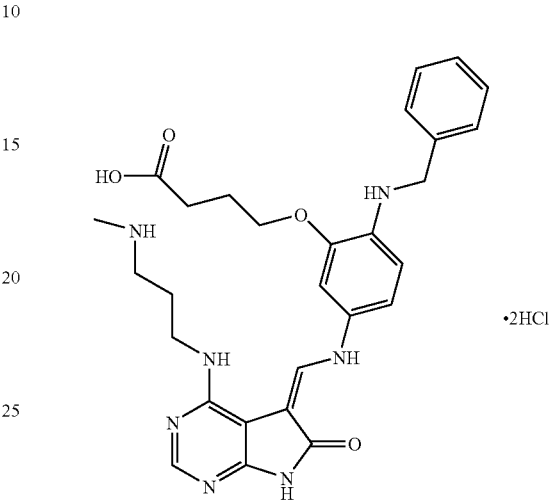

Intermediate 134 (0.36 mmol) was dissolved in dioxane (35 ml) and HCl 5% (7 ml) and the mixture was stirred at room temperature for 20 hours. The reaction mixture was concentrated to dryness. The product was stirred in DIPE, filtered and dried (vacuum, room temperature), yielding intermediate 135 used as such in next step.

Example A38 a) Preparation of Intermediate 136

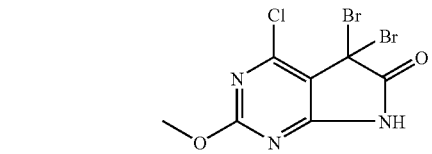

4-Chloro-2-methoxy-1H-pyrrolo[2,3-d]pyrimidine (0.0311 mol) was dissolved in 2-methyl-2-propanol (78.5 ml) and stirred at room temperature. Pyridine hydrobromide perbromide (0.0311 mol) was added portionwise over a 15-min period and the resulting reaction mixture was stirred overnight. H$_2$O (260 ml) was added and the product was extracted with EtOAc (4×80 ml). The organic layers were combined, washed with brine, dried over anhydrous MgSO$_4$, filtered and concentrated to dryness at 45° C. The product was dried (vacuum, room temperature) yielding a violet-white solid. The solid was stirred in DIPE and filtered off. The filtrate was concentrated to dryness and was dried (vacuum, room temperature) yielding 1.6 g (41%) of a pink solid as intermediate 136.

b) Preparation of Intermediate 137

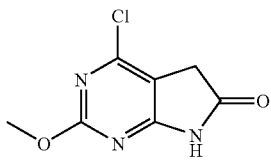

Intermediate 136 (0.0045 mol) was dissolved in HOAc and the mixture was cooled to 0° C. Zn powder (0.0500 mol) was added portionwise over 30 minutes and the reaction mixture was stirred at room temperature overnight. Residual zinc was removed by filtration and the resulting filtrate was concentrated to dryness. H$_2$O (100 ml) was added, followed by the slow addition of an aqueous saturated K$_2$CO$_3$ solution until pH 8. One liter of EtOAc was then added and the mixture was stirred for 15 minutes. The precipitate was filtered off and both phases were separated. The aqueous layer was extracted several times with EtOAc. The organic layers were combined and dried over anhydrous MgSO$_4$, filtered and concentrated to dryness. The residue was purified by flash column chromatography over silica gel (eluent: hexanes/EtOAc gradient: 10:1-5:1-1:1). The product fractions were collected and the solvent was evaporated. The product was dried (vacuum, room temperature) yielding 0.342 g (38%) of a white solid as intermediate 137.

c) Preparation of Intermediate 138

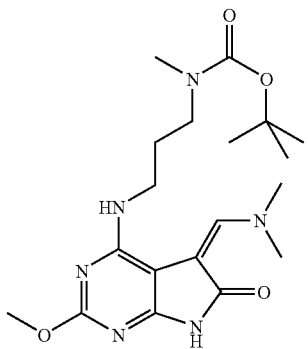

Reaction under N$_2$ atmosphere. Intermediate 137 (0.0019 mol) was dissolved in DMA 99% (7 ml) and stirred at room temperature. DIPEA (0.00226 mol) was added and the mixture was stirred for 5 minutes. Finally, Carbamic acid, N-(3-aminopropyl)-N-methyl-, 1,1-dimethylethyl ester (0.00209 mol) was added and the reaction mixture was stirred for 15 hours at 100° C., under N$_2$ atmosphere. Then, the mixture was cooled to 25-30° C. DMFDMA (0.0057 mol) was added in one portion and the reaction mixture was stirred for 3 hours at room temperature. The mixture was poured out into brine and this mixture was extracted several times with EtOAc The organic layers were combined, washed with brine, dried (MgSO$_4$), filtered and the solvent was evaporated. The residue was purified by flash column chromatography over silica gel (gradient elution with DCM/MeOH). The product fractions were collected and the solvent was evaporated. The residue was dried (vacuum, room temperature), yielding 0.20 g (26%) of intermediate 138.

d) Preparation of Intermediate 139

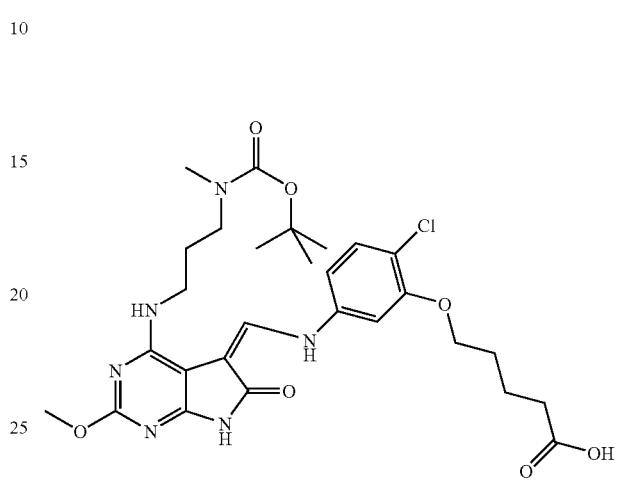

A mixture of intermediate 138 (0.0005 mol), intermediate (70) HCl salt (0.0005 mol) and anhydrous MgSO$_4$ (0.5 g) in a mixture of CH$_3$CN (3 ml) and DMA (3 ml) was stirred overnight at 80° C. The crude reaction mixture was poured out into brine and this mixture was extracted with EtOAc. The organic layer was separated, washed several times with brine, then dried over MgSO$_4$, filtered and the solvent was evaporated. The residue was purified by flash column chromatography over silica gel (gradient elution with eluent mixture DCM/MeOH). The product fractions were collected and the solvent was evaporated, yielding 0.2 g (66%) of intermediate 139.

e) Preparation of Intermediate 140

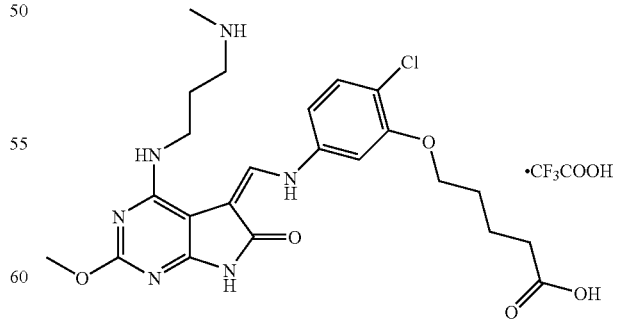

Intermediate 139 (0.00033 mol) was dissolved in DCM (6 ml) and treated with TFA (6 ml). The resultant reaction mixture was stirred for 15 hours at room temperature. The solvent was evaporated. The residue was dried under high-vacuum at 60° C. for 20 hours, yielding intermediate 140 which was used in the next reaction step without further purification.

Example A39 a) Preparation of Intermediate 141

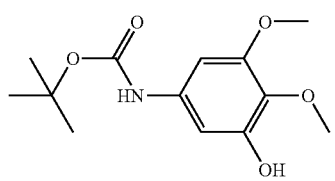

A mixture of 1,2-dimethoxy-5-nitro-3-(phenylmethoxy)benzene (0.1380 mol), Pd(OH)$_2$/C (4.0 g) and di-tert-butyl dicarbonate (also tert-butoxycarbonyl anhydride) (0.1380 mol) in THF (500 ml) was hydrogenated overnight at 50 psi H$_2$ pressure at 50° C. After uptake of H$_2$ (4 eq.), the catalyst was filtered off and the filtrate was evaporated. The residue was purified by flash column chromatography over silica gel (eluent: petroleum ether/EtOAc 4/1). The product fractions were collected and the solvent was evaporated, yielding 28 g (76%) of intermediate 141.

b) Preparation of Intermediate 142

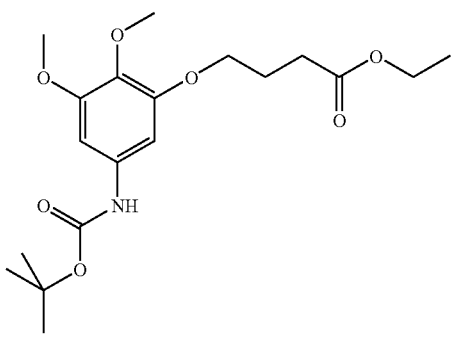

A mixture of intermediate 141 (0.00742 mol), 4-bromo-butanoic acid ethyl ester (1.1 equiv, 0.00817 mol) and K$_2$CO$_3$ (1.1 equiv, 0.00817 mol) in CH$_3$CN (22 ml) was stirred overnight at 80° C. Again 4-bromo-butanoic acid ethyl ester (0.47 equiv, 0.5 ml) was added and the reaction was stirred for 4 hours at 80° C. K$_2$CO$_3$ was removed by filtration. The filtrate was evaporated and the crude residue was purified by flash chromatography (eluent: n-Hexane/EtOAc; gradient 15:1 to 5:1). The combined fractions were concentrated to dryness, yielding: 3 g of intermediate 142 which was used in the next reaction step.

c) Preparation of Intermediate 143

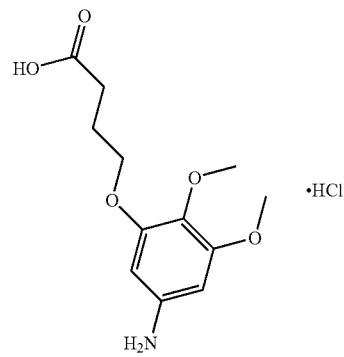

Intermediate 142 (0.00782 mol) was dissolved in HCl (4N in 1,4-dioxane; 39 ml) and the reaction solution was stirred overnight at 55° C. The solvent was evaporated, yielding 2.2 g of intermediate 143 which was used in next the next reaction step without further purification.

d) Preparation of Intermediate 144

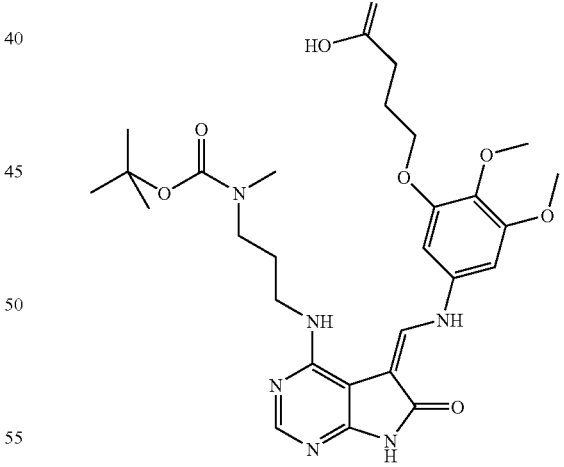

Intermediate 49 (0.00133 mol) was dissolved in DMA (4 ml). Intermediate 143 (0.00159 mol) and anhydrous MgSO$_4$ were added. The resultant reaction mixture was shaken overnight at 80° C. Then, the MgSO$_4$ was removed by filtration. The filtrate was evaporated to dryness. The residue was purified by flash column chromatography over silica gel (eluent:

DCM/MeOH gradient 20/1 to 70/10). The product fractions were collected and the solvent was evaporated, yielding intermediate 144.

e) Preparation of Intermediate 145

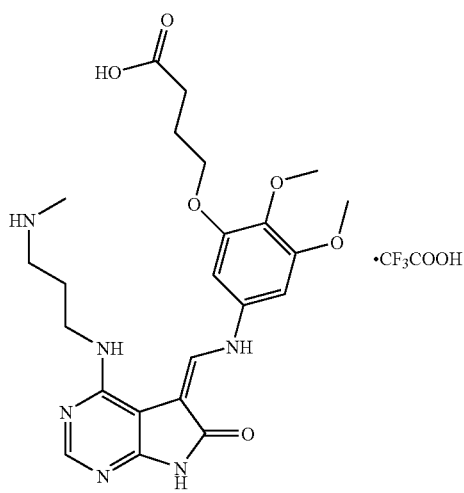

Intermediate 144 (max. 0.00133 mol) was dissolved in a mixture of TFA (5 ml) and DCM (5 ml) and the reaction was stirred overnight at room temperature. The solvents were evaporated. The resulting oil was dried under high vacuum, yielding intermediate 145.

Example A40 a) Preparation of Intermediate 146

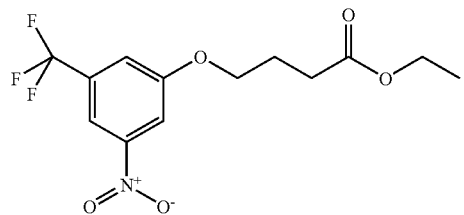

3-Nitro-5-(trifluoromethyl)phenol (0.0154 mol) was dissolved in CH$_3$CN (46 ml), then 4-bromo-butanoic acid ethyl ester (0.0185 mol) was added, followed by the addition of K$_2$CO$_3$ (0.0232 mol). The reaction mixture was heated overnight at 80° C. The solid was filtered off and washed with CH$_3$CN. EtOAc (20 ml) was added and the mixture was washed with brine, dried over anhydrous MgSO$_4$, filtered and concentrated to dryness. The residue was purified by flash column chromatography on silica gel (eluent:hexane/EtOAc ratio: 40/1). The product fractions were collected and the solvent was evaporated. The product was dried (vacuum, room temperature) yielding 4.40 g (89%) of a pale yellow solid as intermediate 146.

b) Preparation of Intermediate 147

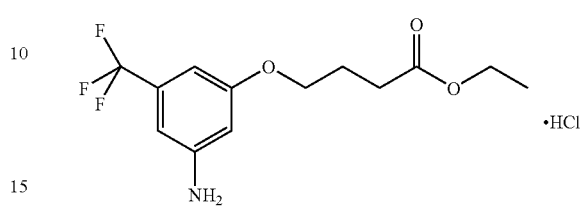

Intermediate 146 (0.0137 mol) was dissolved in THF (48 ml), at room temperature. Then Pt/C$_5$% (0.88 g) was added and the mixture was stirred at room temperature under H$_2$ atmosphere for 15 hours. The mixture was filtered through a Celite pad. The solvent was evaporated under reduced pressure. The product was dried (vacuum, room temperature), yielding a brown oil. The hydrochloric salt was obtained by bubbling HCl gas into a solution of the aniline in diethyl ether, yielding 3.86 g (86%) of intermediate 147.

c) Preparation of Intermediate 148

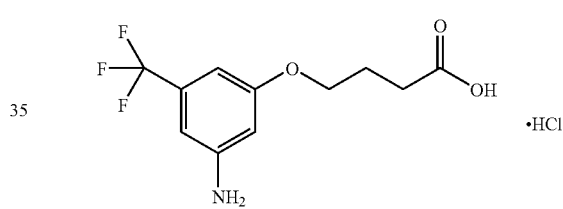

Intermediate 147 (0.0118 mol) was dissolved in HCl (4N in 1,4-dioxane; 30 ml) and the mixture was heated overnight at 60° C. The solvent was evaporated and the residue was stirred with diethyl ether filtered off and dried (vacuum, room temperature) yielding 3.40 g (96%) as intermediate 148.

d) Preparation of Intermediate 149

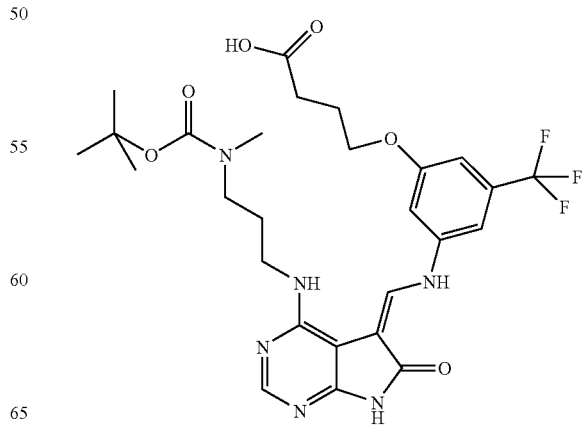

Intermediate 49 (0.00133 mol) was dissolved in DMA (4 ml). Intermediate 148 (0.00159 mol) and anhydrous MgSO₄ were added. The reaction mixture was shaken overnight at 80° C. Then, MgSO₄ was removed by filtration. The solvent was evaporated. The residue was purified by flash column chromatography over silica gel (eluent: DCM/MeOH gradient 20/1 to 70/10). The product fractions were collected and the solvent was evaporated, yielding intermediate 149.

e) Preparation of Intermediate 150

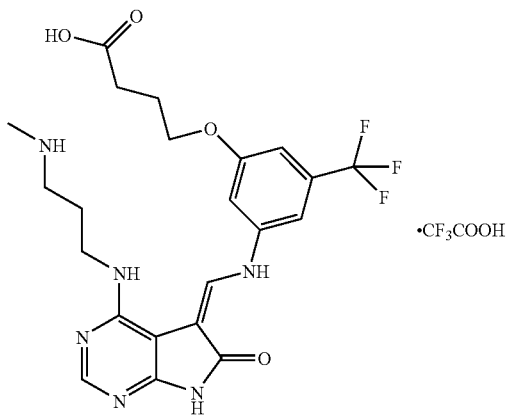

Intermediate 149 (max. 0.00133 mol) was dissolved in a mixture of TFA (5 ml) and DCM (5 ml). and the reaction was stirred overnight at room temperature. The solvents were evaporated. The resulting oil was dried (high-vacuum pump), yielding intermediate 150.

B. PREPARATION OF THE COMPOUNDS

Example B1

Preparation of Compound 1

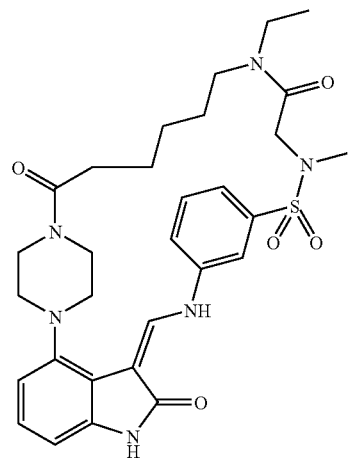

A mixture of PyBOP (1 g) in DMF (20 ml) was stirred at room temperature. Intermediate 12 (0.00055 mol) and Et₃N (3 ml) dissolved in DMF (130 ml) was added dropwise over a period of 4 hours to the reaction mixture. The reaction mixture was stirred at room temperature for 3 hours. The solvent was evaporated. The residue was diluted with H₂O. The precipitate was filtered off, washed with H₂O and dried. The precipitate was purified by reversed-phase column chromatography (Shandon Hyperprep® C18 BDS (Base Deactivated Silica) 8 µM, 250 g, I.D. 5 cm). The mentioned mobile phases were used to apply a gradient (phase A: 90% of a 0.5% N'H₄OAc solution in water+10% CH₃CN; phase B: CH₃OH (optional); phase C: CH₃CN). The first fraction was collected and concentrated by partial evaporation of the solvent (until precipitation). The precipitate was filtered off and dried (vacuum). Yield: 0.007 g of compound 1 (1.8%; Z/E mixture).

Example B2

Preparation of Compound 2

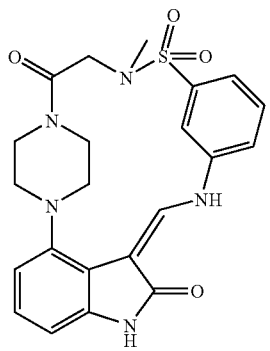

A mixture of PyBOP (0.0027 mol), Et₃N (10 ml) and DMF (50 ml) was stirred at room temperature. A solution of intermediate 15 (0.0006 mol) in DMF (100 ml) was added dropwise in 3 hours. The reaction mixture was stirred at room temperature for 4 hours. The solvent was evaporated. The residue was diluted with H₂O and extracted with DCM (3×). The organic layer was washed with H₂O, dried (MgSO₄), filtered and the organic solvent was evaporated. The residue was suspended in CH₃CN. The precipitate was filtered off and dried. Yield: 0.135 g of compound 2 (±69% Z/31% E).

Example B3

Preparation of Compound 3

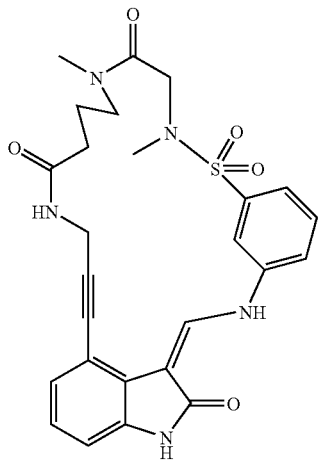

A mixture of PyBOP (0.4 g) in DMF (25 ml) was stirred at room temperature. A solution of intermediate 22 (0.000185 mol) in DMF (75 ml) and Et₃N (3 ml) was added dropwise over a period of 2 hours to the reaction mixture. The reaction mixture was stirred at room temperature for 2 hours. The solvent was evaporated. The residue was diluted with H₂O. The precipitate was filtered off. The precipitate was suspended in CH₃CN. The precipitate was filtered off, washed with CH₃CN and dried (vacuum). Yield: 0.062 g of compound 3 (65%; Z-isomer when measured by NMR in a DMSO-d6 solution at room temperature after equilibrium).

Example B4

Preparation of Compound 4

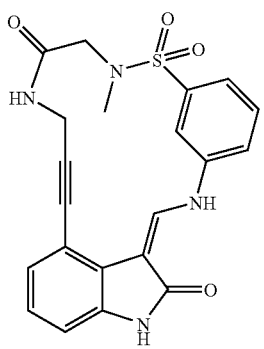

A mixture of PyBOP (0.00035 mol) in Et₃N (10 ml) and DMF was stirred at room temperature. A solution of intermediate 23 (0.000074 mol) in DMF was added dropwise over a period of 3 hours. The solvent was evaporated. The residue was diluted with H₂O. This mixture was extracted (3×) with DCM. The organic layer was separated, washed with H₂O, dried (MgSO₄), filtered and the solvent was evaporated. The residue was purified by reversed-phase high-performance liquid chromatography (Shandon Hyperprep® C18 BDS (Base Deactivated Silica) 8 μm, 250 g, I.D. 5 cm). The mentioned mobile phases were used to apply a gradient (phase A: 90% of a 0.5% NH₄OAc solution in water+10% CH₃CN; phase B: CH₃OH (optional); phase C: CH₃CN). The product fraction groups were collected and the organic solvent was evaporated. The aqueous concentrate was extracted 3× with DCM.

The separated organic layer was washed with water, dried (MgSO₄), filtered and the solvent evaporated. Yield: 0.008 g of compound 4 (25%).

Example B5

Preparation of Compound 5

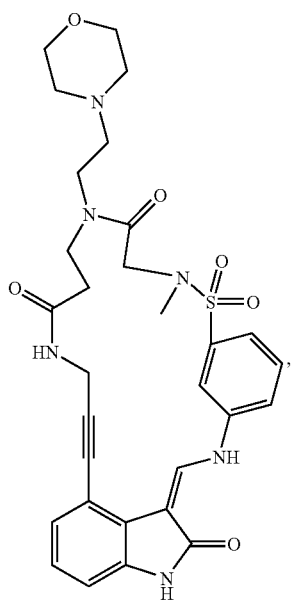

A mixture of PyBOP (0.0027 mol) in DMF (100 ml) and Et₃N (10 ml) was stirred at room temperature. A solution of intermediate 25 (0.0006 mol) in DMF (100 ml) and added dropwise over a period of 3 hours. The reaction mixture was stirred at room temperature for 20 hours. The solvent was evaporated. The residue was diluted with H₂O and extracted with DCM+a small amount of MeOH (2×). The organic layer was separated, washed with H₂O, dried (MgSO₄), filtered and the solvent was evaporated. The residue was purified by high-performance liquid chromatography (Shandon Hyperprep® C18 BDS (Base Deactivated Silica) 8 μm, 250 g, I.D. 5 cm). The mentioned mobile phases were used to apply a gradient (phase A: 90% of a 0.5% NH₄OAc solution in water+10% CH₃CN; phase B: CH₃OH (optional); phase C: CH₃CN). The pure fractions were collected and the organic solvent was evaporated until a precipitate resulted. The precipitate was filtered off, washed with H₂O and dried (vacuum). Yield:

0.073 g of compound 5 (20%; Z-isomer when measured by NMR in a DMSO-d6 solution at room temperature after equilibrium).

Example B6

Preparation of Compound 6

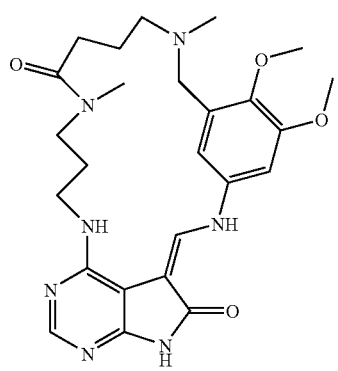

Intermediate 32 (0.00025 mol; crude) was dissolved in DMF (10 ml). This solution was added dropwise to a mixture of HBTU (2.2 eq., 0.00055 mol) and DIPEA (30 eq., 0.0075 mol) in DMF (21 ml), using a Watson-Marlow peristaltic pump (0.50 rpm). The reaction mixture was stirred for one hour at room temperature. The reaction was quenched by addition of $NH_3$/MeOH (1 ml). The resultant mixture was evaporated and the crude residue was then purified by flash column chromatography over silica gel (eluent: DCM/MeOH mixture). The desired fractions were collected and the solvent was evaporated. Yield: 0.040 g of compound 6 (20.2% yield over 3 reaction steps).

Example B7

Preparation of Compound 7

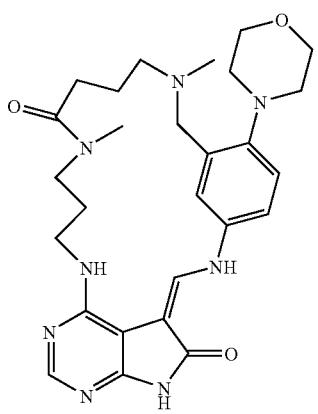

Intermediate 38 (0.00025 mol) was dissolved in DMF (10 ml). This solution was added dropwise to a mixture of HBTU (2.2 eq., 0.00055 mol) and DIPEA (30 eq., 0.0075 mol) in DMF (21 ml), using a Watson-Marlow peristaltic pump (0.50 rpm). The reaction mixture was stirred for one hour at room temperature. The reaction was quenched by addition of $NH_3$/MeOH (1 ml). The resultant mixture was evaporated and the crude residue was then purified by flash column chromatography over silica gel (eluent: DCM/MeOH mixture). The desired fractions were collected and the solvent was evaporated. Yield: 0.018 g of compound 7 (8.6% yield over 3 reactions steps).

Example B8

Preparation of Compound 8

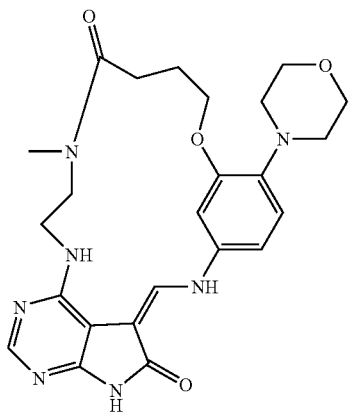

A solution of intermediate 47 (0.00025 mol) in DMF (10 ml) was added dropwise to a mixture of HBTU (2.2 eq.; 0.00055 mol) and DIPEA (30 eq.; 0.0075 mol) in DMF (10 ml), using a Watson-Marlow peristaltic pump (0.50 rpm). The reaction mixture was stirred for an extra hour at room temperature. The reaction was quenched by addition of $NH_3$/MeOH (1 ml). The resultant mixture was evaporated and the crude residue was then purified by flash column chromatography over silica gel (eluent: DCM/MeOH gradient). The product fractions were collected and the solvent was evaporated, yielding compound 8.

Example B9

Preparation of Compound 9

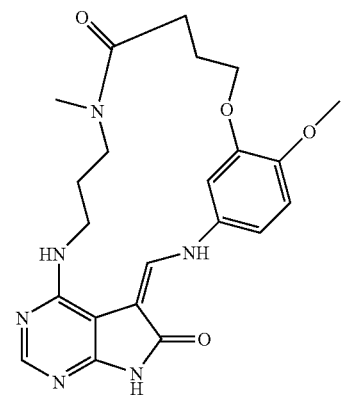

A solution of intermediate 51 (0.0001 mol) in DMA (2 ml) was added dropwise at room temperature under $N_2$ atmosphere to a stirred mixture of PyBOP (0.0005 mol) and $Et_3N$ (0.0005 mol) in DMA (20 ml),. The reaction mixture was stirred for one hour at room temperature. H₂O (10 ml) was added dropwise. The solvent was evaporated. The residue was purified by column chromatography over silica gel (eluent: DCM/MeOH 97.5/2.5). The product fractions were collected and the solvent was evaporated. The residue was stirred in DIPE. The precipitate was filtered off and dried. Yield: 0.021 g of compound 9 (47.95%; Z-isomer when measured by NMR in a DMSO-d6 solution at room temperature after equilibrium).

Example B10

Preparation of Compound 10

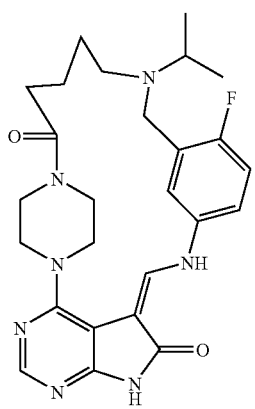

A solution of intermediate 62 (0.00018 mol) in DMF (25 ml; dry) was added dropwise at room temperature under N₂ atmosphere to a stirred mixture of PyBOP (0.0009 mol) and Et₃N (0.0009 mol) in DMF (25 ml; dry). The resultant reaction mixture was stirred for one hour at room temperature. H₂O (10 ml) was added. The solvent was evaporated. The residue was taken up in H₂O, then alkalized with K₂CO₃. This mixture was extracted with DCM/MeOH. The organic layer was separated, dried, filtered and the solvent evaporated. The residue was purified by column chromatography over silica gel (eluent: DCM/MeOH). The product fractions were collected and the solvent was evaporated. Yield: 0.029 g of compound 10 (32.7%; Z/E±78/22).

Example B11

Preparation of Compound 11

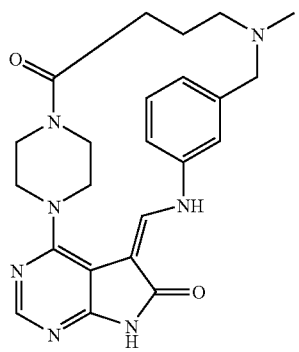

A solution of intermediate 67 (0.0001 mol) in DMF (10 ml; dry) was added dropwise at room temperature under N₂ atmosphere to a stirred mixture of PyBOP (0.0005 mol) and Et₃N (0.0006 mol) in DMF (10 ml; dry). The resultant reaction mixture was stirred overnight at room temperature. The solvent was evaporated. The residue was taken up into H₂O, then alkalized with K₂CO₃. This mixture was extracted with DCM/MeOH. The organic layer was separated and the solvent evaporated. The residue was purified over silica gel on a glass filter (eluent: DCM/MeOH 90/10). The product fractions were collected and the solvent was evaporated. The residue was stirred in DIPE, filtered off and dried. Yield: 0.015 g of compound 11 (34.6%; Z/E t 65/35).

Example B12

Preparation of Compound 12

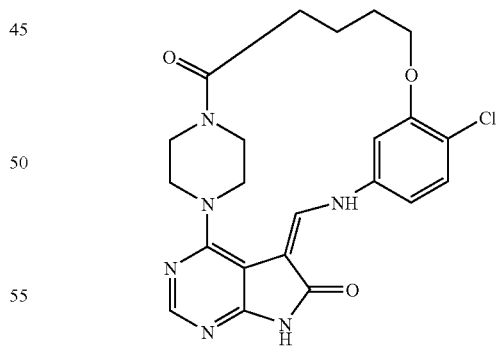

A solution of intermediate 72 (0.00024 mol) in DMF (25 ml; dry) was added dropwise at room temperature under N₂ atmosphere to a stirred mixture of PyBOP (0.0012 mol) and Et₃N (0.0018 mol) in DMF (25 ml; dry). The resultant reaction mixture was stirred for 2 hours at room temperature. H₂O was added and this mixture was stirred for 30 minutes. The solvent was evaporated. The concentrate was stirred in boiling CH₃CN, then cooled and the resulting precipitate was filtered off and dried. This fraction (0.077 g) was taken up into water, then extracted with DCM/MeOH. The organic layer was separated, dried, filtered and the solvent evaporated. The residue was crystallized from $CH_3CN$. The precipitate was filtered off and dried. Yield: 0.055 g of compound 12 (28.5%; Z/E±79/21).

Example B13

Preparation of Compound 13

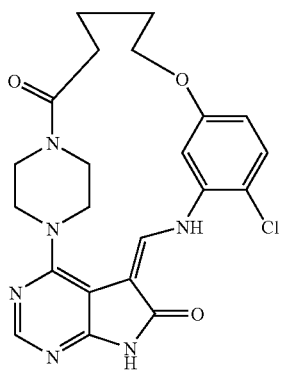

A solution of intermediate 77 (0.0002 mol) in DMF (15 ml; dry) was added dropwise at room temperature under $N_2$ atmosphere to a stirred mixture of PyBOP (0.0005 mol) and $Et_3N$ (0.00075 mol) in DMF (15 ml; dry). The resultant reaction mixture was stirred overnight at room temperature. $H_2O$ (10 ml) was added and this mixture was stirred for 30 minutes. The solvent was evaporated. The concentrate was stirred in boiling $CH_3CN$, then cooled and the resulting precipitate was filtered off and dried. Yield: 0.085 g of compound 13 (Z/E±96/4).

Example B14

Preparation of Compound 14

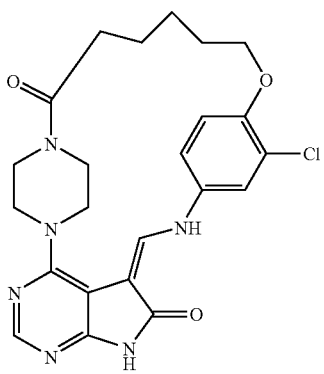

2 Different reaction mixtures. Reaction mixture 1: A solution of intermediate 82 (0.00017 mol) in DMF (25 ml) was added dropwise (in 30 minutes) at room temperature under $N_2$ atmosphere to a stirred mixture of PyBOP (0.00086 mol) and $Et_3N$ (0.0014 mol) in DMF (25 ml). The resultant reaction mixture was stirred overnight at room temperature. $H_2O$ (10 ml) was added. This mixture was stirred for 30 minutes. The solvent was evaporated. The residue contained crude compound 14. Reaction mixture 2: A solution of intermediate 82 (0.00036 mol) in DMF (50 ml) was added dropwise (in 30 minutes) at room temperature under $N_2$ atmosphere to a stirred mixture of PyBOP (0.00188 mol) and $Et_3N$ (0.0031 mol) in DMF (50 ml). The resultant reaction mixture was stirred overnight at room temperature. $H_2O$ (20 ml) was added. This mixture was stirred for 30 minutes. The solvent was evaporated. The residue was taken up into $H_2O$. This mixture was extracted with DCM/MeOH. The organic layer was separated and the solvent evaporated. The residues of reaction mixture 1 and 2 were combined and were purified over silica gel on a glass filter (eluent: DCM/MeOH 95/5). The product fractions were collected and the solvent was evaporated. The residue was stirred in DIPE/EtOAc. The precipitate was filtered off and dried. Yield: 0.025 g of compound 14 (10%; Z/E mixture).

Example B15

Preparation of Compound 15

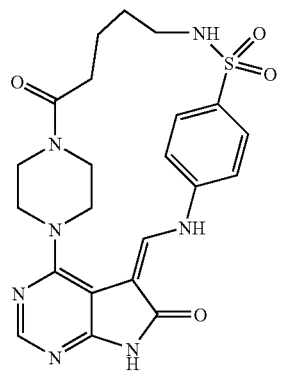

A solution of intermediate 86 (0.000105 mol) in DMF (15 ml; dry) was added dropwise to a mixture of PyBOP (0.00055 mol) and $Et_3N$ (0.000825 mol) in DMF (15 ml; dry), stirred at room temperature under $N_2$ atmosphere. The resultant reaction mixture was stirred overnight at room temperature. $H_2O$ (10 ml) was added and the mixture was stirred. The solvent was evaporated. The residue was stirred in $CH_3CN$. The precipitate was filtered off and dried. Yield: 0.042 g of compound 15 (83%; Z/E mixture).

Example B16 a) Preparation of Compound 99

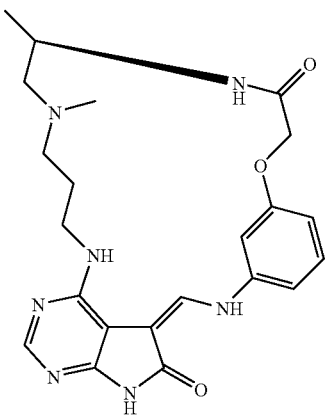

A solution of intermediate 90 (2.3 mmol) in DMF (115 ml) was added very slowly (over 1 hour) using a Marlow peristaltic pump to a solution of HBTU (5.06 mmol) and DIPEA (57.5 mmol) in DMF (57.5 ml). The reaction mixture was stirred for an additional hour before being quenched by 2 ml of 7N NH$_3$ in MeOH. The reaction mixture was concentrated to dryness and the residue was partitioned between DCM and sat. aq. sodium bicarbonate. The aqueous layer was extracted with more DCM. Organic extracts were washed with more sat. sodium bicarbonate, dried and concentrated to dryness. The residue was purified by chromatography (eluent: DCM/MeOH gradient). The pure fractions were combined and concentrated. The resulting residue was crystallized with CH$_3$CN, and filtered off yielding 0.035 g (3.5%) of compound 99.

b) Preparation of Compound 100

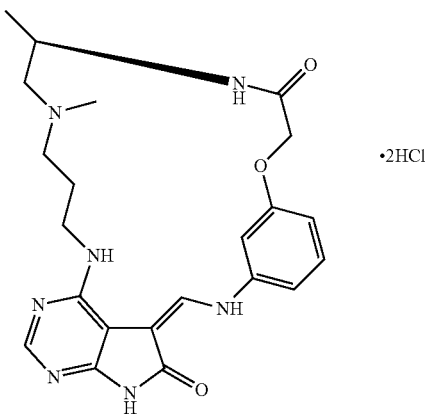

To a solution of compound 99 (0.027 mmol) in MeOH (1 ml) and DCM (1 ml), HCl (4N in dioxane) (0.040 mmol) was added and the mixture was concentrated in the rotatory evaporator until a solid was formed. The mixture was allowed to cool and filtered. The resulting solid was washed with dichloromethane and dried at high vacuum, yielding 0.005 g of compound 100.

Example B17

Preparation of Compound 101

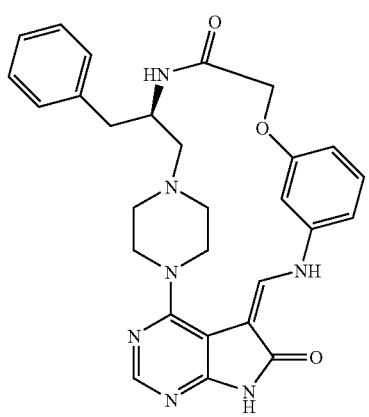

A solution of intermediate 95 (1.02 mmol) in DMF (50 ml) was added very slowly (over 1 hour) using a Marlow peristaltic pump to a solution of HBTU (2.25 mmol) and DIPEA (25 mmol) in DMF (25 ml). The reaction mixture was stirred for an additional 1 hour before being quenched by 6 ml of 7N NH$_3$ in MeOH. The reaction mixture was concentrated to dryness and the residue was partitioned between DCM and sat. aq. sodium bicarbonate. The aqueous layer was extracted with more DCM. The organic extracts were washed with more sat. sodium bicarbonate, dried and concentrated to dryness. The residue was purified by chromatography, (eluent: DCM-MeOH gradient). The pure fractions were combined and concentrated. The residue was crystallized with CH$^3$CN. The solid was filtered off and washed with CH$_3$CN and DIPE. The solid was dried at high vacuum, yielding 0.020 g (4%), yielding of compound 101.

Example B18 a) Preparation of Compound 102

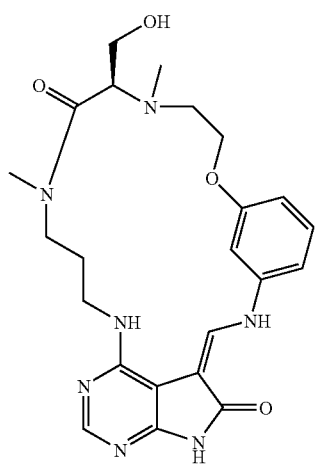

A solution of intermediate 100 (1.12 mmol) in DMF (56.67 ml) was added very slowly (over 1 hour) using a Marlow peristaltic pump to a solution of HBTU (2.49 mmol) and DIPEA (28.5 mmol) in DMF (28.33 ml). The reaction mixture was stirred for an additional hour before being quenched by 2 ml of 7N NH$_3$ in MeOH. The reaction mixture was concentrated to dryness and the residue was partitioned between DCM and sat. aq. K$_2$CO$_3$. The aqueous layer was extracted with more DCM. The organic extracts were washed with more sat. K$_2$CO$_3$, dried and concentrated to dryness. The residue was purified by chromatography (eluent: DCM/MeOH gradient). The pure fractions were combined and concentrated. The resulting residue was crystallized with CH$_3$CN, filtered off and dried in vacuum yielding 0.200 g (38%) of compound 102.

b) Preparation of Compound 103

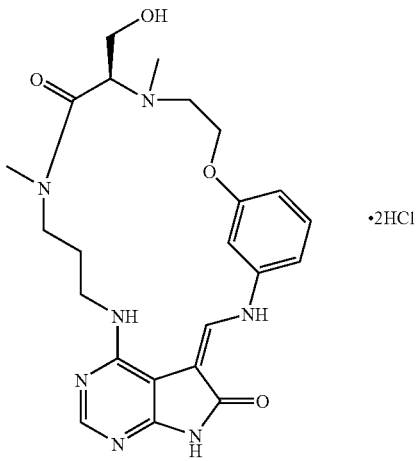

To a solution of compound 102 (0.14 mmol) in MeOH (3 ml) and DCM (3 ml), HCl (4N in dioxane) (0.21 mmol) was added and the mixture was concentrated in the rotatory evaporator until a solid was formed. The mixture was allowed to cool and filtered. The resulting solid was washed with dichloromethane and dried at high vacuum, yielding 0.069 g (98%) of compound 103.

Example B19

Preparation of Compound 104

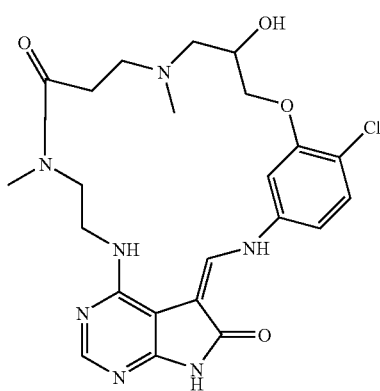

A solution of intermediate 105 (0.00061 mol) in DMF (50 ml) was added very slowly (over a 60-min period)—using a Marlow peristaltic pump—to a solution of HBTU (0.001.5 mol) and DIPEA (0.01525 mol) in DMF (25 ml). Then the reaction mixture was stirred for one hour and the reaction was quenched by addition of 6 ml of NH$_3$ in MeOH (7 N). The solvents were evaporated. The residue was partitioned between DCM and a saturated aqueous NaHCO$_3$ solution. The aqueous phase was re-extracted with DCM. The combined organic phases were washed with a saturated aqueous NaHCO$_3$ solution, dried, filtered and the solvent evaporated. The residue was purified by column chromatography (eluent: DCM/MeOH, gradient elution). The product fractions were collected and the solvent was evaporated. The resultant residue was triturated under hot CH$_3$CN, then the mixture was allowed to cool to room temperature and the solid was filtered off, washed with CH$_3$CN and DIPE, then dried under high-vacuum, yielding 0.125 g (41%) of compound 104.

Example B20

Preparation of Compound 105

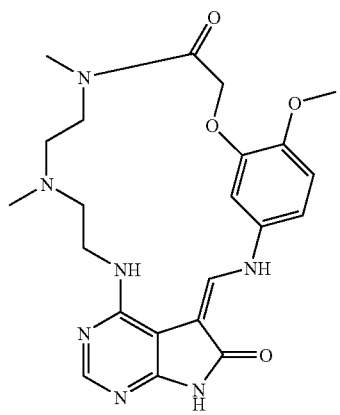

HBTU (0.0017 mol) and DIPEA (0.0228 mol) were dissolved in DMF (50 ml). A solution of intermediate 111 (0.0008 mol) in DMF (50 ml) was added slowly using a Marlow pump. Then the reaction was quenched by addition of 1 ml NH$_3$ in MeOH (7N). The solvents were evaporated. The crude residue was redissolved in DCM and washed with an aqueous Na$_2$CO$_3$ solution. The aqueous phase was re-extracted twice with DCM. The combined organic phases were dried over MgSO$_4$, filtered and concentrated to dryness. The residue was purified by flash chromatography (eluent: DCM/MeOH, gradient 10:1 to 7:1). The product fractions were collected and the solvent was evaporated, yielding 0.048 g (14%) of compound 105.

Example B21

Preparation of Compound 106

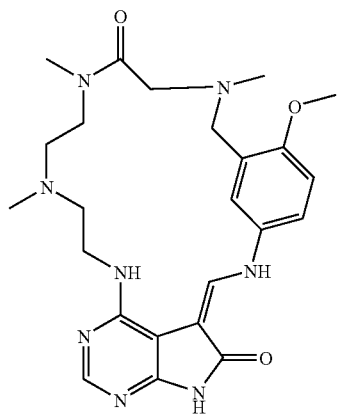

HBTU (0.0010 mol) and DIPEA (0.0141 mol) were dissolved in DMF (50 ml). A solution of intermediate 116

(0.0005 mol) in DMF (50 ml) was added slowly, using a Marlow pump. The reaction was quenched by addition of 1 ml NH₃ in MeOH (7N). The solvents were evaporated. The crude residue was re-dissolved in DCM and it was washed with an aqueous Na₂CO₃ solution. The aqueous phase was re-extracted twice with DCM. The combined organic phases were dried over MgSO₄, filtered and concentrated to dryness. The residue was purified by flash chromatography (eluent: DCM/MeOH:gradient 10:1 to 7:1). The product fractions were collected and the solvent was evaporated, yielding 43 mg (19%) of compound 106.

Example B22

Preparation of Compound 107

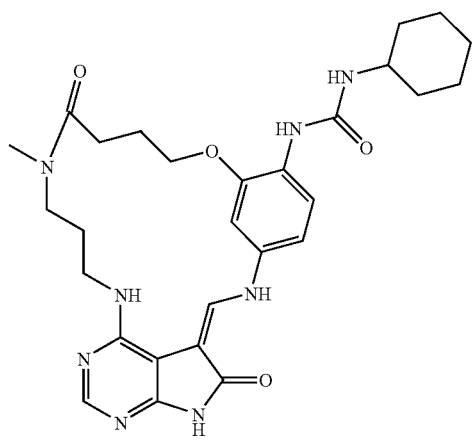

Two reactions of O. 45 g each were set-up in parallel. A solution of intermediate 121 (0.79 mmol) in DMF (15 ml) was added very slowly (4 h) using a Marlow peristaltic pump (0.75 rpm) to a solution of HBTU (1.74 mmol) and DIPEA (19.7 mmol) in DMF (400 ml). After the addition was completed, the reaction mixture was stirred for an additional 1 hour before being quenched with 7N NH₃ in MeOH (2.5 ml). This reaction mixture was concentrated to dryness and the residue, was partitioned between sat. sodium carbonate and DCM. The aqueous layer was extracted with more DCM and the organic extracts were washed with more sodium carbonate, dried and concentrated to dryness. The residue was purified by high-performance liquid chromatography reverse phase (ammonium bicarbonate buffer). The product fractions were collected and the solvent was evaporated, yielding 42 mg of compound 107.

Example B23

Preparation of Compound 108

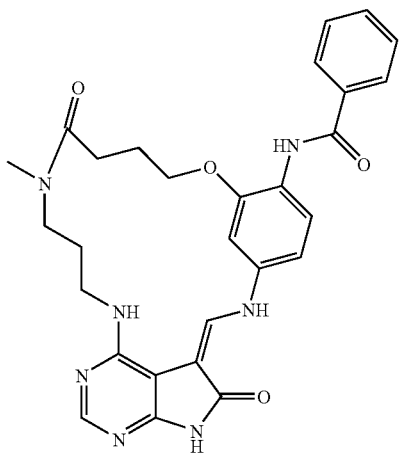

A solution of intermediate 127 (2 mmol) in DMF (100 ml) was added very slowly (1 hour) using a Marlow peristaltic pump to a solution of HBTU (4.4 mmol) and DIPEA (50 mmol) in DMF (50 ml). After the addition was completed, the reaction mixture was stirred for an additional 1 hour before being quenched with 3 ml of 7N NH₃ in MeOH. The reaction mixture was concentrated to dryness and the residue was partitioned between DCM and sat. aq. K₂CO₃. The aqueous layer was extracted with more DCM. The organic extracts were washed with more sat. K₂CO₃, dried and concentrated to dryness. The residue was purified by chromatography (eluent: DCM/MeOH gradient). The pure fractions were combined and concentrated. The residue was recrystallized with CH₃CN, yielding 0.140 g (14%) of compound 108.

Example B24

Preparation of Compound 109

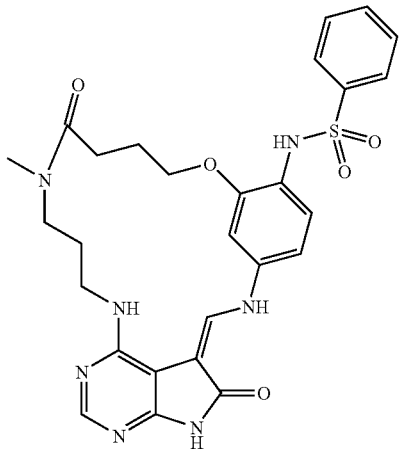

A solution of intermediate 131 (1.6 mmol) in DMF (80 ml) was added very slowly (1 hour) using a Marlow peristaltic pump to a solution of HBTU (3.52 mmol) and DIPEA (40 mmol) in DMF (40 ml). After the addition was completed, the reaction mixture was stirred for an additional 1 hour before being quenched with 3 ml of 7N $NH_3$ in MeOH. The reaction mixture was concentrated to dryness and the residue was partitioned between DCM and sat. aq. $K_2CO_3$. The aqueous layer was extracted with more DCM. The organic extracts were washed with more sat. $K_2CO_3$, dried and concentrated to dryness. The residue was purified by chromatography (eluent: DCM-MeOH gradient). The pure fractions were combined and concentrated. The residue was recrystallized with $CH_3CN$, yielding 0.168 g (19%) of compound 109.

Example B25

Preparation of Compound 110

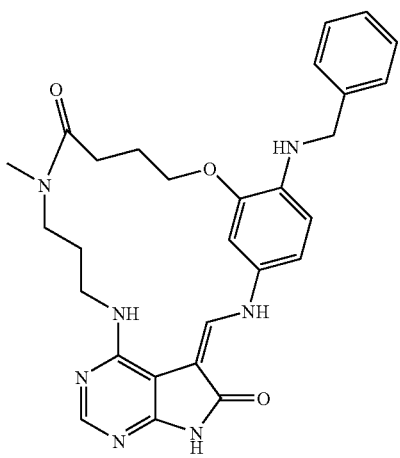

A solution of intermediate 135 (0.36 mmol) in DMF (18.67 ml) was added very slowly (1 hour) using a Marlow peristaltic pump to a solution of HBTU (0.8 mmol) and DIPEA (9.2 mmol) in DMF (9.33 ml). After the addition was completed, the reaction mixture was stirred for an additional 1 hour before being quenched with 1 ml of 7N $NH_3$ in MeOH. The reaction mixture was concentrated to dryness and the residue was partitioned between DCM and sat. aq. $K_2CO_3$. The aqueous layer was extracted with more DCM. The organic extracts were washed with more sat. $K_2CO_3$, dried and concentrated to dryness. The residue was purified by chromatography (eluent: DCM/MeOH gradient). The pure fractions were combined and concentrated, yielding 0.049 g (26.5%) of compound 110.

Example B26

Preparation of Compound 111

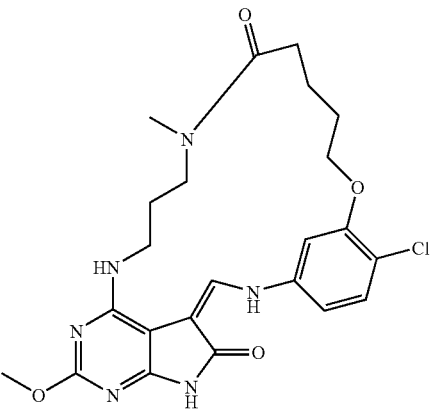

A solution of intermediate 140 (0.00033 mol) in DMF (17 ml) was added very slowly (over a 60-min period)—using a Marlow peristaltic pump—to a solution of HBTU (0.000726 mol) and DIPEA (0.00825 mol) in DMF (8 ml). When addition of intermediate was completed, the reaction mixture was stirred for one hour, then the reaction was quenched by addition of 6 ml of $NH_3$ in MeOH (7N). The solvents were evaporated. The residue was partitioned between DCM and a saturated aqueous $NaHCO_3$ solution. The aqueous phase was re-extracted with DCM. The combined organic phases were washed with a saturated aqueous $NaHCO_3$ solution, dried over $MgSO_4$, filtered and evaporated to dryness. The residue was purified by column chromatography (eluent: DCM/MeOH, gradient elution). The product fractions were collected and the solvent was evaporated. The residue was triturated with hot $CH_3CN$, then the mixture was allowed to cool to room temperature and the solid was filtered off, washed with $CH_3CN$ and DIPE, then dried under high-vacuum, yielding 0.032 g (20%) of compound 111.

Example B27

Preparation of Compound 112

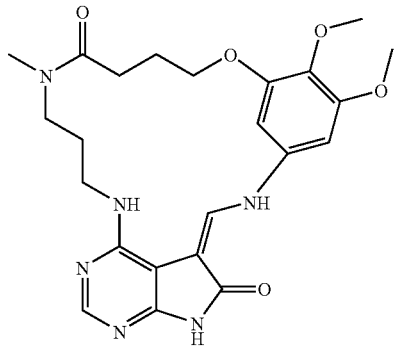

HBTU (0.0006 mol) and DIPEA (0.0084 mol) were dissolved in DMF (50 ml). Intermediate 145 (0.0003 mol) was added slowly using a Watson Marlow pump as a solution in DMF (q.s.). When the addition was completed the reaction mixture was quenched by addition of 1 ml $NH_3$ in MeOH (7N). The solvents were evaporated. The crude was redissolved in DCM and washed with $Na_2CO_3$ aqueous solution. The aqueous phase was re-extracted twice with DCM. The combined organic phases were dried over $MgSO_4$, filtered and evaporated to dryness. The residue was purified by flash chromatography (eluent: DCM/MeOH gradient 10:1 to 7:1). The combined fractions were evaporated to dryness, yielding compound 112.

Example B28

Preparation of Compound 113

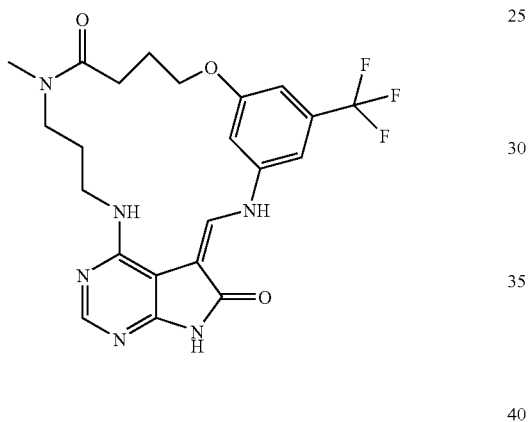

HBTU (0.0006 mol) and DIPEA (0.0084 mol) were dissolved in DMF (50 ml). Intermediate 150 (0.0003 mol) was added slowly as a solution in DMF (q.s.) using a Watson Marlow pump. When the addition was completed the reaction mixture was quenched by addition of 1 ml $NH_3$ in MeOH (7N). The solvents were evaporated. The crude was redissolved in DCM and washed with $Na_2CO_3$ aqueous solution. The aqueous phase was re-extracted twice with DCM. The combined organic phases were dried over $MgSO_4$, filtered and concentrated to dryness. The residue was purified by flash chromatography (eluent: DCM/MeOH gradient 10:1 to 7:1). The combined fractions were evaporated to dryness, yielding compound 113.

The compounds in Table 1 were prepared by analogy to one of the procedures described above, indicated by Ex. No. The exemplified procedures are indicated by a '*'. All the compounds are free bases.

For simplicity the compounds are always drawn as the Z-isomer, but since it was observed that the compounds embraced within the scope of this invention can switch between the Z and E configuration, it is obvious that all stereochemically isomeric forms of the compounds are intended to be embraced within the scope of the present invention.

TABLE 1

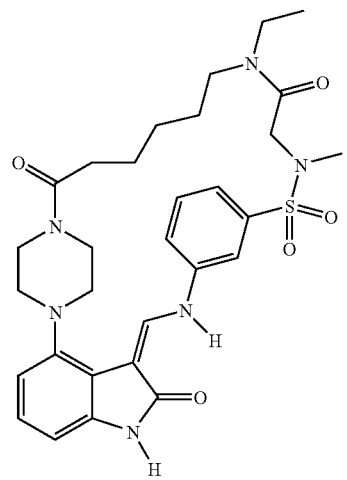

Co. No. 1; Ex. No. B1*

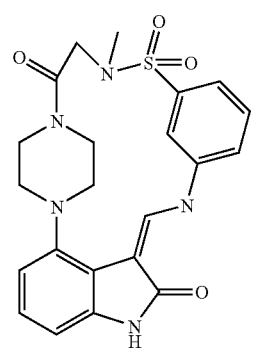

Co. No. 2; Ex. No. B2*

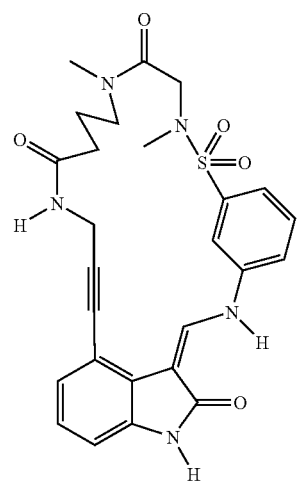

Co. No. 3; Ex. No. B3*

TABLE 1-continued
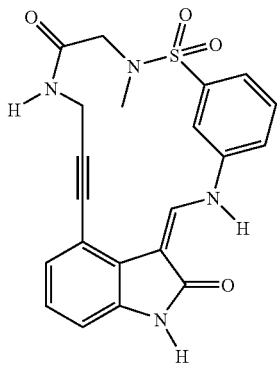
Co. No. 4; Ex. No. B4*
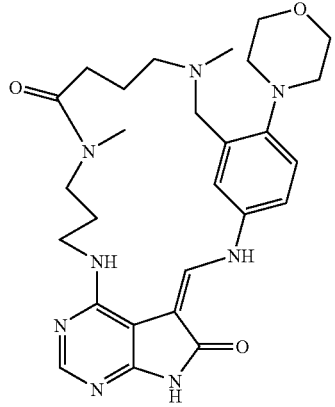
Co. No. 7; Ex. No. B7*
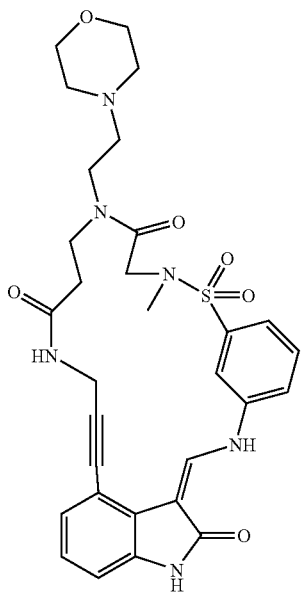
Co. No. 5; Ex. No. B5*
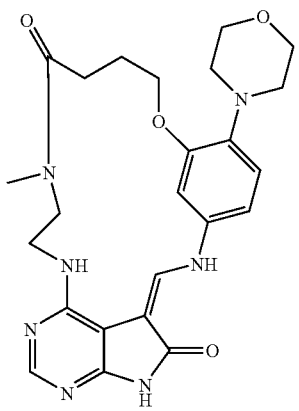
Co. No. 8; Ex. No. B8*
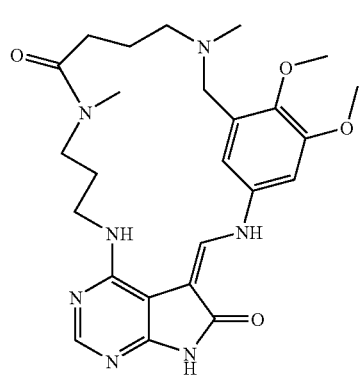
Co. No. 6; Ex. No. B6*
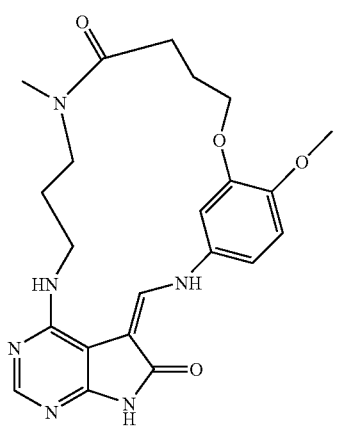
Co. No. 9; Ex. No. B9*

TABLE 1-continued
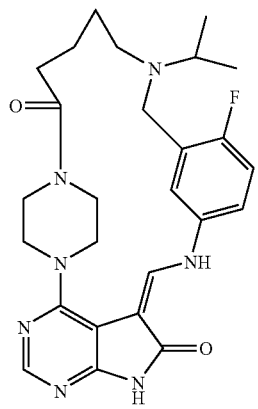
Co. No. 10; Ex. No. B10*
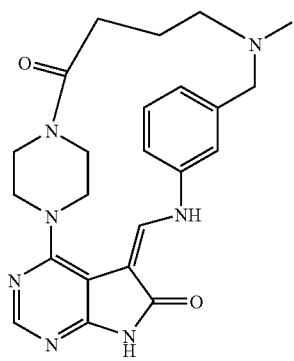
Co. No. 11; Ex. No. B11*
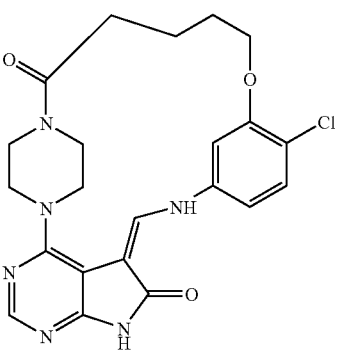
Co. No. 12; Ex. No. B12*
TABLE 1-continued
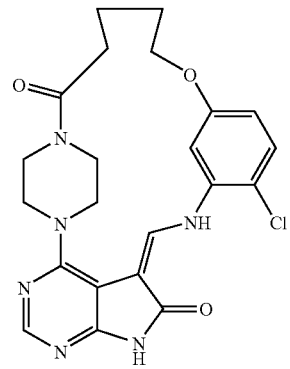
Co. No. 13; Ex. No. B13*
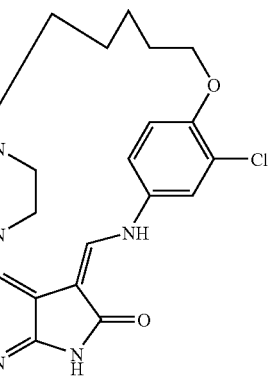
Co. No. 14; Ex. No. B14*
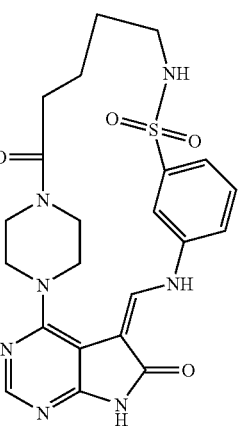
Co. No. 15; Ex. No. B15*

TABLE 1-continued
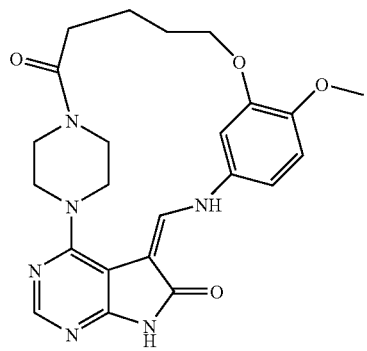
Co. No. 16; Ex. No. B9
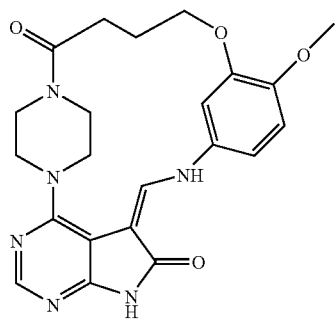
Co. No. 17; Ex. No. B9
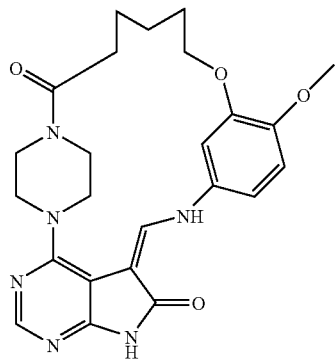
Co. No. 18; Ex. No. B9
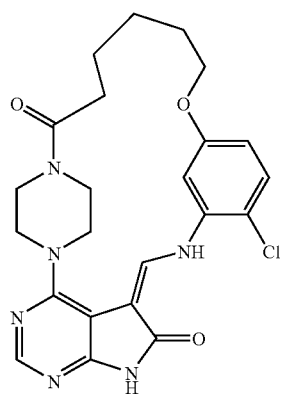
Co. No. 19; Ex. No. B13
TABLE 1-continued
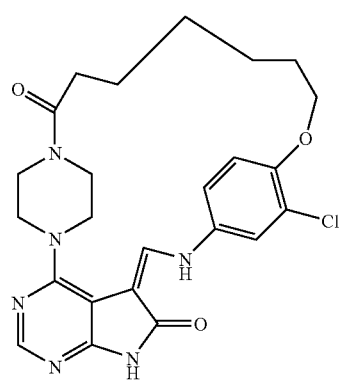
Co. No. 20; Ex. No. B14
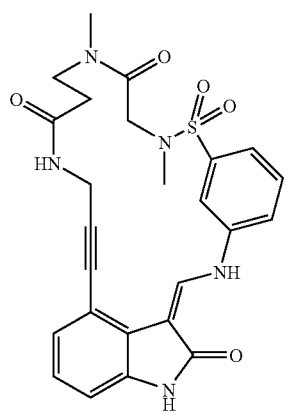
Co. No. 21; Ex. No. B3
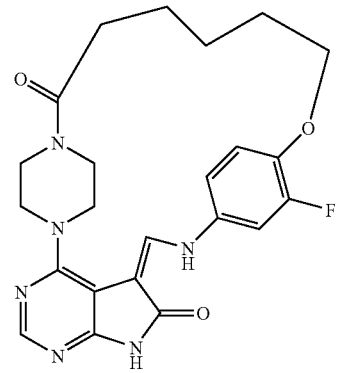
Co. No. 22; Ex. No. B14

TABLE 1-continued
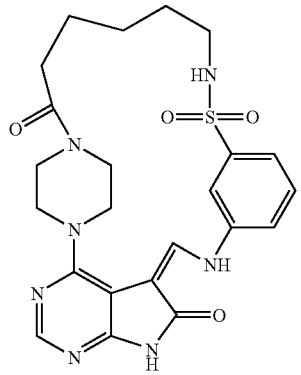
Co. No. 23; Ex. No. B15
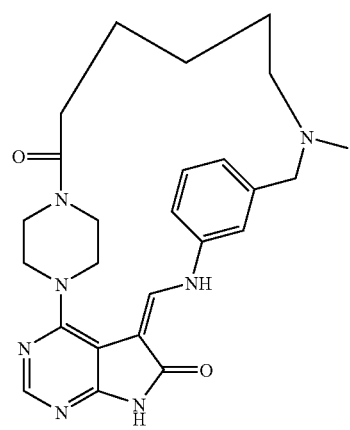
Co. No. 24; Ex. No. B11
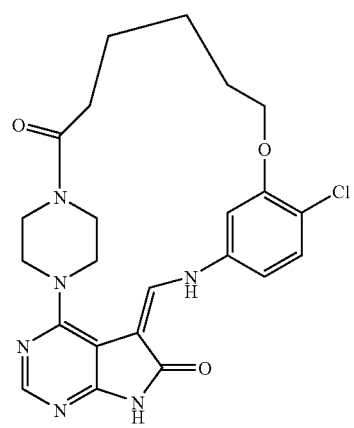
Co. No. 25; Ex. No. B12
TABLE 1-continued
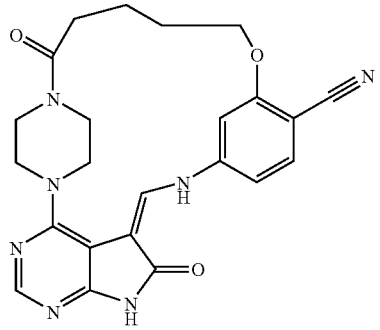
Co. No. 26; Ex. No. B12
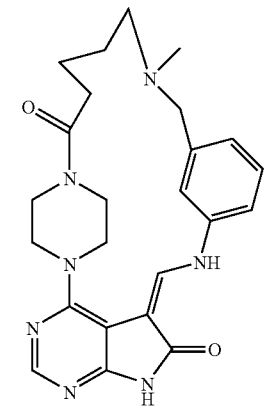
Co. No. 27; Ex. No. B11
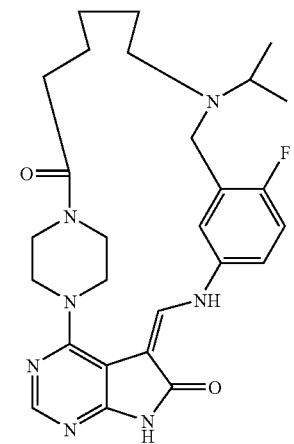
Co. No. 28; Ex. No. B10

TABLE 1-continued
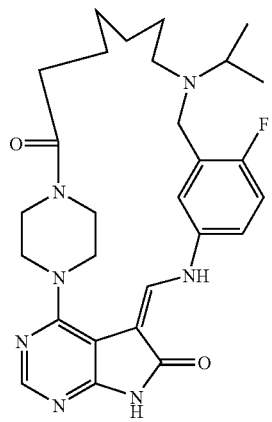
Co. No. 29; Ex. No. B10
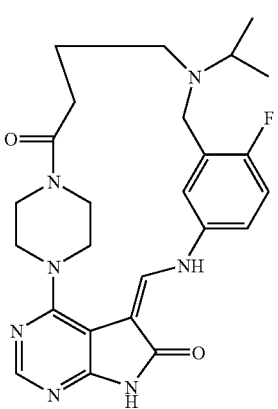
Co. No. 30; Ex. No. B10
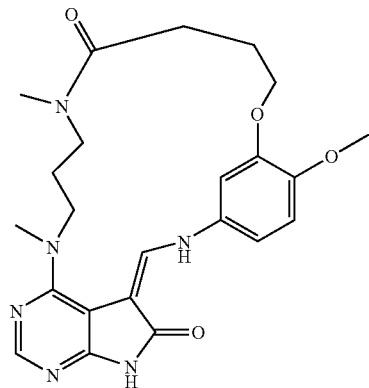
Co. No. 31; Ex. No. B9
TABLE 1-continued
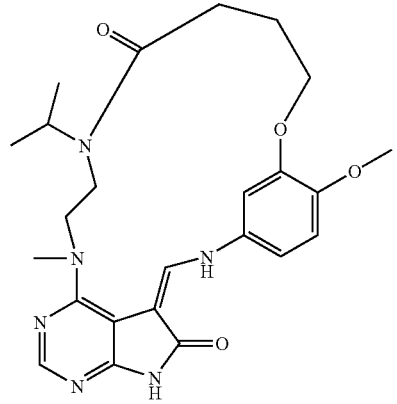
Co. No. 32; Ex. No. B9
Co. No. 33; Ex. No. B9
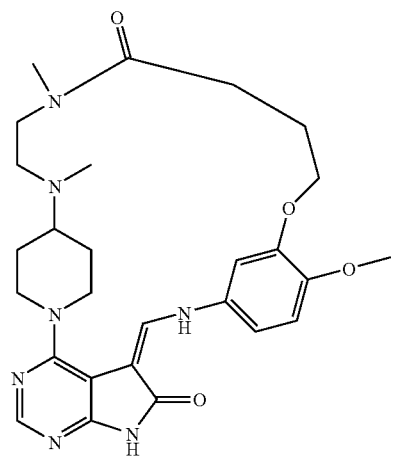
Co. No. 34; Ex. No. B9

TABLE 1-continued
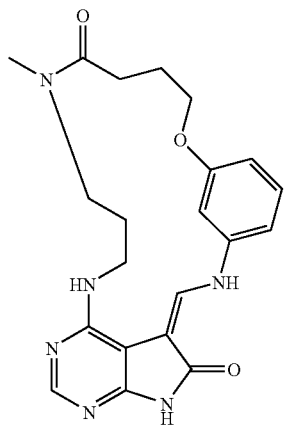
Co. No. 35; Ex. No. B9
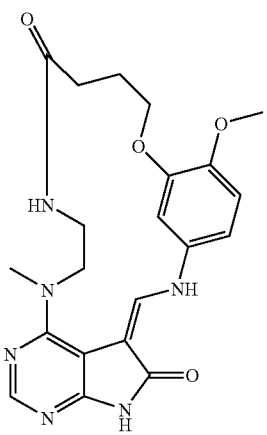
Co. No. 38; Ex. No. B9
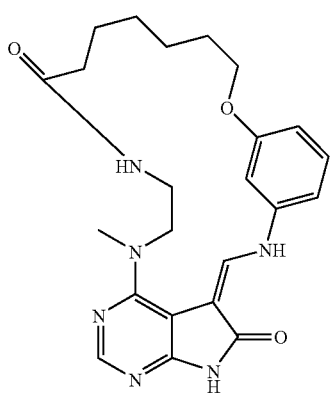
Co. No. 36; Ex. No. B9
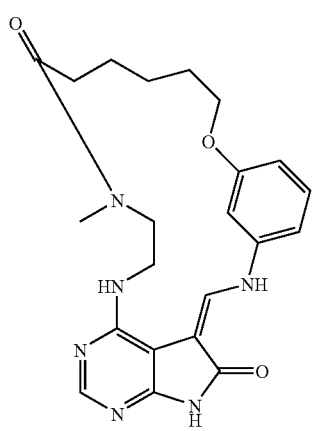
Co. No. 39; Ex. No. B9
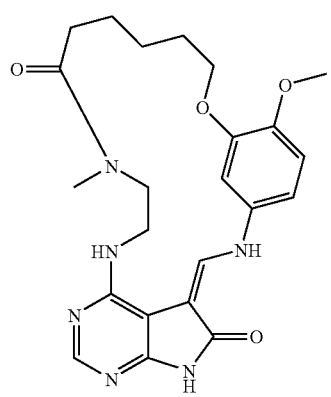
Co. No. 37; Ex. No. B9
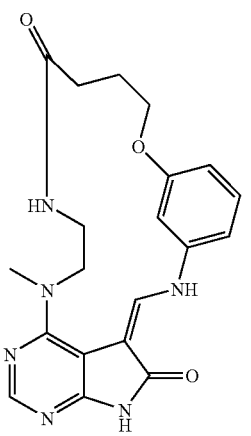
Co. No. 40; Ex. No. B9

TABLE 1-continued
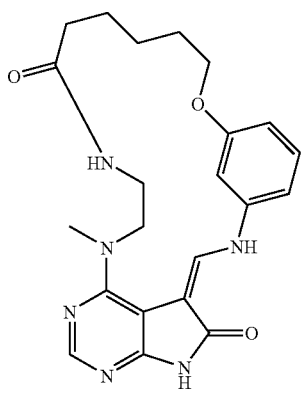
Co. No. 41; Ex. No. B9
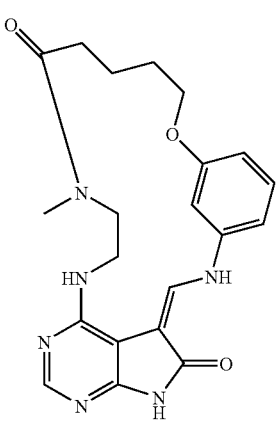
Co. No. 42; Ex. No. B9
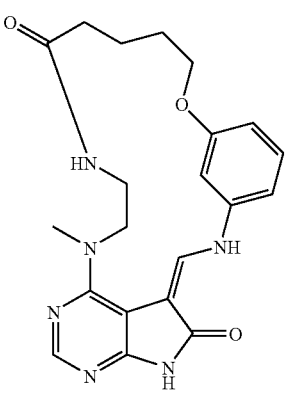
Co. No. 43; Ex. No. B9
TABLE 1-continued
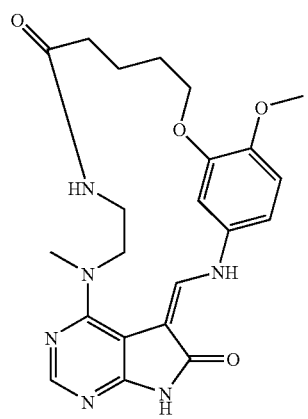
Co. No. 44; Ex. No. B9
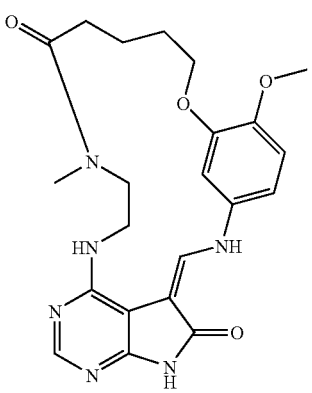
Co. No. 45; Ex. No. B9
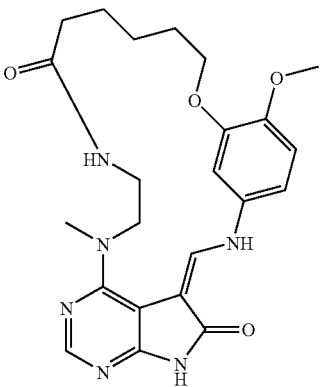
Co. No. 46; Ex. No. B9

TABLE 1-continued
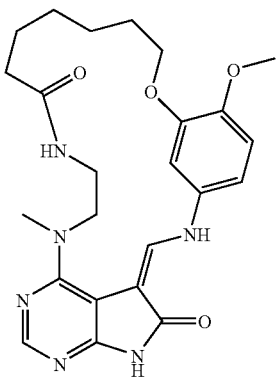
Co. No. 47; Ex. No. B9
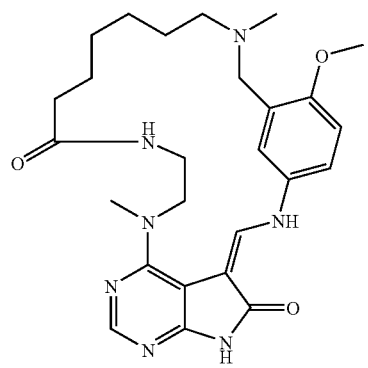
Co. No. 50; Ex. No. B6
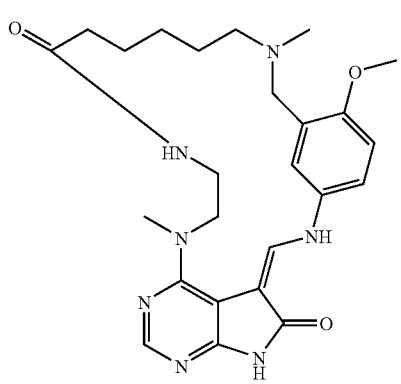
Co. No. 48; Ex. No. B6
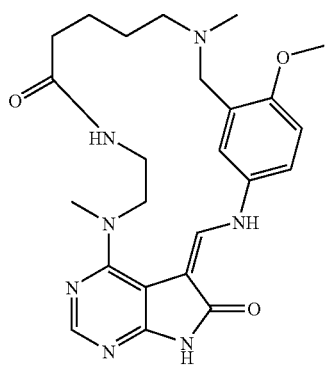
Co. No. 51; Ex. No. B6
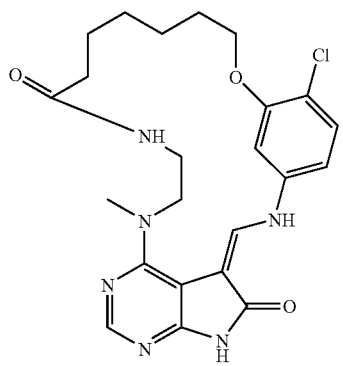
Co. No. 49; Ex. No. B12
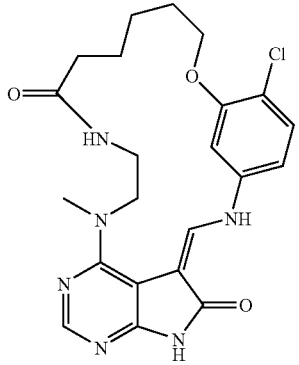
Co. No. 52; Ex. No. B12

TABLE 1-continued
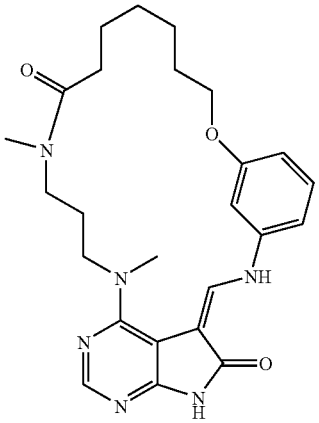
Co. No. 53; Ex. No. B9
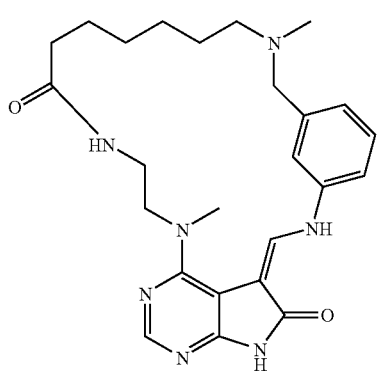
Co. No. 54; Ex. No. B11
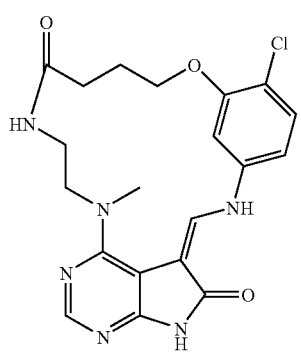
Co. No. 55; Ex. No. B12
TABLE 1-continued
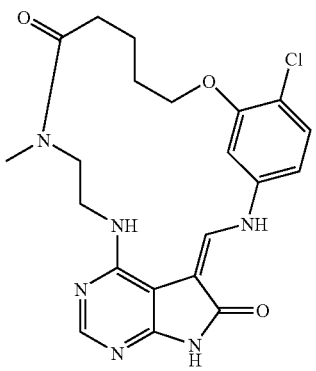
Co. No. 56; Ex. No. B12
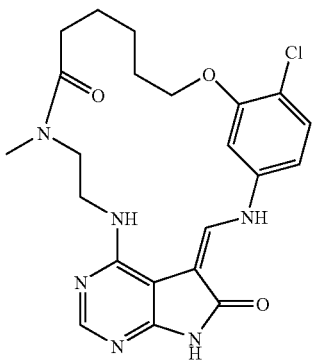
Co. No. 57; Ex. No. B12
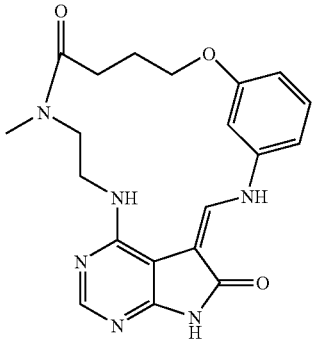
Co. No. 58; Ex. No. B9
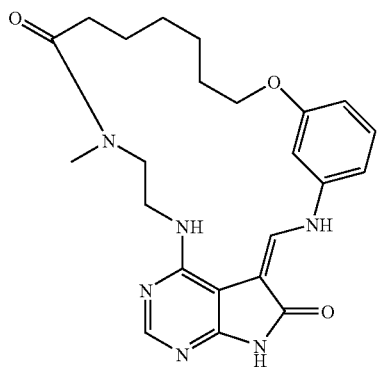
Co. No. 59; Ex. No. B9

TABLE 1-continued
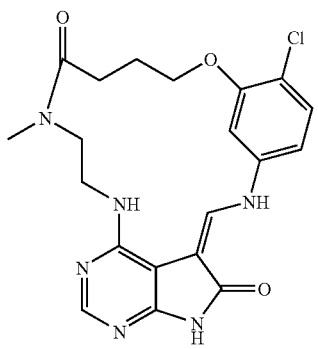
Co. No. 60; Ex. No. B12
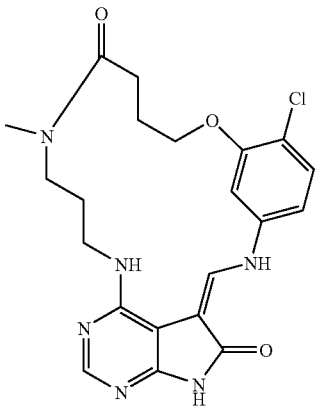
Co. No. 63; Ex. No. B12
TABLE 1-continued
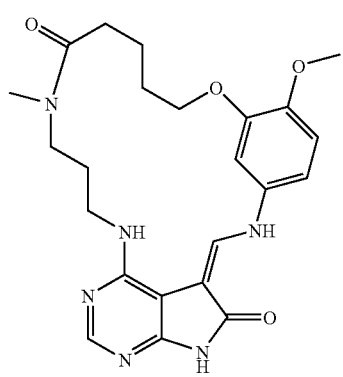
Co. No. 61; Ex. No. B12
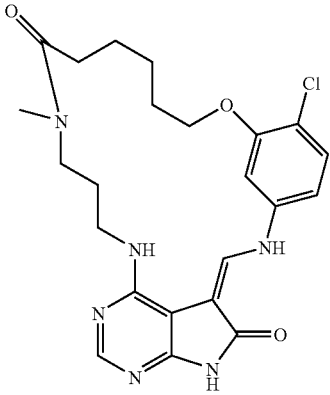
Co. No. 64; Ex. No. B12
Co. No. 62; Ex. No. B9
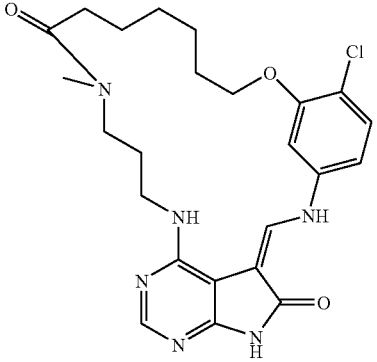
Co. No. 65; Ex. No. B12

TABLE 1-continued
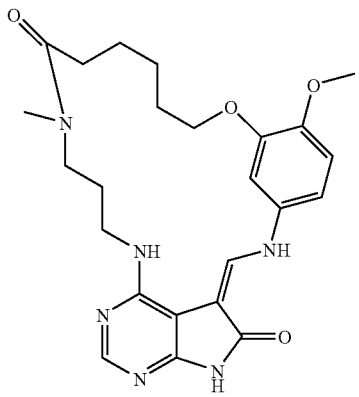
Co. No. 66; Ex. No. B9
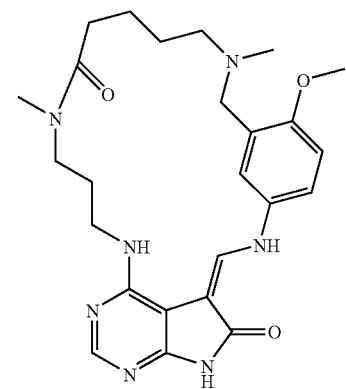
Co. No. 67; Ex. No. B6
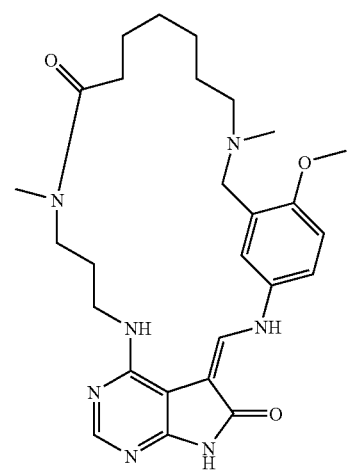
Co. No. 68; Ex. No. B6
TABLE 1-continued
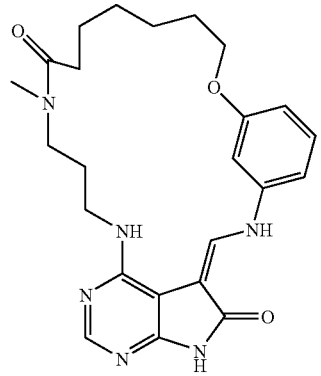
Co. No. 69; Ex. No. B9
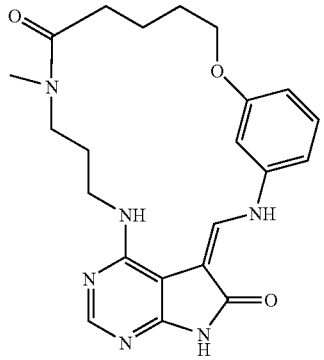
Co. No. 70; Ex. No. B9
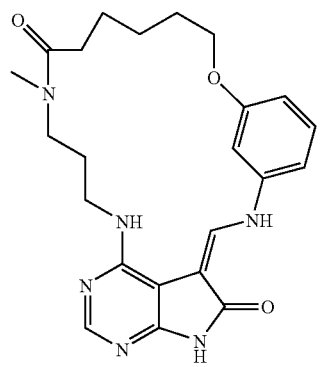
Co. No. 71; Ex. No. B9

TABLE 1-continued
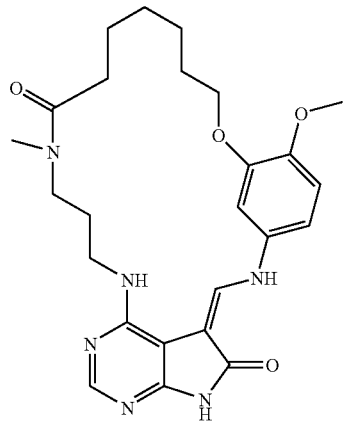
Co. No. 72; Ex. No. B9
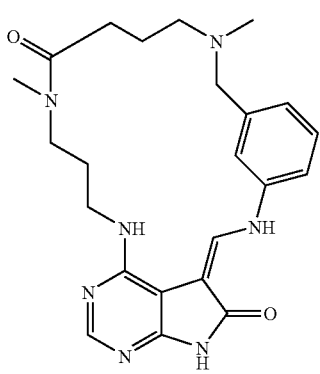
Co. No. 73; Ex. No. B11
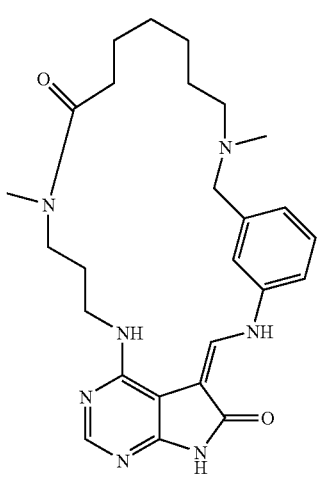
Co. No. 74; Ex. No. B11
TABLE 1-continued
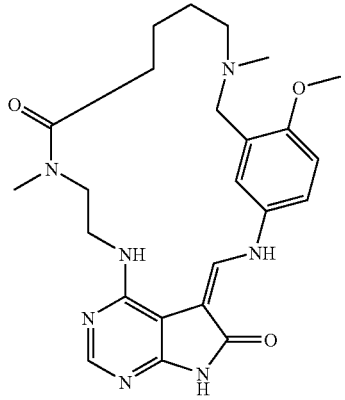
Co. No. 75; Ex. No. B6
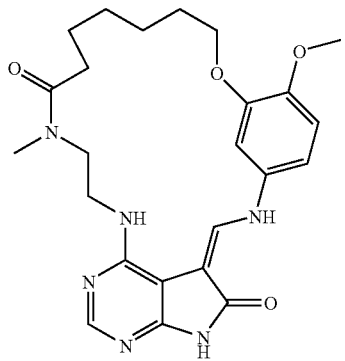
Co. No. 76; Ex. No. B9
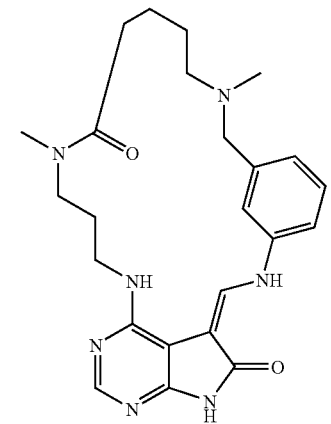
Co. No. 77; Ex. No. B11

TABLE 1-continued
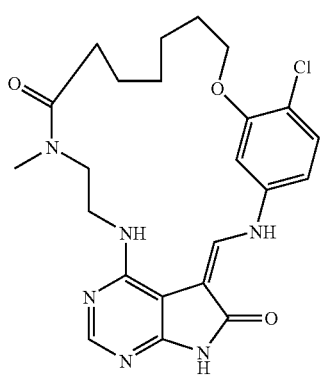
Co. No. 78; Ex. No. B12
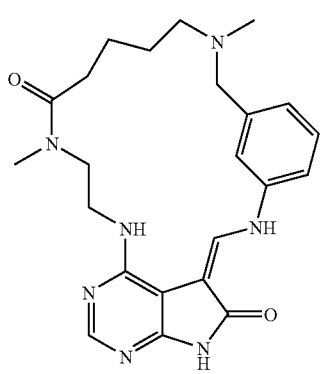
Co. No. 79; Ex. No. B11
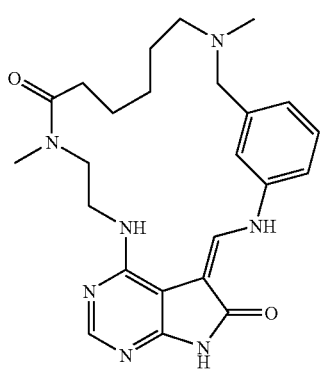
Co. No. 80; Ex. No. B11
TABLE 1-continued
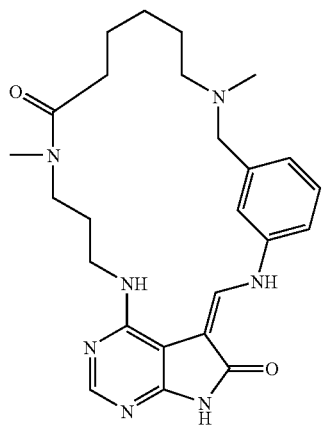
Co. No. 81; Ex. No. B11
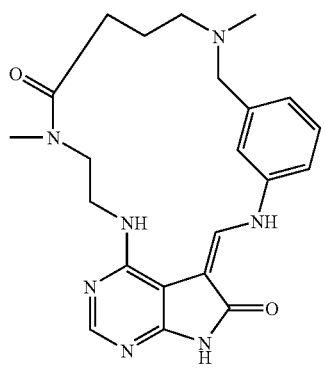
Co. No. 82; Ex. No. B11
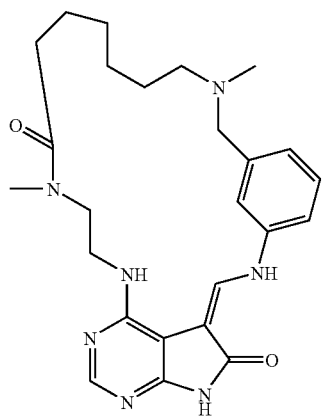
Co. No. 83; Ex. No. B11

TABLE 1-continued
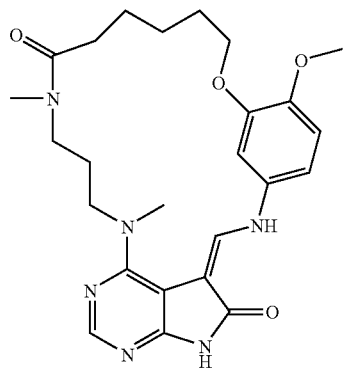
Co. No. 84; Ex. No. B9
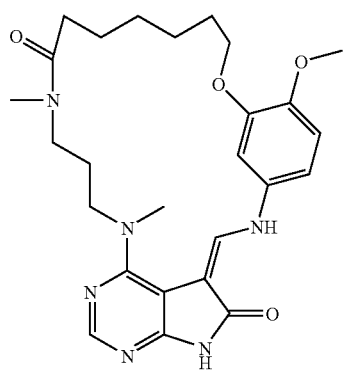
Co. No. 85; Ex. No. B9
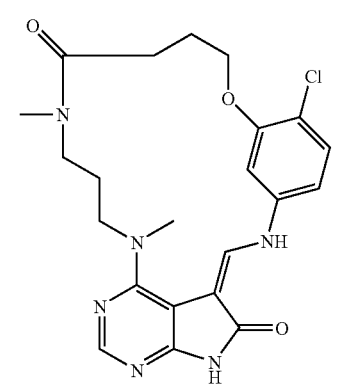
Co. No. 86; Ex. No. B12
TABLE 1-continued
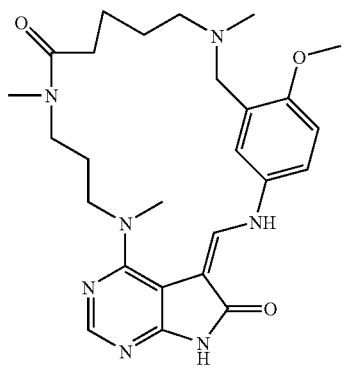
Co. No. 87; Ex. No. B6
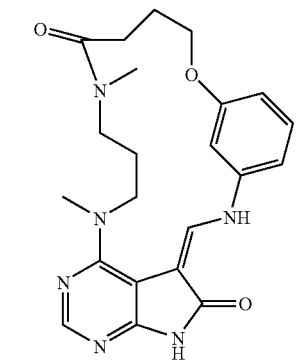
Co. No. 88; Ex. No. B9
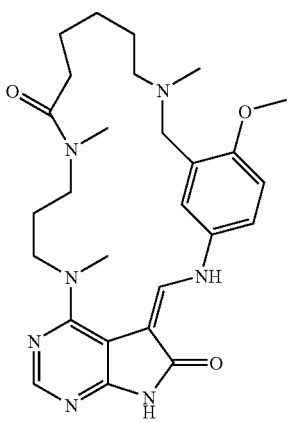
Co. No. 89; Ex. No. B6

TABLE 1-continued
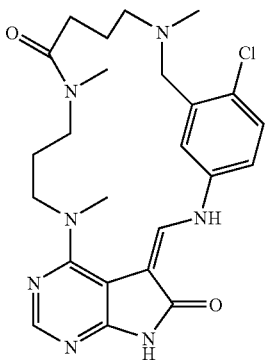
Co. No. 90; Ex. No. B6
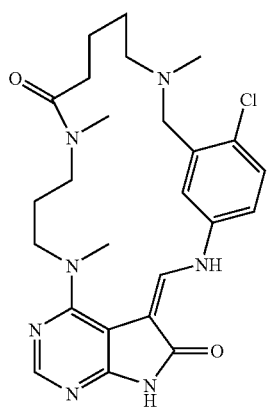
Co. No. 91; Ex. No. B6
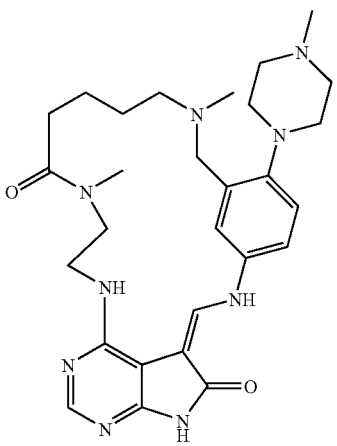
Co. No. 92; Ex. No. B7
TABLE 1-continued
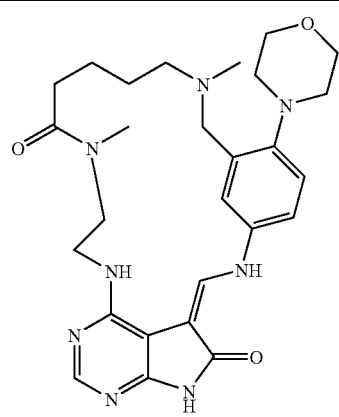
Co. No. 93; Ex. No. B7
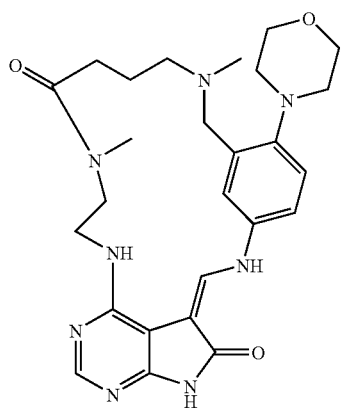
Co. No. 94; Ex. No. B7
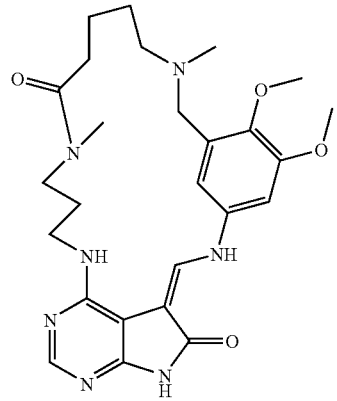
Co. No. 95; Ex. No. B6

TABLE 1-continued
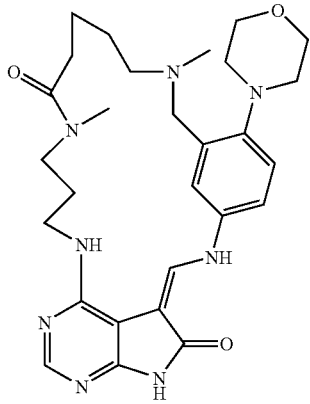
Co. No. 96; Ex. No. B7
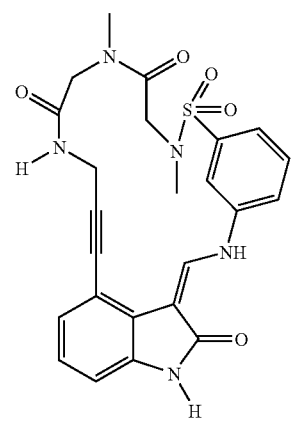
Co. No. 97; Ex. No. B3
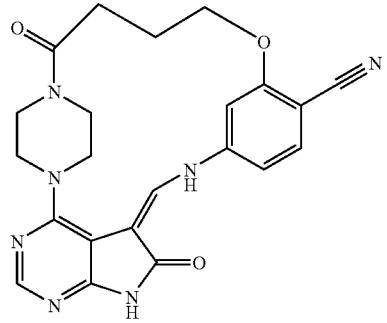
Co. No. 98; Ex. No. B12
TABLE 1-continued
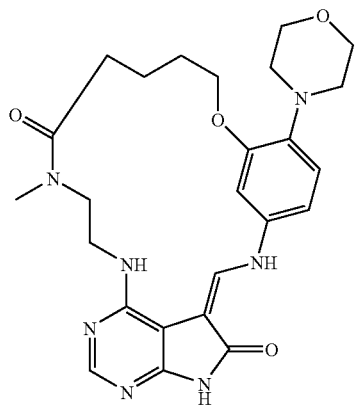
Co. No. 114; Ex. No. B8
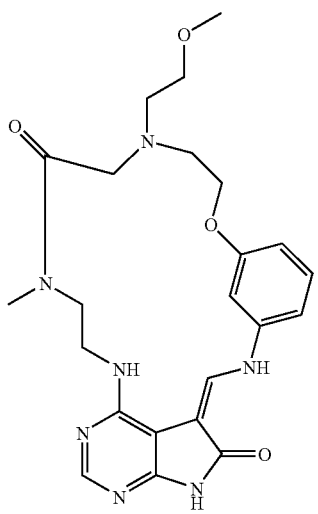
Co. No. 161; Ex. No. B18
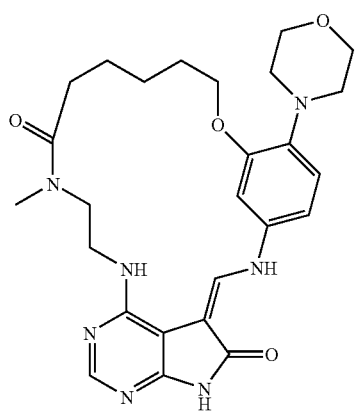
Co. No. 115; Ex. No. B8

TABLE 1-continued
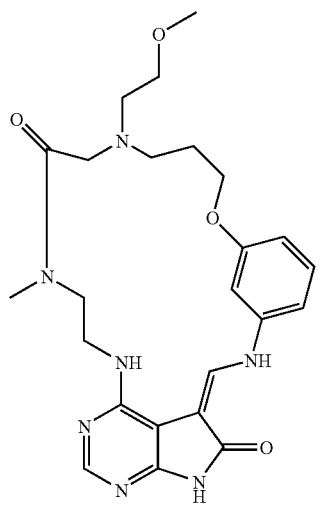
Co. No. 162; Ex. No. B18
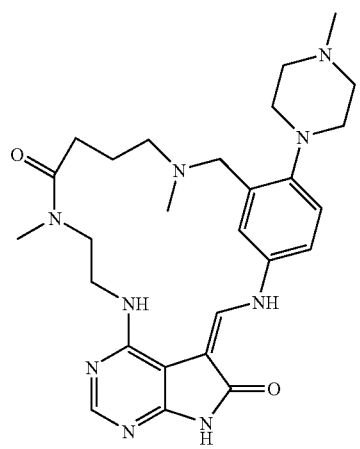
Co. No. 116; Ex. No. B7
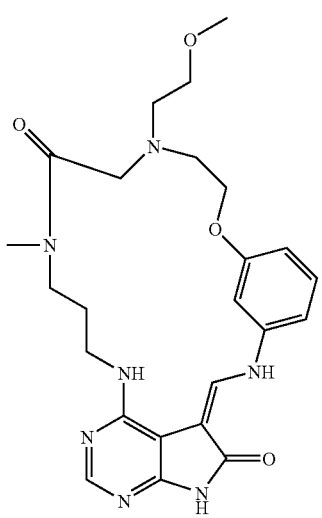
Co. No. 163; Ex. No. B18
TABLE 1-continued
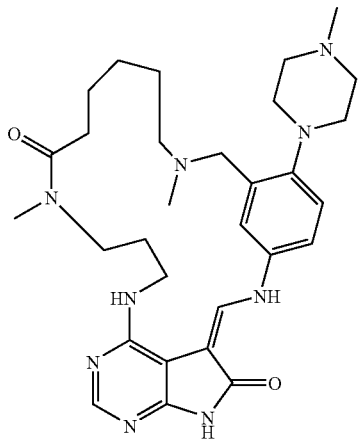
Co. No. 117; Ex. No. B7
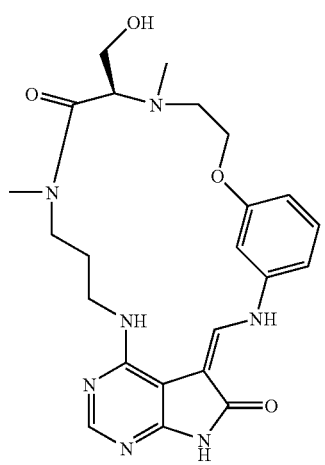
Co. No. 102; Ex. No. B18a*
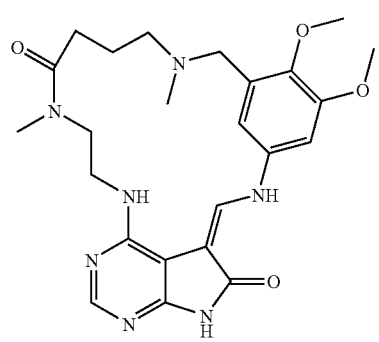
Co. No. 118; Ex. No. B6

TABLE 1-continued
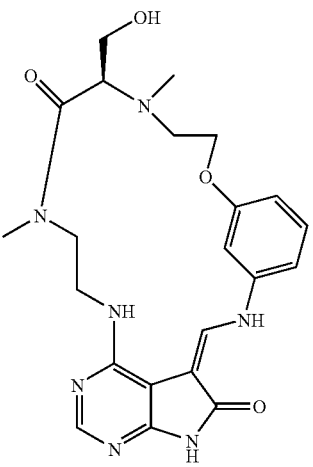
Co. No. 164; Ex. No. B18
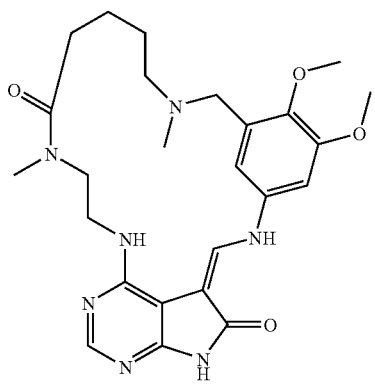
Co. No. 119; Ex. No. B6
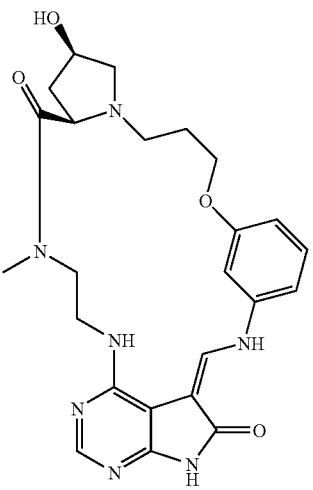
Co. No. 165; Ex. No. B18
TABLE 1-continued
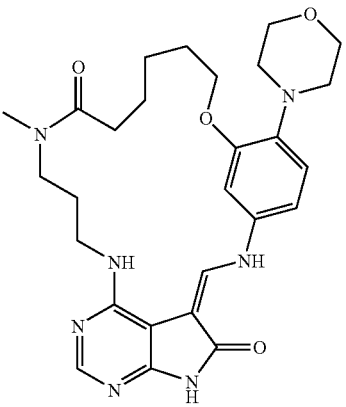
Co. No. 120; Ex. No. B8
Co. No. 166; Ex. No. B18
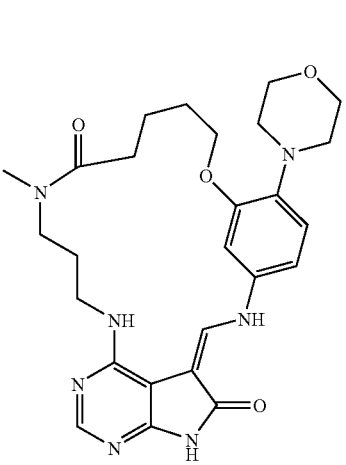
Co. No. 121; Ex. No. B8

TABLE 1-continued
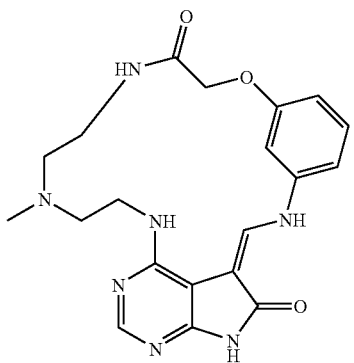
Co. No. 167; Ex. No. B16
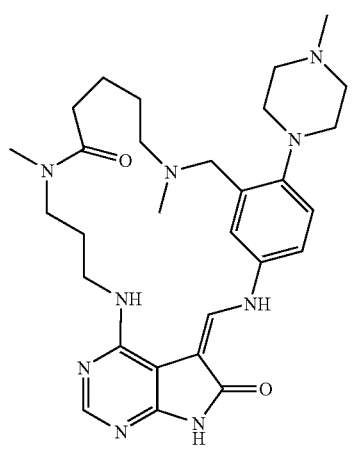
Co. No. 122; Ex. No. B7
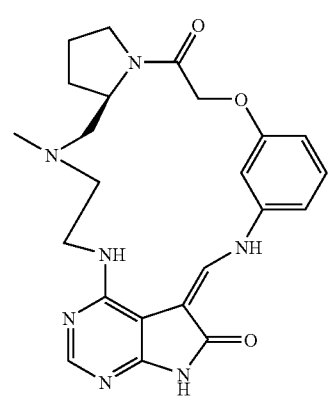
Co. No. 168; Ex. No. B16
TABLE 1-continued
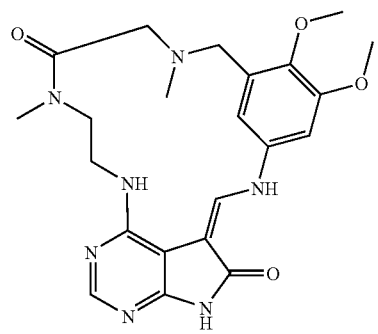
Co. No. 123; Ex. No. B6
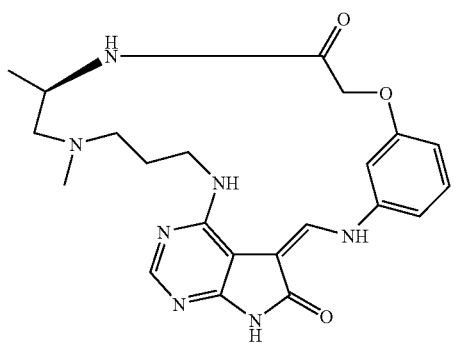
Co. No. 99; Ex. No. B16a*
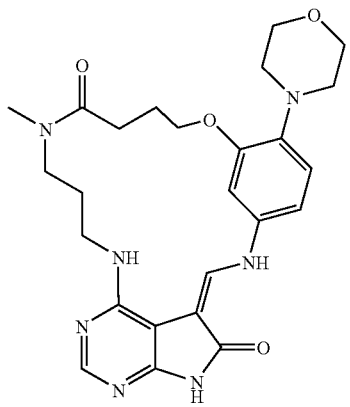
Co. No. 124; Ex. No. B8

TABLE 1-continued
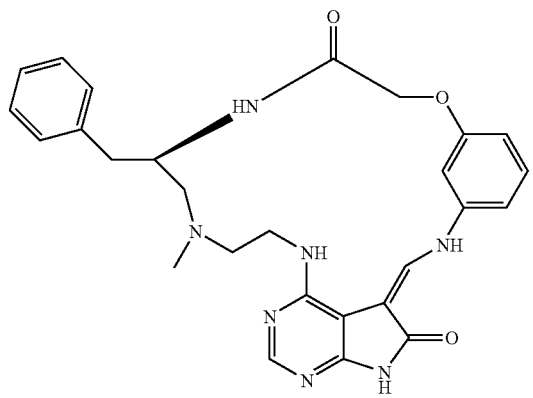
Co. No. 169; Ex. No. B16
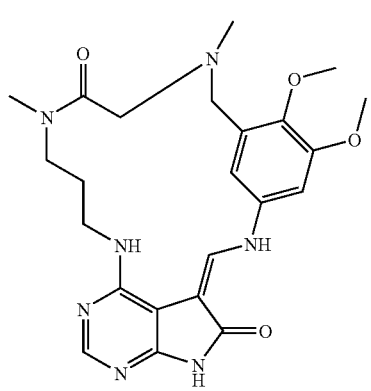
Co. No. 125; Ex. No. B6
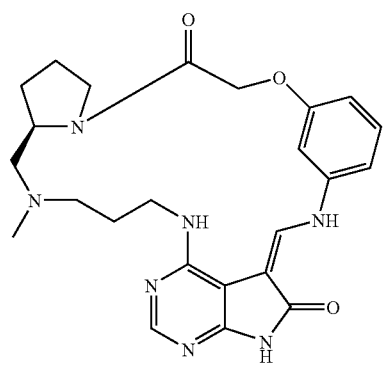
Co. No. 170; Ex. No. B16
TABLE 1-continued
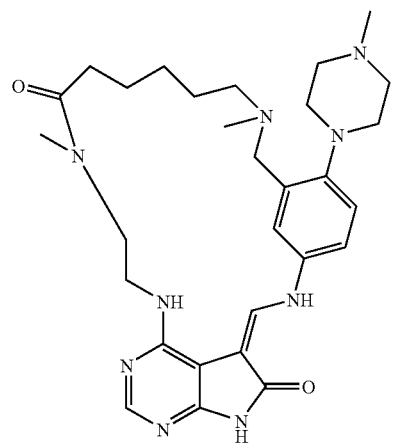
Co. No. 126; Ex. No. B7
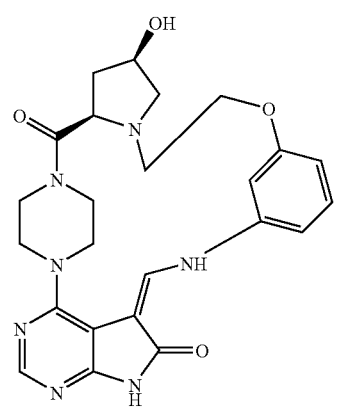
Co. No. 171; Ex. No. B18
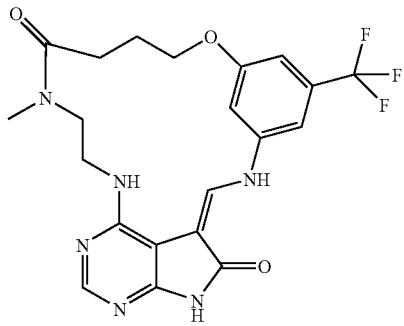
Co. No. 127; Ex. No. B28

TABLE 1-continued
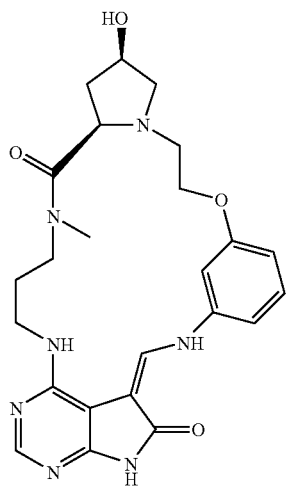
Co. No. 172; Ex. No B18
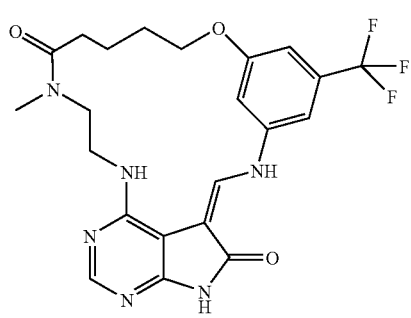
Co. No. 128; Ex. No. B28
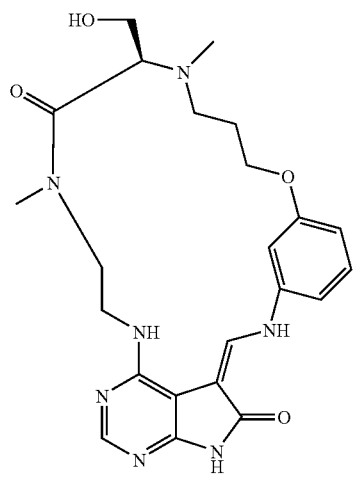
Co. No. 173; Ex. No. B18
TABLE 1-continued
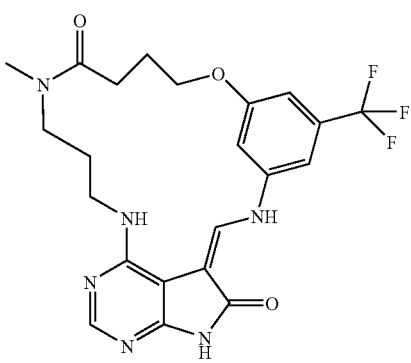
Co. No. 113; Ex. No. B28*
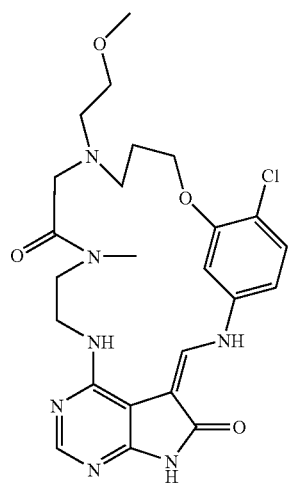
Co. No. 174; Ex. No. B18
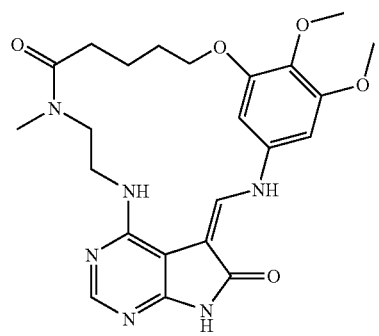
Co. No. 129; Ex. No. B27

TABLE 1-continued
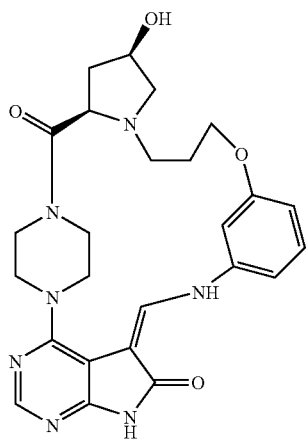
Co. No. 175; Ex. No. B18
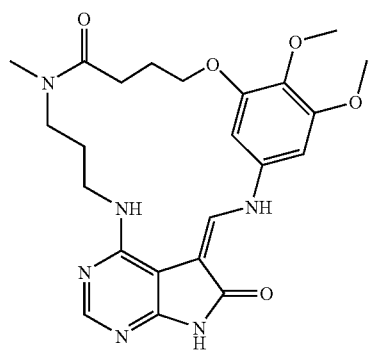
Co. No. 112; Ex. No. B27*
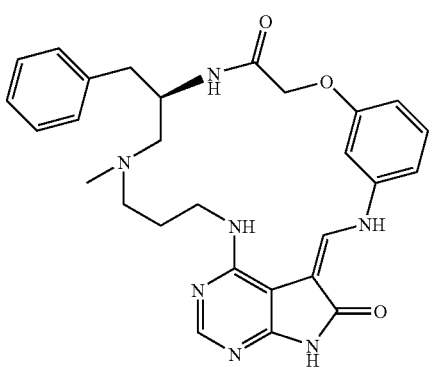
Co. No. 176; Ex. No. B16
TABLE 1-continued
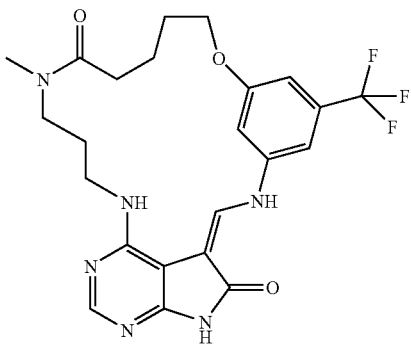
Co. No. 130; Ex. No. B28
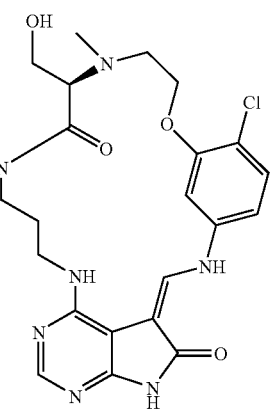
Co. No. 177; Ex. No. B18
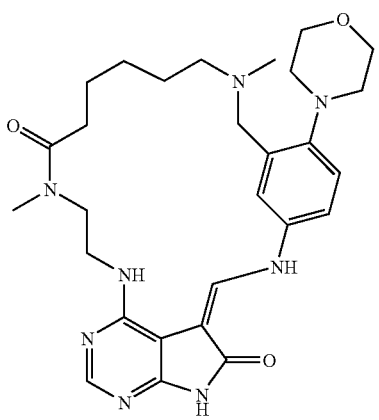
Co. No. 131; Ex. No. B7

TABLE 1-continued
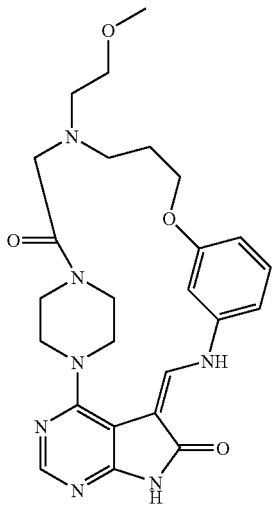
Co. No. 178; Ex. No. B18
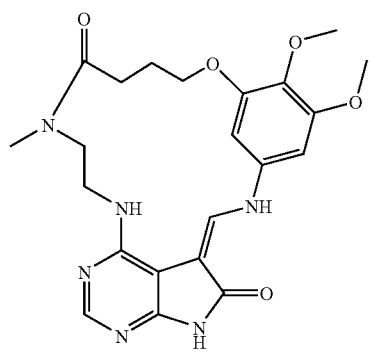
Co. No. 132; Ex. No. B27
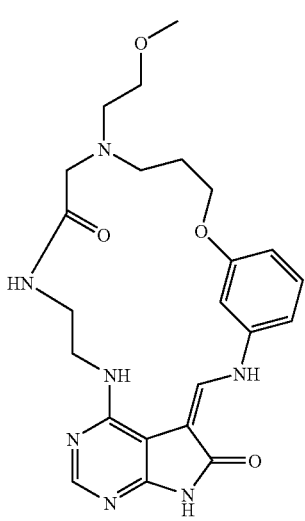
Co. No. 179; Ex. No. B18
TABLE 1-continued
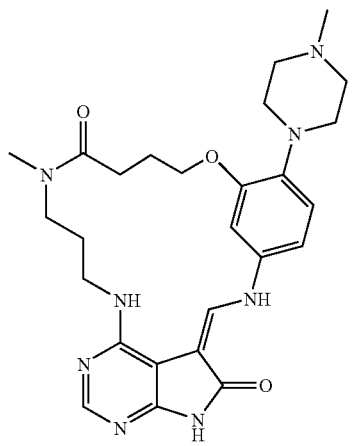
Co. No. 133; Ex. No. B8
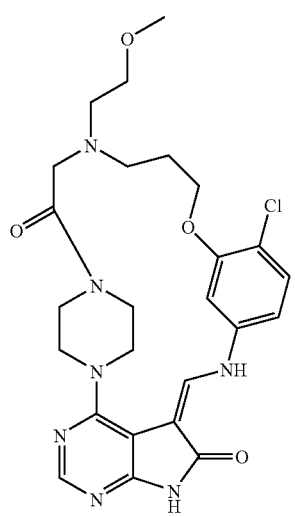
Co. No. 180; Ex. No. B18
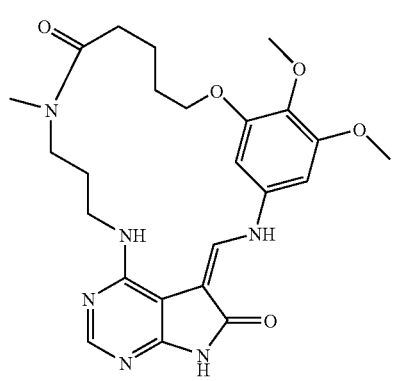
Co. No. 134; Ex. No. B27

TABLE 1-continued
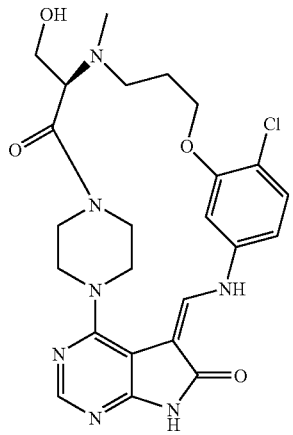
Co. No. 181; Ex. No. B18
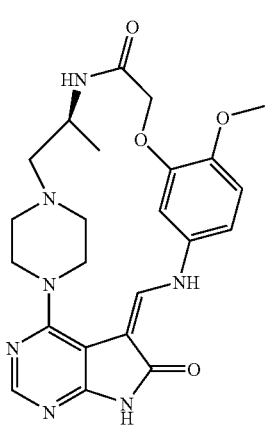
Co. No. 135; Ex. No. B8
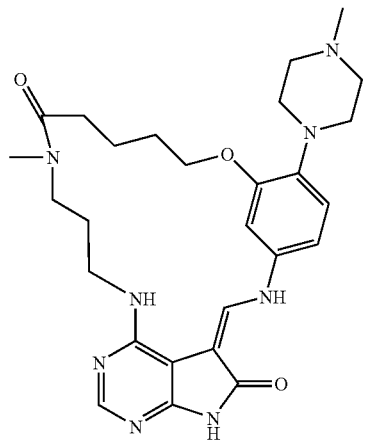
Co. No. 136; Ex. No. B8
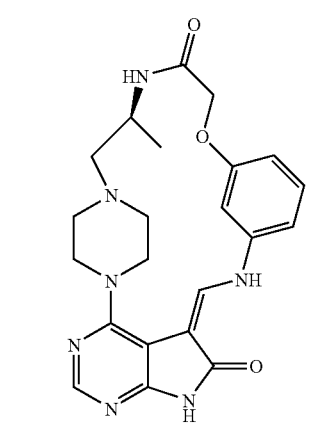
Co. No. 183; Ex. No. B17
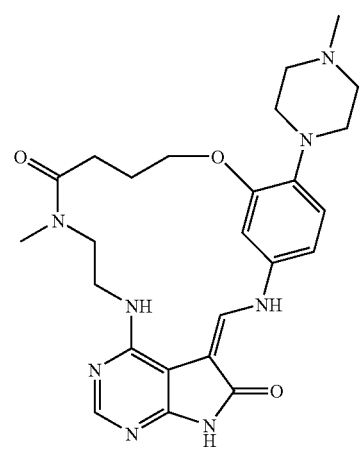
Co. No. 182; Ex. No. B17
Co. No. 137; Ex. No. B8

TABLE 1-continued
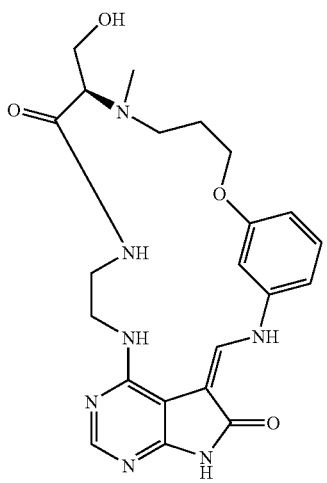
Co. No. 184; Ex. No. B18
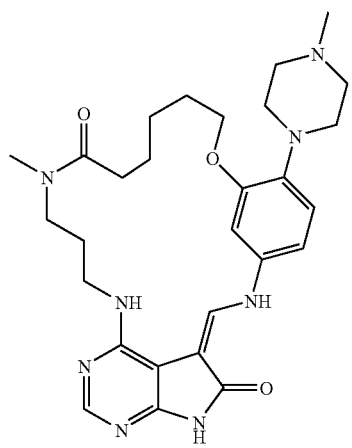
Co. No. 138; Ex. No. B8
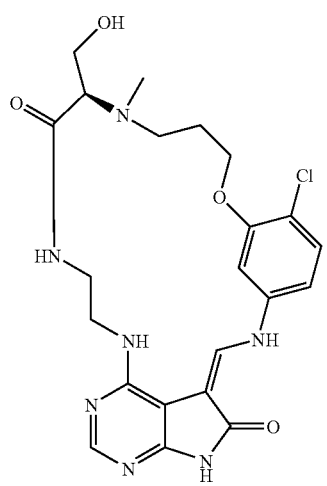
Co. No. 185; Ex. No. B18
TABLE 1-continued
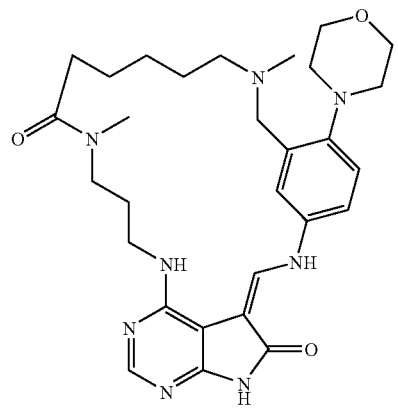
Co. No. 139; Ex. No. B7
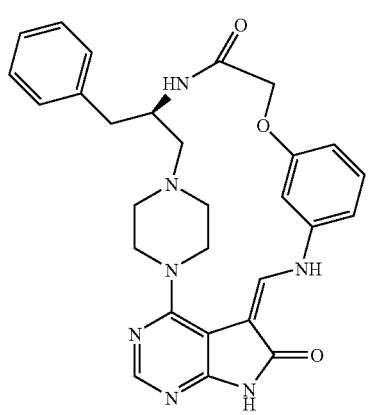
Co. No. 101; Ex. No. B17*
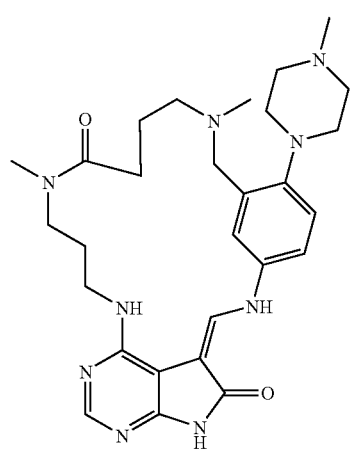
Co. No. 140; Ex. No. B7

TABLE 1-continued
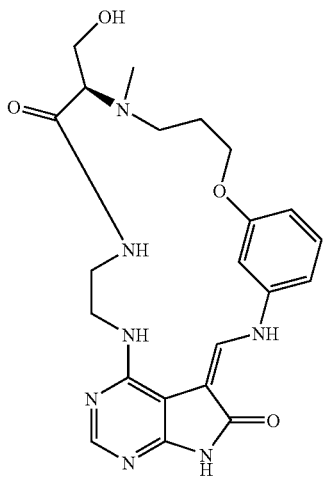
Co. No. 186; Ex. No. B18
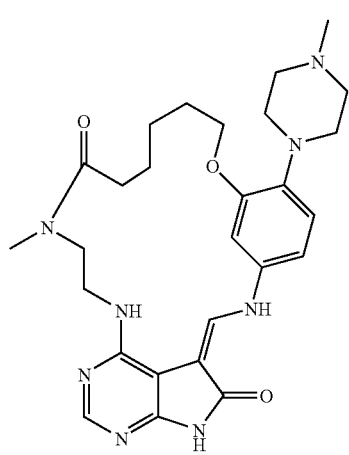
Co. No. 141; Ex. No. B8
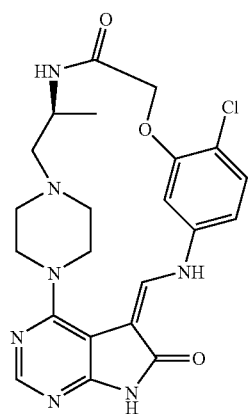
Co. No. 187; Ex. No. B17
TABLE 1-continued
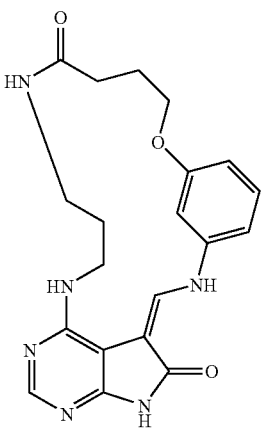
Co. No. 142; Ex. No. B9
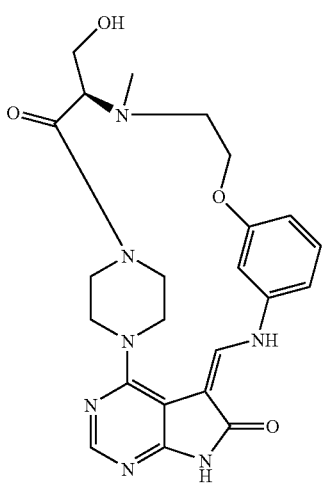
Co. No. 188; Ex. No. B18
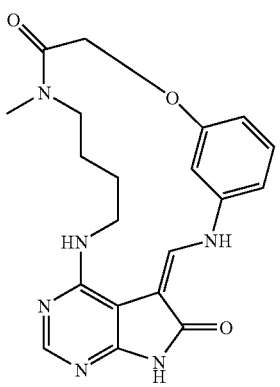
Co. No. 143; Ex. No. B9

TABLE 1-continued
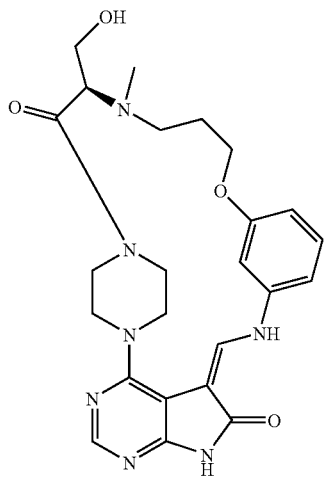
Co. No. 189; Ex. No. B18
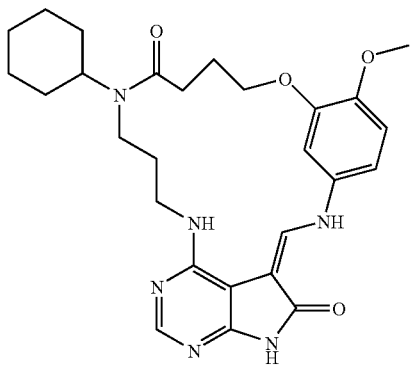
Co. No. 145; Ex. No. B9
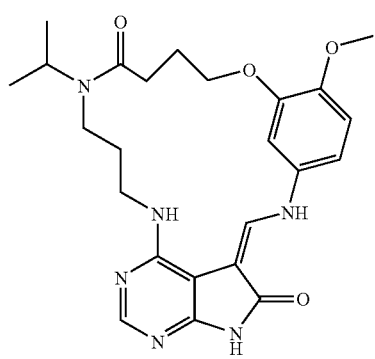
Co. No. 144; Ex. No. B9
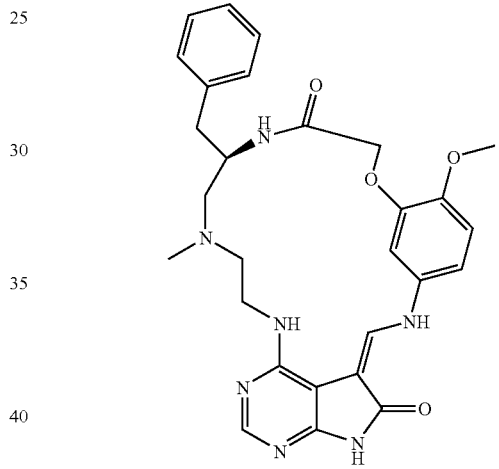
Co. No. 191; Ex. No. B17
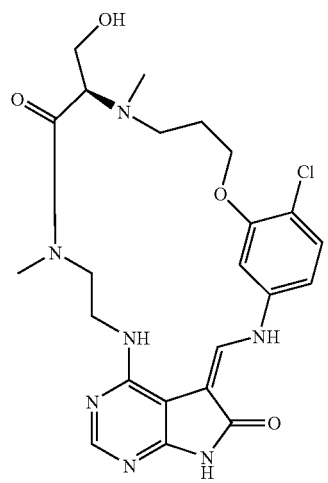
Co. No. 190; Ex. No. B18
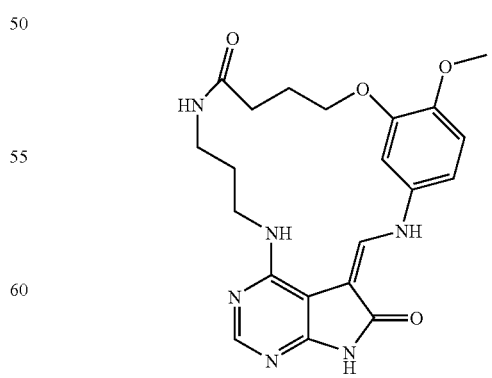
Co. No. 146; Ex. No. B9

TABLE 1-continued
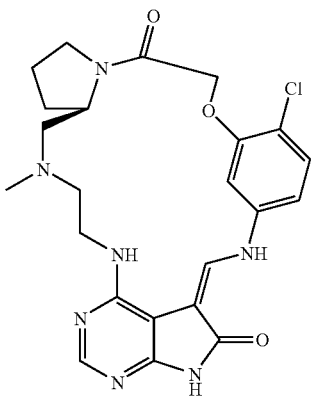
Co. No. 192; Ex. No. B17
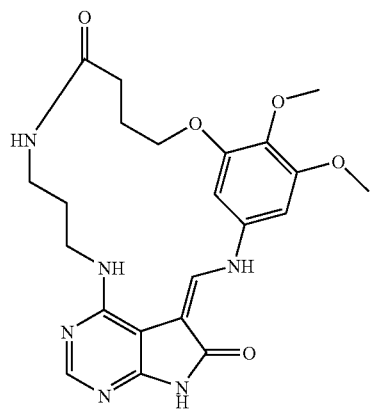
Co. No. 147; Ex. No. B27
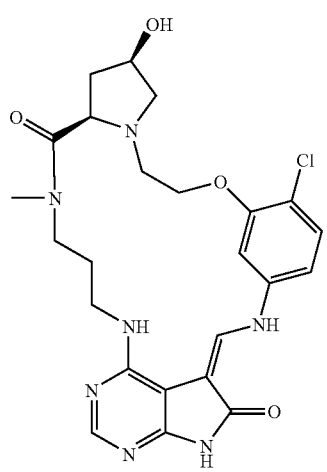
Co. No. 193; Ex. No. B18
TABLE 1-continued
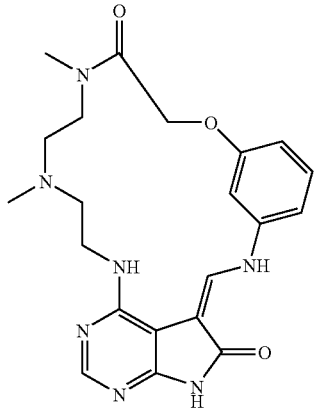
Co. No. 148; Ex. No. B20
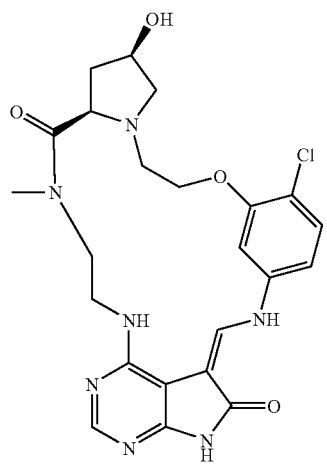
Co. No. 194; Ex. No. B18
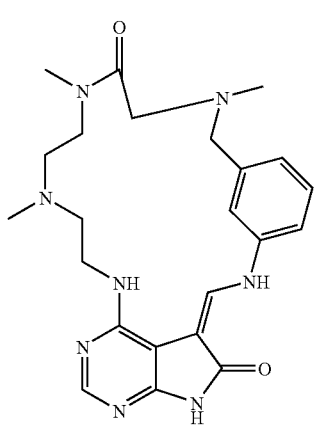
Co. No. 149; Ex. No. B21

TABLE 1-continued
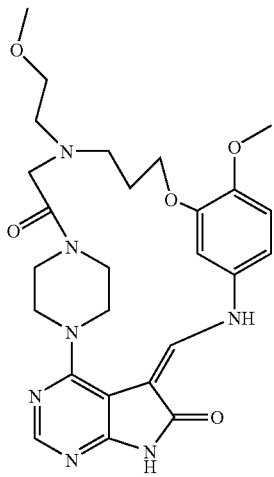
Co. No. 195; Ex. No. B18
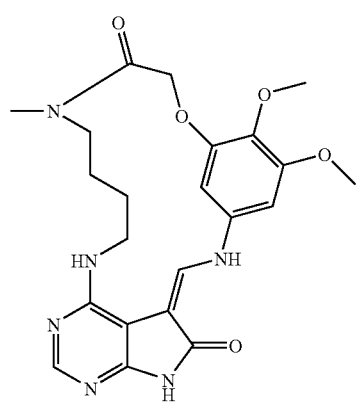
Co. No. 150; Ex. No. B27
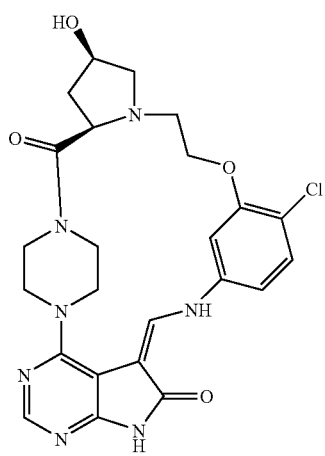
Co. No. 196; Ex. No. B18
TABLE 1-continued
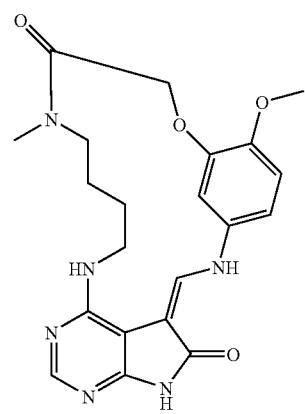
Co. No. 151; Ex. No. B9
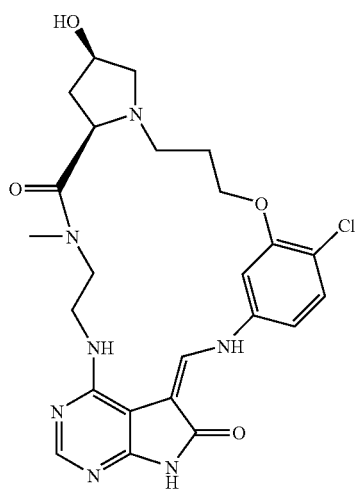
Co. No. 197; Ex. No. B18
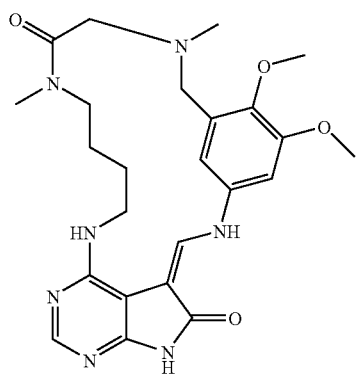
Co. No. 152; Ex. No. B6

TABLE 1-continued
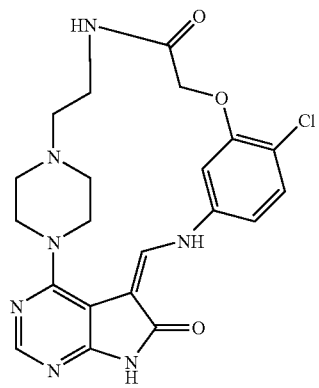
Co. No. 198; Ex. No. B17
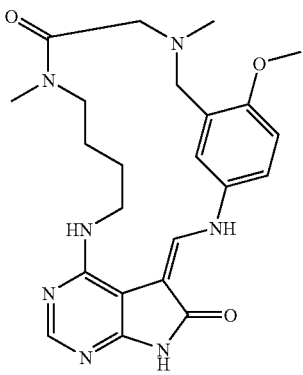
Co. No. 153; Ex. No. B6
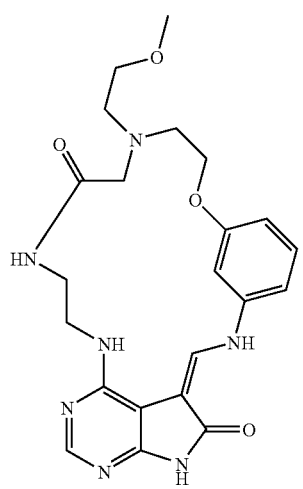
Co. No. 199; Ex. No. B18
TABLE 1-continued
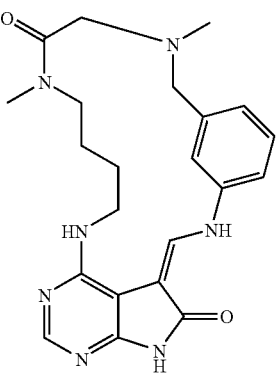
Co. No. 154; Ex. No. B11
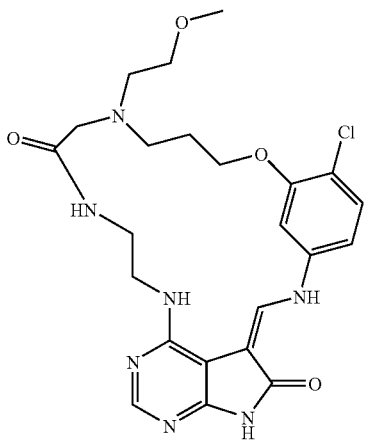
Co. No. 200; Ex. No. B18
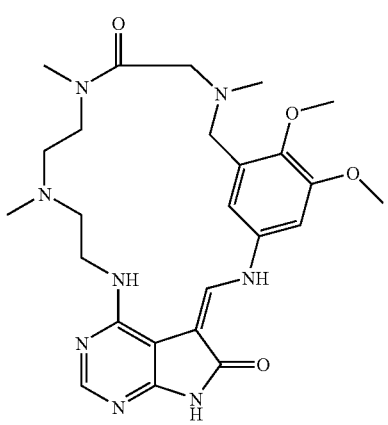
Co. No. 155; Ex. No. B21

TABLE 1-continued
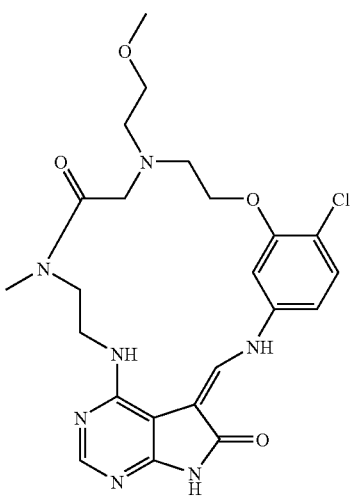
Co. No. 201; Ex. No. B18
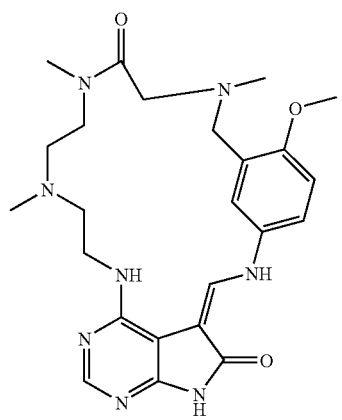
Co. No. 156; Ex. No. B21
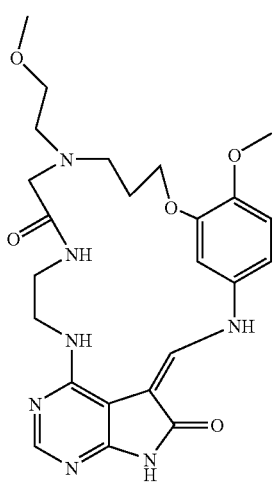
Co. No. 202; Ex. No. B18
TABLE 1-continued
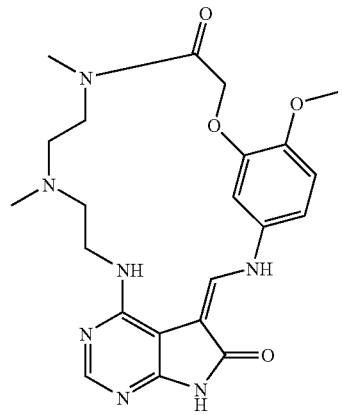
Co. No. 105; Ex. No. B20*
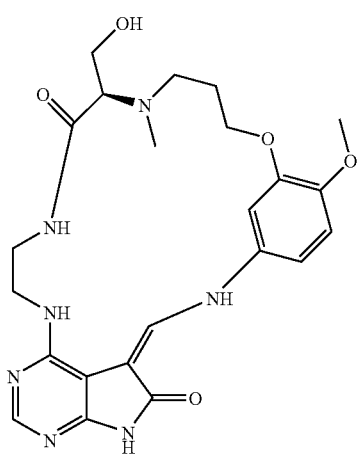
Co. No. 203; Ex. No. B18
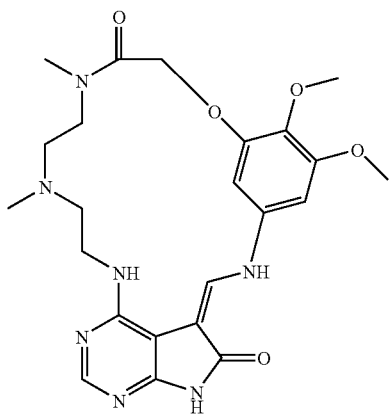
Co. No. 157; Ex. No. B20

TABLE 1-continued
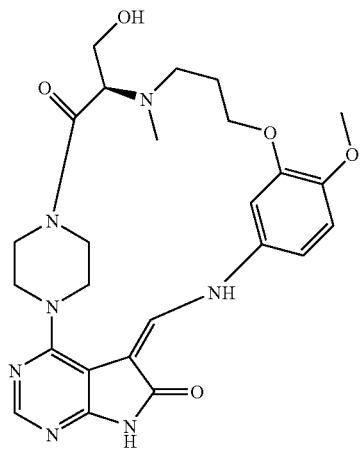
Co. No. 204; Ex. No. B18
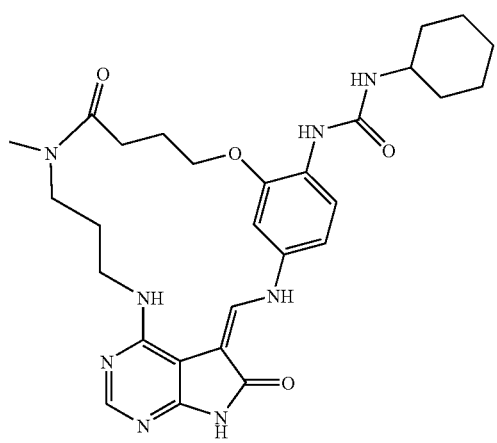
Co. No. 107; Ex. No. B22*
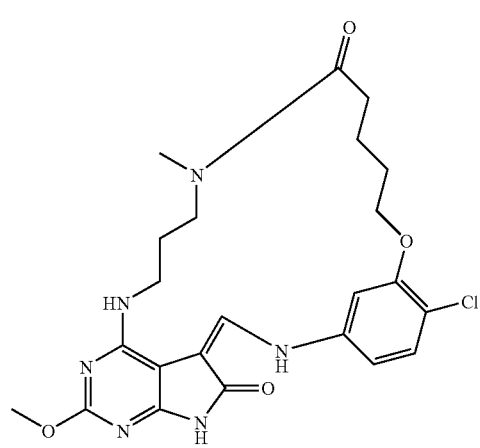
Co. No. 111; Ex. No. B26*
TABLE 1-continued
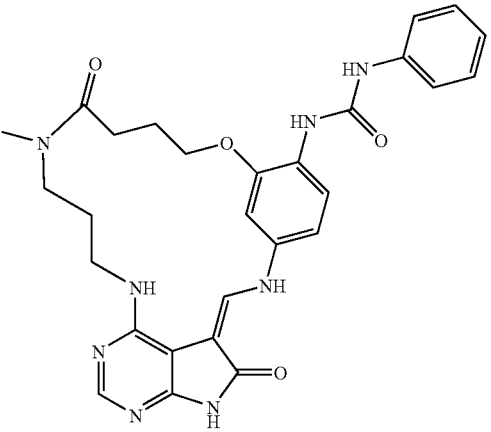
Co. No. 158; Ex. No. B22
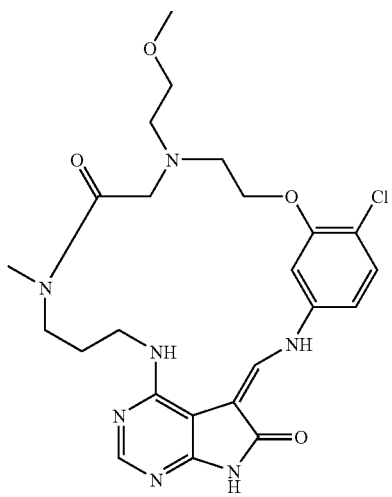
Co. No. 205; Ex. No. B18
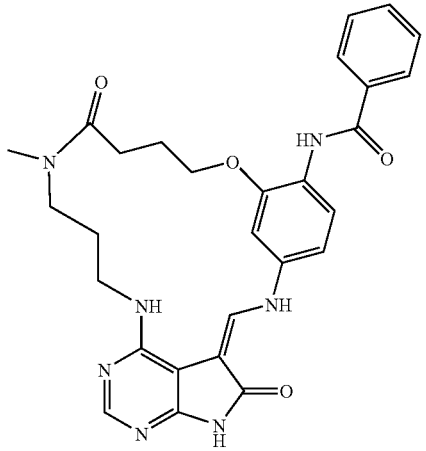
Co. No. 108; Ex. No. B23*

TABLE 1-continued
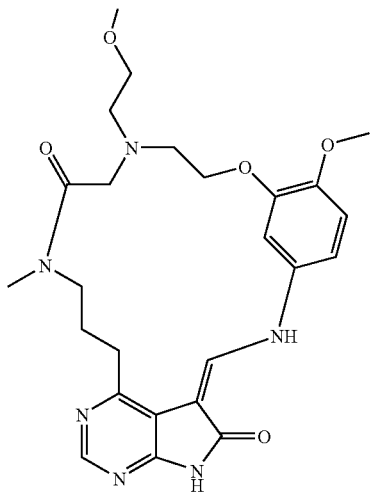
Co. No. 206; Ex. No. B18
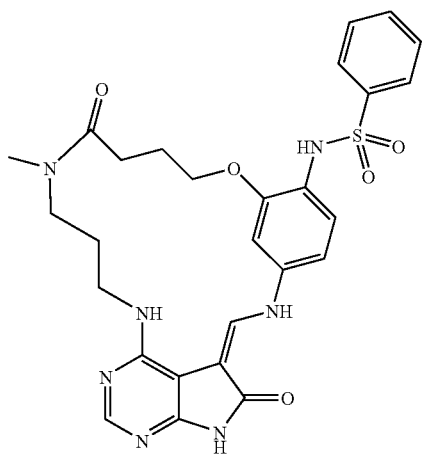
Co. No. 109; Ex. No. B24*
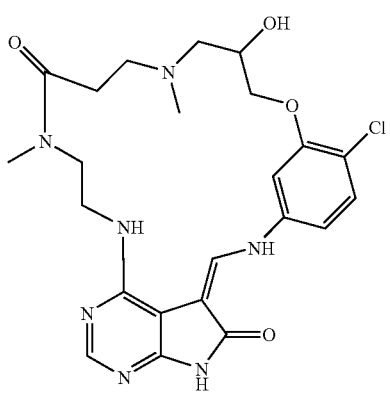
Co. No. 104; Ex. No. B19*
TABLE 1-continued
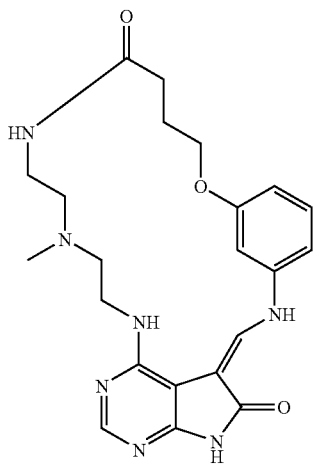
Co. No. 159; Ex. No. B20
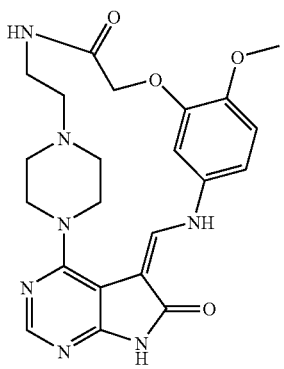
Co. No. 207; Ex. No. B17
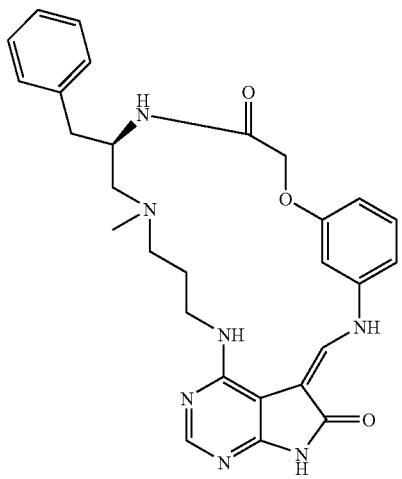
Co. No. 160; Ex. No. B16

TABLE 1-continued

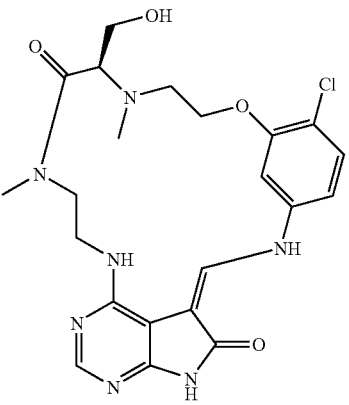

Co. No. 208; Ex. No. B18

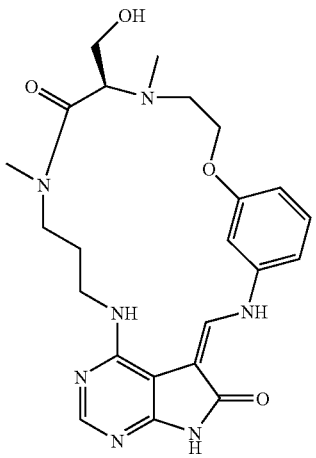

Co. No. 103; Ex. No. B18b*

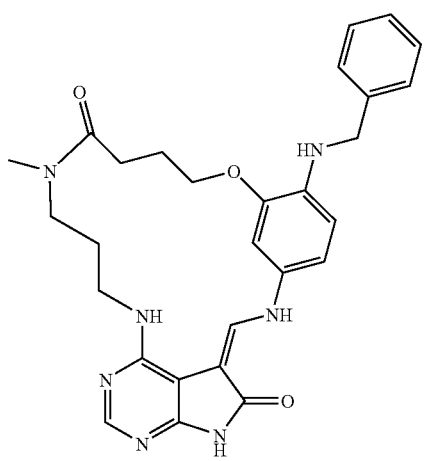

Co. No. 110; Ex. No. B25*

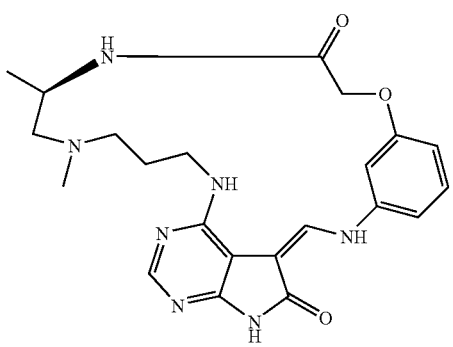

41349568-AACCo. No. 100; Ex. No. B16b*

Analytical Methods

LCMS

The mass of some compounds was recorded with LCMS (liquid chromatography mass spectrometry). The methods used are described below.

General Procedure A

The HPLC measurement was performed using an Alliance HT 2790 (Waters) system comprising a quaternary pump with degasser, an autosampler, a column oven (set at 40° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

General procedure B

The LC measurement was performed using an Acquity HPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

General Procedure C

The HPLC measurement was performed using an Agilent 1100 series liquid chromatography system comprising a binary pump with degasser, an autosampler, a column oven, a UV detector and a column as specified in the respective methods below. Flow from the column was split to a MS spectrometer. The MS detector was configured with an electrospray ionization source. The capillary voltage was 3 kV, the quadrupole temperature was maintained at 100° C. and the desolvation temperature was 300° C. Nitrogen was used as the nebulizer gas. Data acquisition was performed with an Agilent Chemstation data system.

Method 1:

In addition to the general procedure A: Reversed phase HPLC was carried out on an Xterra MS C18 column (3.5 μm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 1 minute, 100% B for 1 minute and reequilibrate with 100% A for 1.5 minutes. An injection volume of 10 μl was used. Cone voltage was 10 V for positive ionization mode and 20 V for negative ionization mode.

Method 2:

In addition to the general procedure A: Reversed phase HPLC was carried out on a Chromolith (4.6×25 mm) with a flow rate of 3 ml/min. Three mobile phases (mobile phase A: 95% 25 mM ammoniumacetate+5% acetonitrile; mobile phase B: acetonitrile; mobile phase C: methanol) were employed to run a gradient condition from 96% A, 2% B and 2% C, to 49% B and 49% C in 0.9 minutes, to 100% B in 0.3 minutes and hold for 0.2 minutes. An injection volume of 2 μl was used. Cone voltage was 10 V for positive ionization mode and 20 V for negative ionization mode.

Method 3:

In addition to the general procedure A: Reversed phase HPLC was carried out on an Xterra MS C18 column (3.5 μm, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 1% A, 49% B and 50% C in 6.5 minutes, to 1% A and 99% B in 1 minute and hold these conditions for 1 minute and reequilibrate with 100% A for 1.5 minutes. An injection volume of 10 μl was used. Cone voltage was 10 V for positive ionization mode and 20 V for negative ionization mode.

Method 4:

In addition to the general procedure B: Reversed phase HPLC was carried out on a bridged ethylsiloxane/silica (BEH) C18 column (1.7 μm, 2.1×50 mm) with a flow rate of 0.8 ml/min. Two mobile phases (mobile phase A: 0.1% formic acid in $H_2O$/methanol 95/5; mobile phase B: methanol) were used to run a gradient condition from 95% A to 5% A, 95% B in 1.3 minutes and hold for 0.2 minutes. An injection volume of 0.5 μl was used. Cone voltage was 10 V for positive ionization mode and 20 V for negative ionization mode.

Method 5:

In addition to general procedure C: Reversed phase HPLC was carried out on a YMC-Pack ODS-AQ C18 column (4.6×50 mm) with a flow rate of 2.6 ml/min. A gradient run was used from 95% water and 5% acetonitrile to 95% acetonitrile in 4.80 minutes and was hold for 1.20 minutes. Mass spectra were acquired by scanning from 100 to 1400. Injection volume was 10 μl. Column temperature was 35° C.

Method 6:

In addition to general procedure C: Reversed phase HPLC was carried out on a YMC-Pack ODS-AQ C18 column (4.6×50 mm) with a flow rate of 2.6 ml/min. A gradient run was used from 88% water and 12% acetonitrile to 88% acetonitrile in 3.40 minutes and was hold for 1.20 minutes. Mass spectra were acquired by scanning from 110 to 1000. Injection volume was 10 μl. Column temperature was 35° C.

Method 7:

In addition to general procedure C: Reversed phase HPLC was carried out on a SB-C18 1 pk column (4.6×30 mm, 1.8 μm) with a flow rate of 4.0 ml/min. A gradient run was used from 88% water and 12% acetonitrile to 88% acetonitrile in 1.10 minutes and was hold for 0.50 minutes. Mass spectra were acquired by scanning from 150 to 1000. Injection volume was 1 μl. Column temperature was 65° C.

Method 8:

Reversed phase HPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (25 mM ammonium acetate in $H_2O$/acetonitrile 95/5; mobile phase B: acetonitrile) were used to run a gradient condition from 95% A and 5% B to 5% A and 95% B in 1.3 minutes and hold for 0.3 minutes. An injection volume of 0.5 μl was used. Cone voltage was 10 V for positive ionization mode and 20 V for negative ionization mode.

Melting Points

For a number of compounds, melting points were obtained with a Kofler hot bench, consisting of a heated plate with linear temperature gradient, a sliding pointer and a temperature scale in degrees Celsius.

When a compound is a mixture of isomers which give different peaks in the LCMS method, only the retention time of the largest peak is given in the LCMS tables below.

For some compounds the Z/E ratio was measured. As was mentioned in the beginning of the experimental part, it was observed that these ratios are dependent on the conditions of the measurement. The reported Z/E ratios in table 2a and 2b, were measured by NMR in a DMSO-d6 solution at room temperature after equilibrium. A compound designated as 'Z-isomer' was characterized using the above mentioned conditions. No Z/E ratio was specified for those compounds from the present invention, for which no Z/E ratio measurement was performed. In such a case the compound can be regarded as a Z/E mixture.

TABLE 2a

LCMS positive ion mode

| Co. Nr. | $R_t$ (min) | (MH$^+$) | LCMS method | Physico-chemical data |
|---|---|---|---|---|
| 16 | 3.57 | 451 | 1 | Z/E (±79/21) |
| 17 | 0.95 | 437 | 4 | Z/E (±16/1) |
| 18 | 1.11 | 465 | 4 | Z/E (±47/1) |
| 14 | 0.81 | 469 | 2 | |
| 20 | 1.17 | 483 | 4 | Z/E (±68/32) |
| 2 | 4.54 | 454 | 3 | |
| 21 | 1.06 | 508 | 4 | |
| 22 | 0.98 | 453 | 4 | |
| 5 | 0.95 | 607 | 4 | m.p.: >240° C. Z-isomer |
| 23 | 0.72 | 498 | 2 | Z/E (±75/25) |
| 24 | 0.82 | 462 | 2 | Z/E (±78/22) |
| 25 | 1.25 | 469 | 4 | Z/E (±93/7) |
| 98 | 0.93 | 432 | 4 | Z/E (±95/5) |
| 26 | 0.76 | 446 | 2 | |
| 11 | 0.54 | 434 | 4 | Z/E (±65/35) |
| 27 | n.d. | n.d. | — | Z/E (±92/8) |
| 1 | 1.21 | 595 | 4 | |
| 10 | 0.98 | 494 | 2 | Z/E (±78/22) |
| 28 | 0.64 | 508 | 4 | Z/E (±52/48) |
| 29 | 0.70 | 522 | 4 | Z/E (±65/35) |
| 31 | 1.14 | 453 | 4 | Z-isomer |
| 32 | 5.33 | 467 | 3 | Z/E (±96/4) |
| 9 | 0.91 | 439 | 2 | Z isomer |
| 34 | 0.76 | 522 | 4 | Z/E (±80/20) |
| 35 | 2.75 | 409 | 5 | |
| 36 | 1.24 | 437 | 4 | |
| 37 | 1.21 | 453 | 4 | |
| 38 | 1.92 | 425 | 5 | |
| 39 | 1.28 | 423 | 4 | |
| 40 | 2.17 | 395 | 5 | |
| 41 | 2.48 | 423 | 5 | |
| 42 | 1.21 | 409 | 4 | |
| 43 | 1.06 | 409 | 4 | |

TABLE 2a-continued

LCMS positive ion mode

| Co. Nr. | Rt (min) | (MH+) | LC/MS method |
|---|---|---|---|
| 45 | 1.55 | 439 | 6 |
| 47 | 1.14 | 467 | 4 |
| 48 | 0.96 | 480 | 6 |
| 49 | 3.13 | 471 | 5 |
| 50 | 0.97 | 494 | 6 |
| 51 | 1.00 | 466 | 6 |
| 52 | 1.24 | 457 | 4 |
| 53 | 2.57 | 465 | 6 |
| 54 | 1.30 | 464 | 5 |
| 55 | 1.98 | 429 | 6 |
| 56 | 0.90 | 443 | 7 |
| 57 | 3.29 | 457 | 5 |
| 58 | 1.20 | 395 | 4 |
| 59 | 3.20 | 437 | 5 |
| 60 | 2.38 | 429 | 6 |
| 61 | 1.37 | 457 | 4 |
| 62 | 2.03 | 453 | 6 |
| 63 | 2.52 | 443 | 6 |
| 64 | 1.41 | 471 | 4 |
| 65 | 1.43 | 485 | 4 |
| 66 | 2.26 | 467 | 6 |
| 67 | 1.05 | 480 | 6 |
| 68 | 1.09 | 508 | 6 |
| 69 | 2.73 | 451 | 6 |
| 70 | 1.29 | 423 | 4 |
| 71 | 2.56 | 437 | 6 |
| 72 | 2.16 | 481 | 6 |
| 73 | 0.99 | 436 | 6 |
| 74 | 0.52 | 478 | 7 |
| 75 | 0.49 | 466 | 7 |
| 76 | 1.25 | 467 | 4 |
| 77 | 1.03 | 450 | 6 |
| 78 | 1.43 | 471 | 4 |
| 79 | 0.99 | 436 | 6 |
| 80 | 0.71 | 450 | 4 |
| 81 | 1.03 | 464 | 6 |
| 82 | 0.66 | 422 | 4 |
| 83 | 1.09 | 464 | 6 |
| 84 | 2.10 | 481 | 6 |
| 85 | 2.19 | 495 | 6 |
| 86 | 1.32 | 457 | 4 |
| 87 | 0.52 | 494 | 7 |
| 88 | 2.28 | 423 | 6 |
| 89 | 1.06 | 508 | 6 |
| 90 | 1.33 | 484 | 6 |
| 91 | 1.34 | 498 | 6 |
| 92 | 0.76 | 534 | 6 |
| 8 | 1.59 | 480 | 6 |
| 93 | 1.10 | 521 | 6 |
| 94 | 1.11 | 507 | 6 |
| 6 | 0.78 | 496 | 4 |
| 95 | 1.23 | 510 | 6 |
| 7 | 1.20 | 521 | 6 |
| 96 | 0.79 | 535 | 4 |
| 114 | 0.79 | 494 | 8 |
| 115 | 0.90 | 508 | 8 |
| 116 | 1.18 | 520 | 5 |
| 117 | 1.25 | 562 | 5 |
| 118 | 0.58 | 482 | 8 |
| 119 | 0.62 | 496 | 8 |
| 120 | 0.95 | 522 | 8 |
| 121 | 0.88 | 508 | 8 |
| 122 | 1.31 | 548 | 5 |
| 123 | 0.66 | 454 | 8 |
| 124 | 0.81 | 494 | 8 |
| 125 | 0.64 | 468 | 8 |
| 126 | 1.19 | 548 | 5 |
| 127 | 1.02 | 463 | 8 |
| 128 | 1.06 | 477 | 8 |
| 113 | 1.08 | 477 | 8 |
| 129 | 0.80 | 469 | 8 |
| 112 | 0.82 | 469 | 8 |
| 130 | 1.13 | 491 | 8 |
| 131 | 1.66 | 535 | 5 |
| 132 | 0.77 | 455 | 8 |
| 133 | 0.63 | 507 | 8 |
| 134 | 2.76 | 483 | 5 |
| 135 | 0.62 | 507 | 8 |
| 136 | 0.69 | 521 | 8 |
| 137 | 0.59 | 493 | 8 |
| 138 | 0.75 | 535 | 8 |
| 139 | 0.68 | 549 | 8 |
| 140 | 1.22 | 534 | 5 |
| 141 | 0.71 | 521 | 8 |
| 142 | 0.80 | 395 | 8 |
| 143 | 0.58 | 395 | 8 |
| 144 | 0.93 | 467 | 8 |
| 145 | 1.11 | 507 | 8 |
| 146 | 0.71 | 425 | 8 |
| 147 | 0.73 | 455 | 8 |
| 148 | 0.55 | 424 | 8 |
| 149 | 0.64 | 451 | 8 |
| 150 | 0.58 | 455 | 8 |
| 151 | 0.55 | 425 | 8 |
| 152 | 0.71 | 482 | 8 |
| 153 | 0.68 | 452 | 8 |
| 154 | 0.66 | 422 | 8 |
| 155 | 0.67 | 511 | 8 |
| 156 | 0.66 | 481 | 8 |
| 105 | 0.53 | 455 | 8 |
| 105 | 1.32 | 455 | 5 |
| 157 | 0.56 | 484 | 8 |
| 107 | 0.94 | 549 | 8 |
| 158 | 0.89 | 543 | 8 |
| 108 | 0.95 | 528 | 8 |
| 109 | 0.87 | 564 | 8 |
| 159 | 0.59 | 438 | 8 |
| 160 | 0.81 | 514 | 8 |
| 110 | 1.07 | 514 | 8 |
| 161 | 0.85 | 468 | 8 |
| 162 | 0.83 | 482 | 8 |
| 163 | 0.88 | 482 | 8 |
| 103 | 1.52 | 468 | 5 |
| 102 | 1.50 | 468 | 5 |
| 164 | 0.74 | 454 | 8 |
| 165 | 0.64 | 480 | 8 |
| 166 | 0.72 | 466 | 8 |
| 167 | 0.52 | 410 | 8 |
| 168 | 0.58 | 450 | 8 |
| 99 | 0.57 | 438 | 8 |
| 100 | | | |
| 169 | 0.82 | 500 | 8 |
| 170 | 0.57 | 464 | 8 |
| 171 | 0.53 | 478 | 8 |
| 172 | 0.67 | 480 | 8 |
| 173 | 0.62 | 468 | 8 |
| 174 | 0.98 | 516 | 8 |
| 175 | 0.67 | 492 | 8 |
| 176 | 0.81 | 514 | 8 |
| 177 | 0.87 | 502 | 8 |
| 178 | 0.82 | 494 | 8 |
| 179 | 0.76 | 468 | 8 |
| 180 | 0.88 | 528 | 8 |
| 181 | 0.84 | 514 | 8 |
| 182 | 1.10 | 466 | 5 |
| 183 | 1.19 | 436 | 5 |
| 184 | 1.37 | 454 | 5 |
| 185 | 1.58 | 488 | 5 |
| 101 | 0.76 | 512 | 8 |
| 186 | 1.32 | 440 | 5 |
| 187 | 1.41 | 470 | 5 |
| 188 | 0.65 | 466 | 8 |
| 189 | 0.77 | 480 | 8 |
| 190 | 0.77 | 502 | 8 |
| 191 | 0.80 | 530 | 8 |
| 192 | 0.67 | 484 | 8 |
| 193 | 0.76 | 514 | 8 |
| 194 | 0.80 | 500 | 8 |
| 195 | 0.72 | 524 | 8 |
| 196 | 0.62 | 512 | 8 |
| 197 | 0.81 | 514 | 8 |
| 198 | 1.34 | 456 | 5 |

TABLE 2a-continued

| | LCMS positive ion mode | | |
|---|---|---|---|
| 199 | 0.75 | 454 | 8 |
| 200 | 0.86 | 502 | 8 |
| 201 | 0.95 | 502 | 8 |
| 202 | 0.67 | 498 | 8 |
| 203 | 0.61 | 484 | 8 |
| 204 | 0.69 | 510 | 8 |
| 111 | 1.15 | 487 | 8 |
| 205 | 0.97 | 516 | 8 |
| 206 | 0.74 | 498 | 8 |
| 104 | 0.70 | 502 | 8 |
| 207 | 0.50 | 452 | 8 |
| 208 | 1.64 | 488 | 5 |

$R_t$ (retention time in minutes),
$(MH^+)$ peak,
LCMS method used and physico-chemical data
(m.p.: melting point).
n.d.: not determined TABLE 2b

| | LCMS negative ion mode | | | |
|---|---|---|---|---|
| Co. Nr. | $R_t$ (min) | $(MH^-)$ | LCMS method | Physico-chemical data |
| 4 | 0.82 | 421 | 2 | |
| 97 | 0.85 | 492 | 2 | m.p.: >240° C. Z-isomer |
| 13 | 0.89 | 453 | 2 | Z/E (±96/4) |
| 12 | 0.87 | 453 | 2 | Z/E (±79/21) |
| 46 | 1.05 | 451 | 4 | |
| 44 | 0.98 | 437 | 4 | |
| 33 | 1.23 | 493 | 4 | Z/E (±82/18) |
| 3 | 0.88 | 520 | 2 | m.p.: >240° C. Z-isomer |

$R_t$ (retention time in minutes),
$(MH^-)$ peak,
LCMS method used and physico-chemical data
(m.p.: melting point).

C. PHARMACOLOGICAL EXAMPLE

C1. Kinase Profiling

The in vitro inhibition of a panel of kinases was assessed using either the scintillation proximity assay (SPA) as described by Cook, N. D. et al., Advances in Experimental Medicine and Biology (1991), 36; p. 525-528; or the Fluorescence Resonance Energy Transfer (FRET) technology as described by Rodems, S. M. et al., Assay Drug Develop. Technol. (2002), 1; p. 9-19.

In the SPA technology the activity of the kinase of interest is measured using an appropriate biotinylated substrate that is incubated with the aforementioned kinase protein in the presence of ($^{33}$P) radiolabeled ATP. ($^{33}$P) Phosporylation of the substrate is subsequently measured through binding of the phosphorylated substrate to streptavidine coated beads that are based on the scintillant poly(vinyl toluene) (PVT-Beads). The scintillation intensity is detected by imaging on Leadseeker.

In the FRET technology the activity of the kinase of interest is measured using an appropriate substrate that is labeled with two fluorophores (coumarin and fluorescein). Phosphorylation is determined using a developing reagent comprising a protease that recognizes and cleaves nonphosphorylated peptides. Cleavage will disturb the FRET between the fluorescein and coumarin on the peptide. Uncleaved, phosphorylated peptides maintain the FRET signal. A ratiometric readout of the donor emission over the acceptor emission quantitates the reaction process.

Detailed Description

All kinases are pre-diluted to a 10× working concentration prior to addition into the assay. The composition of the dilution buffer for each kinase is detailed below.

C1.1 PLK-4 Human

In a final reaction volume of 30 µl PLK4 (h) (19 µg/ml) is incubated with 50 mM Hepes pH 8.0, 10 mM MgCl$_2$, 50 mM NaCl, 1 mM NaF, 1 mM DTT, 10 µM of peptide Biotin-RPRGQRDSSYYWE-OH, 1 µM ATP and 2 nM [γ-$^{33}$P-ATP] (6.0 µCi/ml). After incubation of 60 minutes at room temperature, the reaction is stopped by addition of 40 µl, of stop solution containing 8.7 mM EDTA, BSA 0.17%, 0.17% Triton X-100, 1.7 mg/ml SPA beads (GE-healthcare). The plate is centriguged and read for Scintillation imaging on Leadseeker.

C1.2 Aurora-B Human

In a final reaction volume of 30 µl, AuroraB (h) (0.5 µg/ml) is incubated with 60 mM Hepes pH 7.5, 3 mM MgCl$_2$, 3 mM MnCl$_2$, 3 µM Na$_3$VO$_4$, 0.05 mg/ml PEG, 2 mM DTT, 3 µM Biotin-LRRWSLGLRRWSLGLRRWSLGLRRWSLG-OH, 0.5 µM ATP and 2.2 nM [γ-$^{33}$P-ATP] (6.8 µCi/ml). After incubation of 60 minutes at room temperature, the reaction is stopped by addition of 40 µL of stop solution containing 8.7 mM EDTA, BSA 0.17%, 0.17% Triton X-100, 5 mg/ml SPA beads (GE-healthcare). The plate is centriguged and read for Scintillation imaging on Leadseeker.

C1.3 GSK-3β Human

In a final reaction volume of 30 µl, GSK3β (h) (1 µg/ml) is incubated with 25 mM Tris pH 7.4, 10 mM MgCl$_2$, 1 mM DTT, 1 µM peptide Biotin-KRREILSRRPSYR-OH, 1 µM ATP and 2 nM [γ-$^{33}$P-ATP] (6.0 µCi/ml). After incubation of 60 minutes at room temperature, the reaction is stopped by addition of 40 mL of stop solution containing 8.7 mM EDTA, BSA 0.17%, 0.17% Triton X-100, 6.25 mg/ml SPA beads (GE-healthcare). The plate is centriguged and read for Scintillation imaging on Leadseeker.

C1.4 CDK1/CyclinB Human

In a final reaction volume of 10 µl, CDK1/CyclinB (h) (0.2 µg/ml) is incubated with 50 mM Hepes pH 7.5, 10 mM MgCl$_2$, 1 mM EGTA, 0.01% Brij-35, 2 µM Z'lyte Ser/Thr peptide 12 and 10 µM ATP (Invitrogen's FRET assay). After incubation of 60 minutes at room temperature, the reaction is stopped by addition of 5 µL development reagent containing protease mix. After 60 minutes room temperature the development reaction is stopped by adding 5 µl stop solution. The plate is then read in fluorescence plate reader with excitation: 390 nm and dual emission: 460 and 538 nm. Emission ratio is determined to the formula=Emission signal intensity at 460 nm/Emission signal intensity at 538 nm.

The following table provides the pIC50 values of the compounds according to the invention, obtained using the above mentioned kinase assays.

TABLE 3

| Compound No. | PLK4 pic50 | CDK1 pic50 | AuroraB pic50 | GSK3B pic50 |
|---|---|---|---|---|
| 17 | 5.79 | | <5 | |
| 18 | 5.32 | <5 | <5 | 6.05 |
| 4 | 6.99 | | <5 | |
| 2 | 5.34 | 5.25 | <5 | 5.93 |
| 21 | 5.73 | <5 | <5 | 5.33 |
| 3 | 5.5 | <5 | <5 | 5.73 |
| 5 | 5.38 | <5 | 5.08 | 5.09 |
| 24 | 5.82 | | <5 | |

TABLE 3-continued

| Compound No. | PLK4 pIC50 | CDK1 pIC50 | AuroraB pIC50 | GSK3B pIC50 |
|---|---|---|---|---|
| 15 | 5.26 | | <5 | |
| 98 | <5 | <5 | <5 | 6.11 |
| 26 | <5 | <5 | <5 | 5.58 |
| 11 | 5.51 | | | |
| 1 | 5.16 | <5 | <5 | 5.74 |
| 31 | 6.28 | 5.33 | 5.86 | 6.51 |
| 32 | 5.98 | | | |
| 33 | 5.27 | 5.14 | 5 | 5.33 |
| 9 | 7.28 | 6.92 | 7.29 | 7.63 |
| 35 | 7.01 | 6.56 | 6.88 | 7.4 |
| 36 | 5.65 | <5 | <5 | 5.7 |
| 37 | 6.26 | 5.67 | 6.67 | 7.07 |
| 38 | 5.58 | <5 | <5 | 5.44 |
| 39 | 5.43 | 5.25 | 5.9 | 6.55 |
| 40 | 5.31 | 5.15 | 5.08 | 5.82 |
| 41 | 5.75 | 5.3 | <5 | 5.61 |
| 42 | 5.77 | 5.23 | 5.86 | 6.53 |
| 43 | 5.58 | 5.37 | 5 | 5.6 |
| 44 | 5.22 | <5 | <5 | 5.31 |
| 45 | 6.27 | 5.66 | 6.62 | 6.92 |
| 46 | 5.18 | <5 | 5.13 | 5.07 |
| 47 | 5.64 | <5 | 5.06 | 5.32 |
| 49 | 5.13 | <5 | <5 | <5 |
| 52 | 5.02 | <5 | 5.18 | 5.35 |
| 53 | 5.63 | <5 | <5 | 6.1 |
| 56 | 5.46 | 5.17 | 6.12 | 6.78 |
| 57 | 5.32 | <5 | 5.97 | 6.58 |
| 58 | 6.75 | 6.16 | 6.33 | 6.88 |
| 59 | 5.36 | <5 | 5.29 | 5.98 |
| 60 | 5.76 | 6.64 | 6.05 | 6.58 |
| 61 | 5.75 | <5 | 7.29 | 7.2 |
| 62 | 6.9 | 6.46 | 7.75 | 7.57 |
| 63 | 6.52 | 6.1 | 7.01 | 7.68 |
| 64 | 5.67 | <5 | 6.1 | 7.37 |
| 65 | 5.05 | <5 | <5 | 5.86 |
| 66 | 6.32 | 5.63 | 6.46 | 7.11 |
| 67 | 5.25 | 6.22 | <5 | 6.75 |
| 68 | 5.74 | <5 | <5 | 5.04 |
| 69 | 5.47 | <5 | 5.3 | 5.97 |
| 70 | 6.75 | 5.61 | 6.8 | 7.28 |
| 71 | 6.7 | 5.56 | 6.15 | 7.21 |
| 72 | 5.84 | <5 | 5.72 | 6.24 |
| 73 | 5.43 | 5.75 | <5 | 6.07 |
| 74 | 5.25 | <5 | <5 | <5 |
| 75 | 5.23 | 5.27 | <5 | 6.25 |
| 76 | 5.72 | <5 | 6.28 | 6.54 |
| 78 | <5 | <5 | 5.12 | 5.66 |
| 79 | 5.48 | 5.05 | 5.04 | 6.09 |
| 80 | 5.85 | <5 | <5 | 5.33 |
| 81 | 5.97 | <5 | <5 | 5.56 |
| 82 | 5.21 | <5 | <5 | 5.98 |
| 83 | 5.78 | <5 | <5 | 5.66 |
| 86 | 5.9 | <5 | 5.47 | 6.42 |
| 87 | <5 | <5 | <5 | 6.17 |
| 88 | 5.85 | <5 | 5.33 | 6.26 |
| 90 | 5.26 | <5 | <5 | 6.21 |
| 91 | <5 | <5 | <5 | 6.01 |
| 92 | 5.89 | <5 | <5 | 5.83 |
| 94 | 5.29 | <5 | <5 | 5.98 |
| 6 | 5.21 | 5 | <5 | <5 |
| 95 | 5.57 | 5.94 | <5 | 5.5 |
| 7 | 6.12 | 5.77 | <5 | 7.13 |
| 96 | 6.13 | 5.47 | <5 | 6.15 |

| Compound No. | PLK4 pIC50 | CDK1 pIC50 | AuroraB pIC50 | GSK3B pIC50 |
|---|---|---|---|---|
| 17 | 5.79 | | <5 | |
| 18 | 5.32 | <5 | <5 | 6.05 |
| 14 | <5 | | <5 | |
| 19 | <5 | | <5 | |
| 20 | | | <5 | |
| 13 | <5 | | <5 | |
| 22 | <5 | | <5 | |
| 12 | <5 | | | |
| 24 | 5.82 | | <5 | |
| 15 | | | <5 | |
| 25 | <5 | | | |
| 98 | <5 | <5 | <5 | 6.11 |
| 26 | <5 | <5 | <5 | 5.58 |
| 11 | 5.51 | | | |
| 28 | <5 | <5 | <5 | <5 |
| 29 | <5 | | | |
| 30 | <5 | | | |
| 31 | 6.28 | 5.33 | 5.8 | 6.505 |
| 32 | 5.98 | | | |
| 33 | 5.27 | 5.14 | | |
| 9 | 7.26 | 6.88 | 7.3 | 7.68 |
| 34 | <5 | | | |
| 35 | 7.01 | 6.56 | 6.88 | 7.4 |
| 36 | 5.65 | <5 | <5 | 5.7 |
| 37 | 6.26 | 5.67 | 6.67 | 7.07 |
| 38 | 5.58 | <5 | <5 | 5.44 |
| 39 | 5.43 | 5.25 | 5.9 | 6.55 |
| 40 | 5.31 | 5.15 | 5.08 | 5.82 |
| 41 | 5.75 | 5.3 | <5 | 5.61 |
| 42 | 5.77 | 5.23 | 5.86 | 6.53 |
| 43 | 5.58 | 5.37 | | 5.6 |
| 44 | 5.22 | <5 | <5 | 5.31 |
| 45 | 6.27 | 5.66 | 6.62 | 6.92 |
| 46 | 5.18 | <5 | 5.13 | |
| 47 | 5.64 | <5 | 5.06 | 5.32 |
| 48 | <5 | <5 | <5 | <5 |
| 49 | | <5 | <5 | <5 |
| 50 | <5 | <5 | <5 | <5 |
| 51 | <5 | <5 | <5 | <5 |
| 52 | 5.02 | <5 | 5.18 | 5.35 |
| 53 | 5.63 | <5 | <5 | 6.1 |
| 54 | <5 | <5 | <5 | <5 |
| 55 | <5 | <5 | <5 | <5 |
| 56 | 5.46 | ~5.17 | 6.12 | 6.78 |
| 57 | 5.32 | <5 | 5.97 | 6.58 |
| 58 | 6.75 | 6.16 | 6.33 | 6.88 |
| 59 | 5.36 | <5 | 5.29 | 5.98 |
| 60 | 5.76 | 6.64 | 6.05 | |
| 61 | 5.75 | <5 | 7.29 | 7.2 |
| 62 | 6.9 | 6.46 | 7.75 | 7.57 |
| 63 | 6.52 | 6.1 | 7.01 | 7.68 |
| 64 | 5.67 | <5 | 6.1 | 7.37 |
| 65 | 5.05 | <5 | <5 | 5.86 |
| 66 | 6.32 | 5.63 | 6.46 | 7.11 |
| 67 | 5.25 | 6.22 | <5 | 6.75 |
| 68 | 5.74 | <5 | <5 | |
| 69 | | <5 | 5.3 | 5.97 |
| 70 | 6.75 | 5.61 | 6.8 | 7.28 |
| 71 | 6.7 | 5.56 | 6.15 | 7.21 |
| 72 | | <5 | 5.72 | 6.24 |
| 73 | 5.43 | 5.75 | <5 | 6.07 |
| 74 | 5.25 | <5 | <5 | <5 |
| 75 | 5.23 | 5.27 | <5 | 6.25 |
| 76 | 5.72 | <5 | 6.28 | 6.54 |
| 78 | <5 | <5 | 5.12 | 5.66 |
| 79 | 5.48 | 5.05 | 5.04 | 6.09 |
| 80 | 5.85 | <5 | <5 | 5.33 |
| 81 | 5.97 | <5 | <5 | 5.56 |
| 82 | 5.21 | <5 | <5 | 5.98 |
| 83 | 5.78 | <5 | <5 | 5.66 |
| 84 | 5.53 | | <5 | 6.43 |
| 85 | 5.3 | | <5 | 5.96 |
| 86 | 5.9 | <5 | 5.47 | 6.42 |
| 87 | <5 | <5 | <5 | 6.17 |
| 88 | 5.85 | <5 | 5.33 | 6.26 |
| 89 | <5 | <5 | <5 | <5 |
| 90 | 5.26 | <5 | <5 | 6.21 |
| 91 | <5 | <5 | <5 | 6.01 |
| 92 | 5.89 | <5 | <5 | 5.83 |
| 8 | <5 | <5 | <5 | <5 |
| 93 | 5.14 | <5 | <5 | 5 |
| 94 | 5.29 | <5 | <5 | 5.98 |
| 6 | 5.21 | ~5 | <5 | <5 |
| 95 | 5.57 | 5.94 | <5 | 5.5 |
| 7 | 6.12 | 5.77 | <5 | 7.13 |
| 96 | 6.13 | 5.47 | <5 | 6.15 |
| 114 | 6.585 | <5 | <5 | 6.275 |
| 115 | 6.26 | 5.23 | 5.61 | 6.15 |
| 116 | 5.23 | <5 | <5 | 5.51 |
| 117 | 6.5 | <5 | <5 | 5.58 |
| 118 | <5 | <5 | <5 | <5 |
| 119 | 5.13 | 5.2 | <5 | <5 |
| 120 | 6.67 | 5.86 | 5.58 | 6.73 |

TABLE 3-continued

| | | | | |
|---|---|---|---|---|
| 121 | 7.22 | 6.24 | 6.15 | 7.45 |
| 122 | 6.07 | 5.33 | <5 | 6.24 |
| 123 | <5 | <5 | <5 | <5 |
| 124 | 7.34 | 7.53 | 6.13 | 7.33 |
| 125 | <5 | <5 | <5 | 5.01 |
| 126 | 6.17 | <5 | <5 | 5.41 |
| 127 | <5 | <5 | <5 | <5 |
| 128 | <5 | <5 | <5 | <5 |
| 113 | | <5 | 5.86 | <5 |
| 129 | 5.71 | <5 | 5.26 | <5 |
| 112 | 6.98 | 7.32 | 6.72 | 6.94 |
| 130 | 5.31 | <5 | 6.51 | <5 |
| 131 | 6.345 | <5 | <5 | 5.195 |
| 132 | 6.38 | <5 | <5 | <5 |
| 133 | 7.21 | 6.8 | 5.81 | 6.95 |
| 134 | 6.6 | 5.68 | 6.59 | 5.35 |
| 135 | 6.67 | <5 | <5 | 6.2 |
| 136 | 7.19 | 5.88 | 5.55 | 7.23 |
| 137 | 7.3 | 5.83 | ~5 | 6.405 |
| 138 | 6.74 | 5.8 | <5 | 6.75 |
| 139 | 6.64 | <5 | <5 | 5.87 |
| 140 | 6.28 | 5.81 | <5 | 7.29 |
| 141 | 6.16 | 5.12 | <5 | 6.35 |
| 142 | 7.3 | 6.83 | 6.93 | 7.7 |
| 143 | 5.5 | <5 | 5.63 | 6.44 |
| 144 | 7.03 | 6.12 | 7.25 | 7.32 |
| 145 | 6.61 | <5 | 6.41 | 6.4 |
| 146 | 7.34 | 7.21 | 7.24 | 7.56 |
| 147 | 6.95 | 6.91 | 6.6 | 6.5 |
| 148 | 5.74 | <5 | 5.35 | 6 |
| 149 | 5.3 | <5 | <5 | 6.52 |
| 150 | <5 | <5 | 5.23 | <5 |
| 151 | 5.46 | <5 | 5.54 | 6.03 |
| 152 | 5.3 | <5 | <5 | <5 |
| 153 | 5.59 | <5 | <5 | 5.79 |
| 154 | 5.55 | <5 | <5 | 6.18 |
| 155 | 5.06 | <5 | <5 | 5.22 |
| 156 | 5.2 | <5 | <5 | 6.24 |
| 105 | 6.1 | <5 | 5.94 | 6.24 |
| 157 | 5.35 | <5 | 5.28 | <5 |
| 107 | 5.98 | | 6.56 | 5.7 |
| 158 | 5.56 | | 6.48 | 5.45 |
| 108 | 6.05 | | 6.21 | 5.81 |
| 109 | 6.65 | | 7.04 | 6.85 |
| 159 | 5.36 | | <5 | 5.54 |
| 160 | 5.93 | | <5 | 5.31 |
| 110 | 6.39 | | 6.27 | 6.04 |
| 161 | 5.29 | | 5.13 | 6.08 |
| 162 | 5.51 | | <5 | 5.6 |
| 163 | 6.23 | | 5.19 | 7.2 |
| 102 | 5.71 | | 5.19 | 7.11 |
| 103 | 5.73 | | 5.06 | 6.96 |
| | 5.38 | | 5.11 | 6.1 |
| 164 | 5.44 | | 5.28 | 6.12 |
| 165 | 5.14 | | <5 | 5.21 |
| | | | <5 | 5.24 |
| | 5.64 | | <5 | 6.19 |
| 166 | 5.66 | | <5 | 5.99 |
| 167 | 5.62 | | 5.17 | 6.03 |
| | 5.62 | | 5.49 | 5.95 |
| 168 | <5 | | <5 | 5.12 |
| | 5.21 | | <5 | 5.24 |
| 99 | 6.38 | | <5 | 5.69 |
| 169 | 5.74 | | 5.45 | 5.73 |
| | 5.7 | | 5.45 | 5.49 |
| 170 | 5.13 | | <5 | 5.05 |
| 171 | <5 | | <5 | 6.51 |
| 172 | <5 | | <5 | 5.18 |
| 173 | 5.37 | | <5 | 6.24 |
| 174 | <5 | | <5 | 5.79 |
| | <5 | | <5 | 5.73 |
| 175 | <5 | | <5 | 5.8 |
| | <5 | | <5 | 5.87 |
| 176 | 6.33 | | 5.17 | 5.02 |
| 177 | 5.36 | | 5.6 | 7.18 |
| | 5.14 | | 5.19 | 7.34 |
| 178 | 5.24 | | <5 | 5.63 |
| | 5.13 | | <5 | 5.47 |
| 179 | 6.27 | | 5.59 | 5.55 |
| | 6.12 | | 5.37 | 5.73 |
| 180 | <5 | | <5 | 5.46 |
| | <5 | | <5 | 5.27 |
| 181 | <5 | | <5 | 5.65 |
| 101 | 5.5 | | <5 | 6.34 |
| 188 | <5 | | <5 | 6.4 |
| 189 | <5 | | <5 | 6.37 |
| 190 | <5 | | <5 | 5.81 |
| 191 | 5.78 | | 5.47 | 6.06 |
| | 5.68 | | 5.45 | 5.99 |
| | <5 | | <5 | 5.23 |
| 192 | <5 | | <5 | 5.3 |
| 193 | <5 | | <5 | 6.11 |
| | 5.16 | | <5 | 6.52 |
| 194 | 5.29 | | <5 | 6.34 |
| | | | | <5 |
| 196 | | | <5 | 5.82 |
| 197 | | | <5 | 5.45 |
| 199 | | | 5.25 | 6.08 |
| 200 | | | 4.99 | 5.77 |
| 201 | | | | 6.02 |
| 202 | | | 5.4 | 5.33 |
| 203 | | | 6.03 | 5.76 |
| 204 | | | <5 | 5.87 |
| 111 | | | <5 | 5.51 |
| 205 | | | <5 | 7.03 |
| 206 | | | 5.61 | 5.91 |
| 104 | | | 5.47 | 5.96 |
| 207 | | | 5.73 | 5.39 |

C.2. Cellular Proliferation Assay

In vivo functional properties of these compounds was tested in cellular proliferation assays on a panel of different cell lines in the presence of 10% FCS serum (37° C. and 5% (v/v) $CO_2$). In a first step these cells were seeded and incubated for 24 hours in the absence of compound. In the second step the cells were incubated for 72 hours with the compounds to be tested for 72 hours. The viable cell number was finally assessed in a standard Alamar blue cell viability assay.

Detailed Description

The viable cell number was assessed by incubation for either 4 h (HCT-116, H1299, H460) 6 h (SKOV3, HT29, U87-MG, Colo205) or 24 h (A2780, PC3, MDA-MB-231, A549, MCF-7) with Alamar blue (Resazurin 9 μg/ml, K-Ferrocyanide 90 μM K-Ferricyanide 90 μM) and the converted fluorescent product was quantified on a fluorescent plate readed (544 nm/590 nm). Effect of the compounds is calculated as of on control cells.

pIC50 values obtained for compounds tested are presented in Table 4.

TABLE 4

| Co. No. | A2780 | SKOV3 | HT-29 | HCT-116 | Colo205 | H1299 | A549 | H460 | MDA/MB231 | MCF-7 | DU-145 | A431 | U87MG | PC-3 | SK-N-SH |
|---|---|---|---|---|---|---|---|---|---|---|---|---|---|---|---|
| 17 | <5 | 5.33 | <5 | <5 | <5 | | 5.46 | <5 | <5 | 5.09 | <5 | <5 | 5.11 | 4.97 | 5.48 |
| 18 | | 5.68 | <5 | <5 | <5 | <5 | <5 | <5 | <5 | 5.24 | <5 | <5 | | 5.63 | <5 |
| 14 | | <5 | <5 | <5 | <5 | <5 | <5 | <5 | <5 | <5 | <5 | <5 | | <5 | <5 |
| 20 | | <5 | <5 | <5 | 5.11 | <5 | <5 | <5 | <5 | <5 | <5 | <5 | | <5 | 5.18 |
| 13 | <5 | <5 | <5 | <5 | <5 | | <5 | <5 | <5 | <5 | <5 | <5 | <5 | <5 | <5 |

TABLE 4-continued

| Co. No. | A2780 | SKOV3 | HT-29 | HCT-116 | Colo205 | H1299 | A549 | H460 | MDA/MB231 | MCF-7 | DU-145 | A431 | U87MG | PC-3 | SK-N-SH |
|---|---|---|---|---|---|---|---|---|---|---|---|---|---|---|---|
| 22 |  | <5 | <5 | <5 | <5 | <5 |  | <5 | <5 | <5 | <5 | <5 |  | <5 | <5 |
| 24 | <5 | <5 | <5 | <5 | <5 |  | <5 | <5 | <5 | <5 | <5 | <5 | <5 | <5 | <5 |
| 15 | <5 | <5 | <5 | <5 | <5 |  | <5 | <5 | <5 | <5 | <5 | <5 | <5 | <5 | <5 |
| 25 | <5 |  |  |  |  |  |  |  | <5 |  |  |  | <5 | <5 |  |
| 28 |  | <5 | <5 |  | <5 |  | <5 | <5 |  | <5 | <5 | <5 |  | <5 | <5 |
| 29 | <5 |  |  | <5 |  |  |  |  | <5 |  |  |  | <5 | <5 |  |
| 30 |  | <5 | <5 |  | <5 |  | <5 | <5 |  | <5 | <5 | <5 |  | <5 | <5 |
| 31 | 5.54 | 5.87 | 5.55 | 5.80 | 5.71 | 6.19 | 6.27 | 6.00 | 5.72 | 6.24 | 5.91 | <5 | 5.79 | 5.78 | >6.52 |
| 32 |  | 5.48 | 5.60 |  | 5.69 |  | 5.67 | 5.63 |  | 5.80 | 5.40 | 5.88 |  | 6.00 | 5.79 |
| 33 |  | <5 | <5 |  | <5 |  | <5 | <5 |  | 4.99 | <5 | <5 |  |  | 5.27 |
| 9 | 6.55 | 6.47 | 6.28 | 6.34 | 6.451 | 6.39 | >6.52 | 6.43 | 5.86 | >6.52 | >6.52 | 5.84 | 5.65 | 6.34 | >6.52 |
| 34 |  | <5 | ~5.08 |  | <5 |  | <5 |  |  | <5 | <5 |  |  |  | 5.28 |
| 35 | 5.17 |  |  | 5.85 |  | 5.62 |  |  | <5 |  |  |  | 5.50 | 5.31 |  |
| 36 | <5 |  |  | <5 |  | <5 |  |  | <5 |  |  |  | <5 | <5 |  |
| 37 | 5.12 |  |  | 5.22 |  | 5.50 |  |  | <5 |  |  |  | 5.74 | 5.02 |  |
| 38 | <5 |  |  | <5 |  | <5 |  |  | <5 |  |  |  | <5 | <5 |  |
| 39 | <5 |  |  | 5.42 |  | <5 |  |  | <5 |  |  |  | 5.10 | <5 |  |
| 40 | <5 |  |  | <5 |  | <5 |  |  | <5 |  |  |  | <5 | <5 |  |
| 41 | <5 |  |  | <5 |  | <5 |  |  | <5 |  |  |  | <5 | <5 |  |
| 42 | <5 |  |  | 5.66 |  | <5 |  |  | <5 |  |  |  | <5 | <5 |  |
| 43 | <5 |  |  | <5 |  | <5 |  |  | <5 |  |  |  | <5 | <5 |  |
| 44 | <5 |  |  | <5 |  | <5 |  |  | <5 |  |  |  | <5 | <5 |  |
| 45 | <5 |  |  | 5.72 |  | 5.55 |  |  | <5 |  |  |  | 5.78 | 5.04 |  |
| 46 | <5 |  |  | <5 |  | <5 |  |  | <5 |  |  |  | 5.04 | <5 |  |
| 47 | <5 |  |  | <5 |  | <5 |  |  | <5 |  |  |  | <5 | <5 |  |
| 48 | <5 |  |  | <5 |  | <5 |  |  | <5 |  |  |  | <5 | <5 |  |
| 49 | <5 |  |  | <5 |  | <5 |  |  | <5 |  |  |  | <5 | <5 |  |
| 50 | <5 |  |  | <5 |  | <5 |  |  | <5 |  |  |  | <5 | <5 |  |
| 51 | <5 |  |  | <5 |  | <5 |  |  | <5 |  |  |  | <5 | <5 |  |
| 52 | <5 |  |  | 5.71 |  | <5 |  |  | <5 |  |  |  | 5.14 | <5 |  |
| 53 | <5 |  |  | <5 |  | <5 |  |  | <5 |  |  |  | <5 | <5 |  |
| 54 | <5 |  |  | <5 |  | <5 |  |  | <5 |  |  |  | <5 | <5 |  |
| 55 | <5 |  |  | <5 |  | <5 |  |  | <5 |  |  |  | <5 | <5 |  |
| 58 | 6.2 |  |  | 6.17 |  | 5.89 |  |  | <5 |  |  |  | 5.13 | <5 |  |
| 61 | <5 |  |  | 5.06 |  | <5 |  |  | <5 |  |  |  | <5 | <5 |  |
| 69 | <5 |  |  | <5 |  | <5 |  |  |  |  |  |  | <5 |  |  |
| 114 | <5 | 5.18 |  | <5 |  | <5 |  |  | <5 |  |  |  | <5 | <5 |  |
| 115 | <5 | <5 |  | <5 |  | 5.51 |  |  | 5.28 |  |  |  | <5 | <5 |  |
| 116 | 5.43 | <5 |  | 5.19 |  | 5.01 |  |  | 5.28 |  |  |  | 5.49 | <5 |  |
| 117 | 5.63 | <5 |  |  |  | 5.15 |  |  | 5.06 |  |  |  | 5.55 | <5 |  |
| 118 | <5 | <5 |  | <5 |  | <5 |  |  | <5 |  |  |  | <5 | <5 |  |
| 119 | 5.59 | <5 |  |  |  | <5 |  |  | <5 |  |  |  | <5 | <5 |  |
| 120 | 5.95 | 5.02 |  | 5.38 |  | 5.68 |  |  | 5.03 |  |  |  | 5.99 | <5 |  |
| 121 | 6.48 | 5.78 |  | 5.99 |  | 6.32 |  |  | 5.20 |  |  |  | 6.66 | 5.19 |  |
| 122 | 6.54 | 5.08 |  |  |  | 5.92 |  |  | 5.71 |  |  |  | 6.15 | 5.10 |  |
| 123 | <5 | <5 |  | <5 |  | <5 |  |  | <5 |  |  |  | <5 | <5 |  |
| 124 | 5.94 |  |  | 6.21 |  | 6.89 |  |  | 5.37 |  |  |  | 6.16 | 6.02 |  |
| 125 | <5 |  |  | <5 |  | <5 |  |  | <5 |  |  |  | <5 | <5 |  |
| 126 | <5 |  |  | <5 |  | <5 |  |  | <5 |  |  |  | 5.20 | <5 |  |
| 113 | <5 |  |  | <5 |  | <5 |  |  | <5 |  |  |  | <5 | <5 |  |
| 129 | <5 |  |  | <5 |  | 5.65 |  |  | <5 |  |  |  | 5.42 | <5 |  |
| 112 | <5 |  |  | 6.26 |  | 6.25 |  |  | <5 |  |  |  | 5.28 | <5 |  |
| 130 | <5 |  |  | 5.31 |  | 5.05 |  |  | <5 |  |  |  | 5.20 | 5.09 |  |
| 132 | <5 |  |  | 6.04 |  | <5 |  |  | <5 |  |  |  | <5 | <5 |  |
| 133 | 6.00 |  |  | 6.16 |  | 5.17 |  |  |  |  |  |  | 5.65 | 5.02 |  |
| 134 | 5.07 |  |  | 5.79 |  | 5.76 |  |  | 5.03 |  |  |  | <5 | 5.44 |  |
| 135 | <5 |  |  | 5.21 |  | 5.31 |  |  | <5 |  |  |  | <5 | <5 |  |
| 136 | 5.89 |  |  | 6.44 |  | 5.67 |  |  | 5.55 |  |  |  | 6.54 | 5.39 |  |
| 137 | 5.61 |  |  | 6.04 |  | 5.73 |  |  | 5.31 |  |  |  | 5.94 | <5 |  |
| 138 | 5.16 |  |  | 5.52 |  | <5 |  |  | <5 |  |  |  | 6.05 | <5 |  |
| 139 | 5.08 |  |  | 5.51 |  | <5 |  |  | <5 |  |  |  | 5.35 | <5 |  |
| 140 | 5.91 |  |  |  |  | 5.58 |  |  |  |  |  |  | 6.30 | 5.21 |  |
| 142 | <5 |  |  |  |  | 6.14 |  |  | <5 |  |  |  | 5.19 | 5.75 |  |
| 143 | <5 |  |  | <5 |  | <5 |  |  | <5 |  |  |  | <5 | <5 |  |
| 144 | 5.87 |  |  | 6.32 |  | 6.56 |  |  | 5.92 |  |  |  | 5.89 | 6.14 |  |
| 145 | 5.53 |  |  | 6.04 |  | 6.08 |  |  | 5.73 |  |  |  | 5.45 | 6.04 |  |
| 146 | 5.83 |  |  | 6.15 |  | 6.41 |  |  |  |  |  |  | 5.80 | 6.22 |  |
| 147 | 5.37 |  |  | 5.90 |  | 5.97 |  |  | <5 |  |  |  | 5.35 | 5.42 |  |
| 148 | <5 |  |  | <5 |  | <5 |  |  | <5 |  |  |  | <5 | <5 |  |
| 149 | <5 |  |  | <5 |  | <5 |  |  | <5 |  |  |  | <5 | <5 |  |
| 150 | <5 |  |  | <5 |  | <5 |  |  | <5 |  |  |  | <5 | <5 |  |
| 151 | <5 |  |  | <5 |  | <5 |  |  | <5 |  |  |  | <5 | <5 |  |
| 152 | <5 |  |  | <5 |  | <5 |  |  | <5 |  |  |  | <5 | <5 |  |
| 153 | <5 |  |  | <5 |  | <5 |  |  | <5 |  |  |  | <5 | <5 |  |
| 154 | <5 |  |  | <5 |  | <5 |  |  | <5 |  |  |  | <5 | <5 |  |
| 155 | <5 |  |  | <5 |  | <5 |  |  | <5 |  |  |  | <5 | <5 |  |
| 156 | <5 |  |  | <5 |  | 5.03 |  |  | <5 |  |  |  | <5 | <5 |  |

TABLE 4-continued

| Co. No. | A2780 | SKOV3 | HT-29 | HCT-116 | Colo205 | H1299 | A549 | H460 | MDA/MB231 | MCF-7 | DU-145 | A431 | U87MG | PC-3 | SK-N-SH |
|---|---|---|---|---|---|---|---|---|---|---|---|---|---|---|---|
| 105 | <5 | | | <5 | <5 | | | | <5 | | | | <5 | <5 | |
| 157 | <5 | | | <5 | <5 | | | | <5 | | | | <5 | <5 | |
| 107 | 7.14 | | | 6.77 | 6.56 | | | | 5.63 | | | | 5.69 | 5.80 | |
| 158 | 6.78 | | | 6.64 | 6.26 | | | | 5.36 | | | | 5.91 | 5.88 | |
| 108 | <5 | | | <5 | <5 | | | | 5.08 | | | | <5 | <5 | |
| 109 | 6.06 | | | 6.22 | <5 | | | | <5 | | | | <5 | <5 | |
| 159 | <5 | | | <5 | <5 | | | | <5 | | | | <5 | <5 | |
| 160 | <5 | | | <5 | <5 | | | | <5 | | | | <5 | <5 | |
| 110 | 5.93 | | | 5.78 | 5.58 | | | | <5 | | | | 5.06 | 5.3 | |
| 167 | 5.23 | | | 5.26 | <5 | | | | <5 | | | | <5 | <5 | |
|  | 5.13 | | | 5.06 | <5 | | | | <5 | | | | <5 | <5 | |
| 168 | <5 | | | <5 | <5 | | | | <5 | | | | <5 | <5 | |
|  | <5 | | | <5 | <5 | | | | <5 | | | | <5 | <5 | |
| 99 | <5 | | | <5 | <5 | | | | <5 | | | | <5 | <5 | |
| 169 | 5.04 | | | <5 | 5.08 | | | | <5 | | | | 5.13 | <5 | |
|  | 5.08 | | | 5.07 | <5 | | | | <5 | | | | <5 | <5 | |
| 170 | <5 | | | <5 | <5 | | | | <5 | | | | <5 | <5 | |
| 176 | <5 | | | <5 | <5 | | | | <5 | | | | <5 | <5 | |
| 191 | 5.61 | | | 5.62 | <5 | | | | 5.55 | | | | 5.81 | 5.57 | |
|  | 5.47 | | | 5.55 | <5 | | | | 5.42 | | | | 5.69 | 5.44 | |
|  | 5.61 | | | 5.77 | <5 | | | | <5 | | | | <5 | <5 | |
| 192 | 5.51 | | | 5.66 | 5.6 | | | | <5 | | | | <5 | <5 | |
| 111 | 5.49 | | | 5.44 | <5 | | | | <5 | | | | 5.57 | 5.19 | |
| 207 | <5 | | | <5 | <5 | | | | <5 | | | | <5 | <5 | |

The invention claimed is:

1. A compound of formula

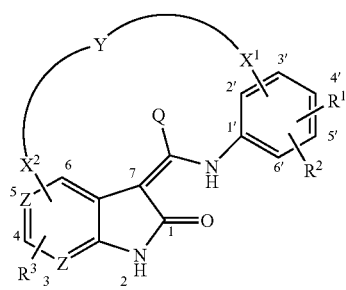

(I)

a N-oxide form, a quaternary amine or a stereochemically isomeric form thereof, wherein
Z represents N or CH;
Y represents —$C_{1-6}$alkanediyl-O—;
—$C_{1-6}$alkanediyl-NR$^{15}$—;
—$C_{1-6}$alkanediyl-NR$^{24}$—CO—$C_{1-6}$alkanediyl-;
—NR$^{5}$—CO—$C_{1-6}$alkanediyl-;
—NR$^{20}$—CO—$C_{1-6}$alkanediyl-NR$^{4}$—;
—NR$^{7}$—CO—$C_{1-6}$alkanediyl-NR$^{8}$—CO—$C_{1-6}$alkanediyl;
—NR$^{25}$—CO—$C_{1-6}$alkanediyl-NR$^{26}$—$C_{1-6}$alkanediyl;
—NR$^{16}$—$C_{1-6}$alkanediyl-NR$^{17}$—CO—$C_{1-6}$alkanediyl-NR$^{21}$—;
—NR$^{9}$—CO—$C_{1-6}$alkanediyl-NR$^{10}$—CO—$C_{1-6}$alkanediyl-NR$^{11}$—;

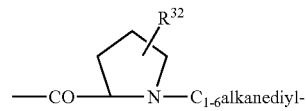

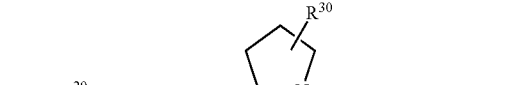

—CO—$C_{1-6}$alkanediyl-;
—CO—$C_{1-6}$alkanediyl-NR$^{6}$—;
—CO—$C_{1-6}$alkanediyl-NR$^{31}$—$C_{1-6}$alkanediyl- ;
—CO—$C_{1-6}$alkanediyl-NR$^{12}$—CO—$C_{1-6}$alkanediyl-NR$^{13}$—; or

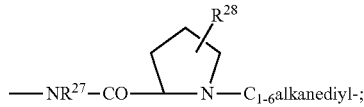

wherein each of said $C_{1-6}$alkanediyl may optionally be substituted with hydroxy or Ar$^{11}$;
X$^{1}$ represents a $C_{1-4}$alkanediyl, —O— or —S(O)$_{2}$—;
X$^{2}$ represents a $C_{1-4}$alkanediyl, Het$^{1}$, $C_{2-4}$alkynediyl, or —$C_{1-4}$alkyl-NR$^{14}$—;
Q represents hydrogen, $C_{1-4}$alkyl or Ar;
R$^{1}$ and R$^{2}$ each independently represent hydrogen; halo; $C_{1-4}$alkyl optionally substituted with one or where possible two, three or more substituents selected from the group consisting of halo, Ar$^{3}$ and Het$^{3}$; Ar$^{1}$—$C_{3-6}$cycloalkyl-O—; $C_{1-4}$alkyl-O— optionally substituted with one or where possible two, three or more substituents selected from the group consisting of halo, Ar$^{4}$ and Het$^{4}$; Ar$^{2}$—O—; —NR$^{18}$R$^{19}$; Het$^{2}$; cyano or —NR$^{33}$—W$^{1}$—Ar$^{10}$;
R$^{3}$ represents hydrogen, $C_{1-4}$alkyl-, Ar$^{5}$, Het$^{5}$, —NR$^{23}$R$^{22}$, $C_{1-4}$alkyl-O—, Ar$^{6}$—O—, $C_{1-4}$alkyl-S—, Ar$^{7}$—S—, $C_{1-4}$alkyl-S(O)$_{1-2}$—, Ar$^{8}$—S(O)$_{1-2}$—;
R$^{4}$, R$^{5}$, R$^{6}$, R$^{7}$, R$^{8}$, R$^{9}$, R$^{10}$, R$^{11}$, R$^{12}$, R$^{13}$, R$^{15}$, R$^{16}$, R$^{17}$, R$^{18}$, R$^{19}$, R$^{20}$, R$^{21}$, R$^{22}$, R$^{23}$, R$^{24}$, R$^{25}$, R$^{26}$, R$^{27}$, R$^{29}$ and R$^{31}$ each independently represent hydrogen; $C_{1-4}$alkyl; $C_{3-6}$cycloalkyl; $C_{1-4}$alkyl substituted with $C_{1-4}$alkyloxy, morpholinyl, piperazinyl or $C_{1-4}$alkylpiperazinyl wherein the $C_{1-4}$alkyl substituted on the piperazinyl may optionally be further substituted with one or where possible two, three or more substituents selected from the group consisting of halo, $Ar^9$ and $Het^6$;

$R^{14}$ and $R^{33}$ each independently represent hydrogen or $C_{1-4}$alkyl;

$R^{28}R^{30}$ and $R^{32}$ each independently represent hydrogen or OH;

$W^1$ represents —CO—NH—, —CO—, —SO$_2$— or —$C_{1-4}$alkanediyl-;

$Het^1$ represents piperidinyl, piperazinyl, pyrrolidinyl or azetidinyl;

$Het^2$ and $Het^5$ each independently represent morpholinyl, thiomorpholinyl, pyrrolidinyl, piperazinyl or piperidinyl wherein said $Het^2$ and $Het^5$ are optionally substituted with one or where possible two or more substituents selected from $C_{1-4}$alkyl, $C_{3-6}$cycloalkyl, hydroxy$C_{1-4}$alkyl or $C_{1-4}$alkyloxy$C_{1-4}$alkyl;

$Het^3$, $Het^4$ and $Het^6$ each independently represent morpholinyl, thiomorpholinyl, pyrrolidinyl, piperazinyl or piperidinyl wherein said $Het^3$, $Het^4$ and $Het^6$ are optionally substituted with one or where possible two or more substituents selected from $C_{1-4}$alkyl, $C_{3-6}$cycloalkyl, hydroxy$C_{1-4}$alkyl or $C_{1-4}$alkyloxy$C_{1-4}$alkyl;

Ar represents an aryl or heteroaryl ring selected from the group consisting of phenyl, naphthyl, quinolinyl, benzoxazolyl, pyridyl, pyrazinyl, furanyl, thienyl, pyrimidinyl, isoxazolyl, isothiazolyl, oxazolyl, thiazolyl, pyrrolyl, pyrazolyl, indolyl, pyridazinyl, benzimidazolyl, benzothienyl and benzothiazolyl;

$Ar^1$, $Ar^2$, $Ar^3$, $Ar^4$ and $Ar^9$ each independently represent an aryl or heteroaryl ring system selected from the group consisting of phenyl, naphthyl, quinolinyl, benzoxazolyl, pyridyl, pyrazinyl, furanyl, thienyl, pyrimidinyl, isoxazolyl, isothiazolyl, oxazolyl, thiazolyl, pyrrolyl, pyrazolyl, indolyl, pyridazinyl, benzimidazolyl, benzothienyl and benzothiazolyl;

$Ar^5$, $Ar^6$, $Ar^7$ and $Ar^8$ each independently represent an aryl or heteroaryl ring system selected from the group consisting of phenyl, naphthyl, quinolinyl, benzoxazolyl, pyridyl, pyrazinyl, furanyl, thienyl, pyrimidinyl, isoxazolyl, isothiazolyl, oxazolyl, thiazolyl, pyrrolyl, pyrazolyl, indolyl, pyridazinyl, benzimidazolyl, benzothienyl and benzothiazolyl;

$Ar^{10}$ and $Ar^{11}$ each independently represent a ring system selected from the group consisting of phenyl and $C_{3-6}$cycloalkyl;

or a pharmaceutically acceptable addition salt thereof.

2. A compound according to claim 1 wherein

Z represents N or CH;

Y represents —$NR^{20}$—CO—$C_{1-6}$alkanediyl-$NR^4$—; —$NR^5$—CO—$C_{1-6}$alkanediyl-; —CO—$C_{1-6}$alkanediyl-$NR^6$—; —$NR^7$—$C_{1-6}$alkanediyl-$NR^8$—CO—$C_{1-6}$alkanediyl; —CO—$C_{1-6}$alkanediyl-; —$C_{1-6}$alkanediyl-O—; —$C_{1-6}$alkanediyl-$NR^{15}$—; —$NR^9$—CO—$C_{1-6}$alkanediyl-$NR^{10}$—CO—$C_{1-6}$alkanediyl-$NR^{11}$—; —CO—$C_{1-6}$alkanediyl-$NR^{12}$—CO—$C_{1-6}$alkanediyl-$NR^{13}$—; —$NR^{16}$—$C_{1-6}$alkanediyl-$NR^{17}$—CO—$C_{1-6}$alkanediyl-$NR^{21}$—;

$X^1$ represents a $C_{1-4}$alkanediyl, —O— or —S(O)$_2$—;

$X^2$ represents a $C_{1-4}$alkanediyl, $Het^1$, $C_{2-4}$alkynediyl, or —$C_{1-4}$alkanediyl-$NR^{14}$—;

Q represents hydrogen, $C_{1-4}$alkyl or Ar;

$R^1$ and $R^2$ each independently represent hydrogen; halo; $C_{1-4}$alkyl optionally substituted with one or where possible two, three or more substituents selected from the group consisting of halo, $Ar^3$ and $Het^3$; $Ar^1$—$C_{3-6}$cycloalkyl-O—; $C_{1-4}$alkyl-O— optionally substituted with one or where possible two, three or more substituents selected from the group consisting of halo, $Ar^4$ and $Het^4$; $Ar^2$—O—; —$NR^{18}R^{19}$; $Het^2$ or cyano;

$R^3$ represents hydrogen, $C_{1-4}$alkyl-, $Ar^5$, $Het^5$, —$NR^{23}R^{22}$, $C_{1-4}$alkyl-O—, $Ar^6$—O—, $C_{1-4}$alkyl-S—, $Ar^7$—S—, $C_{1-4}$alkyl-S(O)$_{1-2}$—, $Ar^8$—S(O)$_{1-2}$—;

$R^4$, $R^5$, $R^6$, $R^7$, $R^8$, $R^9$, $R^{10}$, $R^{11}$, $R^{12}$, $R^{13}$, $R^{15}$, $R^{16}$, $R^{17}$, $R^{18}$, $R^{19}$, $R^{20}$, $R^{21}$, $R^{22}$ and $R^{23}$ each independently represent hydrogen; $C_{1-4}$alkyl; $C_{3-6}$cycloalkyl; $C_{1-4}$alkyl substituted with morpholinyl, piperazinyl or $C_{1-4}$alkylpiperazinyl wherein the $C_{1-4}$alkyl substituted on the piperazinyl may optionally be further substituted with one or where possible two, three or more substituents selected from the group consisting of halo, $Ar^9$ and $Het^6$;

$R^{14}$ represents hydrogen or $C_{1-4}$alkyl;

$Het^1$ represents piperidinyl, piperazinyl, pyrrolidinyl or azetidinyl;

$Het^2$ and $Het^5$ each independently represent morpholinyl, thiomorpholinyl, pyrrolidinyl, piperazinyl or piperidinyl wherein said $Het^2$ and $Het^5$ are optionally substituted with one or where possible two or more substituents selected from $C_{1-4}$alkyl, $C_{3-6}$cycloalkyl, hydroxy$C_{1-4}$alkyl or $C_{1-4}$alkyloxy$C_{1-4}$alkyl;

$Het^3$, $Het^4$ and $Het^6$ each independently represent morpholinyl, thiomorpholinyl, pyrrolidinyl, piperazinyl or piperidinyl wherein said $Het^3$, $Het^4$ and $Het^6$ are optionally substituted with one or where possible two or more substituents selected from $C_{1-4}$alkyl, $C_{3-6}$cycloalkyl, hydroxy$C_{1-4}$alkyl or $C_{1-4}$alkyloxy$C_{1-4}$alkyl;

Ar represents an aryl or heteroaryl ring selected from the group consisting of phenyl, naphthyl, quinolinyl, benzoxazolyl, pyridyl, pyrazinyl, furanyl, thienyl, pyrimidinyl, isoxazolyl, isothiazolyl, oxazolyl, thiazolyl, pyrrolyl, pyrazolyl, indolyl, pyridazinyl, benzimidazolyl, benzothienyl and benzothiazolyl;

$Ar^1$, $Ar^2$, $Ar^3$, $Ar^4$ and $Ar^9$ each independently represent an aryl or heteroaryl ring system selected from the group consisting of phenyl, naphthyl, quinolinyl, benzoxazolyl, pyridyl, pyrazinyl, furanyl, thienyl, pyrimidinyl, isoxazolyl, isothiazolyl, oxazolyl, thiazolyl, pyrrolyl, pyrazolyl, indolyl, pyridazinyl, benzimidazolyl, benzothienyl and benzothiazolyl;

$Ar^5$, $Ar^6$, $Ar^7$ and $Ar^8$ each independently represent an aryl or heteroaryl ring system selected from the group consisting of phenyl, naphthyl, quinolinyl, benzoxazolyl, pyridyl, pyrazinyl, furanyl, thienyl, pyrimidinyl, isoxazolyl, isothiazolyl, oxazolyl, thiazolyl, pyrrolyl, pyrazolyl, indolyl, pyridazinyl, benzimidazolyl, benzothienyl and benzothiazolyl.

3. A compound according to claim 1 wherein Z represents N.

4. A compound according to claim 1 wherein Z represents CH.

5. A compound according to claim 1 wherein

Y represents —$NR^{20}$—CO—$C_{1-6}$alkanediyl-$NR^4$—; —$NR^5$—CO—$C_{1-6}$alkanediyl-; —CO—$C_{1-6}$alkanediyl-$NR^6$—; —CO—$C_{1-6}$alkanediyl-; —$NR^9$—CO—$C_{1-6}$alkanediyl-$NR^{10}$—CO—$C_{1-6}$alkanediyl-$NR^{11}$—; or —CO—$C_{1-6}$alkanediyl-$NR^{12}$—CO—$C_{1-6}$alkanediyl-$NR^{13}$—;

$X^1$ represents $C_{1-4}$alkanediyl, —O— or —S(O)$_2$—;

$X^2$ represents $Het^1$, $C_{2-4}$alkynediyl, or —$C_{1-4}$alkanediyl-$NR^{14}$—;

Q represents hydrogen;

$R^1$ and $R^2$ each independently represent hydrogen, halo, $C_{1-4}$alkyl-O—, cyano or $Het^2$; in particular $R^1$ represents $Het^2$, $C_{1-4}$alkyl-O—, cyano or halo and $R^2$ represents hydrogen, halo or $C_{1-4}$alkyl-O—;

$R^3$ represents hydrogen;

$R^5$, $R^9$, $R^{10}$, $R^{12}$ and $R^{20}$ each independently represent hydrogen, $C_{1-4}$alkyl or $C_{1-4}$alkyl substituted with morpholinyl or piperazinyl; in particular $R^5$, $R^9$, $R^{12}$ and $R^2$ each independently represent hydrogen or $C_{1-4}$alkyl and $R^{10}$ represents hydrogen, $C_{1-4}$alkyl or $C_{1-4}$alkyl substituted with morpholinyl or piperazinyl; more in particular $R^{10}$ represents $C_{1-4}$alkyl substituted with morpholinyl;

$R^4$, $R^6$, $R^{11}$ and $R^{13}$ each independently represent hydrogen or $C_{1-4}$alkyl;

$R^{14}$ represents hydrogen or $C_{1-4}$alkyl;

$Het^1$ represents piperidinyl or piperazinyl; and $Het^2$ represents morpholinyl.

6. A compound according to claim 1 wherein

Y represents —$NR^{20}$—CO—$C_{1-6}$alkanediyl-$NR^4$—; —$NR^5$—CO—$C_{1-6}$alkanediyl-; —CO—$C_{1-6}$alkanediyl-$NR^6$—; —CO—$C_{1-6}$alkanediyl-; or –$NR^9$—CO—$C_{1-6}$alkanediyl-$NR^{10}$—CO—$C_{1-6}$alkanediyl-$NR^{11}$—;

$X^1$ represents $C_{1-4}$alkanediyl, —O— or —$S(O)_2$—;

$X^2$ represents $Het^1$, $C_{2-4}$alkynediyl or —$C_{1-4}$alkanediyl-$NR^{14}$—;

Q represents hydrogen;

$R^1$ represents hydrogen, $Het^2$, $C_{1-4}$alkyl-O—, cyano or halo;

$R^2$ represents hydrogen or $C_{1-4}$alkyl-O—;

$R^3$ represents hydrogen;

$R^5$, $R^9$, $R^{10}$ and $R^{20}$ each independently represent hydrogen or $C_{1-4}$alkyl; in particular $R^5$, $R^9$, $R^{10}$ and $R^{20}$ each independently represent hydrogen, methyl or isopropyl;

$R^4$, $R^6$ and $R^{11}$ each independently represent $C_{1-4}$alkyl; in particular methyl or isopropyl;

$R^{14}$ represents hydrogen or $C_{1-4}$alkyl;

$Het^1$ represents piperazinyl; and $Het^2$ represents morpholinyl.

7. A compound according to claim 1 wherein

Y represents —$NR^{20}$—CO—$C_{1-6}$alkanediyl-$NR^4$—; —$NR^5$—CO—$C_{1-6}$alkanediyl-; or —CO—$C_{1-6}$alkanediyl-;

$X^1$ represents $C_{1-4}$alkanediyl, —O— or —$S(O)_2$—;

$X^2$ represents $Het^1$, $C_{2-4}$alkynediyl or -$C_{1-4}$alkanediyl-$NR^{14}$—;

Q represents hydrogen;

$R^1$ represents hydrogen, $Het^2$, $C_{1-4}$alkyl-O—, cyano or halo;

$R^2$ represents hydrogen;

$R^3$ represents hydrogen;

$R^5$, $R^9$, $R^{10}$ and $R^{20}$ each independently represent hydrogen or $C_{1-4}$alkyl; in particular $R^5$, $R^9$, $R^{10}$ and $R^{20}$ each independently represent hydrogen, methyl or isopropyl;

$R^4$, $R^6$ and $R^{11}$ each independently represent $C_{1-4}$alkyl; in particular methyl or isopropyl;

$R^{14}$ represents hydrogen or $C_{1-4}$alkyl;

$Het^1$ represents piperazinyl; and $Het^2$ represents morpholinyl.

8. A compound according to claim 1 wherein

Y represents —$NR^5$—CO—$C_{1-6}$alkyl- with $R^5$ being selected from hydrogen, methyl or isopropyl;

$X^1$ represents —O—;

$X^2$ represents —$C_{1-4}$alkyl-$NR^{14}$— with $R^{14}$ being selected from hydrogen or methyl;

$R^1$ represents hydrogen, $C_{1-4}$alkyl-O—, or halo; in particular $R^1$ represents hydrogen, methoxy, ethoxy or halo; and $R^2$ and $R^3$ represent hydrogen.

9. A compound according to claim 1 wherein

Y represents —$NR^{20}$—CO—$C_{1-6}$alkanediyl-$NR^4$—; —$NR^5$—CO—$C_{1-6}$alkanediyl-; or —CO—$C_{1-6}$alkanediyl-; in particular Y represents —$NR^5$—CO—$C_{1-6}$alkanediyl-;

$X^1$ represents $C_{1-4}$alkanediyl, —O— or —$S(O)_2$—; in particular $X^1$ represents —O—;

$X^2$ represents $Het^1$, $C_{2-4}$alkynediyl, or —$C_{1-4}$alkanediyl-$NR^{14}$—; in particular $X^2$ represents —$C_{1-4}$alkanediyl-$NR^{14}$—;

Q represents hydrogen;

$R^1$ and $R^2$ each independently represent hydrogen, halo, $C_{1-4}$alkyl-O—, cyano or $Het^2$; in particular $R^1$ represents $Het^2$, $C_{1-4}$alkyl-O—, cyano or halo and $R^2$ represents hydrogen; in an even further embodiment $R^1$ and $R^2$ each independently represent hydrogen, halo, or $C_{1-4}$alkyl-O—;

$R^3$ represents hydrogen;

$R^5$ and $R^{20}$ each independently represent hydrogen or $C_{1-4}$alkyl;

$R^4$ represents hydrogen or $C_{1-4}$alkyl;

$R^{14}$ represents hydrogen or $C_{1-4}$alkyl;

$Het^1$ represents piperidinyl or piperazinyl; in particular $Het^1$ represents piperazinyl; and $Het^2$ represents morpholinyl.

10. A compound according to claim 1 wherein $R^1$ represents hydrogen, morpholinyl, halo, cyano or methoxy; in particular hydrogen $R^2$ represents hydrogen, halo or methoxy; in particular $R^2$ represents hydrogen;

$R^3$ represents hydrogen;

$R^9$, $R^{10}$ and $R^{20}$ each independently represent hydrogen, methyl or isopropyl; more in particular $R^9$, $R^{10}$ and $R^{20}$ each independently represent hydrogen or methyl;

$R^4$ and $R^6$ each independently represents hydrogen or methyl;

$R^{14}$ represents hydrogen or methyl; and $Het^1$ represents piperazinyl.

11. A compound according to claim 1 wherein Y represents —$NR^5$—CO—$C_{1-6}$alkanediyl-; $X^1$ represents —O13 ; $X^2$ represents -$C_{1-4}$alkanediyl-$NR^{14}$—; $R^5$ represents hydrogen or $C_{1-4}$alkyl and $R^{14}$ represents hydrogen or $C_{1-4}$alkyl. More in particular, those compounds of formula (I), (Ia) or (Ib) wherein Y represents —$NR^5$—CO—$(CH_2)_{3-4}$—; $X^1$ represents —O—; $X^2$ represents —$(CH_2)_3$—$NR^{14}$—; $R^5$ represents hydrogen, methyl or isopropyl and $R^{14}$ represents hydrogen or methyl.

12. A compound according to claim 1 wherein $X^1$ is attached at position 2', $R^1$ is at position 3' and $X^2$ is at position 6.

13. A compound of formula (I), according to claim 1 including the N-oxide forms and stereochemically isomers thereof, selected from the group consisting of:

6,9-ethano-17,20-etheno-1H-16-oxa-2,3,5,6,9,21-hexaazacycloeicos[1,2,3-cd]indene-1,10(11H)-dione, 18-chloro-2,7,8,12,13,14,15,21-octahydro-;

1H-6,9-ethano-16,20-metheno-10H-15-oxa-2,3,5,6,9,21-hexaazacycloeicos[1,2,3-cd]indene-1,10-dione, 19-chloro-2,7,8,11,12,13,14,21-octahydro-;

1H-6,9-ethano-16,20-metheno-10H-15-oxa-2,3,5,6,9,21-hexaazacycloeicos[1,2,3-cd]indene-1,10-dione, 17-chloro-2,7,8,11,12,13,14,21-octahydro-;

1H-6,9-ethano-17,21-metheno-16-thia-2,3,5,6,9,15,22-heptaazacycloheneicos[1,2,3-cd]indene-1,10(11H)-dione, 2,7,8,12,13,14,15,22-octahydro-, 16,16-dioxide;

1H-6,9-ethano-17,21-metheno-16-oxa-2,3,5,6,9,22-hexaazacycloheneicos[1,2,3-cd]indene-1,10(11H)-dione, 18-chloro-2,7,8,12,13,14,15,22-octahydro-;

1H-6,9-ethano-15,19-metheno-14-oxa-2,3,5,6,9,20-hexaazacyclononadec[1,2,3-cd]indene-16-carbonitrile, 2,7,8,10,11,12,13,20-octahydro-1,10-dioxo-;

1H-6,9-ethano-16,20-metheno-10H-15-oxa-2,3 ,5,6,9,21-hexaazacycloeicos[1,2,3-cd]indene-17-carbonitrile, 2,7,8,11,12,13,14,21-octahydro-1,10-dioxo-;

1H-6,9-ethano-16,20-metheno-2,3,5,6,9,14,21-heptaazacycloeicos[1,2,3-cd]indene-1,10(11H)-dione, 2,7,8,12,13,14,15,21-octahydro-14-methyl-;

10H-6,9-ethano-21,17-metheno-1H-2,3,5,6,9,15,22-heptaazacycloheneicos[1,2,3-cd]indene-1,10-dione, 18-fluoro-2,7,8,11,12,13,14,15,16,22-decahydro-15-(1-methylethyl)-;

20,16-metheno-16H-15-oxa-2,3,5,6,10,21-hexaazacycloeicos[1,2,3-cd]indene-1,11(2H,12H)-dione, 6,7,8,9,10,13,14,21-octahydro-17-methoxy-6,10-dimethyl-;

1H-19,15-metheno-14-oxa-2,3,5,6,9,20-hexaazacyclononadec[1,2,3-cd]indene-1,10(11H)-dione, 2,6,7,8,9,12,13,20-octahydro-16-methoxy-6-methyl-9-(1-methylethyl)-;

20,16-metheno-16H-15-oxa-2,3,5,6,10,21-hexaazacycloeicos[1,2,3-cd]indene-1,11(2H,12H)-dione, 6,7,8,9,10,13,14,21-octahydro-17-methoxy-10-methyl-;

20,16-metheno-16H-15-oxa-2,3,5,6,10,21-hexaazacycloeicos[1,2,3-cd]indene-1,11(2H,12H)-dione, 6,7,8,9,10,13,14,21-octahydro-10-methyl-;

1H-21,17-metheno-16-oxa-2,3,5,6,9,22-hexaazacycloheneicos[1,2,3-cd]indene-1,10(11H)-dione, 2,6,7,8,9,12,13,14,15,22-decahydro-18-methoxy-9-methyl-;

20,16-metheno-16H-15-oxa-2,3,5,6,9,21-hexaazacycloeicos[1,2,3-cd]indene-1,10-dione, 2,6,7,8,9,11,12,13,14,21-decahydro-17-methoxy-9-methyl-;

1H-21,17-metheno-16-oxa-2,3,5,6,9,22-hexaazacycloheneicos[1,2,3-cd]indene-1,10(11H)-dione, 18-chloro-2,6,7,8,9,12,13,14,15,22-decahydro-6-methyl-;

20,16-metheno-16H-15-oxa-2,3,5,6,10,21-hexaazacycloeicos[1,2,3-cd]indene-1,11(2H,12H)-dione, 17-chloro-6,7,8,9,10,13,14,21-octahydro-10-methyl-;

21,17-metheno-17H-2,3,5,6,10,15,22-heptaazacycloheneicos[1,2,3-cd]indene-1,11(2H,12H)-dione, 6,7,8,9,10,13,14,15,16,22-decahydro-10,15-dimethyl-;

1H-19,15-metheno-14-oxa-2,3,5,6,9,20-hexaazacyclononadec[1,2,3-cd]indene-1,10(11H)-dione, 2,6,7,8,9,12,13,20-octahydro-9-methyl-16-(4-morpholinyl)-;

21,17-metheno-17H-2,3,5,6,10,15,22-heptaazacycloheneicos[1,2,3-cd]indene-1,11(2H,12H)-dione, 6,7,8,9,10,13,14,15,16,22-decahydro-18,19-dimethoxy-10,15-dimethyl-;

21,17-metheno-17H-2,3,5,6,10,15,22-heptaazacycloheneicos[1,2,3-cd]indene-1,11(2H,12H)-dione, 6,7,8,9,10,13,14,15,16,22-decahydro-10,15-dimethyl-18-(4-morpholinyl)-;

or the pharmaceutically acceptable addition salts thereof.

14. A compound of formula (I) according to claim 1, including the N-oxide forms and stereochemically isomers thereof, selected from the group consisting of:

1H-21,17-metheno-16-oxa-2,3,5,6,9,22-hexaazacycloheneicos[1,2,3-cd]indene-1,10(11H)-dione, 18-chloro-2,6,7,8,9,12,13,14,15,22-decahydro-6-methyl-;

20,16-metheno-16H-15-oxa-2,3,5,6,10,21-hexaazacycloeicos[1,2,3-cd]indene-1,11(2H,12H)-dione, 6,7,8,9,10,13,14,21-octahydro-10-methyl-;

1H-21,17-metheno-16-oxa-2,3,5,6,9,22-hexaazacycloheneicos[1,2,3-cd]indene-1,10(11H)-dione, 2,6,7,8,9,12,13,14,15,22-decahydro-18-methoxy-9-methyl-;

20,16-metheno-16H-15-oxa-2,3,5,6,9,21-hexaazacycloeicos[1,2,3-cd]indene-1,10-dione, 2,6,7,8,9,11,12,13,14,21-decahydro-17-methoxy-9-methyl-;

20,16-metheno-16H-15-oxa-2,3,5,6,10,21-hexaazacycloeicos[1,2,3-cd]indene-1,11(2H,12H)-dione, 6,7,8,9,10,13,14,21-octahydro-17-methoxy-6,10-dimethyl-;

1H-19,15-metheno-14-oxa-2,3,5,6,9,20-hexaazacyclononadec[1,2,3-cd]indene-1,10(11H)-dione, 2,6,7,8,9,12,13,20-octahydro-16-methoxy-6-methyl-9-(1-methylethyl)-;

20,16-metheno-16H-15-oxa-2,3,5,6,10,21-hexaazacycloeicos[1,2,3-cd]indene-1,11(2H,12H)-dione, 6,7,8,9,10,13,14,21-octahydro-17-methoxy-10-methyl-;

or the pharmaceutically acceptable addition salts thereof.

15. A method of treating colon, lung, ovarian, prostate cancers or glioblastoma and melanoma cancers in a subject in need of such treatment, said method comprising administering to the subject a therapeutically effective amount of a pharmaceutical composition comprising a compound of claim 1 and a pharmaceutically acceptable carrier.

16. A pharmaceutical composition comprising a compound as claimed in claim 1 and a pharmaceutically acceptable carrier.

17. A compound of formula (I) according to claim 1, including the N-oxide forms and stereochemically isomers thereof, selected from the group consisting of:

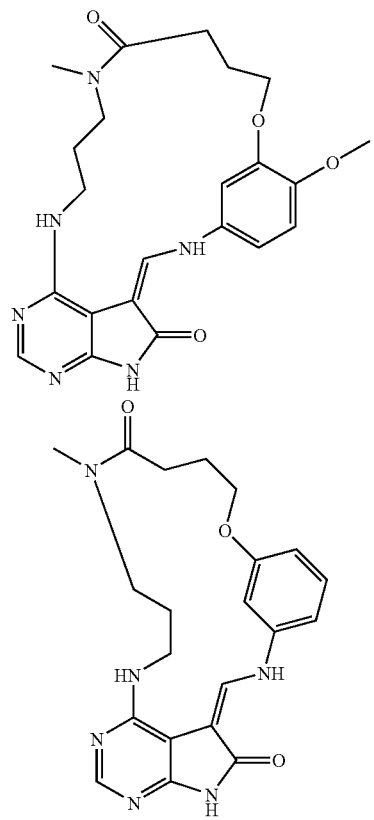

223
-continued
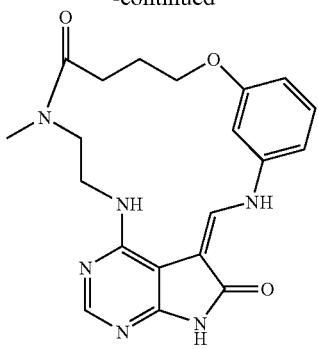
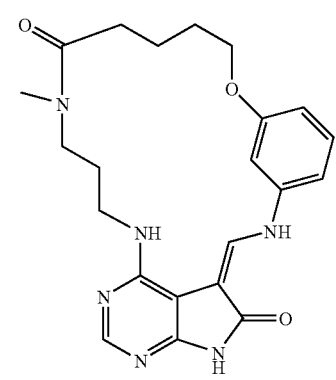
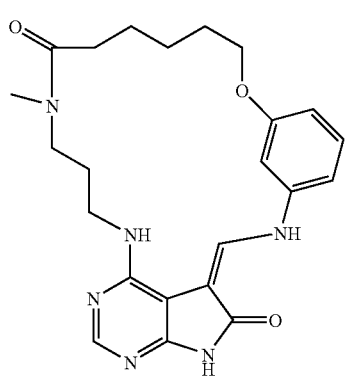
224
-continued
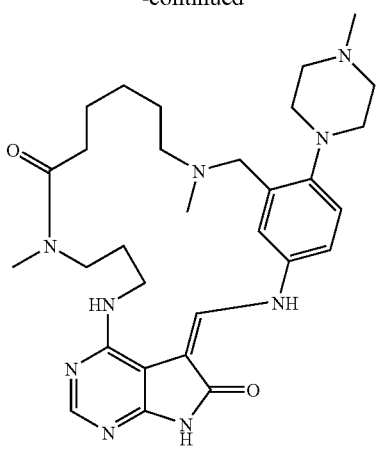
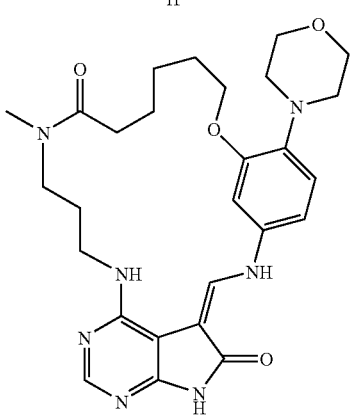
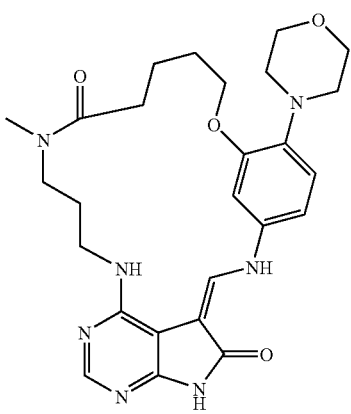
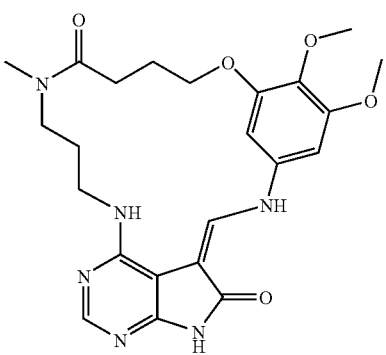

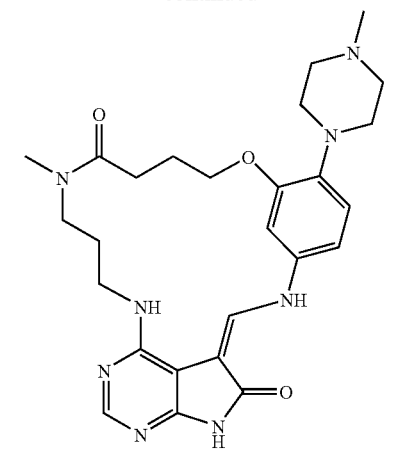
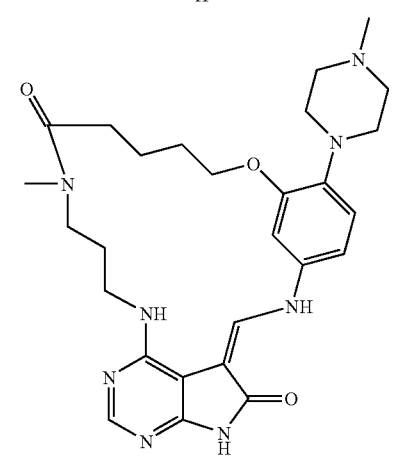
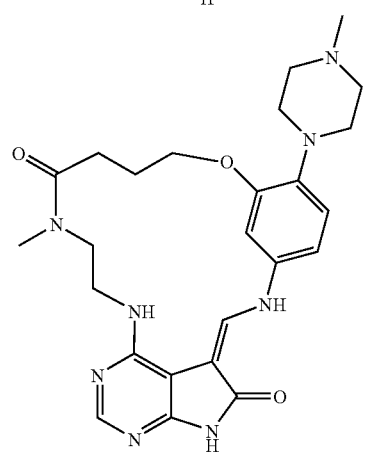
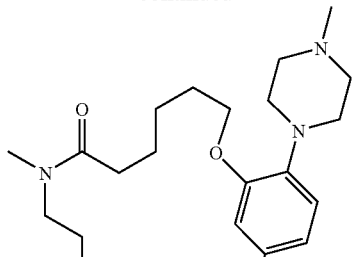
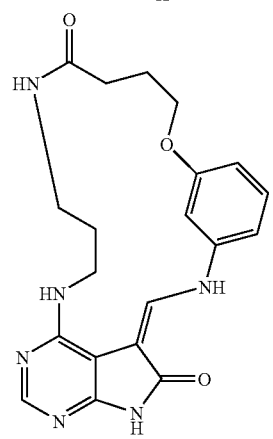
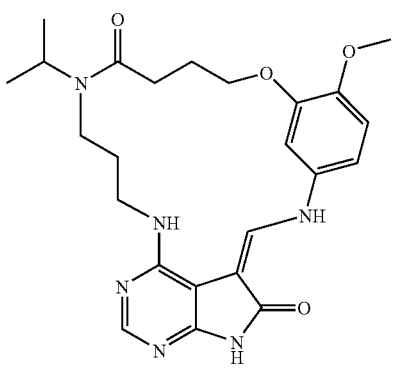
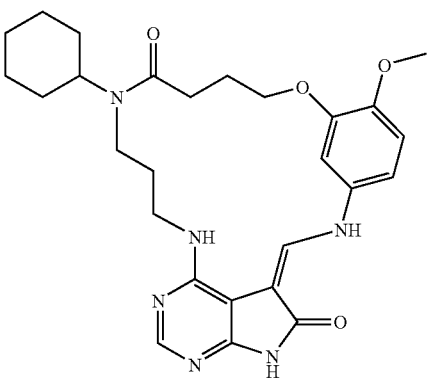

227
-continued
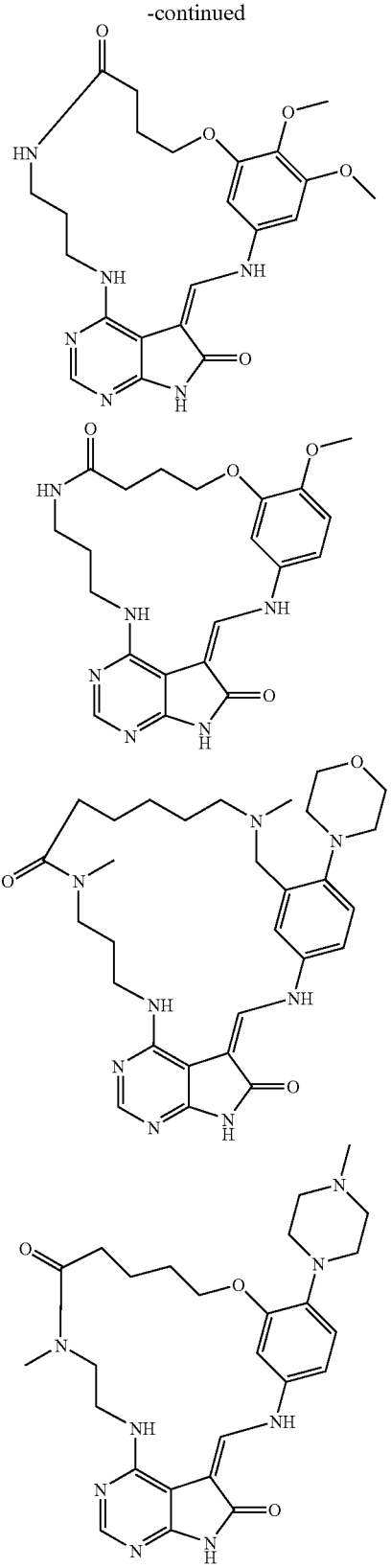
228
-continued
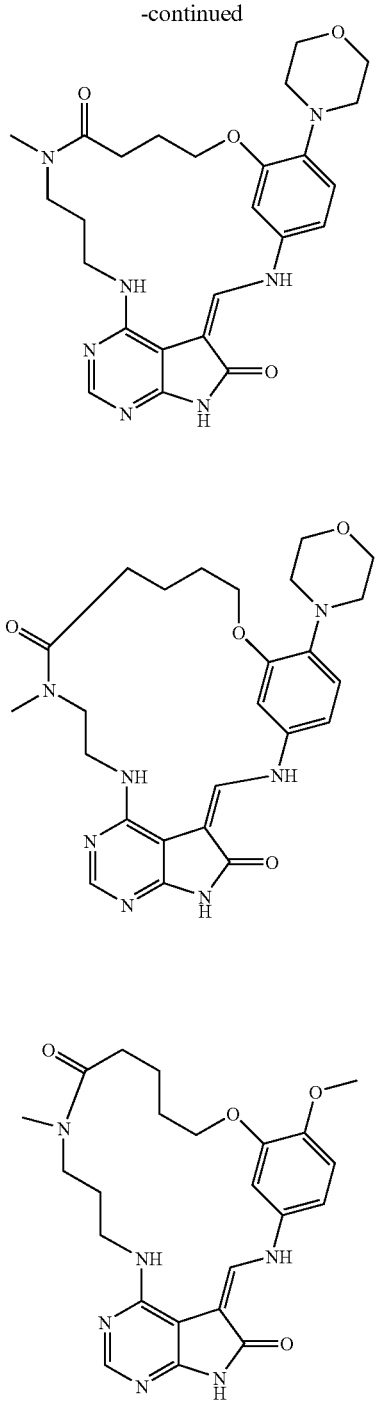
or the pharmaceutically acceptable addition salts thereof.
18. A compound according to claim 2 wherein Z represents N.
19. A compound according to claim 2 wherein Z represents CH.
* * * * *